US012773205B2

(12) United States Patent
Bedoya et al.

(10) Patent No.: US 12,773,205 B2
(45) Date of Patent: Oct. 27, 2026

(54) RUNNING STITCH SUTURING INSTRUMENT

(71) Applicant: HOLOGIC, INC., Marlborough, MA (US)

(72) Inventors: Marco Bedoya, Marlborough, MA (US); Catherine Withers, Marlborough, MA (US); Matt Laplaca, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 133 days.

(21) Appl. No.: 18/494,779

(22) Filed: Oct. 26, 2023

(65) Prior Publication Data

US 2024/0050087 A1 Feb. 15, 2024

Related U.S. Application Data

(63) Continuation of application No. PCT/US2022/034611, filed on Jun. 22, 2022.

(Continued)

(51) Int. Cl.

*A61B 17/29* (2006.01)
*A61B 17/04* (2006.01)
*A61B 17/062* (2006.01)

(52) U.S. Cl.

CPC ...... *A61B 17/0469* (2013.01); *A61B 17/0625* (2013.01); *A61B 2017/2926* (2013.01)

(58) Field of Classification Search

CPC ............ A61B 17/0469; A61B 17/0625; A61B 2017/2926; A61B 2017/047;

(Continued)

(56) References Cited

U.S. PATENT DOCUMENTS

2003/0181924 A1 9/2003 Yamamoto
2004/0049207 A1 * 3/2004 Goldfarb ............... A61F 2/2463 606/139

(Continued)

FOREIGN PATENT DOCUMENTS

EP 0684012 A2 * 11/1995 ......... A61B 17/0483
EP 1629780 A1 3/2006
WO WO 2017/044838 A1 3/2017

OTHER PUBLICATIONS

Espacenet translation of EP-0684012-A2 (Year: 1999).*

(Continued)

*Primary Examiner* — Katherine H Schwiker
*Assistant Examiner* — Zehra Jaffri
(74) *Attorney, Agent, or Firm* — Vista IP Law Group, LLP

(57) ABSTRACT

A laparoscopic tissue suturing instrument comprises a shaft and a tissue grasper coupled to the shaft. The tissue grasper defines a tissue receiving gap and defining a shuttling element retention cavity. The instrument further comprises a suture shuttling element configured for being removably retained at least partially within the shuttling element retention cavity, and a needle having a needle shaft, a shuttling element coupler disposed at a distal end of the needle shaft, and a shuttling element release mechanism disposed on the needle shaft proximal to the shuttling element coupler. The instrument further comprises a shuttling element retainer mechanism adjacent to the shuttling element retention cavity. The shuttling element release mechanism is configured for interacting with the shuttling element retainer mechanism to alternately transition the shuttling element retention cavity between a retention state that securely retains the suture shuttling element, and a release state that releases the suture shuttling element.

20 Claims, 96 Drawing Sheets

Related U.S. Application Data

(60) Provisional application No. 63/311,399, filed on Feb. 17, 2022, provisional application No. 63/279,638, filed on Nov. 15, 2021, provisional application No. 63/218,223, filed on Jul. 2, 2021.

(58) Field of Classification Search
CPC .......... A61B 17/062; A61B 2017/0609; A61B 17/0482; A61B 17/0491
See application file for complete search history.

(56) References Cited

U.S. PATENT DOCUMENTS

| | | | | |
|---|---|---|---|---|
| 2011/0276064 | A1 | 11/2011 | Henrichsen | |
| 2013/0317291 | A1 | 11/2013 | Yamamoto | |
| 2016/0000445 | A1 * | 1/2016 | Raybin | A61B 17/1285 606/157 |
| 2017/0071597 | A1 | 3/2017 | Gorski et al. | |

OTHER PUBLICATIONS

PCT International Search Report for PCT/US2022/034611, Applicant: Hologic, Inc., Form PCT/ISA/210 and 220, dated Oct. 17, 2022 (5 pages).
PCT Written Opinion of the International Search Authority for PCT/US2022/034611, Applicant: Hologic, Inc., Form PCT/ISA/237, dated Oct. 17, 2022 (10 pages).

* cited by examiner

RUNNING STITCH SUTURING INSTRUMENT

RELATED APPLICATIONS

The present application is a continuation of International Application No. PCT/US2022/034611, filed Jun. 22, 2022, which claims the benefit under 35 U.S.C. § 119(e), to U.S. Provisional Application Ser. No. 63/218,223, filed Jul. 2, 2021, U.S. Provisional Application Ser. No. 63/279,638, filed Nov. 15, 2021, and U.S. Provisional Application Ser. No. 63/311,399, filed Feb. 17, 2022, the contents of all of which are hereby expressly incorporated herein by reference in their entirety into the present application.

FIELD

The present disclosure relates generally to surgical devices and surgical techniques, and more specifically, to laparoscopic tissue suturing devices and related methods.

BACKGROUND

Laparoscopic suturing is challenging and may take years for a surgeon to master. For example, suturing the vaginal cuff during a total laparoscopic hysterectomy (TLH) is one of the most challenging steps of TLH due to the dexterity and coordination required for suturing. In the United States alone, there are approximately 500,000 laparoscopic or robotic hysterectomies performed annually. In such procedures, the cervix is severed from the vagina and removed with the uterus, leaving behind the opening in the vaginal wall that must be closed. However, the geometry of this opening can make it difficult to suture effectively using laparoscopy tools. Consequently, vaginal cuff dehiscence, which is a potentially catastrophic event where the vaginal cuff opens such that the bowel may herniate through the vagina, may occur, thereby requiring immediate surgery. The incidence of vaginal cuff dehiscence after a TLH has been found to be approximately 0.5-4%. A modifiable risk factor for vaginal cuff dehiscence is surgical technique, which can vary significantly among surgeons.

Thus, there remains a need to provide a more efficient and efficacious tissue suturing instrument that minimizes inter-operator variability in laparoscopic suturing procedures, for example, post-TLH vaginal cuff suturing procedures.

SUMMARY

In accordance with a first aspect of the present inventions, a laparoscopic tissue suturing instrument comprises an elongated shaft and a tissue grasper coupled to a distal end of the elongated shaft. The tissue grasper defines a tissue receiving gap and defines a shuttling element retention cavity. The laparoscopic tissue suturing instrument further comprises a suture shuttling element configured for being removably retained at least partially within the shuttling element retention cavity, and a needle having a needle shaft, a shuttling element coupler disposed at a distal end of the needle shaft, and a shuttling element release mechanism disposed on the needle shaft proximal to the shuttling element coupler.

The laparoscopic tissue suturing instrument further comprises a shuttling element retainer mechanism adjacent to the shuttling element retention cavity. The shuttling element release mechanism is configured for interacting with the shuttling element retainer mechanism of the needle to alternately transition the shuttling element retention cavity between a retention state that securely retains the suture shuttling element, and a release state that releases the suture shuttling element.

The shuttling element coupler is configured for engaging the suture shuttling element when the needle shaft is transitioned from a proximal position to a first distal position, such that the shuttling element release mechanism interacts with shuttling element retainer mechanism to transition the shuttling element retention cavity from the retention state to the release state, removing the suture shuttling element from the shuttling element retention cavity when the needle shaft is transitioned from the first distal position to the proximal position, inserting the suture shuttling element back into the shuttling element retention cavity when the needle shaft is transitioned from the proximal position to a second distal position proximal to the first distal position, and disengaging the suture shuttling element when the needle shaft is transitioned from the second distal position to the proximal position. The laparoscopic tissue suturing instrument may further comprise a suture affixed to the suture shuttling element, such that the when the needle is transitioned from the first distal position to the proximal position, the suture is drawn from the tissue grasper to the distal end of the elongated shaft.

In one embodiment, the shuttling element retention cavity is biased to be maintained in the retention state, the shuttling element retention cavity is configured for returning from the release state to the retention state when the needle shaft is transitioned from the first distal position to the proximal position, and the shuttling element release mechanism is configured for not interacting with the shuttling element retainer mechanism to maintain the shuttling element retention cavity in the retention state when the needle shaft is transitioned from the proximal position to the second distal position.

In another embodiment, the shuttling element release mechanism is a sleeve that is configured for being inserted within the shuttling element retention cavity to interact with the shuttling element retainer mechanism when the needle shaft is transitioned from the proximal position to the first distal position. In this embodiment, the sleeve may be slidably disposed along a length of the needle shaft, such that the sleeve continues to interact with the shuttling element release mechanism to maintain the shuttling element retention cavity in the release state as the shuttling element coupler removes the suture shuttling element from the shuttling element retention cavity. In this embodiment, the needle may further have a stop affixed to the needle shaft proximal to the sleeve. In this case, the stop is configured for abutting the sleeve to forcibly insert the sleeve within the shuttling element retention cavity to interact with the shuttling element retainer mechanism when the needle is transitioned from the proximal position to the first distal position.

In still another embodiment, the suture shuttling element has a cavity, and the shuttling element coupler has a tip configured for being inserted into the cavity to engage the suture shuttling element, and for being removed from the cavity to disengage the suture shuttling element. In this embodiment, the cavity of the suture shuttling element may have an inner annular ledge, and the tip of the shuttling element coupler may have an enlarged bullet-shaped tip, in which case, the enlarged bullet-shaped tip may have an outer annular ledge configured for engaging the inner annular ledge of the suture shuttling element, thereby allowing the shuttling element coupler to remove the suture shuttling element from the cavity.

In yet another embodiment, the tissue grasper comprises a jaw assembly having first and second jaws hingedly associated with each other. The jaw assembly may be configured for being transitioned between an open state for grasping tissue and a closed state for delivery through a laparoscope. In this embodiment, the shuttling element retainer mechanism may comprise a pair of parallel resilient members formed on the first jaw, and the cavity may comprise a pair of cavity portions formed on ends of the resilient members. The resilient members may be configured for being flexed away from each other to translate the pair of cavity portions away from each other, thereby transitioning the shuttling element retention cavity from the retention state to the release state, and the resilient members are configured for being relaxed to translate the pair of cavity portions toward each other, thereby transitioning the shuttling element retention cavity from the released state to the retention state. In this embodiment, the shuttling element release mechanism may comprise a sleeve configured for being inserted within the cavity to flex the resilient members, and removed from the cavity to relax the resilient members. The needle may be hingedly coupled to the second jaw for, when the jaw assembly is in the open state, being alternately hinged between a retracted state. The needle may be stowed in the second jaw, and a deployed state, such that the needle extends from the second jaw towards the first jaw.

In yet another embodiment, the tissue grasper comprises a clamp arm hingedly associated with the distal end of the elongated shaft. The clamp arm is configured for being transitioned between a retracted state for grasping tissue and an extended state for delivery through a laparoscope. In this embodiment, the shuttling element retainer mechanism may comprise a latch contained within the clamp arm. The latch may be configured for being translated from the cavity, thereby transitioning the shuttling element retention cavity from the retention state to the release state, and translated into the cavity, thereby transitioning the shuttling element retention cavity from the release state to the retention state. In this embodiment, the shuttling element retainer mechanism may further comprise a spring affixed to the latch. The spring may be configured for being compressed to translate the latch from the cavity, and for being relaxed to translate the latch into the cavity. In this embodiment, the shuttling element release mechanism may comprise a sleeve configured for being inserted within the cavity to compress the spring, and removed from the cavity to relax the spring. In this embodiment, the needle may be slidably coupled to the elongated shaft, such that the needle may be proximally slid between the proximal position, in which case, the needle may be stowed in the distal end of the elongated shaft, and the first and second distal positions.

In accordance with a second aspect of the present inventions, a method of suturing tissue (e.g., a vaginal cuff) using the laparoscopic tissue suturing instrument comprises (a) introducing the laparoscopic tissue suturing instrument through a laparoscopic port in a patient adjacent tissue to be sutured, (b) locating the tissue within the tissue gap, and (c) grasping the tissue located within the tissue gap with the tissue grasper. The method further comprises (d) transitioning the needle from the proximal position to the first distal position, thereby passing the needle through the tissue via a first entry point, engaging the suture shuttling element with the shuttling element coupler, and transitioning the shuttling element retention cavity from the retention state to the release state, (e) transitioning the needle from the first distal position to the proximal position, thereby removing the suture shuttling element from the shuttling element retention cavity and drawing the suture through the tissue, (f) releasing the sutured tissue from the tissue grasper, (g) transitioning the needle from the proximal position to the second distal position, thereby inserting the suture shuttling element back into the shuttling element retention cavity, and (h) transitioning the needle from the second distal position to the proximal position, thereby disengaging the shuttling element coupler from the suture shuttle. One method further comprises repeating steps (b)-(h) for a second entry point of the tissue different from the first entry point, thereby creating a stitch between the first and second entry points of the tissue.

In accordance with a third aspect of the present inventions, a method of suturing tissue (e.g., a vaginal cuff) using a laparoscopic tissue suturing instrument having a tissue grasper, needle, and a shuttling element coupled to the tissue grasper is provided. The method comprises (a) introducing the laparoscopic tissue suturing instrument through a laparoscopic port in a patient, and (b) grasping the tissue to be sutured with the tissue grasper. The method further comprises (c) transitioning the needle from a proximal position to a first distal position, thereby passing the needle through the tissue via a first entry point, and engaging the shuttling element, (d) transitioning the needle from the first distal position to the proximal position, thereby decoupling the suture shuttling element from the tissue grasper and drawing the suture through the tissue, (e) releasing the sutured tissue from the tissue grasper, (f) transitioning the needle from the proximal position to a second distal position proximal to the first distal position, thereby inserting the suture shuttling element back into the shuttling element retention cavity, and (g) transitioning the needle from the second distal position to the proximal position, thereby disengaging the suture shuttle. One method further comprises repeating steps (b)-(g) for a second entry point of the tissue different from the first entry point, thereby creating a stitch between the first and second entry points of the tissue.

In accordance of a fourth aspect of the present inventions, a laparoscopic tissue suturing instrument comprises an elongated shaft and a tissue grasper coupled to a distal end of the elongated shaft. The tissue grasper defines a tissue receiving gap and defining a shuttling element retention cavity. The laparoscopic tissue suturing instrument further comprises a suture shuttling element configured for being removably retained at least partially within the shuttling element retention cavity, and a needle having a needle shaft, a shuttling element coupler disposed at a distal end of the needle shaft, and a shuttling element release mechanism disposed on the needle shaft proximal to the shuttling element coupler.

The laparoscopic tissue suturing instrument further comprises a shuttling element retainer mechanism adjacent to the shuttling element retention cavity. The shuttling element release mechanism is configured for interacting with the shuttling element retainer mechanism of the needle to alternately transition the shuttling element retention cavity between a retention state that securely retains the suture shuttling element, and a release state that releases the suture shuttling element.

The shuttling element coupler is configured for engaging the suture shuttling element when the needle shaft is transitioned from a proximal position to a first distal position, such that the shuttling element release mechanism interacts with shuttling element retainer mechanism to transition the shuttling element retention cavity from the retention state to the release state. The shuttling element coupler is further configured for removing the suture shuttling element from the shuttling element retention cavity when the needle shaft is transitioned from the first distal position to the proximal position. The shuttling element release mechanism is slidably disposed along a length of the needle shaft, such that the shuttling element release mechanism continues to interact with the shuttling element retainer mechanism to maintain the shuttling element retention cavity in the release state as the shuttling element coupler removes the suture shuttling element from the shuttling element retention cavity. For example, the shuttling element release mechanism may be a sleeve that is configured for being inserted within the shuttling element retention cavity to interact with the shuttling element retainer mechanism when the needle shaft is transitioned from the proximal position to the first distal position. The laparoscopic tissue suturing instrument may further comprise a suture affixed to the suture shuttling element, such that the when the needle is transitioned from the first distal position to the proximal position, the suture is drawn from the tissue grasper to the distal end of the elongated shaft.

In one embodiment, the shuttling element coupler is further configured for inserting the suture shuttling element back into the shuttling element retention cavity when the needle shaft is transitioned from the proximal position to a second distal position proximal to the first distal position, and disengaging the suture shuttling element when the needle shaft is transitioned from the second distal position to the proximal position.

In another embodiment, the shuttling element retention cavity is biased to be maintained in the retention state, the shuttling element retention cavity is configured for returning from the release state to the retention state when the needle shaft is transitioned from the first distal position to the proximal position, and the shuttling element release mechanism is configured for not interacting with the shuttling element retainer mechanism to maintain the shuttling element retention cavity in the retention state when the needle shaft is transitioned from the proximal position to the second distal position.

In still another embodiment, the needle further has a stop affixed to the needle shaft proximal to the sleeve. In this case, the stop may be configured for abutting the shuttling element release mechanism to forcibly cause the shuttling element release mechanism to interact with the shuttling element retainer mechanism when the needle is transitioned from the proximal position to the first distal position.

In yet another embodiment, the suture shuttling element has a cavity, and the shuttling element coupler has a tip configured for being inserted into the cavity to engage the suture shuttling element, and for being removed from the cavity to disengage the suture shuttling element. In this embodiment, the cavity of the suture shuttling element may have an inner annular ledge, and the tip of the shuttling element coupler may have an enlarged bullet-shaped tip, in which case, the enlarged bullet-shaped tip may have an outer annular ledge configured for engaging the inner annular ledge of the suture shuttling element, thereby allowing the shuttling element coupler to remove the suture shuttling element from the cavity.

In yet another embodiment, the tissue grasper comprises a jaw assembly having first and second jaws hingedly associated with each other. The jaw assembly may be configured for being transitioned between an open state for grasping tissue and a closed state for delivery through a laparoscope. In this embodiment, the shuttling element retainer mechanism may comprise a pair of parallel resilient members formed on the first jaw, and the cavity may comprise a pair of cavity portions formed on ends of the resilient members. The resilient members may be configured for being flexed away from each other to translate the pair of cavity portions away from each other, thereby transitioning the shuttling element retention cavity from the retention state to the release state, and the resilient members are configured for being relaxed to translate the pair of cavity portions toward each other, thereby transitioning the shuttling element retention cavity from the released state to the retention state. In this embodiment, the shuttling element release mechanism may comprise a sleeve configured for being inserted within the cavity to flex the resilient members, and removed from the cavity to relax the resilient members. The needle may be hingedly coupled to the second jaw for, when the jaw assembly is in the open state, being alternately hinged between a retracted state. The needle may be stowed in the second jaw, and a deployed state, such that the needle extends from the second jaw towards the first jaw.

In yet another embodiment, the tissue grasper comprises a clamp arm hingedly associated with the distal end of the elongated shaft. The clamp arm is configured for being transitioned between a retracted state for grasping tissue and an extended state for delivery through a laparoscope. In this embodiment, the shuttling element retainer mechanism may comprise a latch contained within the clamp arm. The latch may be configured for being translated from the cavity, thereby transitioning the shuttling element retention cavity from the retention state to the release state, and translated into the cavity, thereby transitioning the shuttling element retention cavity from the release state to the retention state. In this embodiment, the shuttling element retainer mechanism may further comprise a spring affixed to the latch. The spring may be configured for being compressed to translate the latch from the cavity, and for being relaxed to translate the latch into the cavity. In this embodiment, the shuttling element release mechanism may comprise a sleeve configured for being inserted within the cavity to compress the spring, and removed from the cavity to relax the spring. In this embodiment, the needle may be slidably coupled to the elongated shaft, such that the needle may be proximally slid between the proximal position, in which case, the needle may be stowed in the distal end of the elongated shaft, and the first and second distal positions.

In accordance with a fifth aspect of the present inventions, a method of suturing tissue (e.g., a vaginal cuff) using the laparoscopic tissue suturing instrument comprises (a) introducing the laparoscopic tissue suturing instrument through a laparoscopic port in a patient adjacent tissue to be sutured, (b) locating the tissue within the tissue gap, and (c) grasping the tissue located within the tissue gap with the tissue grasper. The method further comprises (d) transitioning the needle from the proximal position to the first distal position, thereby passing the needle shaft through the tissue via a first entry point, engaging the suture shuttling element with the shuttling element coupler, and transitioning the shuttling element retention cavity from the retention state to the release state. The method further comprises (e) transitioning the needle from the first distal position to the proximal position, thereby allowing the shuttling element release mechanism to slide relative to the needle shaft, such that the shuttling element retention cavity is maintained in the release state, removing the suture shuttling element from the shuttling element retention cavity, and drawing the suture through the tissue.

In accordance with a sixth aspect of the present inventions, a laparoscopic tissue suturing instrument comprises an elongated shaft and a jaw assembly coupled to a distal end of the elongated shaft. The jaw assembly comprises first and second jaws hingedly associated with each other, and is configured for being transitioned between an open state for grasping tissue and a closed state for delivery through a laparoscopic port.

The laparoscopic tissue suturing instrument further comprises a suture shuttling element configured for being removably coupled to the first jaw, and a needle hingedly coupled to the second jaw for being alternately hinged between a retracted state, wherein the needle is stowed in the second jaw, and a deployed state, wherein the needle is configured for being inserted within and engaged to the suture shuttling element when the jaw assembly is in a first one of at least one intermediate state between the open state and the closed state, decoupling the engaged shuttling element from the first jaw when the jaw assembly is transitioned from the first intermediate state towards the open state, recoupling the suture shuttling element to the first jaw when the jaw assembly is transitioned from the open state to a second one of the at least one intermediate state, and for being removed and disengaged from the suture shuttling element when the jaw assembly is transitioned from the second intermediate state toward the open state.

In one embodiment, the first intermediate state and second intermediate state are different from each other. In another embodiment, the first intermediate state is between the second intermediate state and the open state. In still another embodiment, the first jaw comprises a shuttling element retention cavity configured for retaining the suture shuttling element when the suture shuttling element is removably coupled to the first jaw.

In yet another embodiment, the shuttling element retention cavity is configured for being transitioned between a retention state for securely retaining the suture shuttling element therein, and a release state for allowing the suture shuttling element to be removed from the shuttling element retention cavity. In this embodiment, the first jaw may comprise a pair of parallel resilient members that respectively include a pair of cavity portions that form the shuttling element retention cavity. The pair of parallel resilient members may be configured for being urged away from each other to translate the pair of cavity portions away from each other, thereby transitioning the shuttling element retention cavity from the retention state to the release state, and for being relaxed to translate the pair of cavity portions toward each other, thereby transitioning the shuttling element retention cavity from the release state to the contract state.

In this embodiment, the needle may comprise a needle shaft, a shuttling element coupler disposed at the distal end of the needle shift, and a sleeve disposed on the needle shaft above the shuttling element coupler. The shuttling element coupler may be configured for being inserted within and engage the suture shuttling element when the jaw assembly is in the first intermediate state, and removed from and disengage the suture shuttling element when the jaw assembly is transitioned from the first intermediate state toward the open state. The sleeve may be configured for cooperating with the first jaw to transition the shuttling element retention cavity from the retention state to the release state, thereby allowing the shuttling element coupler to remove the suture shuttling element from the shuttling element retention cavity and decouple the suture shuttling element from the first jaw when the jaw assembly is transitioned from the first intermediate state toward the open state. The laparoscopic tissue suturing may further comprise a suture affixed to the suture shuttling element, such that the when the jaw assembly is transitioned from the first intermediate state towards the open state, the suture is drawn from the first jaw towards the second jaw.

In this embodiment, the shuttling element retention cavity may have a proximal chamber and a distal chamber in communication with each other. The proximal chamber may have a reduced inner diameter relative to an inner diameter of the distal chamber, thereby forming an inner annular ledge between the proximal chamber and the distal chamber. The inner annular ledge may be configured for retaining the suture shuttling element within the distal chamber when the shuttling element retention cavity is in the retention state. The sleeve may have an outer diameter greater than the inner diameter of the proximal chamber when the shuttling element retention cavity is in the retention state, such that when the sleeve is inserted into the proximal chamber. The shuttling element retention cavity may be transitioned from the retention state to the release state, thereby allowing the shuttling element coupler to translate the suture shuttling element from the distal chamber, past the inner annular ledge, into the proximal chamber. The outer diameter of the sleeve may be greater than an outer diameter of the suture shuttling element, such that the diameter of the proximal chamber is greater than the outer diameter of the suture shuttling element when the shuttling element retention cavity is in the expand state. The suture shuttling element may have an inner annular ledge, and the shuttling element coupler may comprise is an enlarged bullet-shaped tip. The enlarged bullet-shaped tip may have an outer annular ledge configured for engaging the inner annular ledge of the suture shuttling element, thereby allowing the shuttling element coupler to remove the suture shuttling element from the shuttling element retention cavity and decouple the suture shuttling element from the first jaw. The suture shuttling element may be configured for being disposed within the distal chamber without disposing the sleeve within the proximal chamber, such that the shuttling element retention cavity remains in the retention state, thereby recoupling the suture shuttling element to the first jaw. The sleeve may be configured for sliding toward the second jaw when the sleeve contacts the proximal chamber and as jaw assembly is transitioned from the open state to the second intermediate state. The needle may comprise a stop configured for abutting the slidable sleeve to forcibly insert the slidable sleeve into the proximal chamber as the jaw assembly is transitioned from the second intermediate state to the first intermediate state.

In accordance with a seventh aspect of the present inventions, a method of suturing tissue (e.g., a vaginal cuff) using the laparoscopic tissue suturing instrument comprises (a) introducing the laparoscopic tissue suturing instrument through a laparoscopic port in a patient adjacent tissue to be sutured while the jaw assembly is in the closed state, (b) transitioning the jaw assembly from the closed state to the open state, (c) hinging the needle from the retracted state to the deployed state, and (d) locating the jaw assembly such that the tissue to be sutured is between the jaws when the jaw assembly is in the open state. The method further comprises (e) transitioning the jaw assembly from the open state to a first one of the at least one intermediate state, thereby passing the needle through the tissue via a first entry point and inserting the needle within and engaging the suture shuttling element, and (f) transitioning the jaw assembly from the first intermediate state to the open state, thereby decoupling the engaged shuttling element from the first jaw and drawing the suture through the tissue. The method further comprises (g) locating the jaw assembly such that the tissue to be sutured is not between the jaws when the jaw assembly is in the open state, (h) transitioning the jaw assembly from open state to a second one of the at least one intermediate state, thereby recoupling the engaged shuttling element to the first jaw, and (i) transitioning the jaw assembly from the second intermediate state to the open state, thereby removing the needle from and disengaging the suture shuttling element. The first intermediate state and second intermediate state may be different from each other. The method further comprises (j) repeating steps (d)-(h) for a second entry point of the tissue different from the first entry point, thereby creating a stitch between the first and second entry points of the tissue. One method further comprises (k) hinging the needle from the deployed state to the retracted state, (l) transitioning the jaw assembly from the open state to the closed state, and (m) withdrawing the laparoscopic tissue suturing instrument from the patient via the laparoscopic port while the jaw assembly is in the closed state.

In accordance with an eighth aspect of the present inventions, a method of suturing tissue (e.g., a vaginal cuff) using a laparoscopic tissue suturing instrument comprises (a) introducing the laparoscopic tissue suturing instrument through a laparoscopic port in a patient while a jaw assembly having a first jaw and a second jaw is in a closed state, (b) transitioning the jaw assembly from the closed state to an open state, and (c) locating the jaw assembly, such that the tissue is between the jaws when the jaw assembly is in an open state. The method further comprises (d) transitioning the jaw assembly from the open state to a first one of the at least one intermediate state, thereby passing a needle coupled to the second jaw through a first entry point of the tissue and inserting the needle within and engaging a shuttling element coupled to the first jaw, and (e) transitioning the jaw assembly from the first intermediate state to the open state, thereby decoupling the engaged shuttling element from the first jaw and drawing a suture affixed to the suture shuttling element through the tissue. The method further comprises (f) locating the jaw assembly such that the tissue is not between the jaws when the jaw assembly is in the open state, (g) transitioning the jaw assembly from open state to a second one of the at least one intermediate state, thereby recoupling the engaged shuttling element to the first jaw, and (h) transitioning the jaw assembly from the second intermediate state to the open state, thereby removing the needle from and disengaging the suture shuttling element. The method further comprises (i) repeating steps (c)-(h) for a second entry point of the tissue, thereby creating a stitch between the first and second entry points of the tissue.

One method further comprises hinging the needle from a retracted state to a deployed state prior to subsequent to step (b) and prior to step (d). This method may further comprise (j) hinging the needle from the deployed state to the retracted state, (k) transitioning the jaw assembly from the open state to the closed state, and (l) withdrawing the laparoscopic tissue suturing instrument from the patient via the laparoscopic port while the jaw assembly is in the closed state.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages of the disclosed inventions are obtained, a more particular description of the disclosed inventions briefly described above will be rendered by reference to specific embodiments thereof, which are illustrated in the accompanying drawings. Understanding that these drawings depict only typical embodiments of the disclosed inventions and are not therefore to be considered limiting of their scope, the disclosed inventions will be described and explained with additional specificity and detail through the use of the accompanying drawings, in which.

DETAILED DESCRIPTION OF THE ILLUSTRATED EMBODIMENTS

Figure 1:
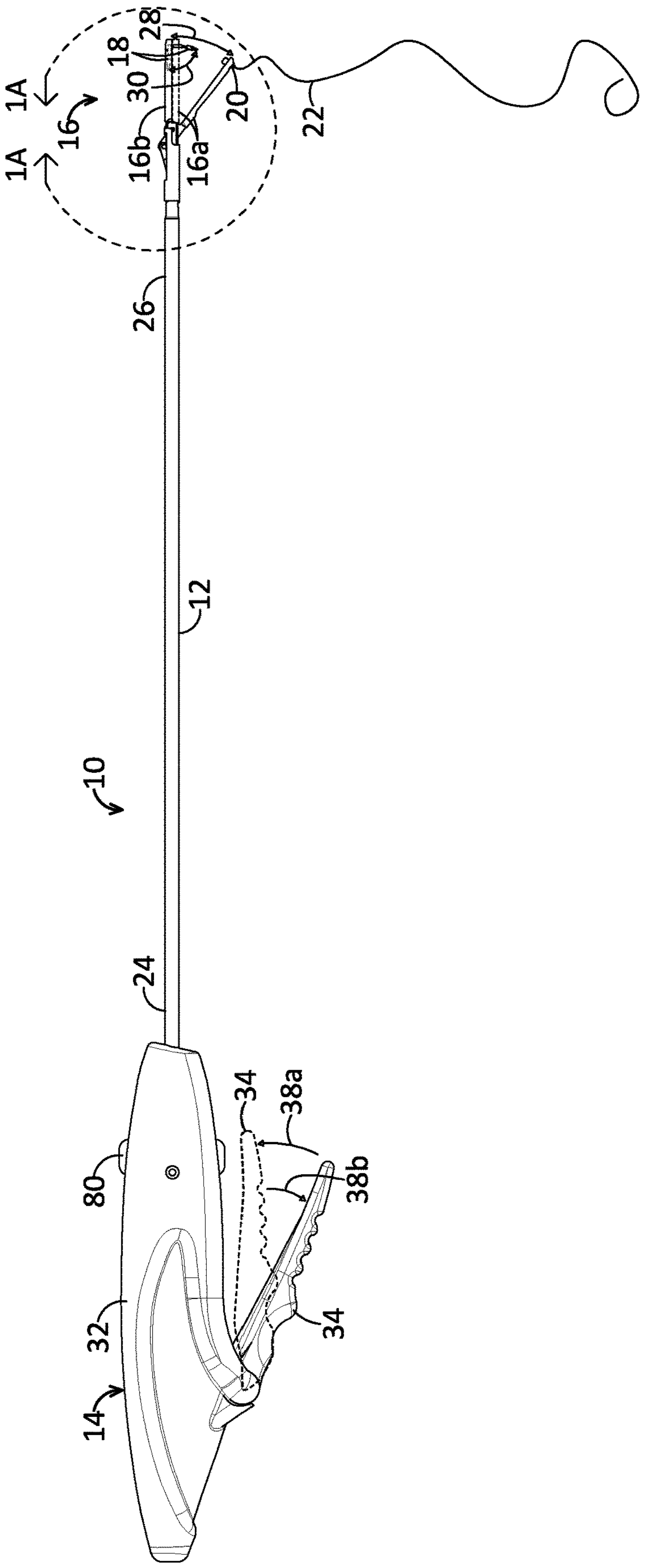
FIG. 1 is a schematic diagram of an exemplary laparoscopic tissue suturing instrument constructed in accordance with one embodiment of the disclosed inventions.
Figure 1A:
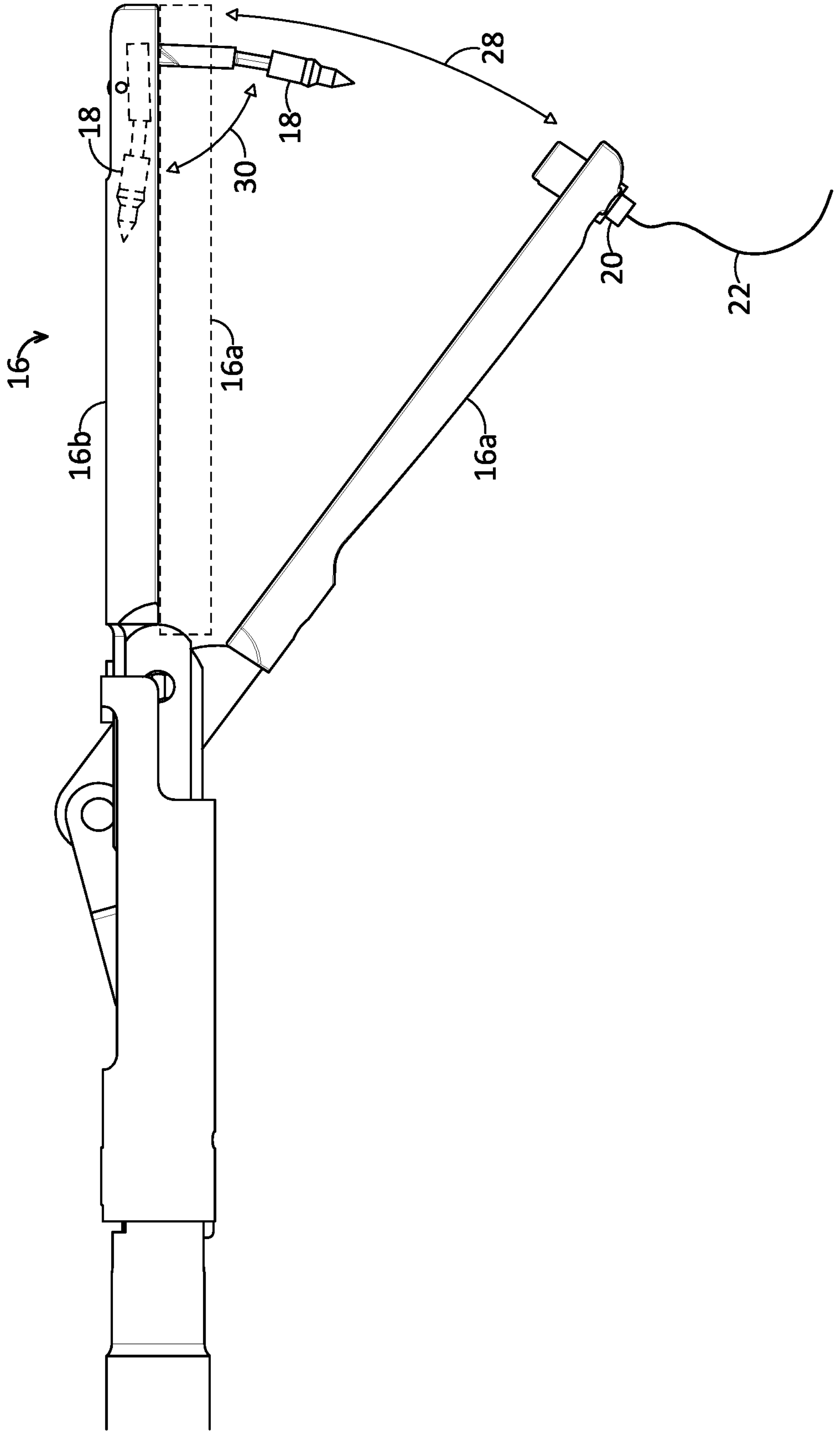
FIG. 1A is a close-up view of the distal end of the laparoscopic tissue suturing instrument of FIG. 1.
Figure 2:
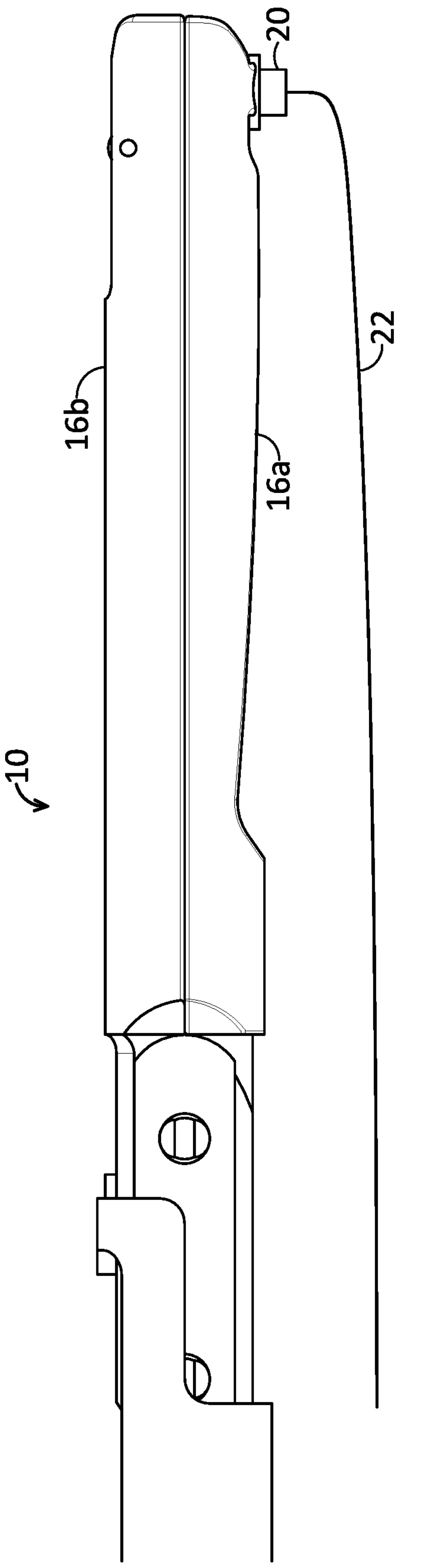
FIG. 2 is a profile view of the distal end of laparoscopic tissue suturing instrument of FIG. 1, particularly showing a jaw assembly of the laparoscopic tissue suturing instrument in a closed state, while a needle of the laparoscopic tissue suturing instrument is in a retracted state.

Referring to FIGS. 1 and 1A, one embodiment of a laparoscopic tissue suturing instrument 10 generally comprises: an elongated, hollow, rigid shaft 12 having a proximal end 24 and a distal end 26; a handle assembly 14 affixed to the proximal end 24 of the rigid shaft 12; a tissue grasper, and in particular, a jaw assembly 16 including a pair of opposable lower (first) and upper (second) jaws 16*a*, 16*b* hingedly associated with each other, such that the jaw assembly 16 may be transitioned (shown by the arrow 28) between a closed state (shown in phantom in FIGS. 1 and 1A), two intermediate states (shown in further detail below), and an open state (shown in solid in FIGS. 1 and 1A) via manipulation of the handle assembly 14; a needle 18 operatively associated with the lower jaw 16*a*, such that the needle 18 may be transitioned (shown by the arrow 30) between a retracted state (shown in phantom in FIGS. 1 and 1A) and a deployed state (shown in solid in FIGS. 1 and 1A) vis manipulation of the handle assembly 14; a suture shuttling element 20 configured for being removably coupled to the lower jaw 16*a* (shown in FIG. 2); and a suture 22 affixed to the shuttling element 20.

The rigid shaft 12 is preferably cylindrical (i.e., has a circular cross-section), although in alternative embodiments, the rigid shaft 12 may have any suitable cross-sectional geometry. The rigid shaft 12 is preferably narrow enough (e.g., less than 10 mm in diameter, and preferably 5 mm or less in diameter), such that the laparoscopic tissue suturing instrument 10 may be introduced through a separate conventional laparoscopic port (not shown) into the patient; and may have a suitable length, e.g., in the range of 18 cm-45 cm.

The handle assembly 14 comprises a handle 32 configured for being ergonomically grasped by the palm of a hand, and a finger piece 34 configured for being ergonomically grasped by the fingers of the hand. The finger piece 34 is pivotably affixed to the handle 32 and is operably associated with the lower jaw 16*b* via a linkage 36 (illustrated in FIGS. 14-16) extending through the rigid shaft 12. Details on the linkage 36 will be described in further detail below. Manual displacement of the pivotable finger piece 34 towards the handle 32 (in the direction of arrow 38*a*) pivots the lower jaw 16*a* towards the upper jaw 16*b* to transition the jaw assembly 16 to the closed state (or either of the two intermediate states), while manual displacement of the pivotable finger piece 34 away from the handle 32 (in the direction of arrow 38*b*) pivots the jaws 16*a*, 16*b* away from each other to transition the jaw assembly 16 to the open state.

The pivotable finger piece 34 may be biased away from the handle 32, e.g., via a spring mechanism (not shown), such that the jaw assembly 16 is biased to the open state. In this case, the pivotable finger piece 34 may be manually pivoted towards the handle 32 (e.g., by firmly grasping the handle 32 with a single hand and squeezing the finger piece 34 with the fingers) in opposition to the biasing force applied by the spring mechanism to transition the jaw assembly 16 to the closed state. The jaw assembly 16 can also be transitioned to different positions between the open state and the closed state to grasp and release tissue of varying thickness, as well as to enable the suturing functionality of the laparoscopic tissue suturing instrument 10, via incremental manual displacement of the pivotable finger piece 34 towards or away from the handle 32. An optional locking mechanism (e.g., a ratchet (not shown)) may be employed to lock the jaw assembly 16 in any position between the open state and the closed state, and to unlock the jaw assembly 16 to allow the biasing force applied to the pivotable finger piece 34 (e.g., by grasping the handle 32 and releasing the finger piece 34 with the fingers) to place the jaw assembly 16 in the open state.

Figure 3:
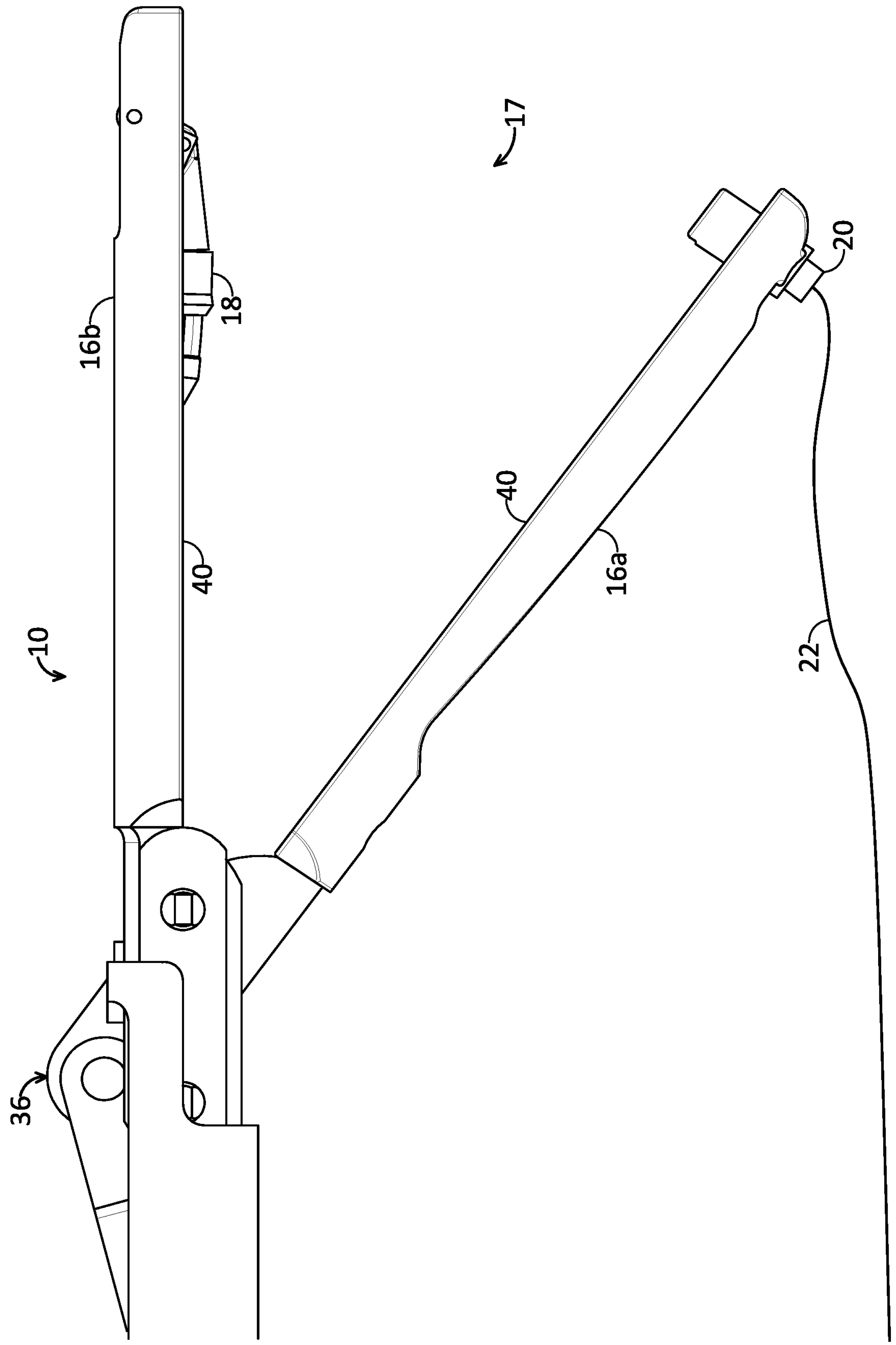
FIG. 3 is a profile view of the distal end of the laparoscopic tissue suturing instrument of FIG. 1, particularly showing the jaw assembly in an open state, while the needle is in the retracted state.
Figure 4:
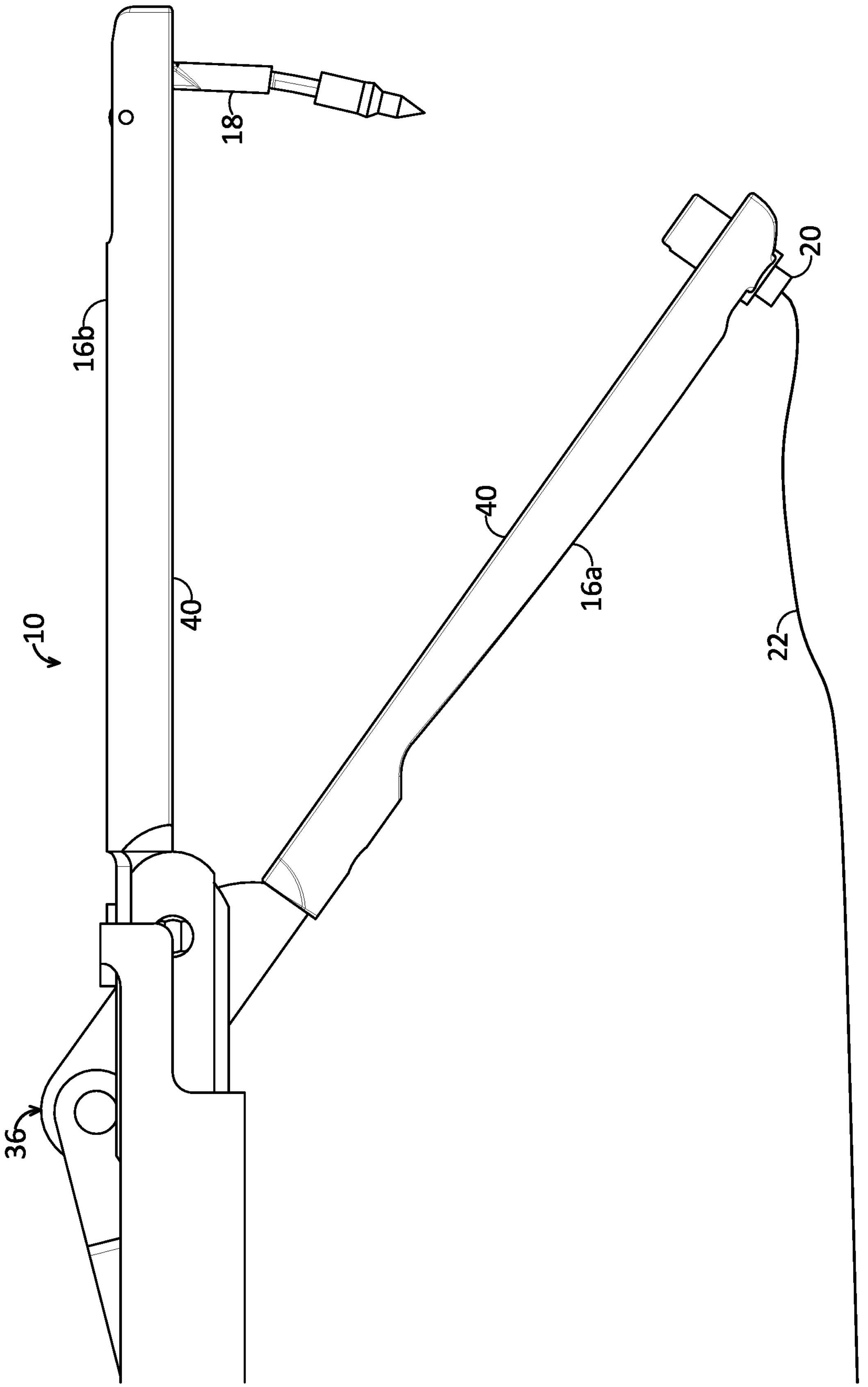
FIG. 4 is a profile view of the distal end of the laparoscopic tissue suturing instrument of FIG. 1, particularly showing the jaw assembly in an open state, while the needle is in a deployed state.
Figure 5:
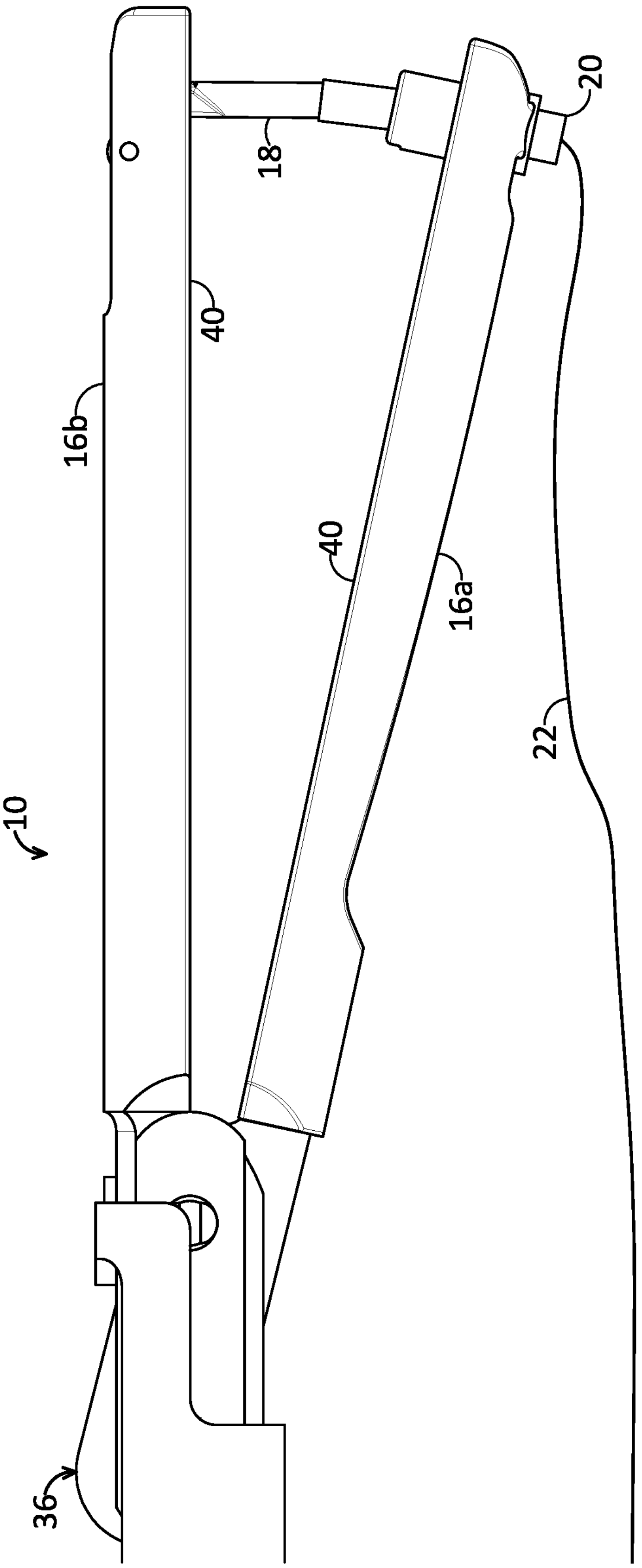
FIG. 5 is a profile view of the distal end of the laparoscopic tissue suturing instrument of FIG. 1, particularly showing the jaw assembly in a first one of two intermediate states between the open state and the closed state, while the needle is in the deployed state.
Figure 6:
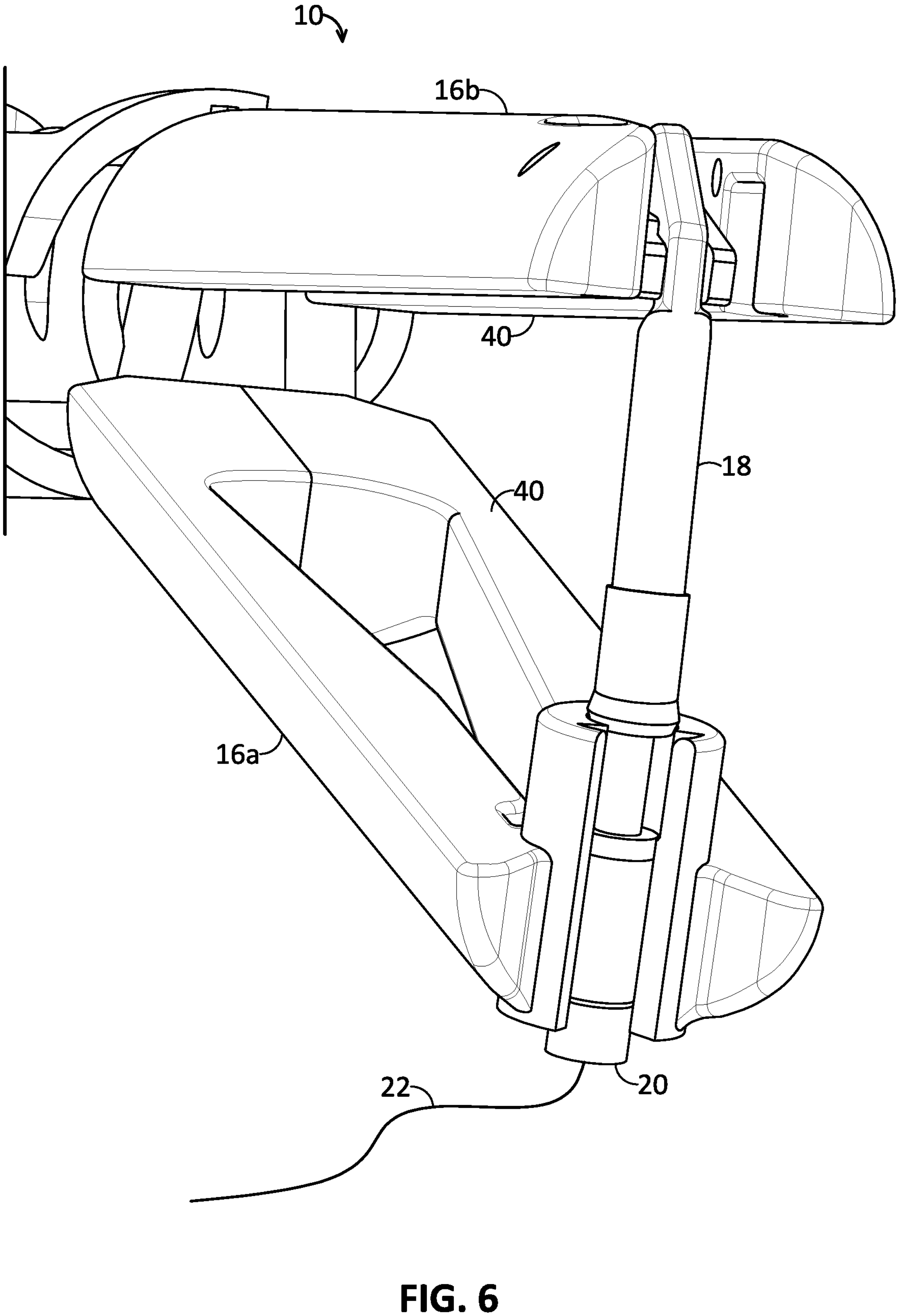
FIG. 6 is a perspective view of the jaw assembly of the laparoscopic tissue suturing instrument of FIG. 1 in the first intermediate state, while the needle is engaged with a suture shuttling element coupled to a lower jaw of the jaw assembly.
Figure 7:
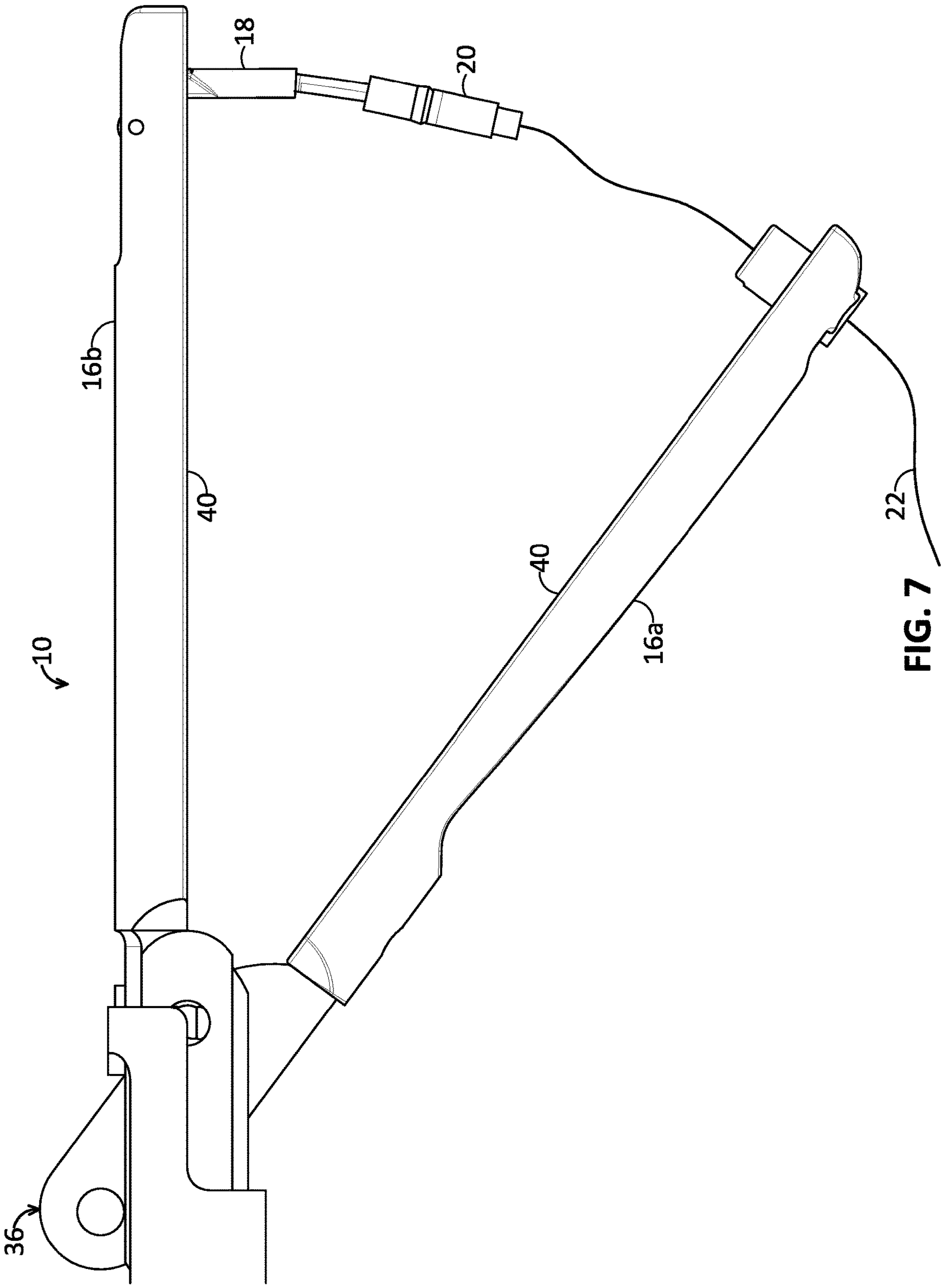
FIG. 7 is a perspective view of the jaw assembly of the laparoscopic tissue suturing instrument of FIG. 1 in the open state after the shuttling element has been decoupled from one of the jaws of the jaw assembly by the needle.

In the illustrated embodiment, the jaw 16*b* is pivotably attached to the distal end 26 of the rigid shaft 12, while the jaw 16*a* is fixed to the distal end 26 of the rigid shaft 12, such that jaw 16*a* may be alternately transitioned relative to jaw 16*b* (shown by the arrow 28) to transition the jaw assembly 16 between a closed state (see FIG. 2) and an open state (see FIGS. 3 and 4). As best shown in FIGS. 3-8, the jaws 16*a*, 16*b* respectively comprise opposing inner surfaces 40. In an optional embodiment not shown, the inner surfaces 40 are textured or have teeth (not shown), to facilitate grasping of tissue between the jaws 16*a*, 16*b*. In such an embodiment, the teeth of the upper jaw 16*b* intermesh together with the teeth of the lower jaw 16*a* when the jaw assembly 16 is in the closed state, such that the jaw assembly 16 has an integrated outer cylindrical surface that matches the outer cylindrical surface of the rigid shaft 12.

Although, in the illustrated embodiment, the lower jaw 16*a* is pivotably affixed to the distal end 26 of the rigid shaft 12, while the upper jaw 16*b* is immovably affixed to the distal end 26 of the rigid shaft 12, in an alternative embodiment, the lower jaw 16*a* may be immovably affixed to the distal end 26 of the rigid shaft 12, while the upper jaw 16*b* may be pivotably affixed to the distal end 26 of the rigid shaft 12. In another alternative embodiment (not shown), both jaws 16*a*, 16*b* are pivotably attached to the distal end 26 of the rigid shaft 12. Ultimately, the jaws 16*a*, 16*b* may be arranged in any suitable manner with the distal end 26 of the rigid shaft 12 as long as the needle 18 may be transitioned between the retracted or stowed position (FIG. 3) when in the deployed state (FIG. 4) while the jaw assembly 16 is in the open state. When in the open state, the jaw assembly 16 defines a tissue receiving gap 17 (best shown in FIG. 3) between the jaws 16*a*, 16*b*. As will be described in further detail below, the jaw assembly 16 may be transitioned to at least two intermediate states (see FIGS. 5, 6, and 8), the open state (FIGS. 3 and 4) and the closed state (FIG. 2) to enable the suturing functionality of the laparoscopic tissue suturing instrument 10.

Figure 9:
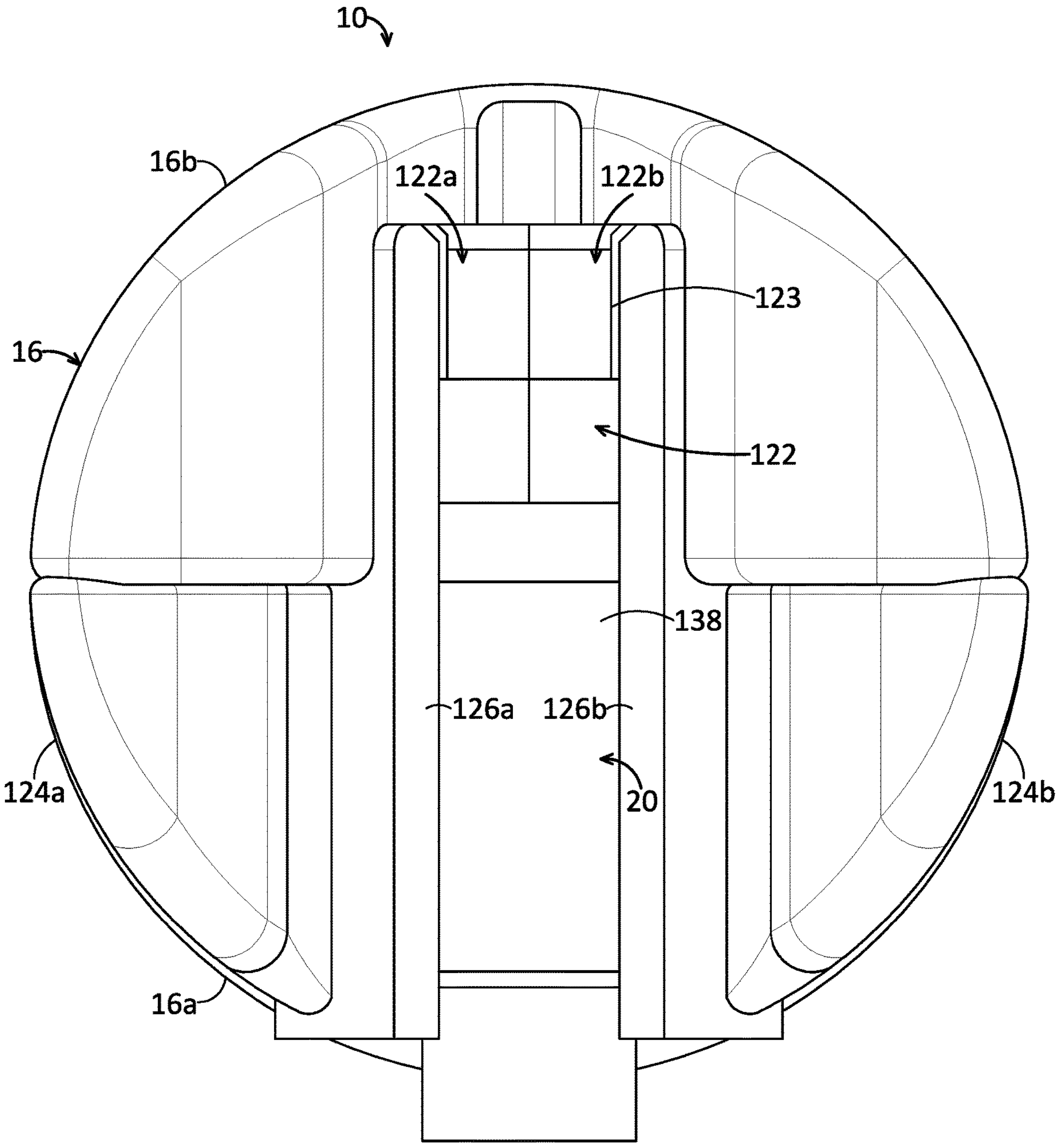
FIG. 9 is an axial view of the jaw assembly of the laparoscopic tissue suturing instrument of FIG. 1.

While in the closed state, the jaw assembly 16 preferably has a profile that is equal to or less than the diameter of the rigid shaft 12, such that the jaw assembly 16 along with the rigid shaft 12 may be introduced through the laparoscopic port. As best shown in FIG. 9, each of the jaws 16*a*, 16*b* preferably has a hemi-spherical cross-section, with the diameters of the hemi-spherical cross-sections, such that the jaws 16*a*, 16*b*, when in the closed state, form a cylindrical member having a diameter no greater than the diameter of the rigid shaft 12 (i.e., the outer envelopes of the rigid shaft 12 and closed jaw assembly 16 are contiguous).

Figure 10:
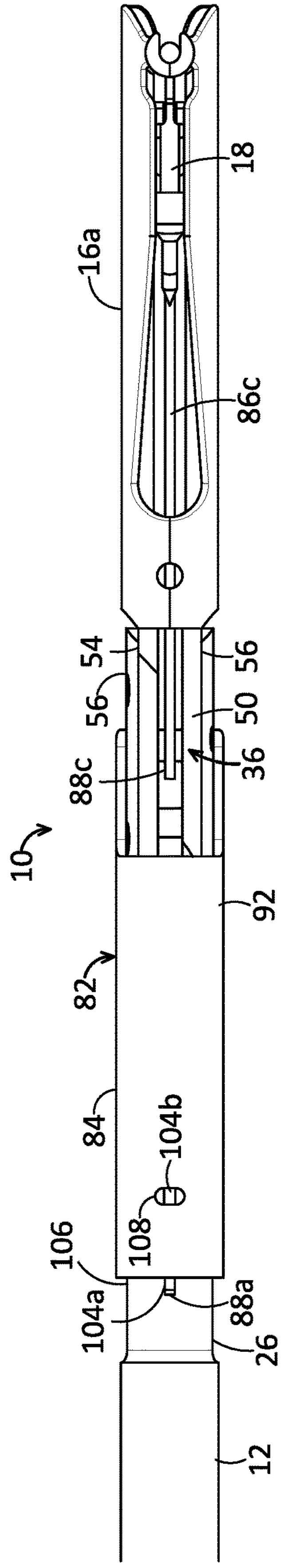
FIG. 10 is a bottom view of the distal end of the laparoscopic tissue suturing instrument of FIG. 1.
Figure 11:
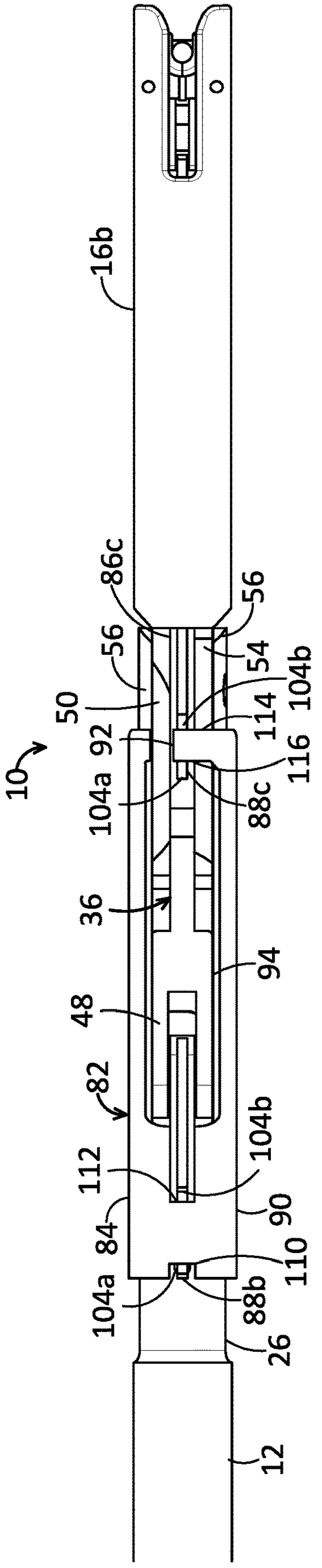
FIG. 11 is a top view of the distal end of the laparoscopic tissue suturing instrument of FIG. 1.
Figure 12:
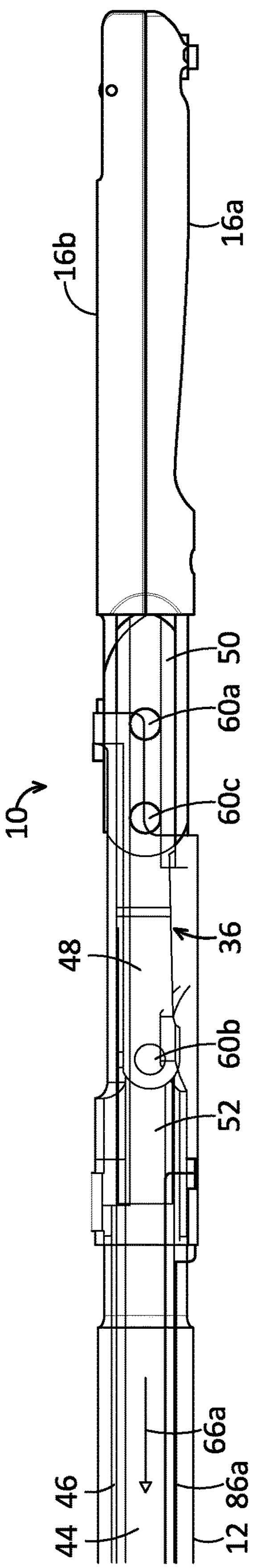
FIG. 12 is a profile of the distal end of the laparoscopic tissue suturing instrument of FIG. 1, particularly showing the jaw assembly in the closed state, wherein the shaft of the laparoscopic tissue suturing instrument is shown in phantom.
Figure 13:
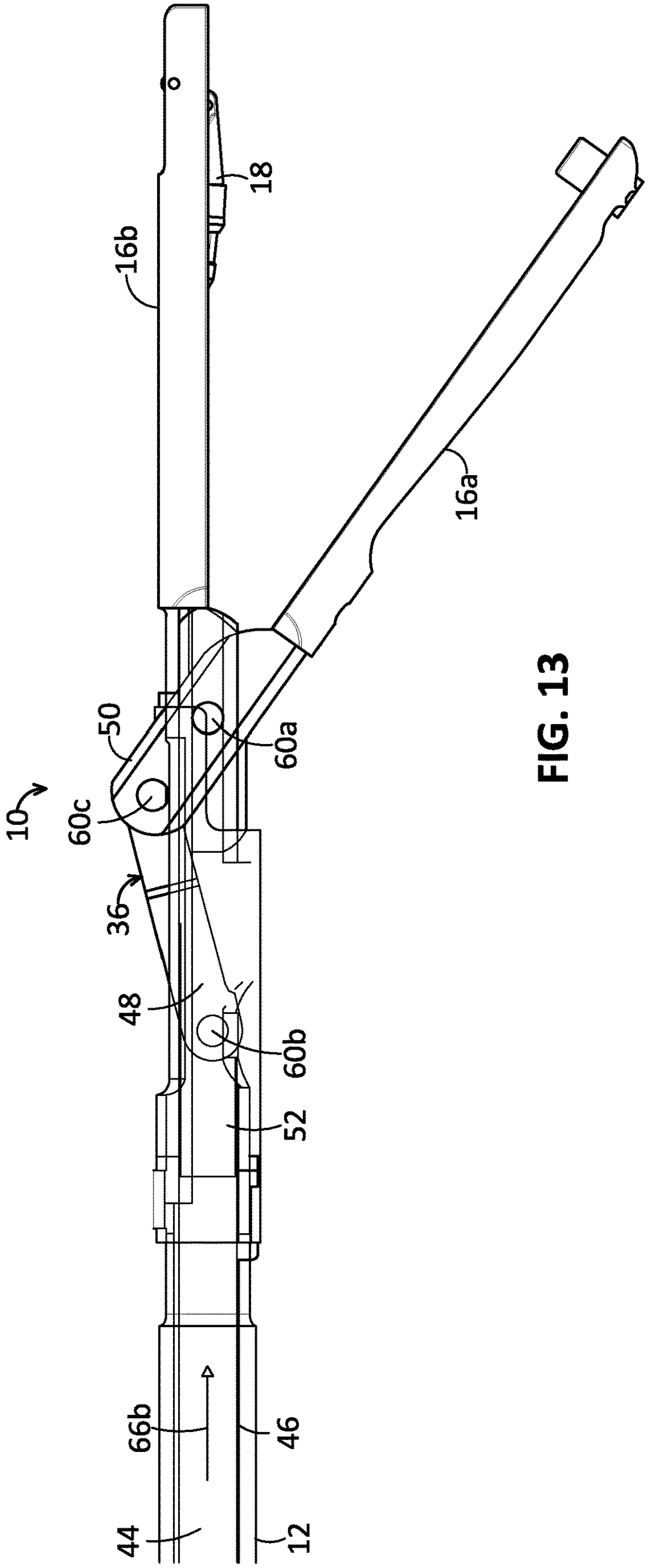
FIG. 13 is a profile of the distal end of the laparoscopic tissue suturing instrument of FIG. 1, particularly showing the jaw assembly in the open state, wherein the shaft of the laparoscopic tissue suturing instrument is shown in phantom.
Figure 14:
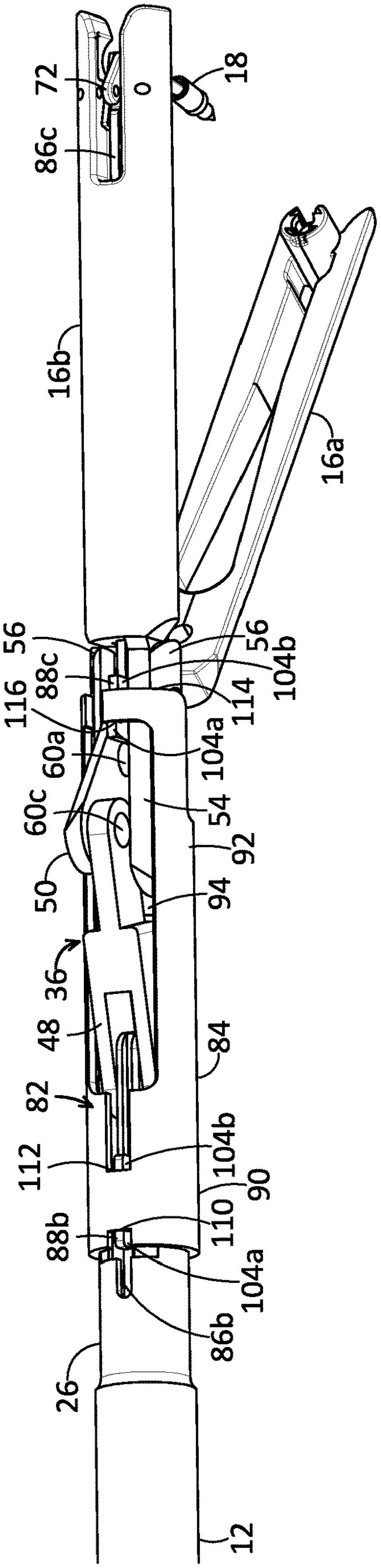
FIG. 14 is a perspective view of the distal end of the laparoscopic tissue suturing instrument of FIG. 1.
Figure 15:
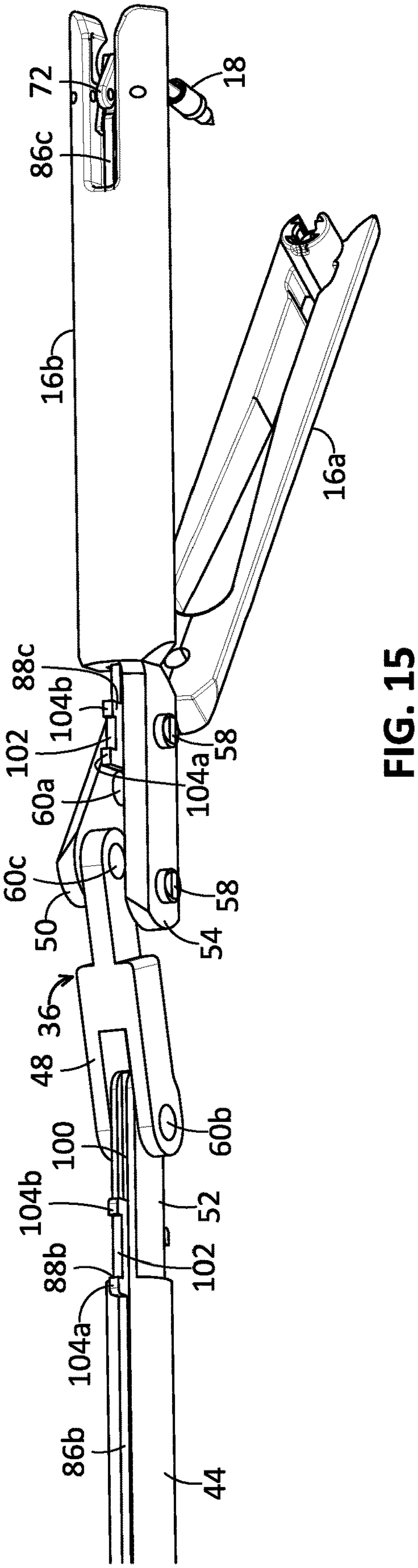
FIG. 15 is a perspective view of a linkage mechanism used to displace the lower jaw relative to the upper jaw of the laparoscopic tissue suturing instrument of FIG. 1.

Referring to FIGS. 10-16, the linkage 36 between the pivotable finger piece 34 (shown in FIG. 16) and the lower jaw 16*a* comprises a generally cylindrical reciprocating rod 44 that resides within a main central lumen 46 extending through the rigid shaft 12 (best shown in FIGS. 12 and 13), a flattened rigid link 48 operatively associated with the reciprocating rod 44, and another flattened rigid link 50 operatively associated (and in particular, integrated) with the lower jaw 16*a*. In the illustrated embodiment, the reciprocating rod 44 has a flattened distal end 52 to which the rigid link 48 is pivotably coupled, as best shown in FIGS. 12, 13, and 15). The proximal end of the upper jaw 16*b* has a flattened flange 54 that is immovably affixed to the distal end 26 of the rigid shaft 12.

As best shown in FIGS. 10, 11, and 14, the distal end 26 of the rigid shaft 12 is cleaved to form two parallel arms 56 for supporting the rigid links 48, 50 therebetween. As shown in FIG. 15, the flattened flange 54 of the upper jaw 16*b* is affixed to one of the distal parallel arms 56 via two rivets 58, such that the upper jaw 16*b* is incapable of moving relative to the distal end 26 of the rigid shaft 12. As best shown in FIG. 14, the rigid link 50 is pivotably coupled between the distal parallel arms 56 of the rigid shaft 12 via a pivot pin 60*a*, and the rigid link 48 is pivotably coupled between the flattened distal end 52 of the reciprocating rod 44 and the rigid link 50 respectively via a pivot pin 60*b* and a pin 60*c*.

Figure 16:
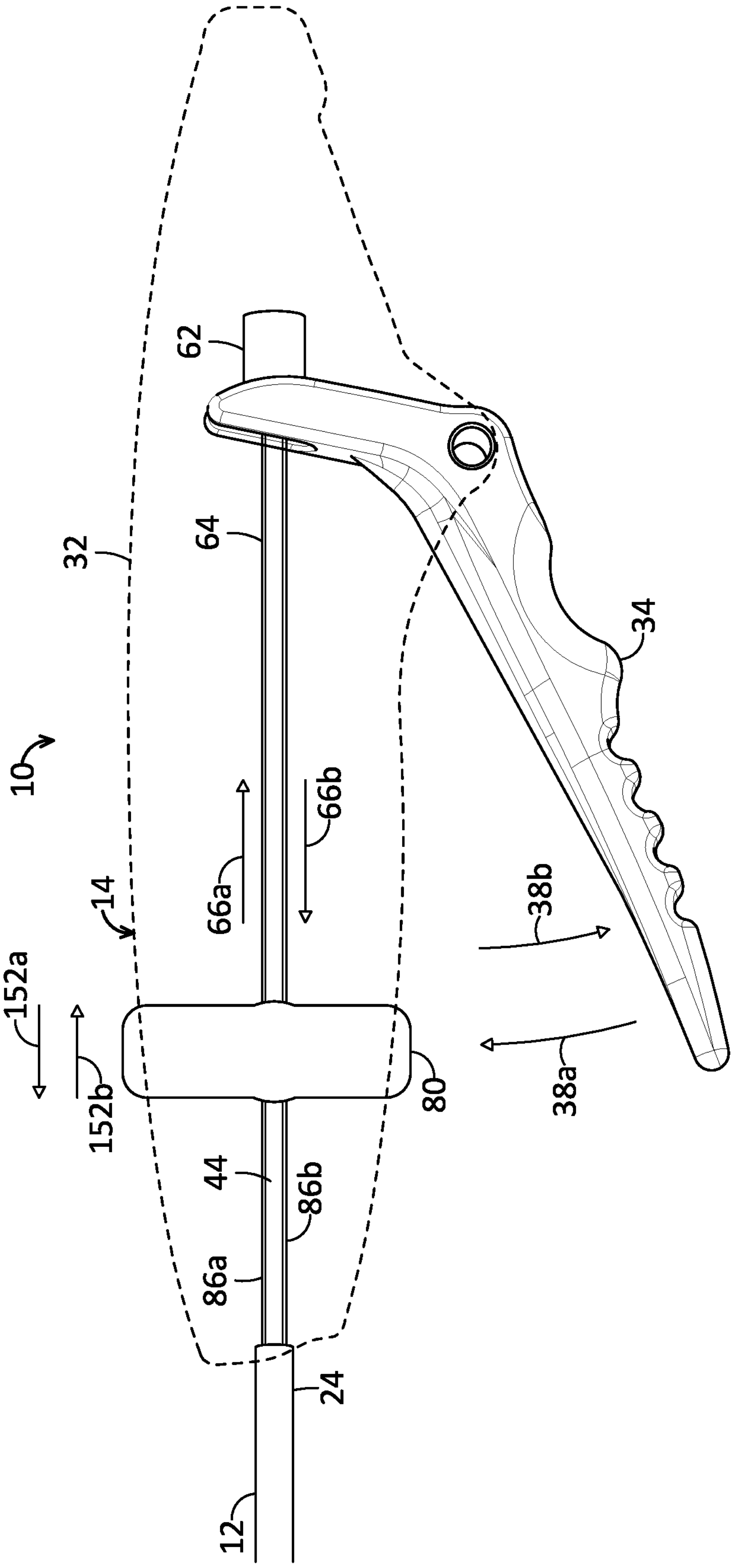
FIG. 16 is a profile view of handle assembly of the laparoscopic tissue suturing instrument of FIG. 1, wherein the handle of the handle assembly is shown in phantom.

In the embodiment illustrated in FIG. 16, the linkage 36 comprises a boss 62 affixed to the proximal end 64 of the reciprocating rod 44. The proximal end 64 of the reciprocating rod 44 extends through the pivotable finger piece 34, with the boss 62 located proximal to the pivotable finger piece 34 and in an interference relationship with the pivotable finger piece 34. When the pivotable finger piece 34 is pivoted toward the handle 32 (shown by the arrow 38*a*), the reciprocating rod 44 is proximally transitioned (shown by the arrow 66*a*) within the central lumen 46 of the rigid shaft 12. Conversely, when the pivotable finger piece 34 is pivoted away from the handle 32 (shown by the arrow 38*b*), the reciprocating rod 44 is distally transitioned (shown by the arrow 66*b*) within the central lumen 46 of the rigid shaft 12.

Thus, displacement of the reciprocating rod 44 in the distal direction 66*b* in response to displacing the pivotable finger piece 34 away from the handle 32 (shown by the arrow 38*b* in FIG. 1), causes the rigid links 48, 50 to pivot as shown in FIG. 13, thereby displacing the lower jaw 16*a* away from the fixed upper jaw 16*b* to transition the jaw assembly 16 to the open state. Conversely, displacement of the reciprocating rod 44 in the proximal direction 66*a* in response to displacing the pivotable finger piece 34 toward the handle 32 (shown by the arrow 38*a* in FIG. 1), causes the rigid links 48, 50 to pivot as shown in FIG. 12, causing the lower jaw 16*a* to be transitioned toward the fixed upper jaw 16*b* to transition the jaw assembly 16 to the closed state.

Notably, as shown in FIG. 12, the rigid links 48, 50 reside completely between the distal parallel arms 56 of the rigid shaft 12 (i.e., the rigid links 48, 50 do not protrude outwardly from the circular cross-sectional envelope of the rigid shaft 12) when the jaw assembly 16 is in the closed state, thereby maintaining the low profile of the laparoscopic tissue suturing instrument 10. It should be appreciated that, although the finger piece 34 and associated linkage (including the reciprocating rod 44 and rigid links 48, 50) are described as actuating the jaw assembly 16 between the open state and the closed state, any suitable proximal actuator and associated linkage may be used to alternately displace the jaw assembly 16 between the open state and closed state.

For example, the handle assembly 14 may alternatively comprise a first finger ring (not shown) immovably affixed to the proximal end 24 of the rigid shaft 12, and a second finger ring (not shown) pivotably affixed to the proximal end 24 of the rigid shaft 12, such that alternate manual displacement of the finger rings towards and away from each other alternately closes and opens the jaws 16*a*, 16*b*.

Figure 17:
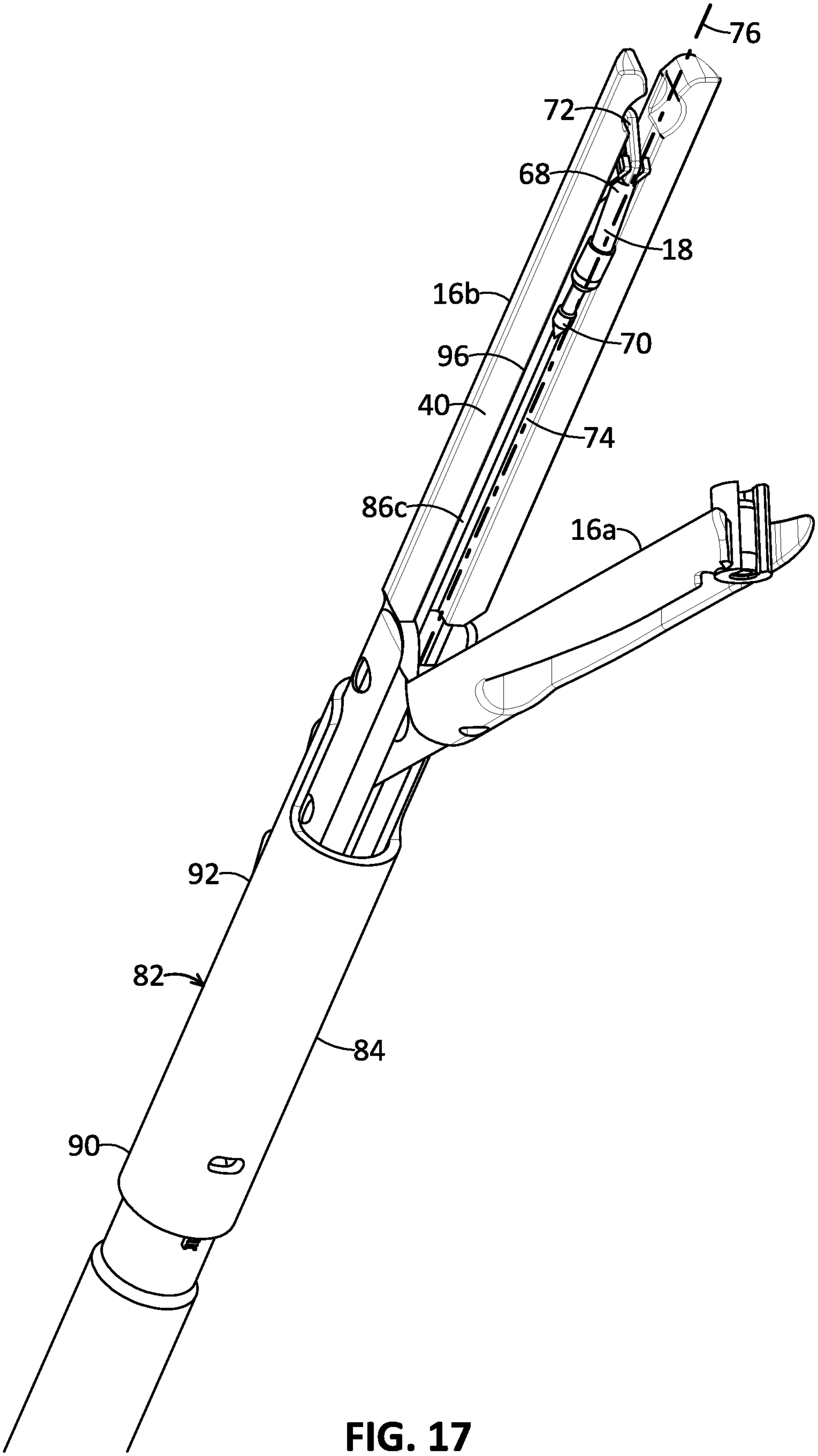
FIG. 17 is a perspective view of the jaw assembly, while the jaw assembly is in the open state.
Figure 18:
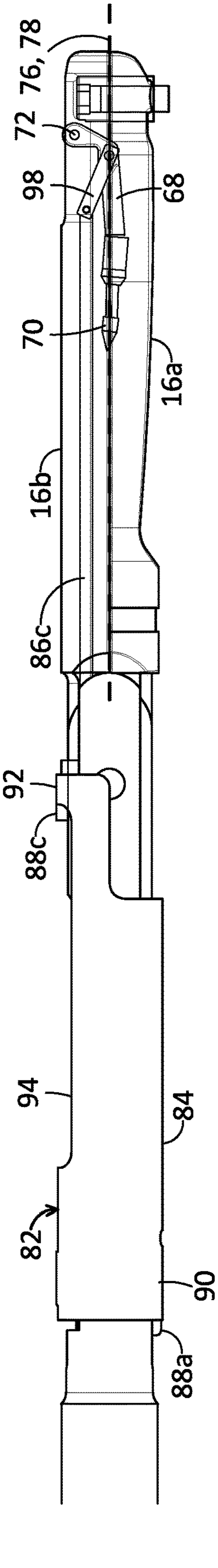
FIG. 18 is a profile of the distal end of the laparoscopic tissue suturing instrument of FIG. 1, particularly showing the jaw assembly in the closed state and the needle in the retracted state, wherein the jaw assembly is shown in phantom.
Figure 19:
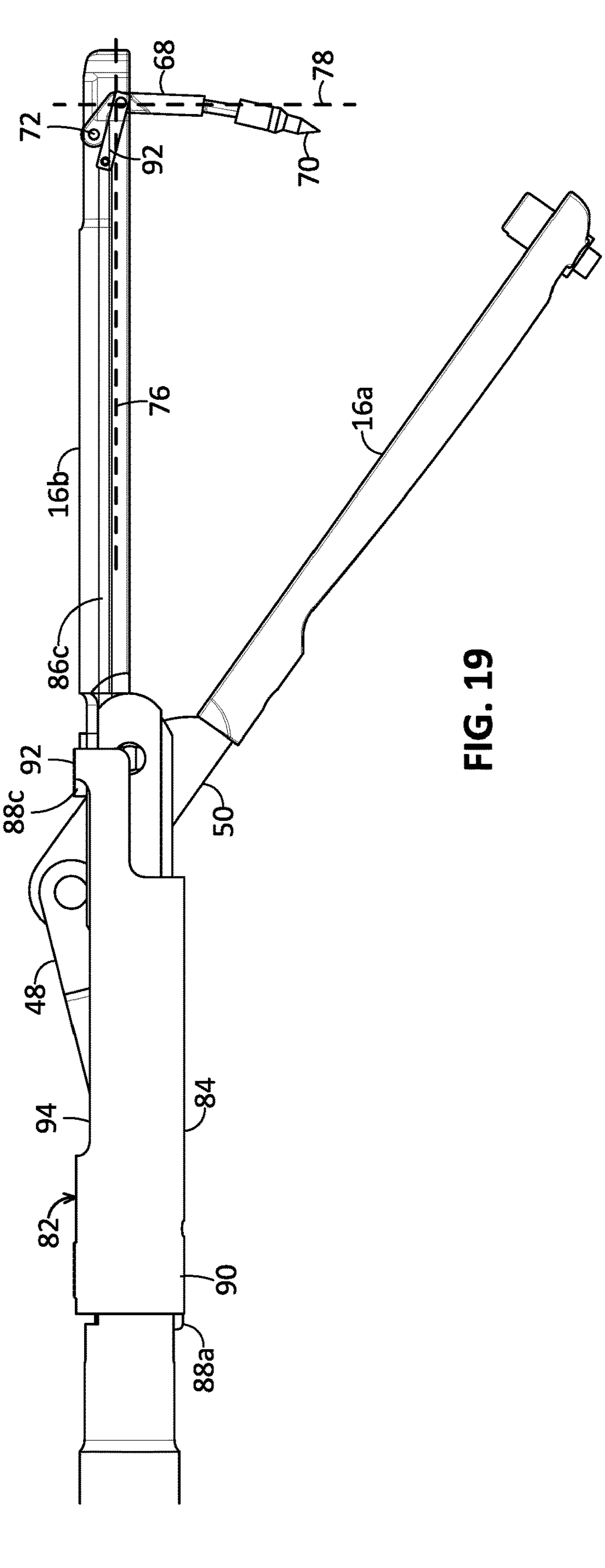
FIG. 19 is a profile of the distal end of the laparoscopic tissue suturing instrument of FIG. 1, particularly showing the jaw members in the open state and the needle in the deployed state, wherein the upper jaw is shown in phantom.
Figure 21:
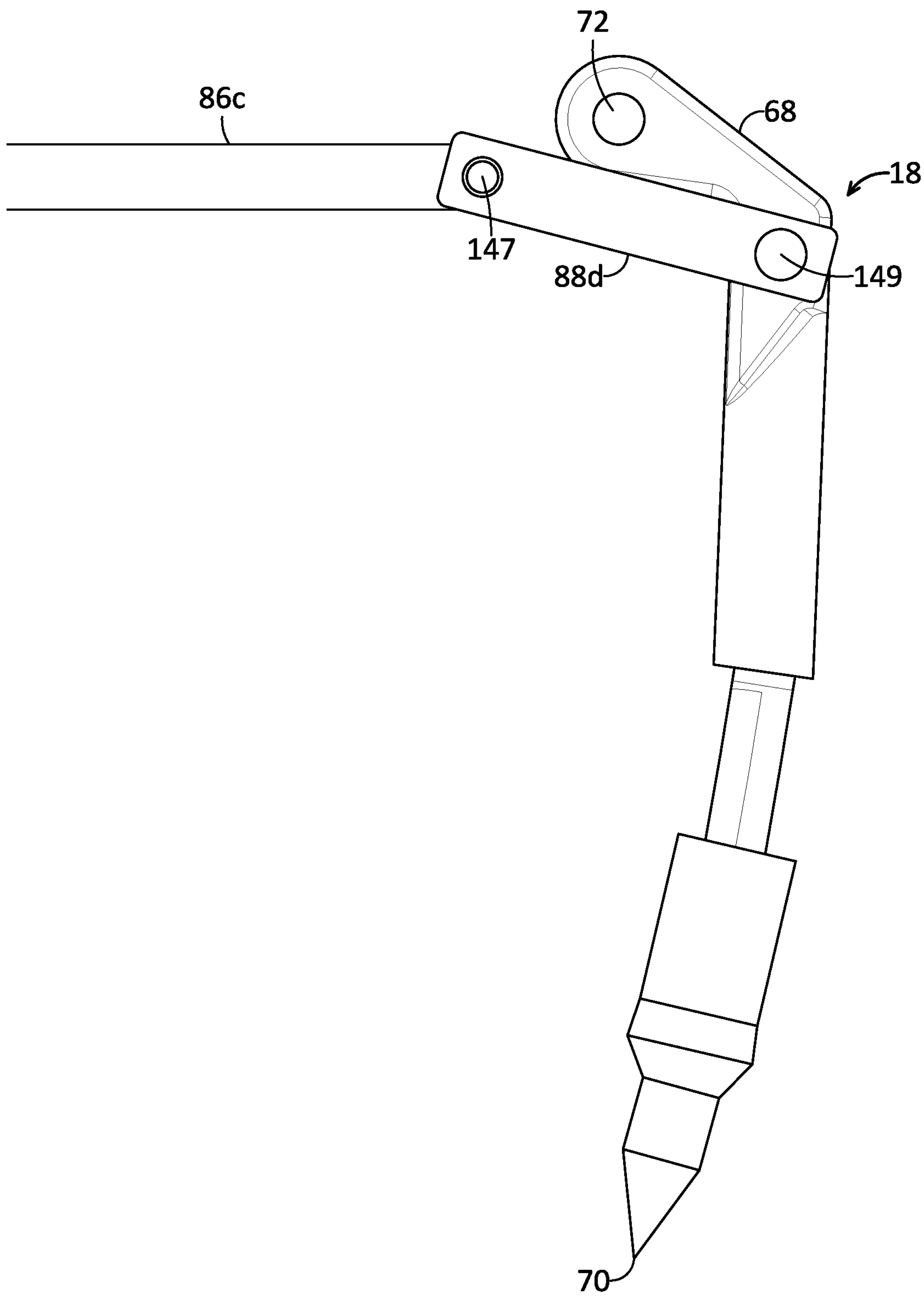
FIG. 21 is a profile view of the needle of the laparoscopic tissue suturing instrument of FIG. 1.
Figure 22:
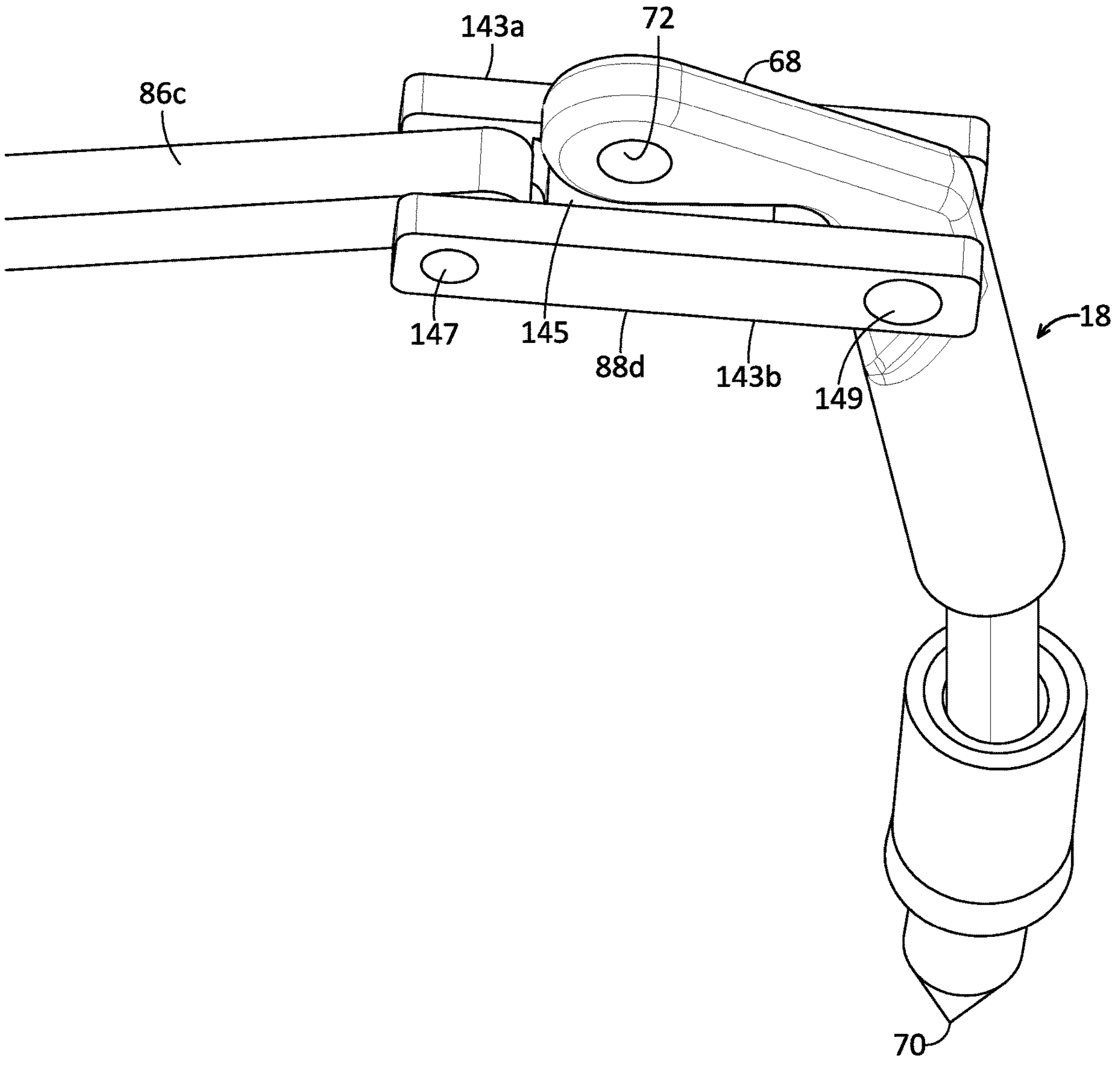
FIG. 22 is another close-up profile view of the needle of the laparoscopic tissue suturing instrument of FIG. 1.

As shown in FIGS. 17-19, the needle 18 comprises a blunt end 68 and a sharp tissue penetrating end 70 opposite of the blunt end 68. The blunt end 68 of the needle 18 is hingedly coupled to the upper jaw 16*b* via a pin 72, such that the needle 18 may be alternately hinged (shown by the arrow 52 in FIG. 1) between the retracted or stowed state (see FIG. 18) and a deployed state (see FIG. 19). As best illustrated in FIGS. 21 and 22, the blunt end 68 of the needle 18 is angled at approximately ninety degrees relative to shaft 12 to facilitate proper orientation of the needle 18 in both the retracted state and deployed state.

When in the retracted state, the needle 18 is stowed within the upper jaw 16*b*, and when in the deployed state, the needle 18 extends away from upper jaw 16*b* toward the lower jaw 16*a*. In alternative embodiments, the blunt end 68 of the needle 18 may be hingedly coupled to the lower jaw 16*a* via a hinge, such that, when in the retracted state, the needle 18 extends along the lower jaw 16*a* when the jaw assembly 16 is in the closed state, and, when in the deployed state, the needle 18 extends from the lower jaw 16*a* toward the upper jaw 16*b*.

To facilitate placement of the jaw assembly 16 into the closed state when the needle 18 is in the retracted state, the upper jaw 16*b* comprises storage channel 74 in which the retracted needle 18 may be at least partially seated, as illustrated in FIG. 17. The storage channel 74 is disposed in the inner surface 40 along the longitudinal axis 76 of the lower jaw 16*a*. In the illustrated embodiment, the entirety of the retracted needle 18 is not seated within the storage channel 74 of the upper jaw 16*b*, as best illustrated in FIG. 18. Thus, as will be described in further detail below, the lower jaw 16*a* is specifically designed to seat the remainder of retracted needle 18 protruding from lower jaw 16*a*.

In the illustrated embodiment, when in the retracted state, the longitudinal axis 78 of the needle 18 is generally parallel to the longitudinal axis 76 of the upper jaw 16*b*, with the sharp end 70 of the needle 18 pointing proximally and parallel with longitudinal axis 76 of the upper jaw 16*b*, as illustrated in FIGS. 17 and 18. In one alternative embodiment, the longitudinal axis 78 of the needle 18 may be arranged at a non-parallel angle (i.e., more than 0 degrees) relative to the longitudinal axis 76 of the upper jaw 16*b* when in the retracted state. In another alternative embodiment, the sharp end 70 of the needle 18 may point distally along the longitudinal axis 76 of the upper jaw 16*b* when in the retracted state.

In the embodiment illustrated in FIG. 19, when in the deployed state, the longitudinal axis 78 of the needle 18 extends perpendicular to the longitudinal axis 76 of the upper jaw 16*b*, with the sharp end 70 of the needle 18 pointing generally towards the lower jaw 16*a*. In alternative embodiments, the longitudinal axis 78 of the needle 18 may be arranged obliquely relative to the longitudinal axis 76 of the upper jaw 16*b*, as long as the sharp end 70 of the needle 18 is capable of penetrating tissue disposed between the jaws 16*a*, 16*b* when the jaw assembly 16 is transitioned from the open state to the closed state. As best shown in FIG. 19, the needle 18 is slightly curved in the proximal direction to facilitate proper insertion into the shuttling element 20, as will be described in further detail below.

The needle 18 is actuated to hinge between the retracted state and the deployed state via a suitable linkage assembly operably associated with a slider mechanism 80 associated with the handle 30 (shown in FIG. 1). As will be described in further detail below, the slider mechanism 80 can be actuated to displace the needle 18 between the retracted state and the deployed state.

In the illustrated embodiment, linkage assembly takes the form of an anti-buckling linkage assembly 82. In particular, referring to FIGS. 10, 11, 14, 15, and 17-20, the linkage assembly 82 comprises a sleeve 84 slidably disposed within the rigid shaft 12, two diametrically opposed proximal push-pull wires 86*a*, 86*b* (shown best in FIGS. 12, 15, and 20) coupled to a proximal end 90 of the sleeve 84 via respective connectors 88*a*, 88*b*, and a distal push-pull wire 86*c* coupled between a distal end 92 of the sleeve 84 via a connector 88*c* and the blunt end 68 of the needle 18 via a connector 88*d*.

The sleeve 84 is generally cylindrically shaped and comprises a sidewall opening 94 through which rigid links 48, 50 pivot outwards when the lower jaw 16*a* is transitioned away from the fixed upper jaw 16*b* to transform the jaw assembly 16 to the open state, as best shown in FIGS. 14 and 17, and through which the links 48, 50 pivot inwards when the lower jaw 16*a* is transitioned toward the fixed upper jaw 16*b* to transition the jaw assembly 16 to the closed state, as best shown in FIG. 18.

The distal push-pull wire 86*c* extends from the blunt end 68 of the needle 18 in the proximal direction to the sleeve 84 along an open pull wire channel 96 formed within the storage channel 74 (shown in FIG. 17) that longitudinally runs along the bottom surface 40 of the upper jaw 16*b*. In the illustrated embodiment, the distal push-pull wire 86*c* is affixed to the blunt end 68 of the needle 18 via the connector 88*d*, as illustrated in FIG. 21. Thus, distal displacement of the distal push-pull wire 86*c*, distally displaces the connector 88*d*, causing the pin 72 to pivot away from the storage channel 74, which in turn, causes the needle 18 to pivot away from the upper jaw 16*b* into its deployed state (FIG. 19). In contrast, proximal displacement of the distal push-pull wire 86*c*, proximally displaces the connector 88*d*, causing the pin 72 to pivot toward the storage channel 74, which in turn, causes the needle 18 to pivot toward the upper jaw 16*b* into its retracted state (FIG. 18).

The proximal push-pull wires 86*a*, 86*b* extend from the slider mechanism 80 (shown in FIG. 16) in the distal direction to the sleeve 84 along open pull wire channels 100 (one shown in FIG. 15) that longitudinally run along the diametrically opposed surfaces of the rod 44. Alternatively, instead of running along the open pull wire channels 100, the proximal push-pull wires 86*a*, 86*b* may be slidably disposed through wire lumens (not shown) that longitudinally extend through the rigid shaft 12 separately from the central lumen 46 of the rigid shaft 12. In the illustrated embodiment, the proximal push-pull wires 86*a*, 86*b* and distal push-pull wire 86*c* are flattened, and the wire channels 96, 100 are rectangular, such that the push-pull wires 86*a*-86*c* conform to and are guided within the wire channels 96, 100. Thus, it can be appreciated that the wire channels 96, 100 (or alternatively the pull wire lumens) provide support to the push-pull wires

86*a*-86*c*, thereby further ensuring that the push-pull wires 86*a*-86*c* do not axially buckle when transitioned in the distal direction.

Figure 20:
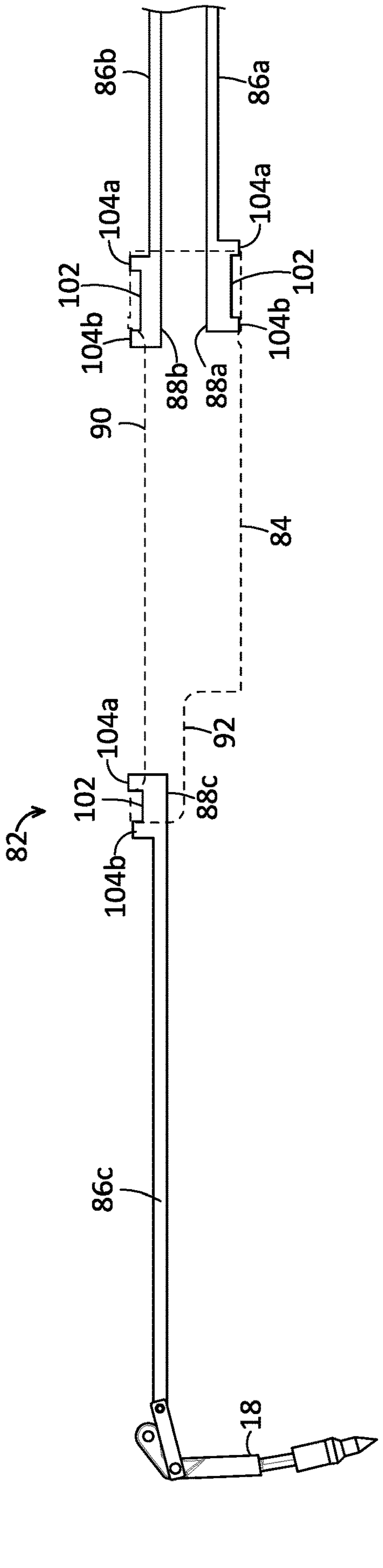
FIG. 20 is a profile view of a linkage mechanism used to displace the needle of the laparoscopic tissue suturing instrument of FIG. 1 between the deployed state and the retracted state.

As best shown in FIG. 20, each connector 88*a*, 88*b* that couples a respective proximal push-pull wire 86*a*, 86*b* to the proximal end 90 of the sleeve 84 comprises a recess 102 flanked by two ridges 104*a*, 104*b*. Diametrically opposed proximal portions of the sleeve 84 respectively fit within the recesses 102 of the diametrically opposed connectors 88*a*, 88*b*. In particular, as further shown in FIG. 10, the two ridges 104*a*, 104*b* of the connector 88*a* respectively engage a proximal-most edge 106 of the sleeve 84 and a small sidewall opening 108 in the sleeve 84, such that the connector 88*a* is interference fit with the sleeve 84. As further shown in FIGS. 11 and 14, the two ridges 104*a*, 104*b* of the connector 88*b* respectively engage a notch 110 of the sleeve 84 and a proximal-most edge 112 of the sidewall opening 94, such that the connector 88*b* is interference fit with the sleeve 84.

Likewise, connector 88*c* that couples the distal push-pull wire 86*c* to the distal end 90 of the sleeve 84 comprises a recess 102 flanked by two ridges 104*a*, 104*b*. The distal portion of the sleeve 84 fits within the recess 102 of the connector 88*c*. In particular, as shown in FIGS. 11 and 14, two ridges 104*a*, 104*b* of the connector 88*c* respectively engage a distal-most edge 114 of the sleeve 84 and a distal-most edge 116 of the sidewall opening 94, such that the connector 88*c* is interference fit with the sleeve 84.

As shown in FIGS. 21 and 22, the connector 88*d* is H-shaped, comprising parallel members 144*a*, 144*b* and a cross-bar 147. The distal end of the distal push-pull wire 86*c* is hingedly affixed between the parallel members 144*a*, 144*b* at one end of the connector 88*d* via a pin 147, and the blunt end 68 of the needle 18 is hingedly affixed between the parallel members 144*a*, 144*b* at the other end of the connector 88*d* via a pin 149.

As illustrated in FIG. 16, manual displacement of the slider mechanism 80 relative to the handle 32 from a distal position to a proximal position (along the arrow 152*a*) axially displaces the proximal push-pull wires 86*a*, 86*b* in the proximal direction, thereby hinging the needle 18 from the retracted state into the deployed state, while manual displacement of the slider mechanism 80 relative to the handle 32 from a proximal position to a distal position (along the arrow 152*b*) axially displaces the proximal push-pull wires 86*a*, 86*b* in the distal direction, thereby hinging the needle 18 from the deployed state back into retracted state. In an optional embodiment, a locking mechanism or spring mechanism (not shown) may be employed in the handle 32 for locking the slider mechanism 80 in the proximal position, and thus, locking the needle 18 in the deployed state.

In an alternative embodiment, rather than employing the sleeve 84 and associated proximal push-pull wires 86*a*, 86*b* and distal push-pull wire 86*c*, as shown in FIGS. 10, 11, 14, and 17-20, the linkage assembly includes a single push-pull wire (not shown) affixed between the blunt end 68 of the needle 18 and the slider mechanism 80 of the handle assembly 14. In this embodiment, the single push-pull wire has the necessary columnar strength to resist buckling when transitioned in the distal direction in response to manual displacement of the slider mechanism 80 relative to the handle 32 from the proximal position to the distal position. A wire channel (not shown) may provide support to the single push-pull wire, thereby further ensuring that the single push-pull wire does not axially buckle when transitioned in the distal direction. In an alternative embodiment, if the single push-pull wire does not have sufficient columnar strength to prevent bucking when transitioned in the distal direction, a spring mechanism (not shown) may be disposed in the lower jaw 16*a* for biasing the needle 18 into the retracted state, and an additional spring mechanism (not shown) associated with the slider mechanism 80 may be disposed in the handle 32 to maintain slight tensioning of the push-pull wire.

Now referring to FIGS. 4-8, the shuttling element 20 is removably coupled to the lower jaw 16*a* in a manner that allows the laparoscopic tissue suturing instrument 10 to pass the shuttling element 20 (and attached suture 22) back and forth between the lower jaw 16*a* and the upper jaw 16*b* to thereby create a running stitch (i.e., a series of connected stitches) within tissue.

Figure 8:
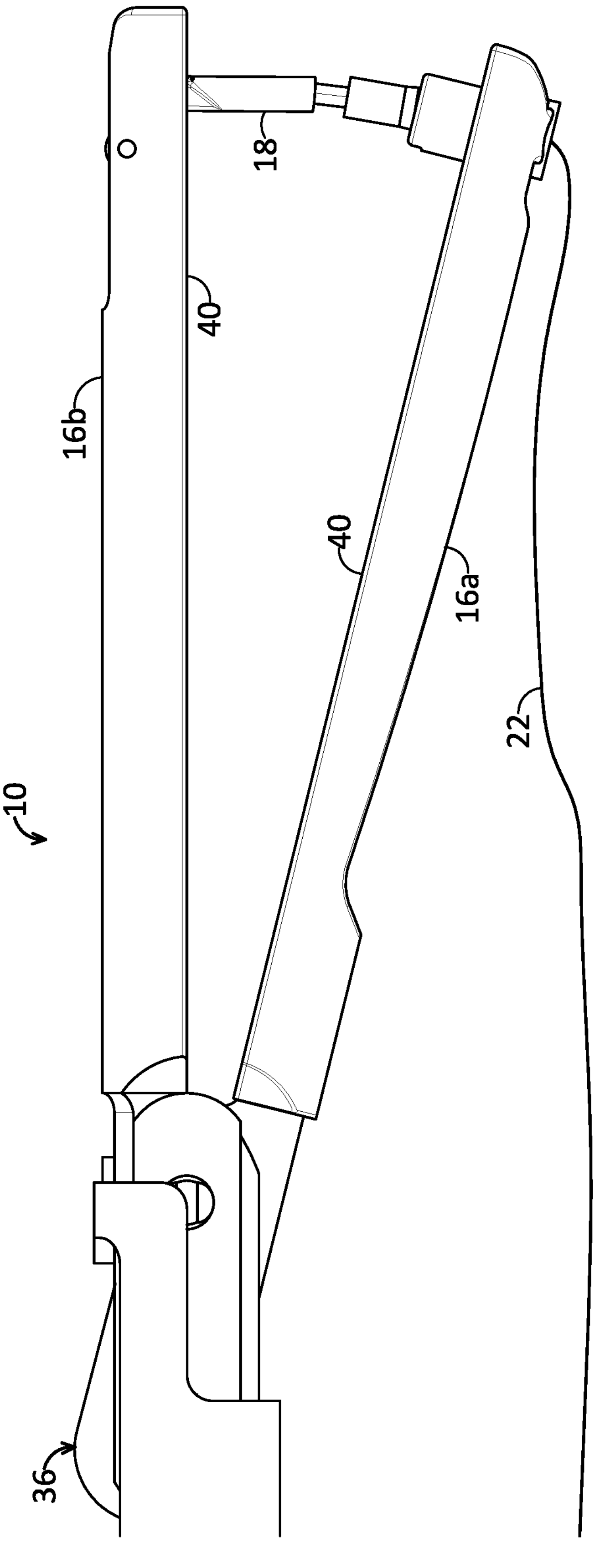
FIG. 8 is a perspective view of the jaw assembly of the laparoscopic tissue suturing instrument of FIG. 1 in a second one of the two intermediate states, while the shuttling element has been recoupled to the lower jaw by the needle.

By transitioning the jaw assembly 16 between the open state and the first and second intermediate states, the needle 18 can be translated between different positions (a proximal position when the jaw assembly 16 is in the open state (see FIG. 4), a first distal position when the jaw assembly 16 is in the first intermediate state (see FIGS. 5 and 6) to effect decoupling and recoupling of the shuttling element 20 to and from the lower jaw 16*a*, and a second distal position when the jaw assembly 16 is in the second intermediate state (see FIG. 8).

In particular, the needle 18, when in the deployed state, is configured for being inserted within and engaged to the shuttling element 20 coupled to the lower jaw 16*a* when the jaw assembly 16 is transitioned from the open state (deployed needle 18 is in the proximal position) (see FIG. 4) to a first intermediate state (deployed needle 18 is in the first distal position) between the open state and the closed state (see FIGS. 5 and 6); decoupling the engaged shuttling element 20 from the lower jaw 16*a* when the jaw assembly 16 is transitioned from the first intermediate state towards the open state, thereby drawing the suture 22 from the lower jaw 16*a* towards the upper jaw 16*b* (see FIG. 7); recoupling the shuttling element 20 to the lower jaw 16*a* when the jaw assembly 16 is transitioned from the open state to a second intermediate state (needle is in the second distal position) (see FIG. 8); and for being removed and disengaged from the shuttling element 20 when the jaw assembly 16 is transitioned from the second intermediate state toward the open state (see FIG. 4). In the illustrated embodiment, the first intermediate state and the second intermediate state of the needle 18 are different from each other. As will be described below, the interaction between the needle 18 and the shuttling element 20 illustrated in FIGS. 4-8 can be repeatedly cycled to create a running stitch within the tissue.

The lower jaw 16*a*, needle 18, and shuttling element 20 have complementary mechanical features that enable the needle 18 to alternately decouple the shuttling element 20 from the lower jaw 16*a* and recouple the shuttling element 20 to the lower jaw 16*a* in the manner illustrated in FIGS. 4-8.

In particular, referring to FIGS. 23-27, the lower jaw 16*a* defines a suture shuttle retention cavity 122 configured for receiving the shuttling element 20. The suture shuttle retention cavity 122 is further configured for being transformed between a retention state for securely retaining the shuttling element 20 (via non-interaction with the needle 18) and a release state for releasing the shuttling element 20 (via interaction with the needle 18), as will be described in further detail below.

The lower jaw 16*a* comprises a shuttling element retainer mechanism in the form of a pair of generally parallel resilient members 124*a*, 124*b* adjacent the shuttling element retention cavity 122. The shuttling element retention cavity 122 includes a pair of hemispherical cavity portions 122*a*, 122*b* respectively formed at the distal ends of the resilient members 124*a*, 124*b*, and are defined by a pair of hemispherical walls 126*a*, 126*b*. The resilient members 124*a*, 124*b* are configured for being urged away from each other (via interaction with the needle 18 as will be described in further detail below) to displace the cavity portions 122*a*, 122*b* away from each other (shown by arrows 128*a* in FIGS. 25 and 27A), thereby expanding the shuttling element retention cavity 122 to transition it from the retention state to the release state, and for being relaxed (via non-interaction with the needle 18 as will be described in further detail below) to displace the cavity portions 122*a*, 122*b* toward each other (shown by arrows 128*b* in FIGS. 25 and 27B), thereby contracting the shuttling element retention cavity 122 to transition it from the release state to the retention state.

Figure 26:
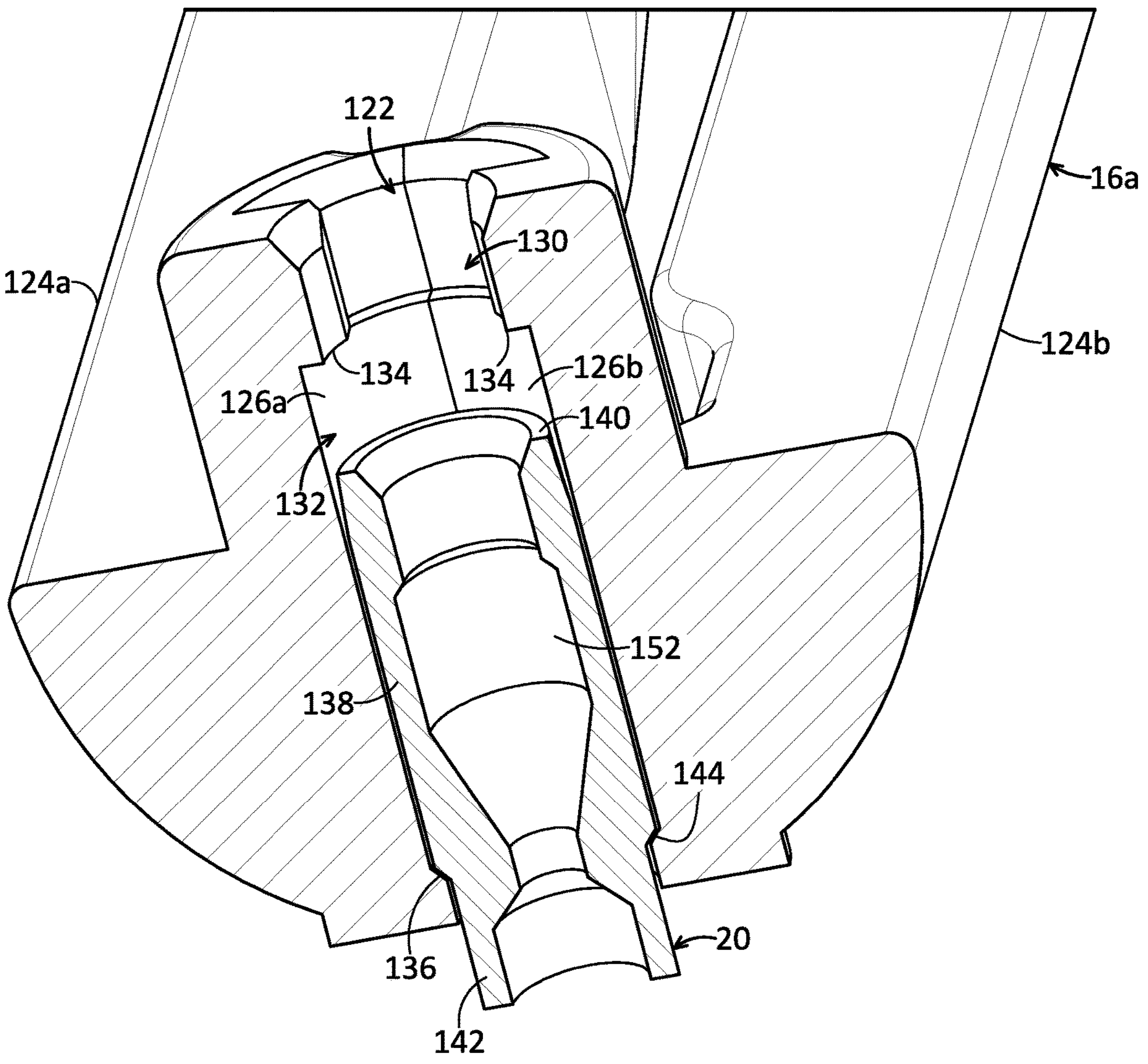
FIG. 26 is a cross-sectional view of the lower jaw and shuttling element of the laparoscopic tissue suturing instrument of FIG. 1.
Figure 27A:
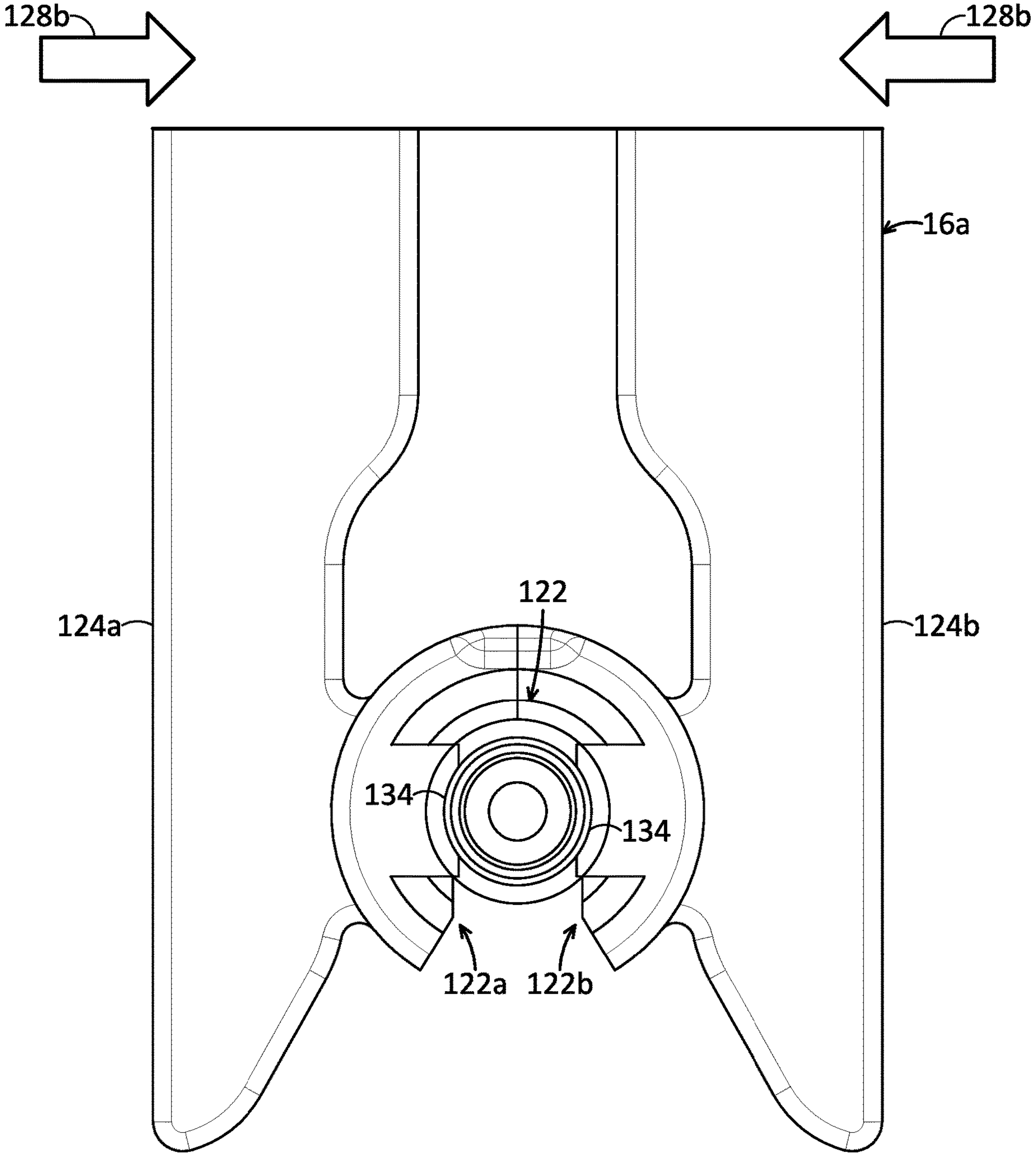
FIG. 27A is a close-up, partially cutaway view, of the lower jaw of the laparoscopic tissue suturing instrument of FIG. 1, particularly showing spring elements of the lower jaw transitioned toward each other to grasp the shuttling element.
Figure 27B:
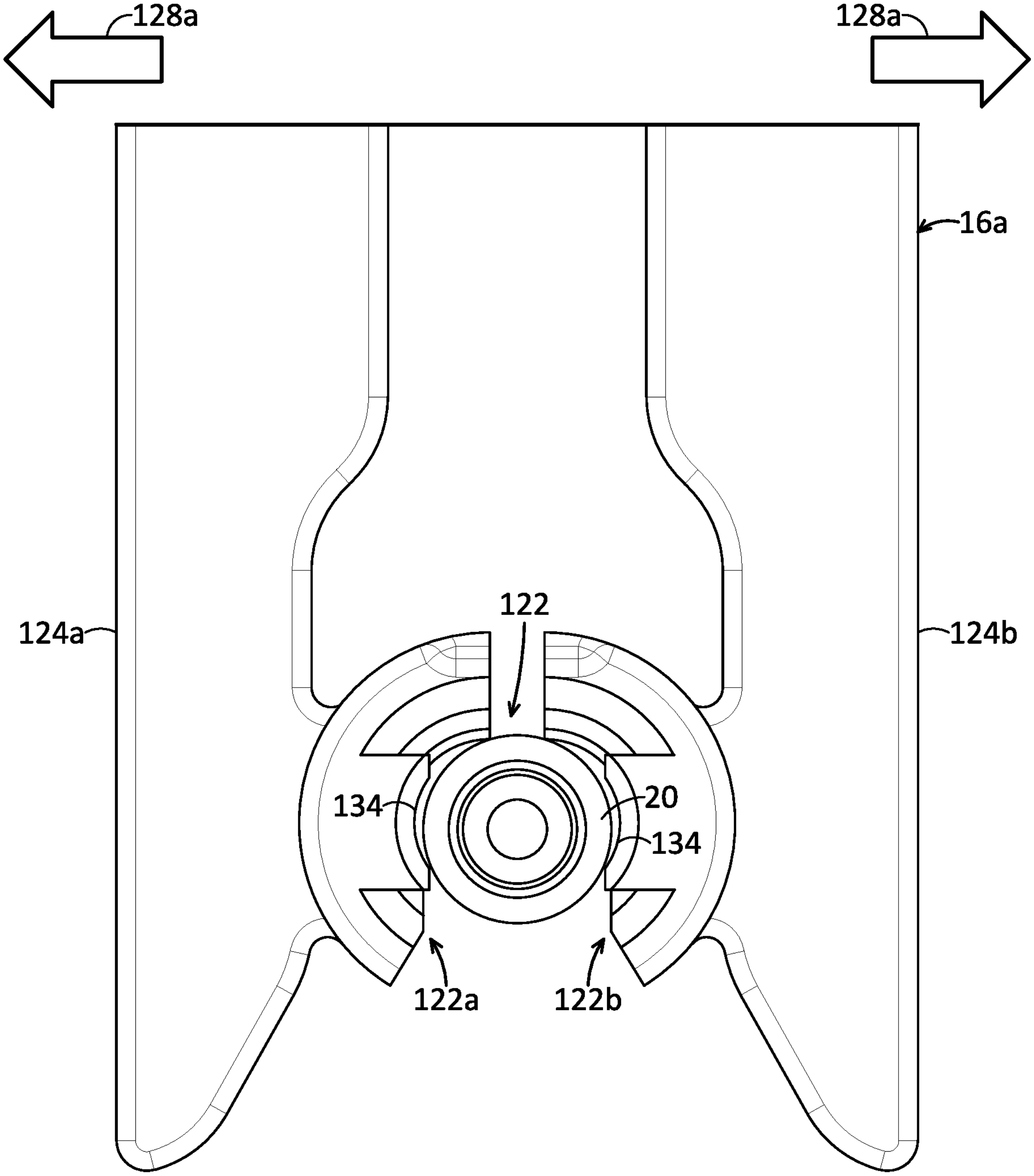
FIG. 27B is a close-up, partially cutaway view, of the lower jaw of the laparoscopic tissue suturing instrument of FIG. 1, particularly showing spring elements of the lower jaw transitioned away from each other to release the shuttling element.

As best shown in FIG. 26, the shuttling element retention cavity 122 comprises a proximal (in this case, upper) chamber 130 and a distal (in this case, lower) chamber 132, which are in communication with each other. For the purposes of this specification, the term "proximal" as it relates to a chamber is the chamber that is closest to the needle 18 when the jaw assembly 16 is in the open state, and the term "distal" as it relates to a chamber is the chamber that is furthest from the needle 18 when the jaw assembly 16 is in the open state. The upper chamber 130 has a reduced inner diameter relative to an inner diameter of the lower chamber 132, thereby forming a proximal (in this case, upper) inner annular ledge 134 on the hemispherical walls 126*a*, 126*b* between the upper chamber 130 and the lower chamber 132. The inner diameter of the lower chamber 132 is further reduced at the lower extremity of the lower chamber 132, thereby forming a distal (in this case, lower) inner annular ledge 136 opposite the upper inner annular ledge 134.

As best shown in FIG. 9, the lower jaw 16*a* comprises a suture clearance slot 123 formed within the shuttling element retention cavity 122 and between the spring members 124*a*, 124*b*. The suture clearance slot 123 is configured for allowing the suture 22 to be displaced from the shuttling element retention cavity 122, so that the suture 22 does not hinder recoupling of the suture sleeve 20 to the lower jaw 16*a*.

Figure 23:
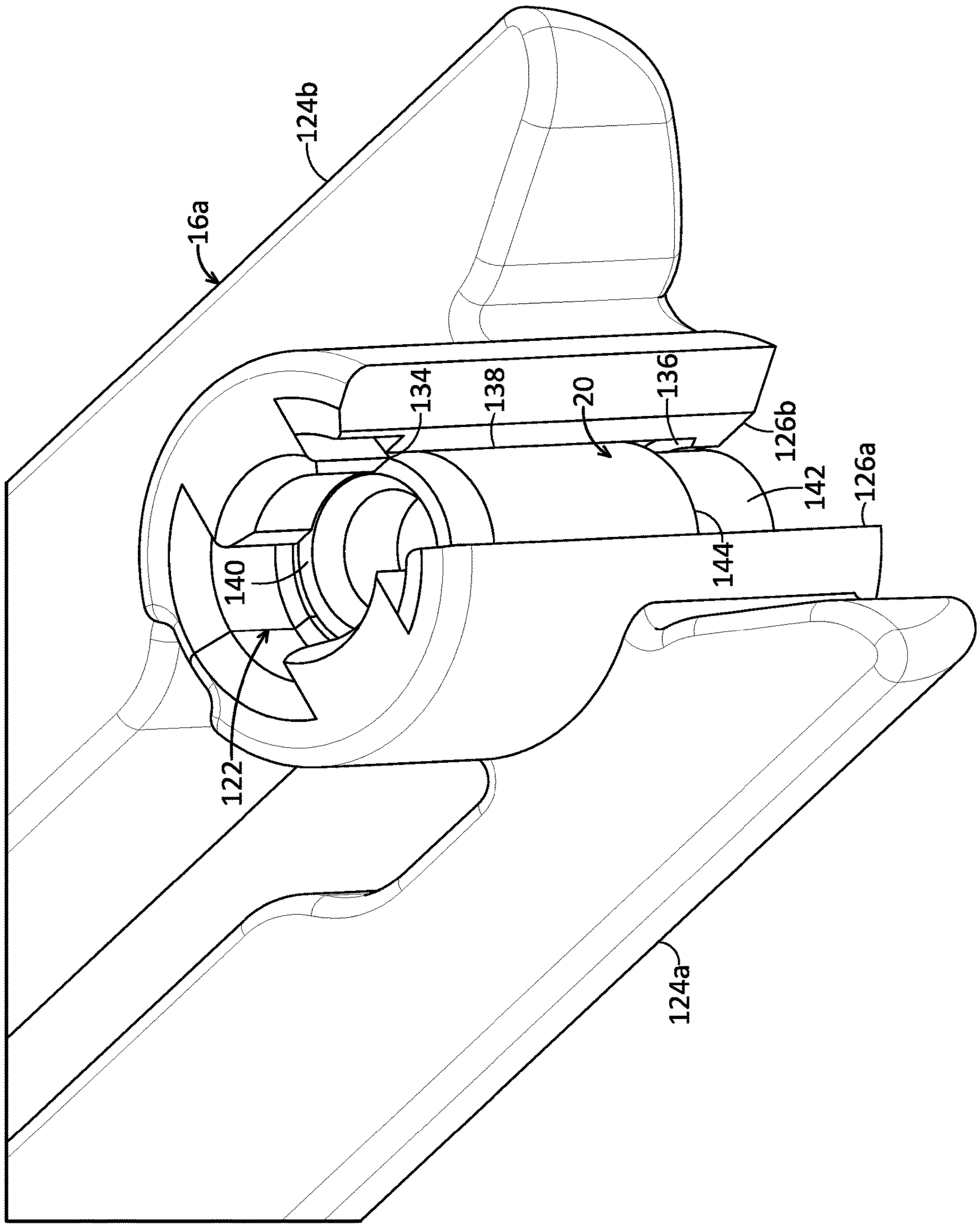
FIG. 23 is a close-up, partially cutaway view, of the lower jaw of the laparoscopic tissue suturing instrument of FIG. 1, particularly showing the shuttling element coupled to the lower jaw.
Figure 24:
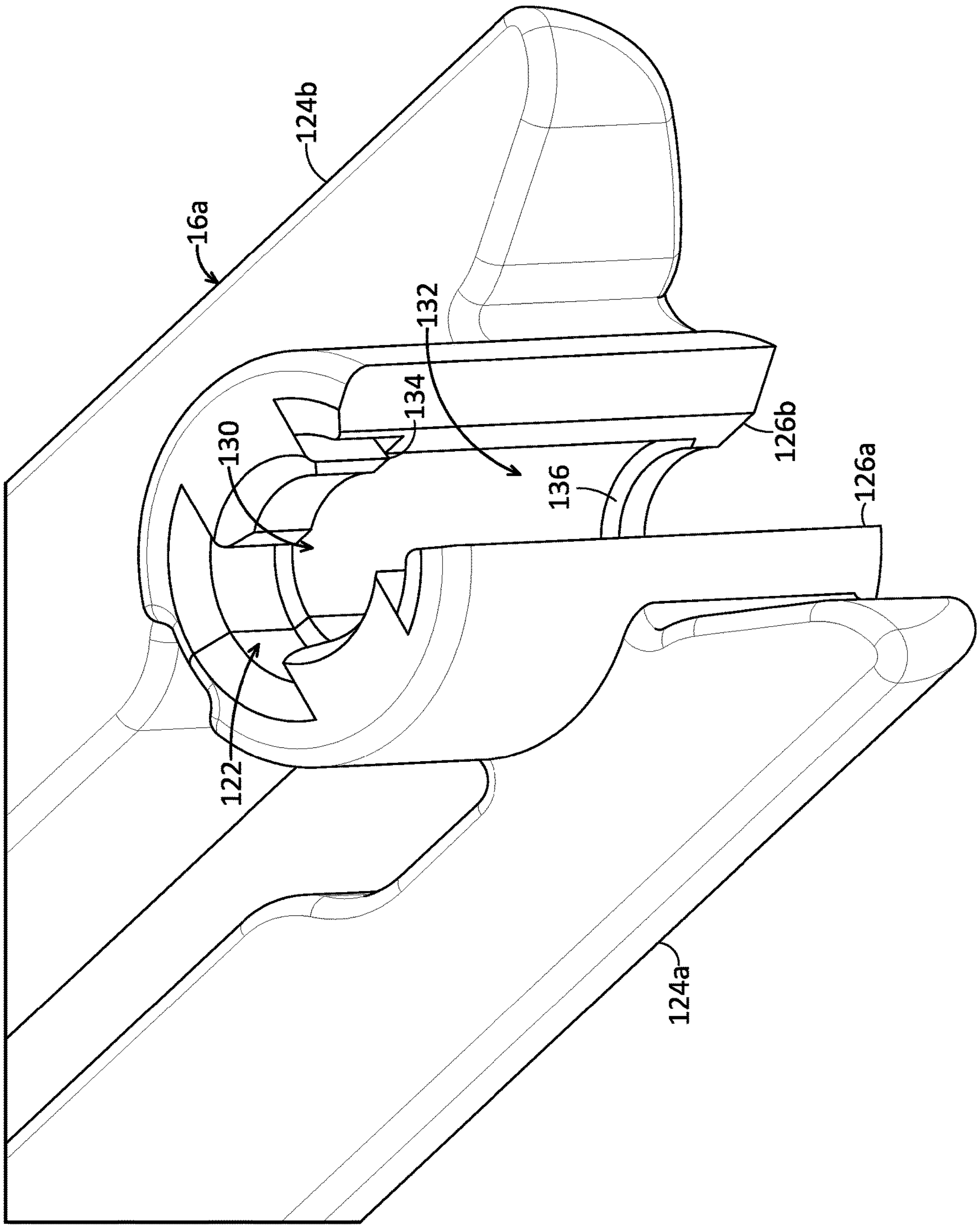
FIG. 24 is a close-up, partially cutaway view, of the lower jaw of the laparoscopic tissue suturing instrument of FIG. 1, particularly showing the lower jaw without the shuttling element.
Figure 28:
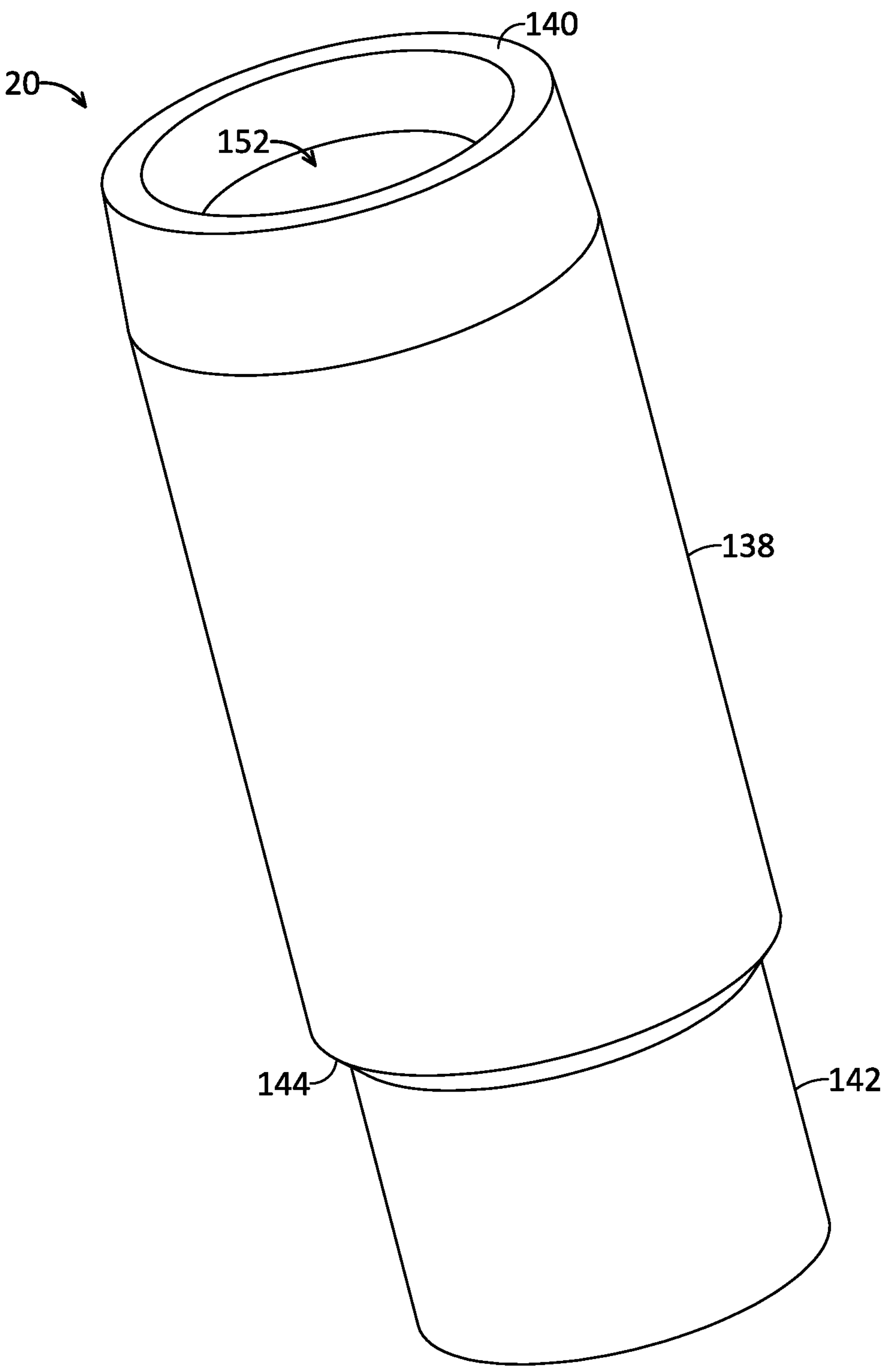
FIG. 28 is a perspective view of the shuttling element of the laparoscopic tissue suturing instrument of FIG. 1.
Figure 29:
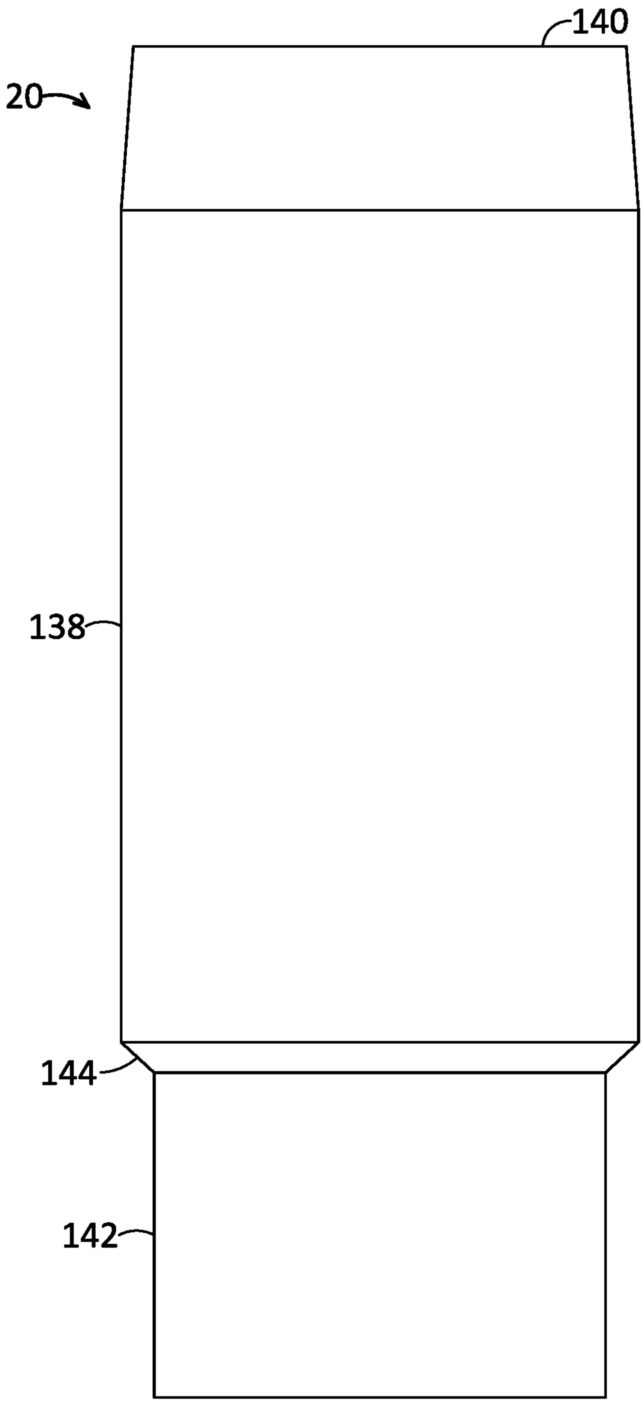
FIG. 29 is a profile view of the shuttling element of the laparoscopic tissue suturing instrument of FIG. 1.
Figure 30:
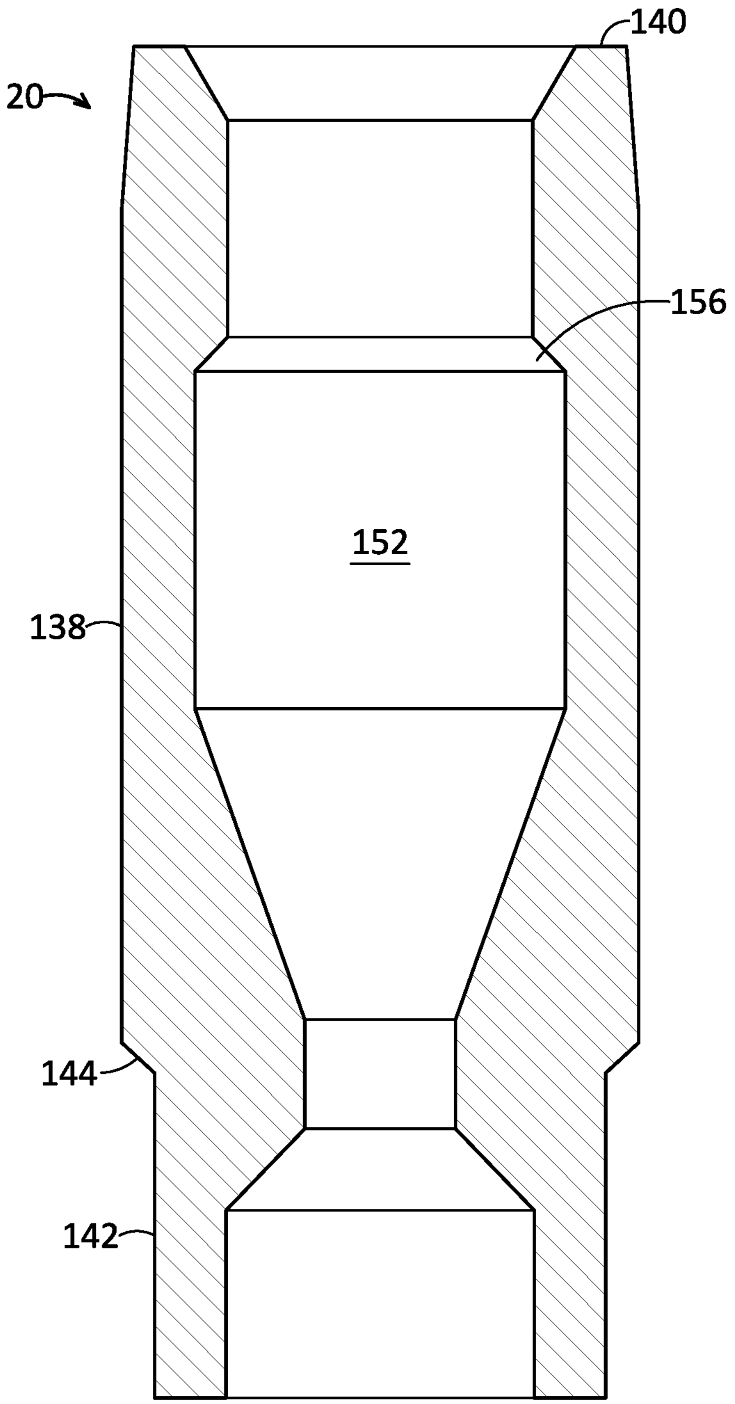
FIG. 30 is a cross-sectional view of the shuttling element of the laparoscopic tissue suturing instrument of FIG. 1.

As further shown in FIGS. 9, 28 and 29, the shuttling element 20 has a retained portion 138. The outer diameter of the retained portion 138 is greater than the inner diameter of the upper chamber 130 when the shuttling element retention cavity 122 is in the retention state, such that an upper edge 140 of the shuttling element 20 abuts the upper ledge 134 of the shuttling element retention cavity 122 when in the retention state, as best illustrated in FIG. 23. The length of the retained portion 138 is equal to or less than the length of the lower chamber 132 (i.e., the distance between the upper and lower ledges 134, 136 of the shuttling element retention cavity 122), such that the retained portion 138 of the shuttling element 20 may freely move in the lower chamber 132 in the linear direction, such that the top surface of the upper edge 140 of the shuttling element 20 may, at times, be spaced from the bottom surface of the upper ledge 134 of the shuttling element retention cavity 122, as shown in FIG. 26.

Figure 25:
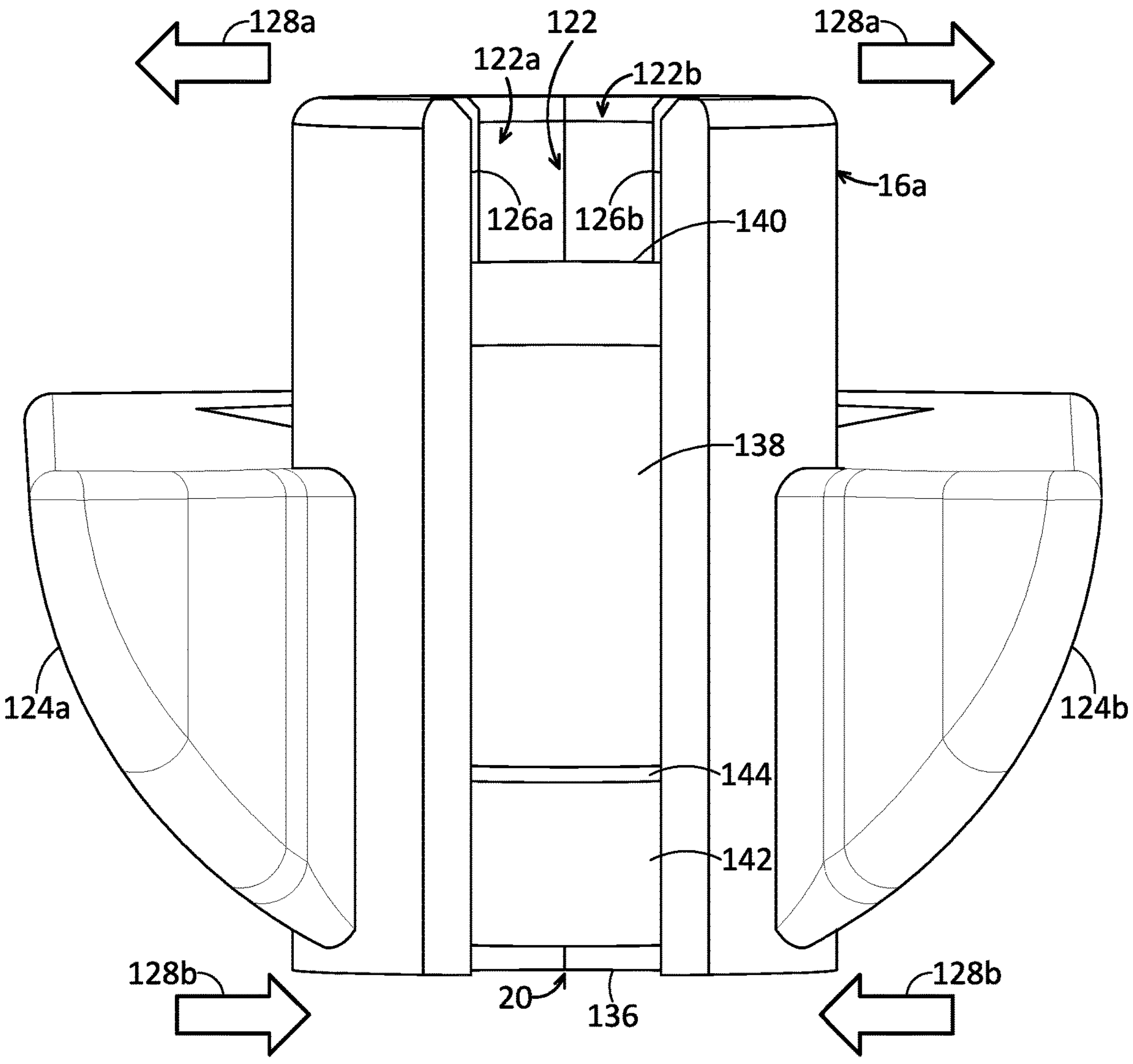
FIG. 25 is an axial view of the lower jaw of the laparoscopic tissue suturing instrument of FIG. 1, particularly showing the shuttling element coupled to the lower jaw.

The shuttling element 20 further comprises a reduced diameter suture affixation portion 142 to which the suture 22 (shown in FIGS. 2-8) is affixed. The outer diameter of the suture affixation portion 142 of the shuttling element 20 is less than the outer diameter of the retained portion 138 of the shuttling element 20, thereby forming an outer annular ledge 144 between the retained portion 138 and the suture affixation portion 142. Thus, the bottom surface of the ledge 144 of the shuttling element 20 abuts the top surface of the lower ledge 136 of the shuttling element retention cavity 122 when in the retention state, as shown in FIG. 26. As discussed above, the length of the retained portion 138 of the shuttling element 20 is less than the length of the lower chamber 132, such that the retained portion 138 of the shuttling element 20 may freely move within the lower chamber 132, as shown in FIG. 26. The bottom surface of the ledge 144 of the shuttling element 20, may at times, be spaced from the top surface of the lower ledge 136 of the shuttling element retention cavity 122 when in the retention state, as illustrated in FIGS. 23 and 25.

The lower ledge 136 of the shuttling element retention cavity 122 and the ledge 144 of the shuttling element 20 are chamfered, thereby reducing the retention force between the lower ledge 136 of the shuttling element retention cavity 122 and the ledge 144 of the shuttling element 20 (i.e., the minimum force required to prevent the shuttling element 20 from being transitioned from the shuttling element retention cavity 122 in the downward direction via mechanical interference between the ledges 136, 144). In this manner, the retained portion 138 of the shuttling element 20 may be at least partially pushed out of the lower chamber 132 by the needle 18 to allow the needle 18 clearance for inserting a slidable shuttling element release mechanism 150 into the upper chamber 130, as will be described in further detail below.

Referring now to FIG. 23, the shuttling element 20 may be securely retained within the lower chamber 132 between the upper and lower ledges 134, 136 of the shuttling element retention cavity 122 in the retention state. Although the retained portion 138 of the shuttling element 20 is retained within the lower chamber 132 when the shuttling element retention cavity 122 is in the retention state, the suture affixation portion 142 extends beyond the lower ledge 136 of the shuttling element retention cavity 122, as illustrated in FIG. 26.

As will be described in further detail below, the outer diameter of the retained portion 138 of the shuttling element 20 is equal to or greater than the outer diameter of the upper chamber 130 when the shuttling element retention cavity 122 is in the release state, thereby allowing the shuttling element 20, via interaction with the needle 18 (as will be described in further detail below), to be translated from the lower chamber 132 and into the upper chamber 130, and then ultimately removed from the shuttling element retention cavity 122 altogether.

Figure 32:
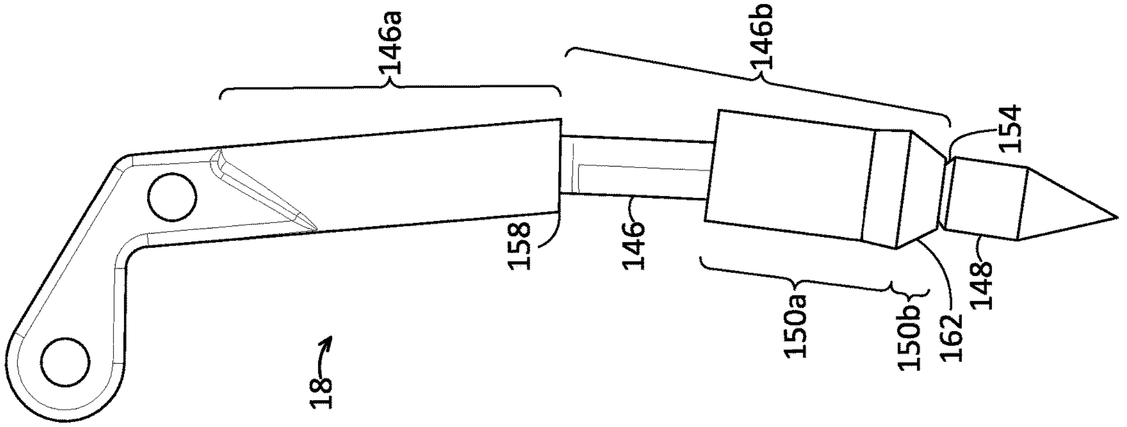
FIG. 32 is a profile view of the needle of the laparoscopic tissue suturing instrument of FIG. 1, particularly showing the slidable sleeve of the needle in its most distal position.
Figure 31:
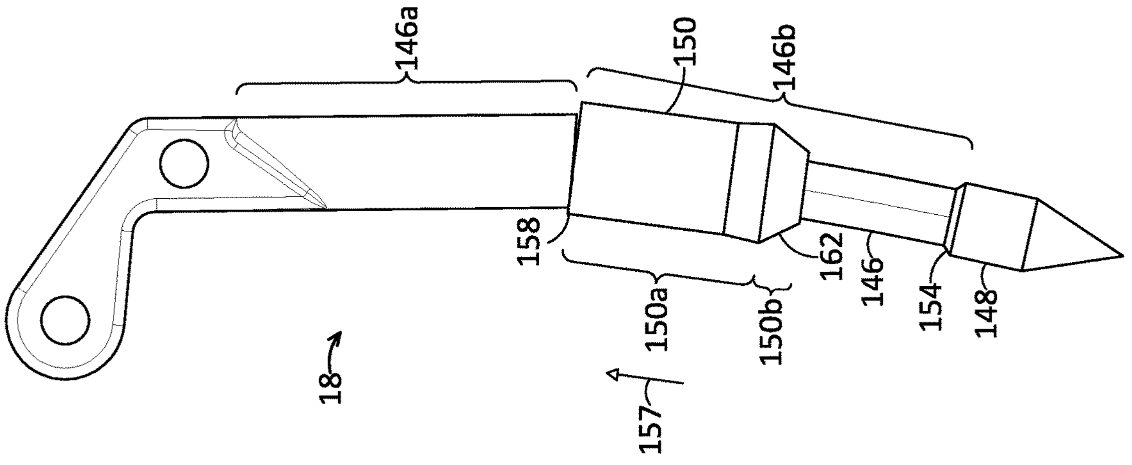
FIG. 31 is a profile view of the needle of the laparoscopic tissue suturing instrument of FIG. 1, particularly showing a slidable sleeve of the needle in its most proximal position.
Figure 33:
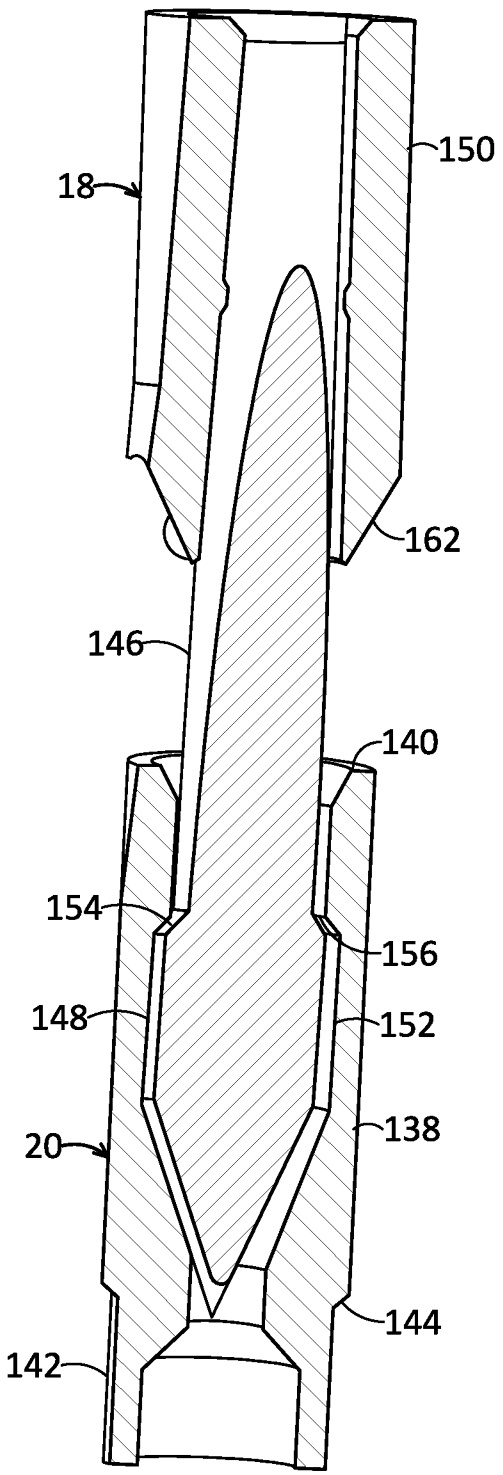
FIG. 33 is a cross-sectional view of the needle and shuttling element of the laparoscopic tissue suturing instrument of FIG. 1, particularly showing the needle engaged with the shuttling element.

Referring to FIGS. 31-33, the needle 18 comprises an elongated needle shaft 146, a shuttling element coupler 148 disposed at the distal end of the needle shaft 146, and the previously mentioned shuttling element release mechanism 150 slidably disposed on the needle shaft 146. In the illustrated embodiment, the shuttling element release mechanism 150 takes the form of a slidable sleeve.

The distal end of the needle 318 is specifically designed to provide a substantially continuous profile to facilitate insertion through tissue while allowing controlled slidability of the sleeve 150. In particular, the needle shaft 146 has a proximal needle shaft section 146*a* and a distal needle shaft section 146*b* having a diameter less than that of the proximal needle shaft section 146*a*. The shuttling element coupler 148 is disposed at the tip of the distal needle shaft section 146*b*. The slidable sleeve 150 has a proximal cylindrical sleeve section 150*a* and a distal tapered sleeve section 150*b*. The outer diameter of the slidable sleeve 150 matches the outer diameter of the proximal needle shaft section 146*a*.

As best shown in FIG. 33, the shuttling element 20 defines a cavity 152 in which the shuttling element coupler 148 is configured for being disposed to engage the shuttling element 20. In the illustrated embodiment, the shuttling element coupler 148 takes the form of an enlarged bullet-shaped tip (corresponding to the sharp end 70 of the needle 18 shown in FIG. 22), the outer diameter of which is greater than the outer diameter of the needle shaft 146, such that an outer annular ledge 154 is formed between the needle shaft 146 and shuttling element coupler 148, as illustrated in FIG. 33. The shuttling element 20 has an inner annular ledge 156 within the cavity 152, such that the ledge 154 of the shuttling element coupler 148 is configured for abutting the ledge 156 of the shuttling element 20. The geometry of the cavity 152 matches the geometry of the shuttling element coupler 148, such that shuttling element coupler 148 may firmly engage the shuttling element 20.

The complementary shapes and sizes of the needle 18 and the cavity 152 of the shuttling element 20, and in particular, the ledge 154 of the shuttling element coupler 148 of the needle 18 and the ledge 156 of the shuttling element 20, can be selected to adjust the desired retention force of the shuttling element coupler 148 of the needle 18 within the cavity 152 of the shuttling element 20 (i.e., the minimum force require to prevent the shuttling element engagement 148 from disengaging the shuttling element 20). In this manner, abutment between the ledge 154 of the shuttling element coupler 148 of the needle and the ledge 156 of the shuttling element 20 may prevent removal of the shuttling element coupler 148 from the cavity 152 of the shuttling element 20 in response to a relatively small opposing force (e.g., a slight frictional force applied on the shuttling element 20 by the walls of the shuttling element retention cavity 122 while in the release state in response to transitioning the jaw assembly 16 from the first intermediate state towards the open state), while allowing removal of the shuttling element coupler 148 from the cavity 152 of the shuttling element 20 in response to a larger force (e.g., the force applied to the shuttling element 20 by the abutment between the upper ledge 134 of the shuttling element retention cavity 122 and the upper edge 140 of the shuttling element 20 when the shuttling element retention cavity 122 is in the retention state in response to transitioning the jaw assembly 16 from the second intermediate state towards the open state). In the illustrated embodiment, the ledge 154 of the shuttling element coupler 148 and the ledge 156 of the shuttling element 20 are both angled in the distal direction to decrease the amount of force necessary to remove the shuttling element coupler 148 from the cavity 152 of the shuttling element 20.

Figure 34:
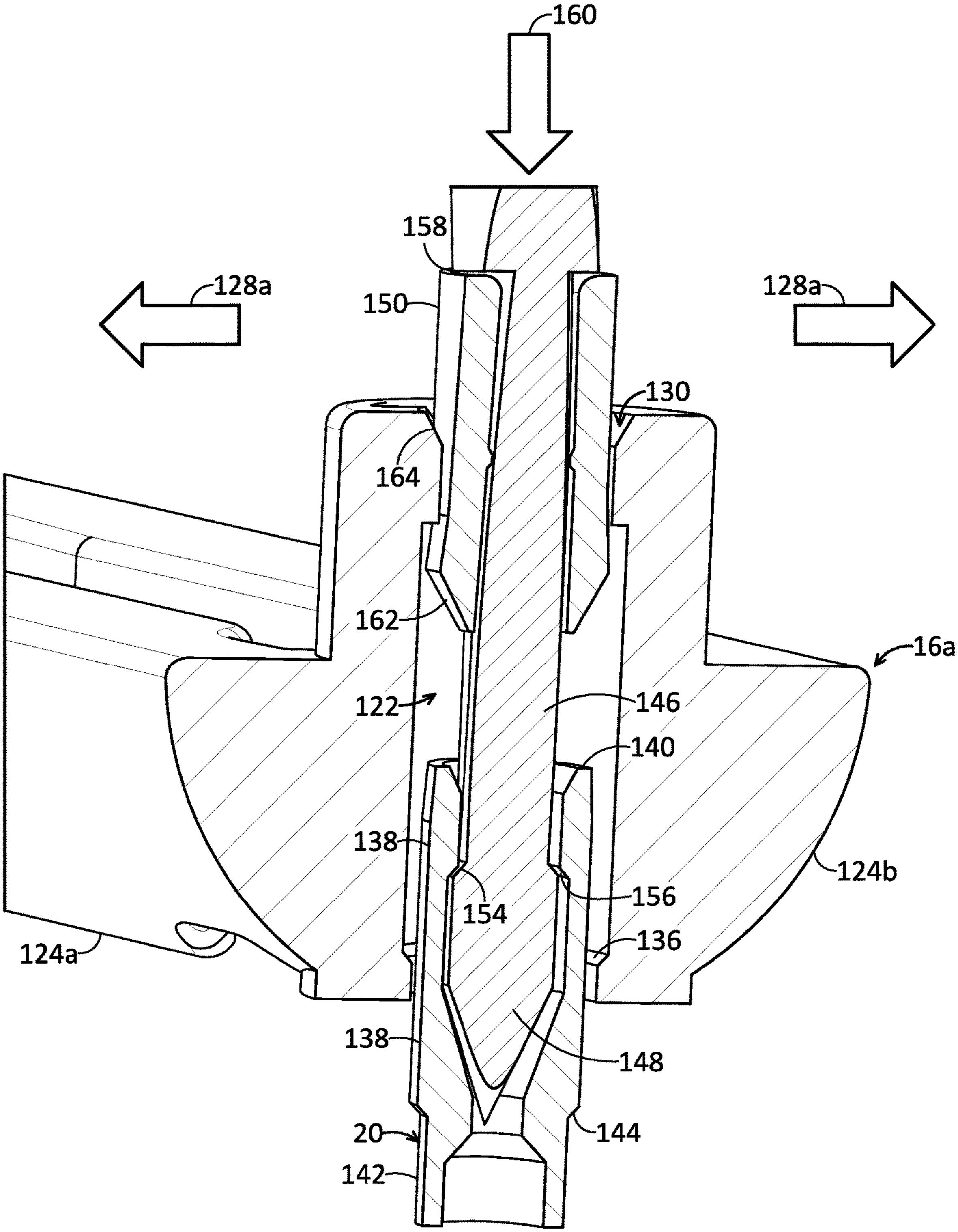
FIG. 34 is a perspective cross-sectional view of the lower jaw, needle, and shuttling element of the laparoscopic tissue suturing instrument of FIG. 1, particularly showing the needle engaging the shuttling element in the lower jaw and the slidable sleeve disposed within a cavity of the lower jaw to transition the cavity from a retention state to a release state when the jaw assembly is in the first intermediate state.

As will be described in further detail below, the slidable sleeve 150 is configured for cooperating with the lower jaw **16*a* to place the shuttling element retention cavity 122 from the retention state to the release state, thereby allowing the shuttling element coupler 148 of the needle 18 to remove the shuttling element 20 from the shuttling element retention cavity 122 and decoupling of the shuttling element 20 from the lower jaw 16*a* when the jaw assembly 16 is transitioned from the first intermediate state toward the open state. As best illustrated in FIG. 31, the sleeve 150 is configured for sliding along the needle shaft 146 upward along arrow 157 when the sleeve 150 contacts the upper chamber 130 of the shuttling element retention cavity 122 and as the jaw assembly 16 is transitioned from the open state to the second intermediate state, as will be described in further detail below. The needle 18 comprises a stop 158 above the needle shaft 146. The stop 158 is configured for abutting the slidable sleeve 150 to forcibly insert the slidable sleeve 150 into the upper chamber 130 of the shuttling element retention cavity 122 (i.e., apply enough axial force to the slidable sleeve 150 to overcome the frictional forces applied to the slidable sleeve 150 by the upper chamber 130 of the shuttling element retention cavity 122) in the direction 160, as illustrated in FIG. 34. In the illustrated embodiment, slidable sleeve 150 and upper chamber 130 of the shuttling element retention cavity 122 have corresponding chamfered edges 162, 164 that engage each other to facilitate insertion of the slidable sleeve 150 into the upper chamber 130 of the shuttling element retention cavity 122**.

Figure 35:
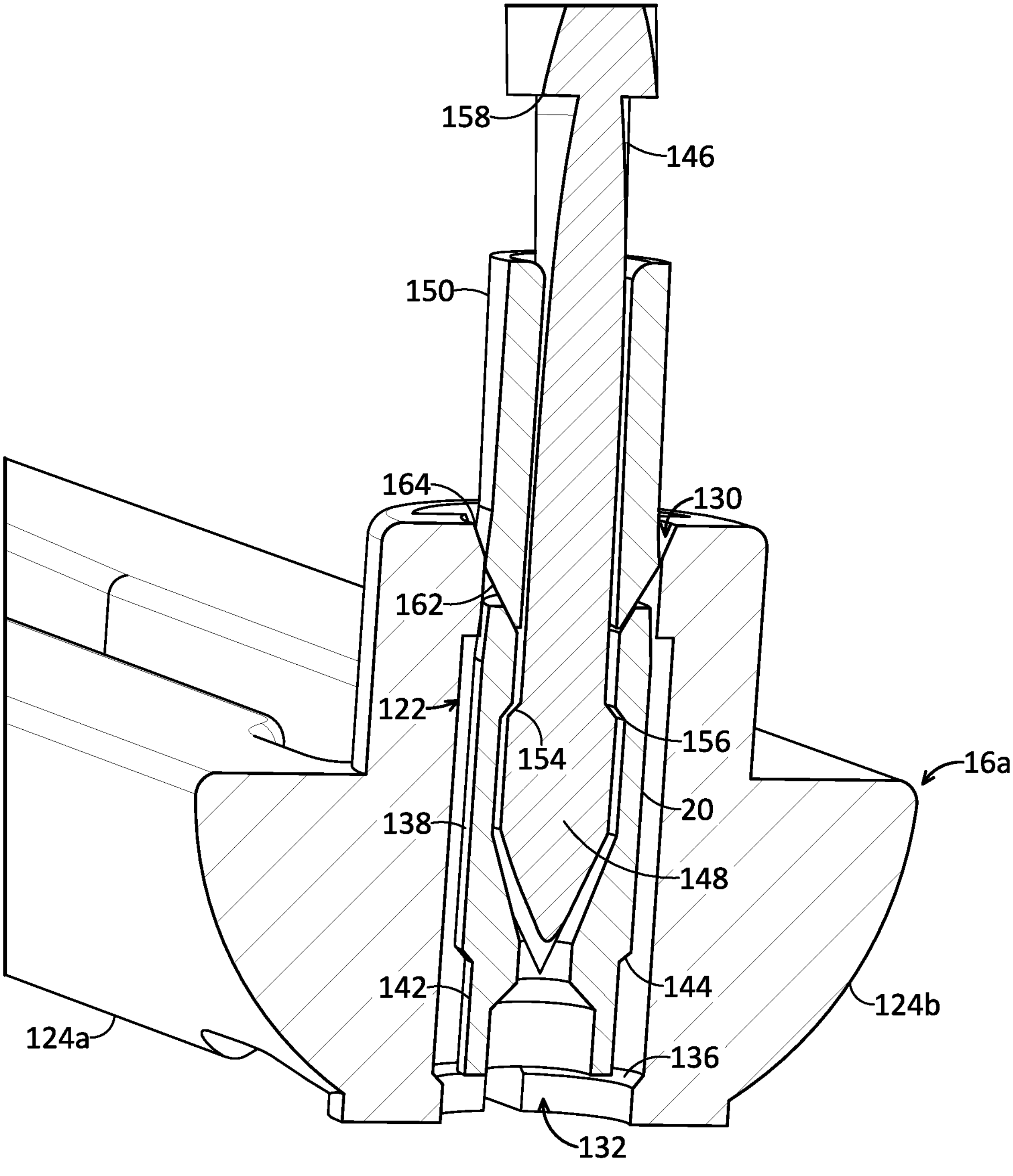
FIG. 35 is a perspective cross-sectional view of the lower jaw, needle, and shuttling element of the laparoscopic tissue suturing instrument of FIG. 1, particularly showing the needle decoupling the shuttling element from the lower jaw as the jaw assembly is transitioned from the first intermediate state to the open state.
Figure 36:
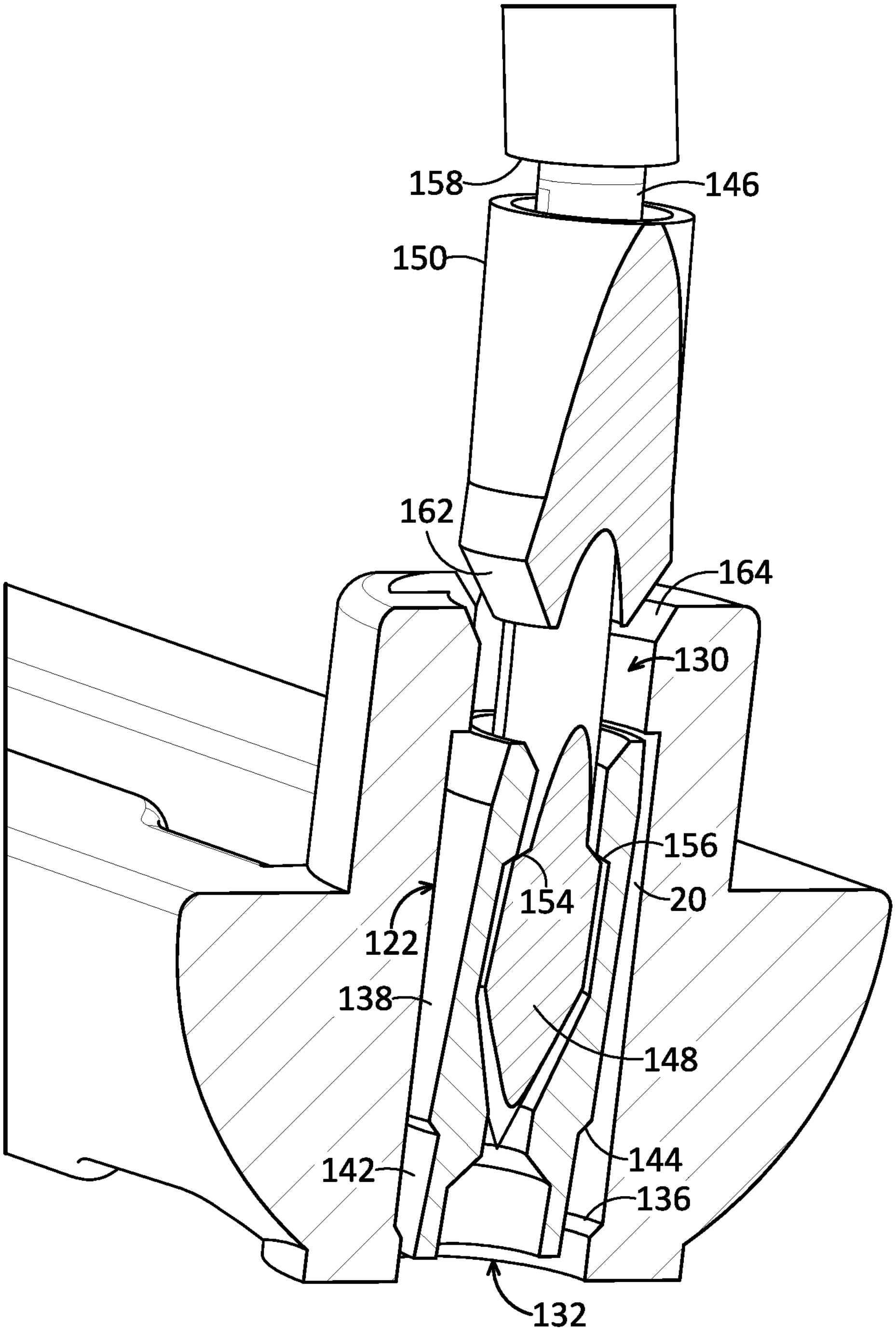
FIG. 36 is a perspective cross-sectional view of the lower jaw, needle, and shuttling element of the laparoscopic tissue suturing instrument of FIG. 1, particularly showing the needle recoupling the shuttling element to the lower jaw when the jaw assembly is in the second intermediate state.

The outer diameter of the slidable sleeve 150 is significantly greater than the outer diameter of the upper chamber 130 when the shuttling element retention cavity 122 is in the retention state, such that when the slidable sleeve 150 is inserted into the upper chamber 130 of the shuttling element retention cavity 122 in the direction 160, the resilient members **124*a*, 124*b* of the lower jaw 16*a* are urged away from each other in the direction 128*a* to transition the shuttling element retention cavity 122 from the retention state to the release state, thereby providing sufficient clearance for the shuttling element 20 to avoid interference with lower jaw 16*a* when being translated from the lower chamber 132 into the upper chamber 130 of the shuttling element retention cavity 122, as illustrated in FIG. 35. Because the slidable sleeve 150 is slidable relative to the needle shaft 146, the shuttling element 20 is configured for being disposed within the lower chamber 132 of the shuttling element retention cavity 122 without disposing the slidable sleeve 150 within the upper chamber 130 of the shuttling element retention cavity 122, as illustrated in FIG. 36. As such, the shuttling element retention cavity 122 will remain in the retention state when the shuttling element 20 is in the lower chamber 132, thereby recoupling the shuttling element 20 to the lower jaw 16*a***.

Referring to FIGS. 37A-37G, the interaction between the specific features of the lower jaw **16*a*, needle 18, and shuttling element 20 will be described. When the jaw assembly 16 is in the open state, the shuttling element retention cavity 122 is in the retention state, the slidable sleeve 150 is at its most distal position (i.e., closest to sharpened tip of needle 18), the sleeve 150 rests against the ledge 154 of the shuttling element coupler 148 of the needle 18, and the shuttling element 20 is securely retained within the lower chamber 132 (shown in FIGS. 23 and 26), with the bottom surface of the ledge 144 of the shuttling element 20 abutting the top surface of the lower ledge 136 of the shuttling element retention cavity 122 (see FIG. 37**A).

Transitioning the jaw assembly 16 from the open state (deployed needle 18 is in the proximal position) to the first intermediate state (deployed needle 18 is in the first distal position) causes the shuttling element coupler 148 of the needle 18 to engage the shuttling element 20, and the slidable sleeve 150 to interact with resilient members **124*a*, 124*b* of the lower jaw 16*a*, thereby transitioning the shuttling element retention cavity 122** from the retention state to the release state.

Figure 37A:
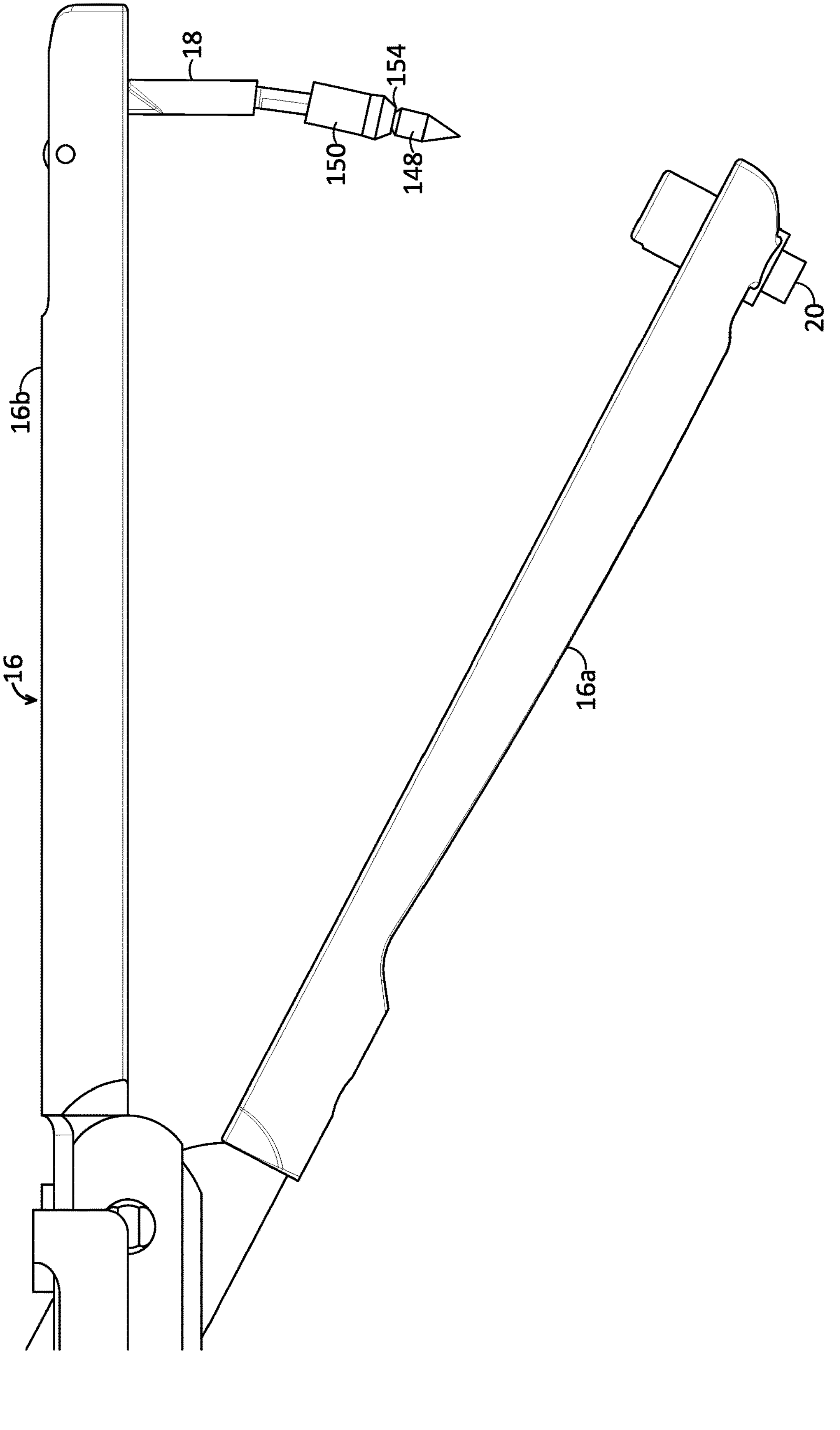
FIGS. 37A-37J are perspective cross-sectional views of the distal end of the laparoscopic tissue suturing instrument of FIG. 1, particularly showing a sequence used to decouple the shuttling element from the lower jaw and recouple the shuttling element to the lower jaw.
Figure 37B:
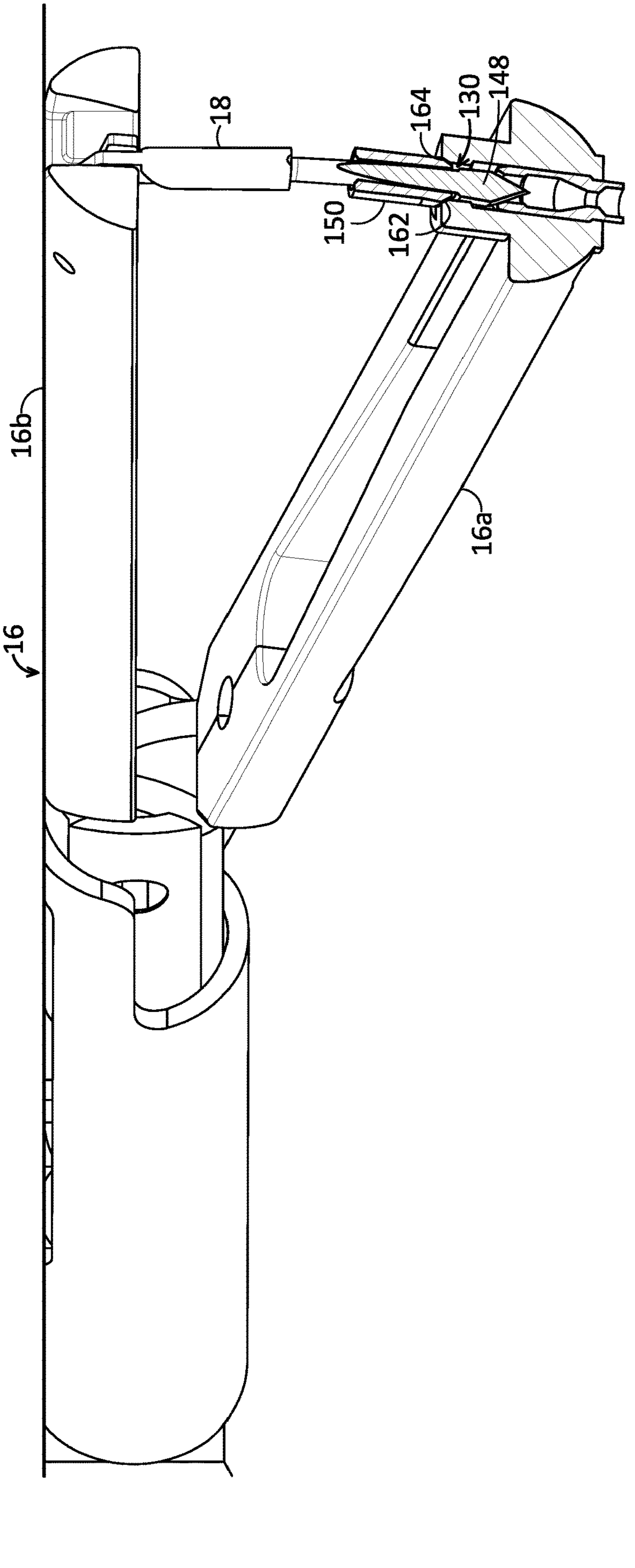
Figure 37C:
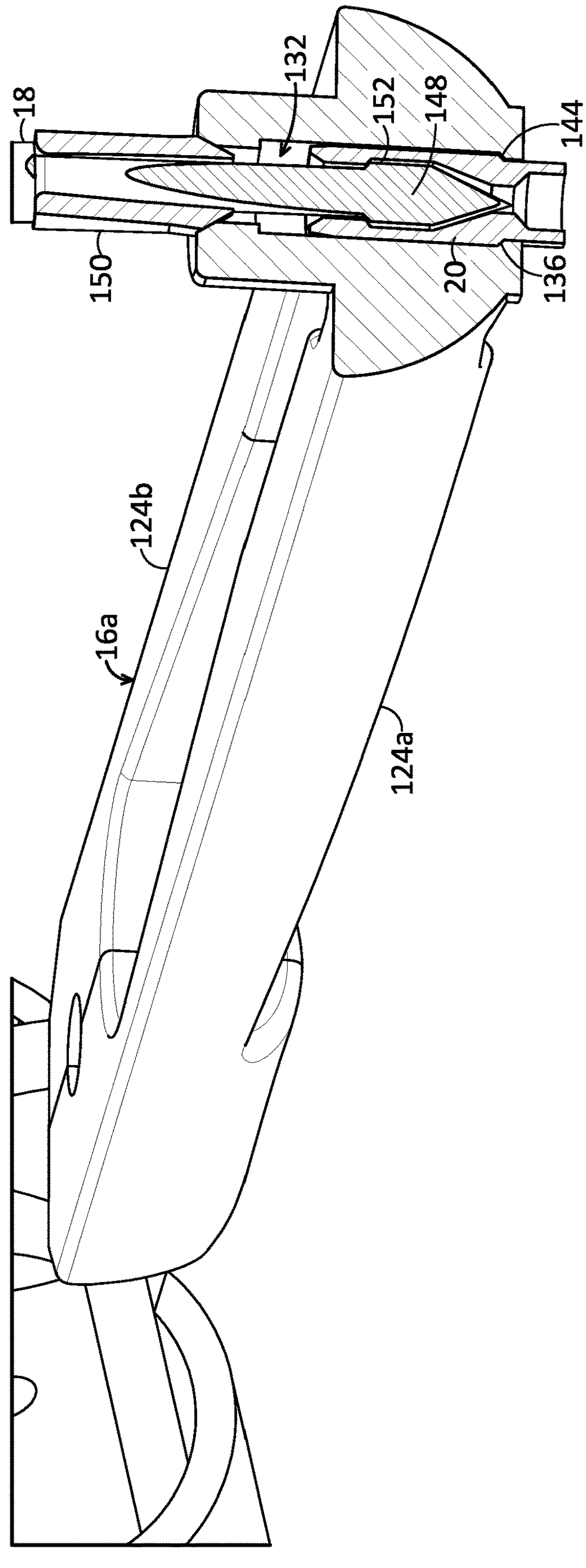
Figure 37D:
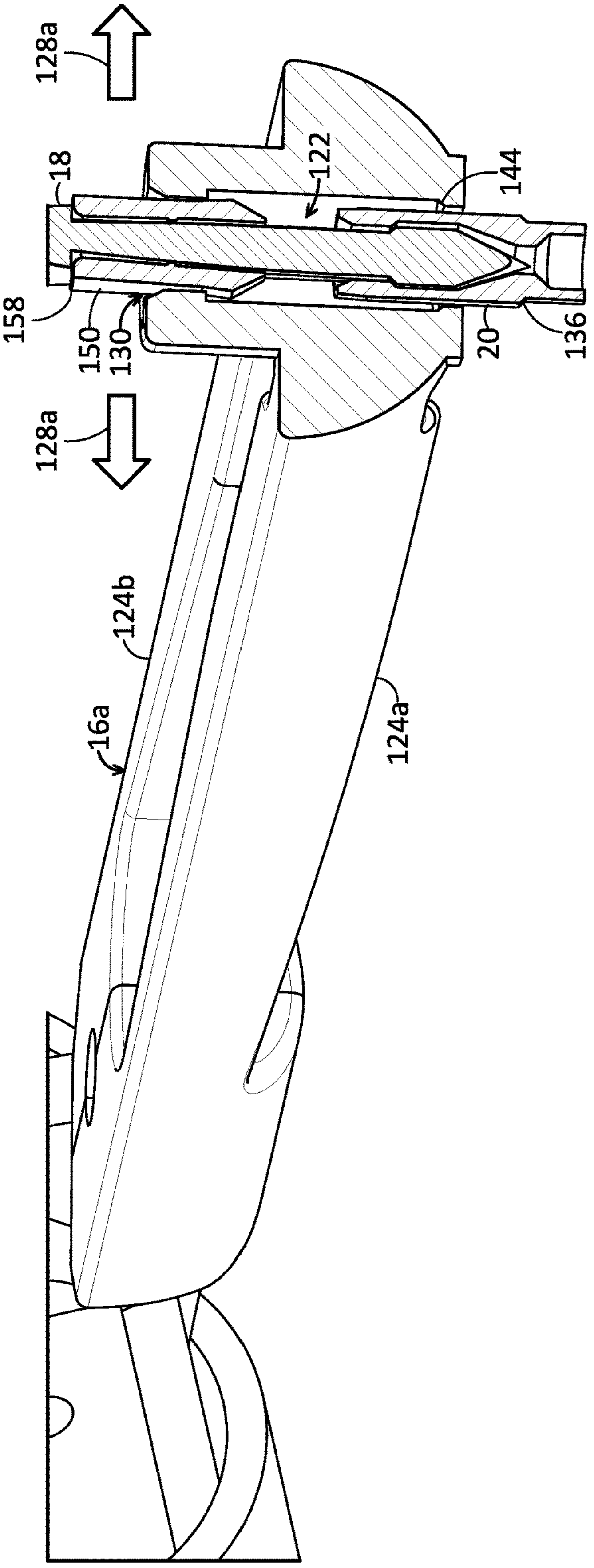

In particular, as the jaw assembly 16 is transitioned from the open state towards the first intermediate state, the lower jaw **16*a* is translated toward the upper jaw 16*b* and thus the needle 18, such that the shuttling element coupler 148 of the needle 18 enters the upper chamber 130 of the shuttling element retention cavity 122, while the bottom edge 162 of the slidable sleeve 150 contacts the lower jaw 16*a* at the top edge 164 of the upper chamber 130 of the shuttling element retention cavity 122 (see FIG. 37B). The shuttling element coupler 148 of the needle 18 is then inserted into the cavity 152 of the shuttling element 20, thereby engaging the shuttling element 20 with the needle 18 (see FIG. 37**C).

In some cases, the bottom surface of the outer annular ledge 144 of the shuttling element 20 may be initially spaced from the inner lower annular ledge 136 of the lower chamber 132 of the shuttling element retention cavity 122. In this case, the shuttling element coupler 148 of the needle 18 will push the shuttling element 20 further into the lower chamber 132 of the shuttling element retention cavity 122 until the bottom surface of the outer annular ledge 144 of the shuttling element 20 abuts the top surface of the inner ledge 136 of the lower chamber 132 of the shuttling element retention cavity 122. The shuttling element coupler 148 of the needle 18 will then be inserted into the cavity 152 of the shuttling element 20.

The shuttling element coupler 148 fits within the cavity 152 of the shuttling element 20, such that translation of the needle 18 correspondingly translates the shuttling element 20 to which it is engaged. The force required to insert the shuttling element coupler 148 into the cavity 152 of the shuttling element 20 is less than the retention force between the lower ledge 136 of the shuttling element retention cavity 122 and the ledge 144 of the shuttling element 20. As such, the shuttling element 20 remains securely retained within the lower chamber 132 of the shuttling element retention cavity 122 until at least after the shuttling element coupler 148 has fully engaged the shuttling element 20. While the shuttling element coupler 148 of the needle 18 is being inserted into the cavity 152 of the shuttling element 20, the sleeve 150 slides upward (i.e., towards the upper jaw 16*b*) along the needle shaft 146 until the sleeve 150 abuts the stop 158 of the needle 18.

The lower jaw 16*a* is further translated toward the upper jaw 16*b*, such that the needle 18 is translated downward relative to the lower jaw 16*a*. As a result, the stop 158 of the needle 18 forcibly inserts the slidable sleeve 150 into the upper chamber 130 of the shuttling element retention cavity 122, thereby displacing the resilient members 124*a*, 124*b* away from each other (shown by arrows 128*a*), and transitioning the shuttling element retention cavity 122 from the retention state to the release state (see FIG. 37D).

The retention force between the lower ledge 136 of the shuttling element retention cavity 122 and the ledge 144 of the shuttling element 20 is less than the force required to insert the slidable sleeve 150 into the upper chamber 130 of the shuttling element retention cavity 122. As such, the retention force between the lower ledge 136 of the shuttling element retention cavity 122 and the ledge 144 of the shuttling element 20 will be broken, such that the retained portion 138 of the shuttling element 20 will momentarily be pushed out of the lower chamber 132 of the shuttling element retention cavity 122, thereby allowing the needle 18 to be translated downward to insert the slidable sleeve 150 into the upper chamber 130 of the shuttling element retention cavity 122 via the stop 158, at which point the jaw assembly 16 will be in the first intermediate state.

Transitioning the jaw assembly 16 from the first intermediate state (deployed needle 18 is in the first distal position) back to the open state (deployed needle 18 is in the proximal position) causes the shuttling element coupler 148 of the needle 18 to remove the shuttling element 20 from the shuttling element retention cavity 122.

In particular, as the jaw assembly 16 is transitioned from the first intermediate state (deployed needle 18 is in the first distal position) back towards the open state (deployed needle 18 is in the proximal position), the lower jaw 16*a* is translated away from the upper jaw 16*b*, such that the needle 18 is translated upward relative to the lower jaw 16*a*. As a result, the shuttling element coupler 148 of the needle 18 pulls the retained portion 138 of the shuttling element 20 (via abutting engagement between the ledge 154 of the shuttling element coupler 148 and the ledge 156 of the shuttling element 20) back into the lower chamber 132 of the shuttling element retention cavity 122 until the top of the shuttling element 20 abuts the bottom edge 162 of the slidable sleeve 150 (see FIG. 37E). As the needle 18 is translated upward relative to the lower jaw 16*a*, the sleeve 150 slides upward (i.e., towards the upper jaw 16*b*) along the needle shaft 146, such that the sleeve 150 remains within the upper chamber 130 of the shuttling element retention cavity 122 to maintain the shuttling element retention cavity 122 in the release state.

As the jaw assembly 16 is further transitioned toward the open state, the lower jaw 16*a* is further translated away from the upper jaw 16*b*, such that the needle 18 is further translated upward relative to the lower jaw 16*a*. As a result, the shuttling element coupler 148 of the needle 18 pulls the retained portion 138 of the shuttling element 20 (via abutting engagement between the ledge 154 of the shuttling element coupler 148 and the ledge 156 of the shuttling element 20) from the lower chamber 132 of the shuttling element retention cavity 122, past the ledge 156 of the shuttling element 20, into the upper chamber 130 of the shuttling element retention cavity 122, while pushing the slidable sleeve 150 out of the upper chamber 130 of the shuttling element retention cavity 122 via abutting engagement between the top of the shuttling element 20 and the bottom edge 162 of the slidable sleeve 150. This allows the resilient members 124*a*, 124*b* of the lower jaw 16*a* to be translated toward each other (shown by arrows 128*b*), thereby transitioning the shuttling element retention cavity 122 from the release state back to the retention state (see FIG. 37F).

As the jaw assembly 16 is further transitioned to the open state, the lower jaw 16*a* is further translated away from the upper jaw 16*b*, such that the needle 18 is further translated upward relative to the lower jaw 16*a*. As a result, the shuttling element coupler 148 of the needle 18 completely removes the shuttling element 20 from the shuttling element retention cavity 122, thereby decoupling the shuttling element 20 from the lower jaw 16*a* (see FIG. 37G). Notably, although the shuttling element retention cavity 122 is in the retention state, and as such the shuttling element 20 is gripped by the resilient members 124*a*, 124*b*, the frictional force between the upper chamber 130 of the shuttling element retention cavity 122 and the shuttling element 20 is less than the retention force between the ledge 154 of the shuttling element coupler 148 and the ledge 156 of the shuttling element 20, thereby maintaining retention of the shuttling element coupler 148 of the needle 18 within the cavity 152, and thus engagement between the needle 18 and the shuttling element 20 as the shuttling element 20 is removed from the shuttling element retention cavity 122.

Transitioning the jaw assembly 16 from the open state (deployed needle 18 is in the proximal position) to the second intermediate state (the needle 18 is in the second distal position) causes the shuttling element coupler 148 of the needle 18 to insert the shuttling element 20 back into the shuttling element retention cavity 122.

In particular, as the jaw assembly 16 is transitioned from the open state toward the second intermediate state, the lower jaw 16*a* is translated back towards the upper jaw 16*b*, such that the needle 18 is translated downward relative to the lower jaw 16*a*. As a result, the suture affixation portion 142 of the shuttling element 20 is inserted into the upper chamber 130 of the shuttling element retention cavity 122 (see FIG. 37H). The outer diameter of the suture affixation portion 142 is less than the diameter of the upper chamber 130 when the shuttling element retention cavity 122 is in the retention state. In this manner, the suture affixation portion 142 may be easily inserted into the upper chamber 130 shuttling element retention cavity 122 to subsequently guide the retained portion 138 of the shuttling element 20 into the upper chamber 130 shuttling element retention cavity 122 shuttling element retention cavity 122.

As the jaw assembly 16 is further transitioned into the second intermediate state, the lower jaw 16*a* is translated further towards the upper jaw 16*b*, such that the needle 18 is translated downward relative to the lower jaw 16*a*. As a result, the shuttling element coupler 148 of the needle 18 pushes the retained portion 138 of the shuttling element 20 through the upper chamber 130 and into the lower chamber 132 of the shuttling element retention cavity 122, thereby recoupling the shuttling element 20 to the lower jaw 16*a* (see FIG. 37I). While the retained portion 138 of the shuttling element 20 is being inserted through the upper chamber 130 and into the lower chamber 132 of the shuttling element retention cavity 122, the sleeve 150 slides upward (i.e., toward the upper jaw 16*b*) along the needle shaft 146, such that the sleeve 150 does not enter the upper chamber 130 when the jaw assembly 16 is in the first intermediate state. As long as the jaw assembly 16 is not further transitioned from the second intermediate state towards the first intermediate state, the sleeve 150 will not be inserted into the upper chamber 130, and thus, the shuttling element retention cavity 122 will remain in the retention state.

Transitioning the jaw assembly 16 from the second intermediate state (deployed needle 18 is in the second distal position) back to the open state (the needle 18 is in the proximal position) causes the shuttling element coupler 148 to disengage the shuttling element 20.

Figure 37E:
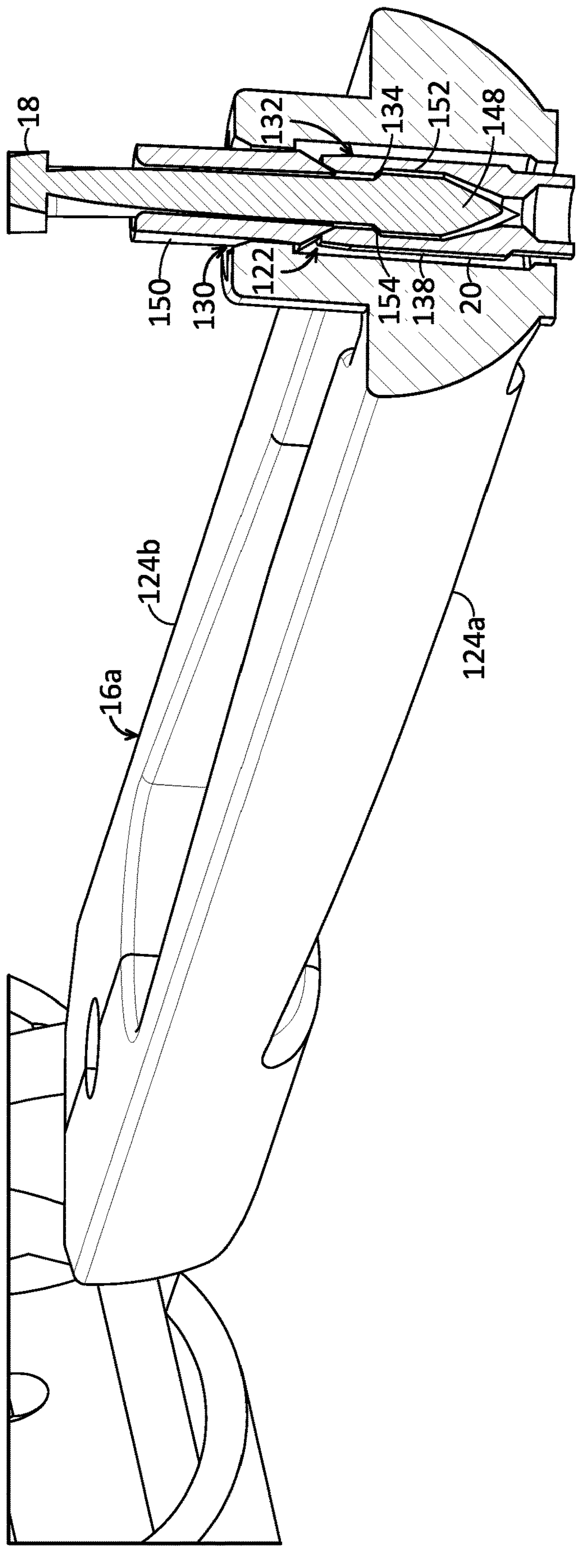
Figure 37F:
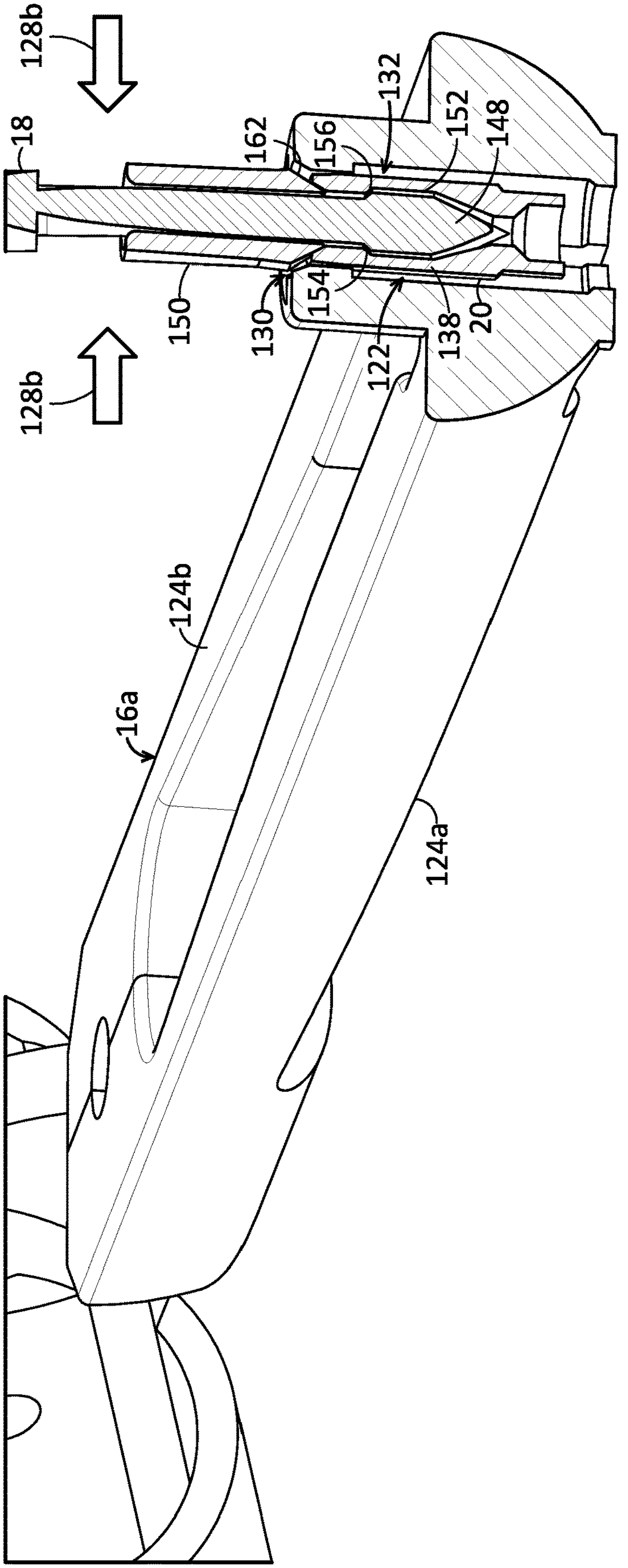
Figure 37G:
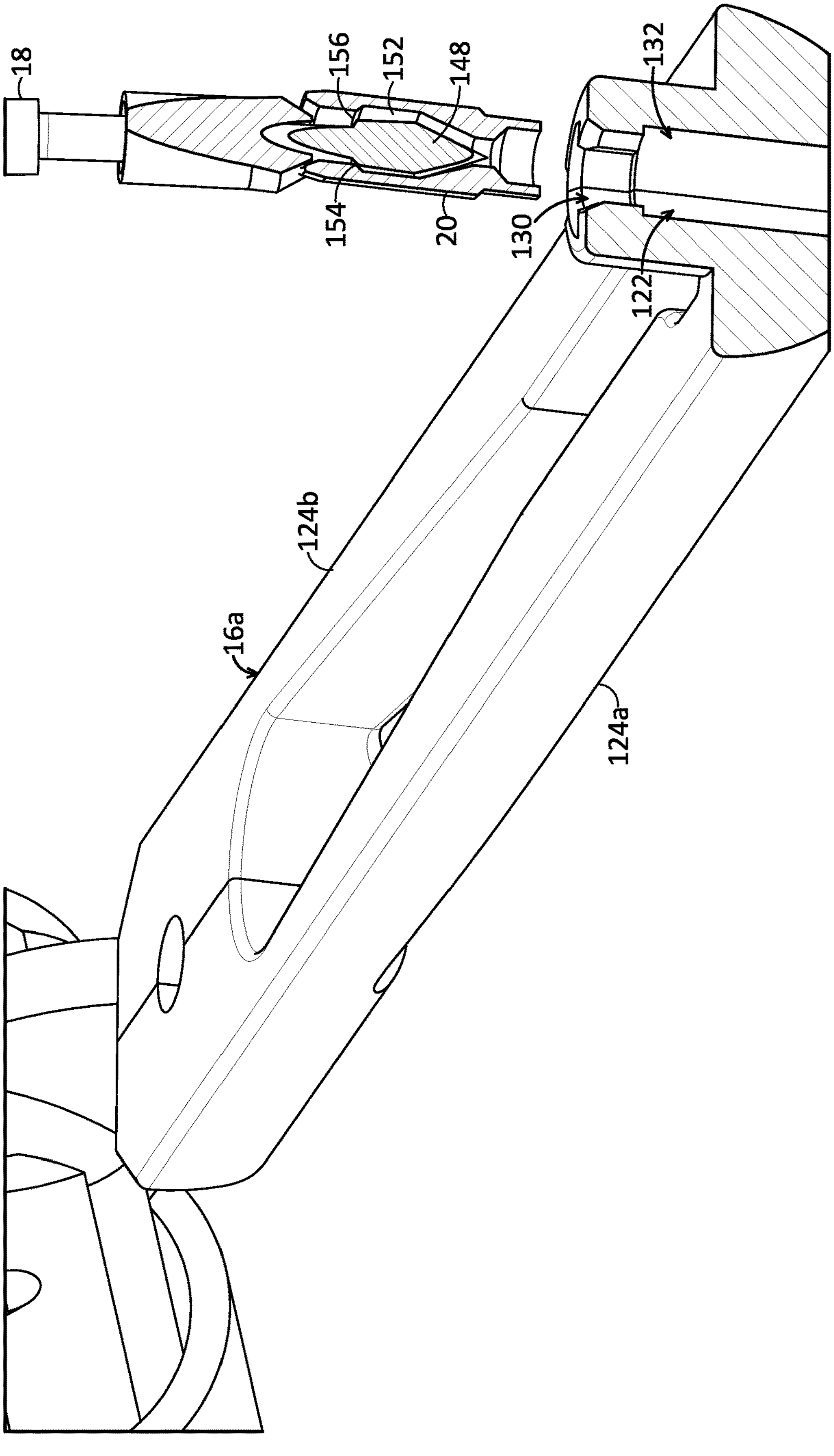
Figure 37H:
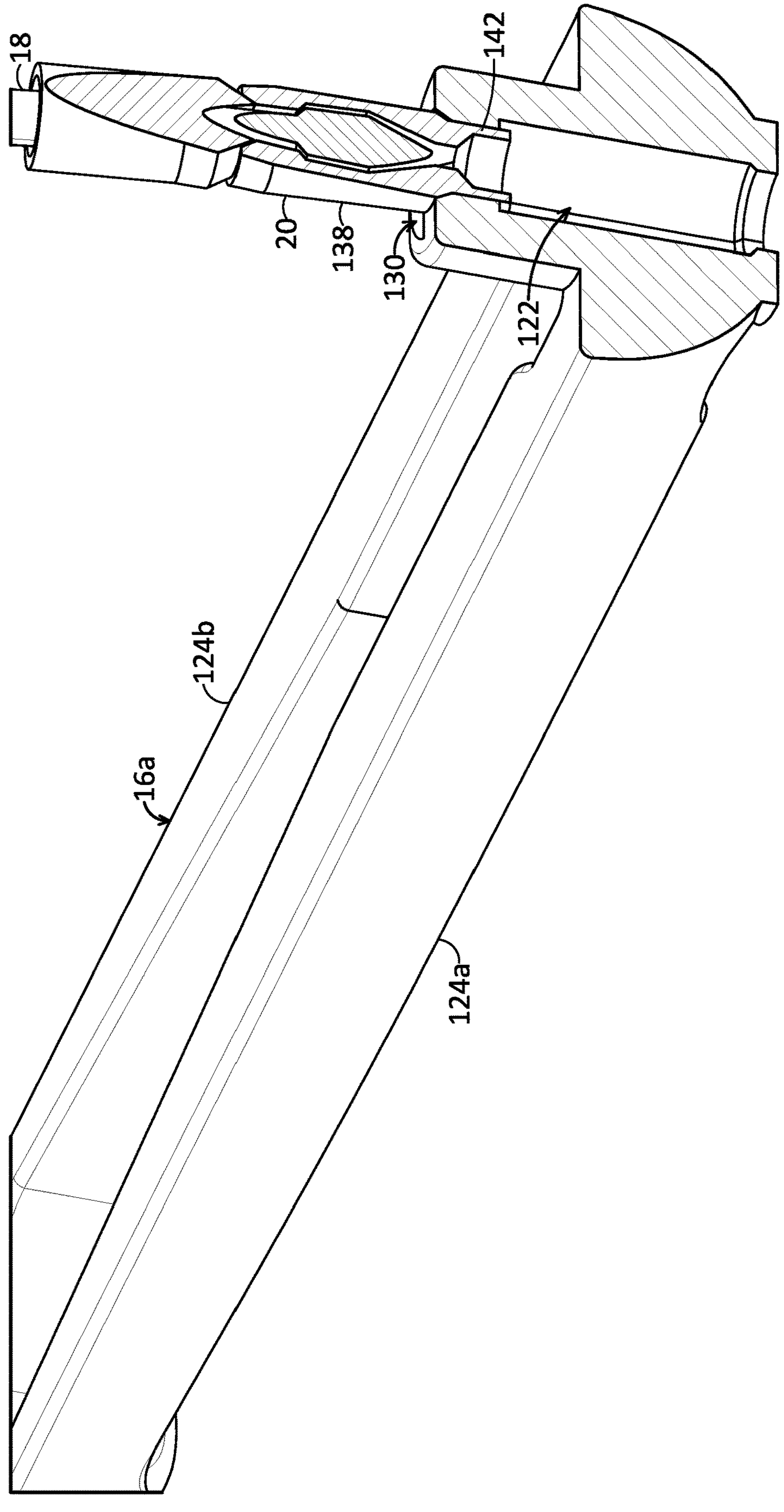
Figure 37I:
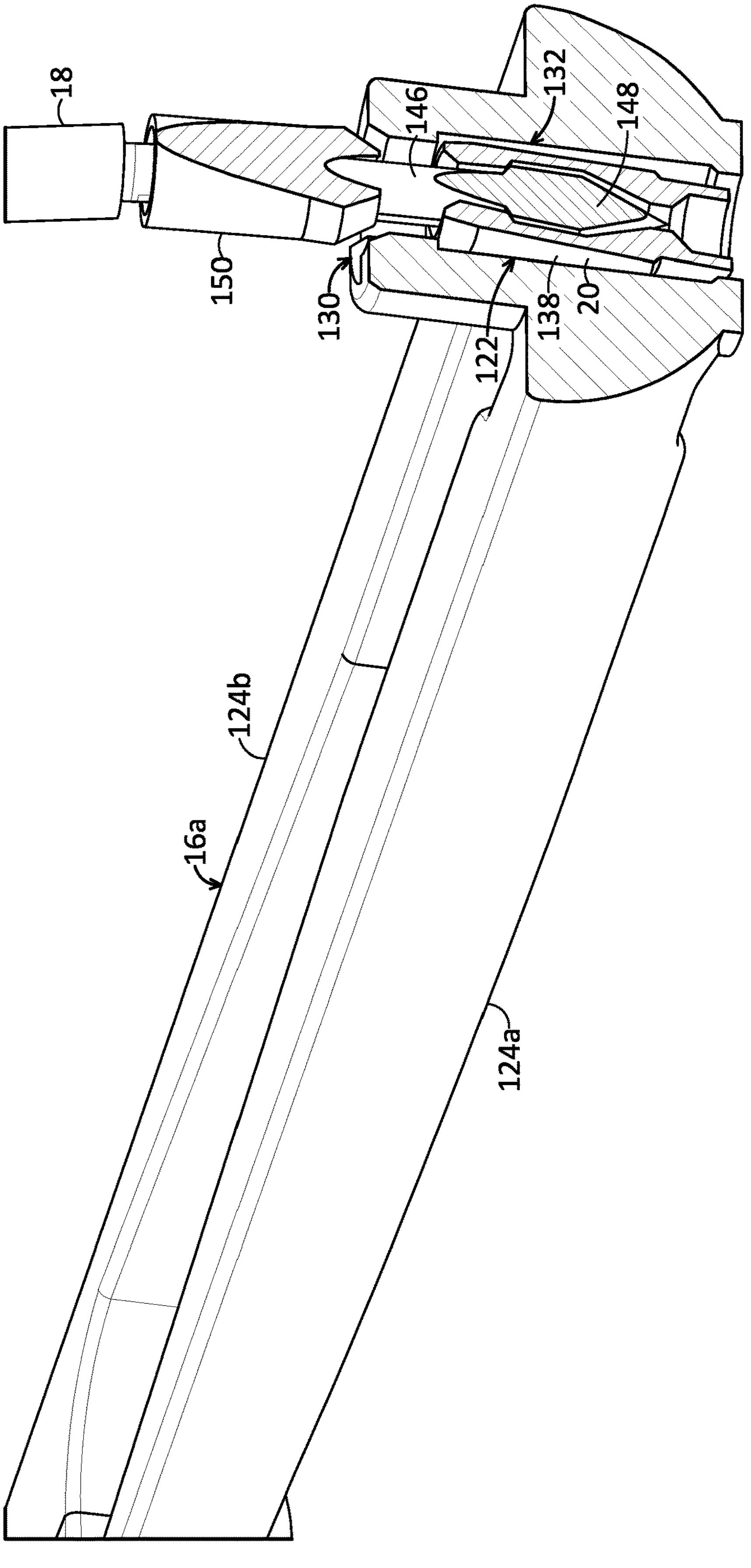
Figure 37J:
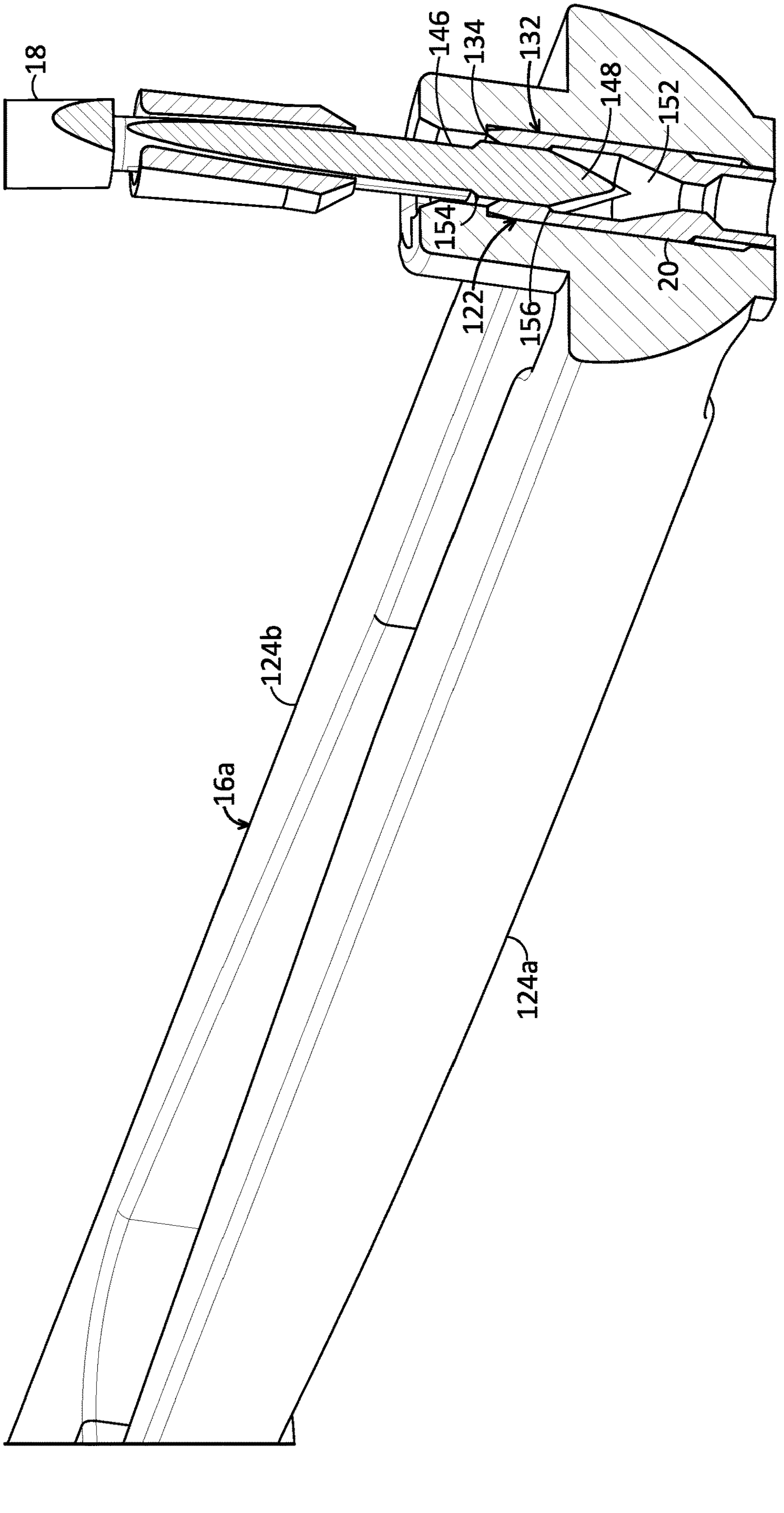
Figure 38:
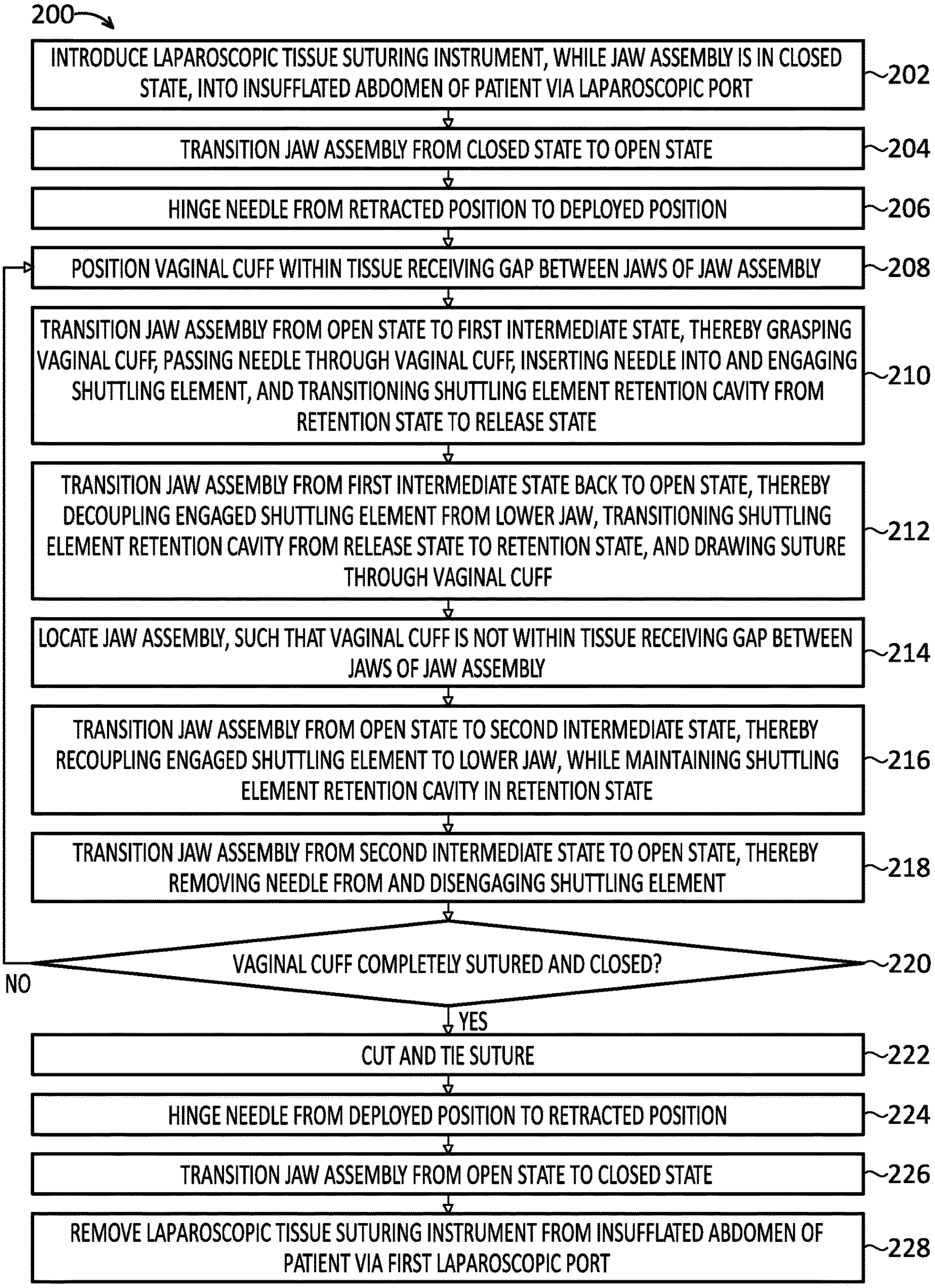
FIG. 38 is a flow diagram illustrating one exemplary method of operating the laparoscopic tissue suturing instrument of FIG. 1 to perform a post-total laparoscopic hysterectomy (TLH) suturing procedure on a vaginal cuff of a patient.

In particular, as the jaw assembly 16 is transitioned from the second intermediate state towards the open state, the lower jaw 16*a* is translated further towards the upper jaw 16*b*, such that the shuttling element coupler 148 of the needle 18 is removed from the cavity 152 of the shuttling element 20, thereby disengaging the needle 18 from the shuttling element 20 (see FIG. 37J). Notably, the retention force between the ledge 154 of the shuttling element coupler 148 of the needle 18 and the ledge 156 of the shuttling element 20 is less than the retention force between the top of the shuttling element 20 and the upper ledge 134 of the shuttling element retention cavity 122 when in the retention state (i.e., the minimum force required to prevent the shuttling element 20 from being translated from the shuttling element retention cavity 122 in the upward direction via mechanical interference between the top of the shuttling element 20 and the upper ledge 134 of the shuttling element retention cavity 122). As such, the lower chamber 132 of the shuttling element coupler 122 will retain the shuttling element 20 as the shuttling element coupler 148 of the needle 18 is pulled out of the cavity 152 of the shuttling element 20.

Referring to FIGS. 38 and 39A-39K, one exemplary method 200 of using the laparoscopic tissue suturing instrument 10 to perform a post-total laparoscopic hysterectomy (TLH) vaginal cuff suturing procedure on a patient will now be described. It is assumed that the uterus of the patient has been removed (either though a transvaginal hysterectomy or laparoscopic hysterectomy), leaving behind an open vaginal cuff 180 that requires suturing.

Figure 39A:
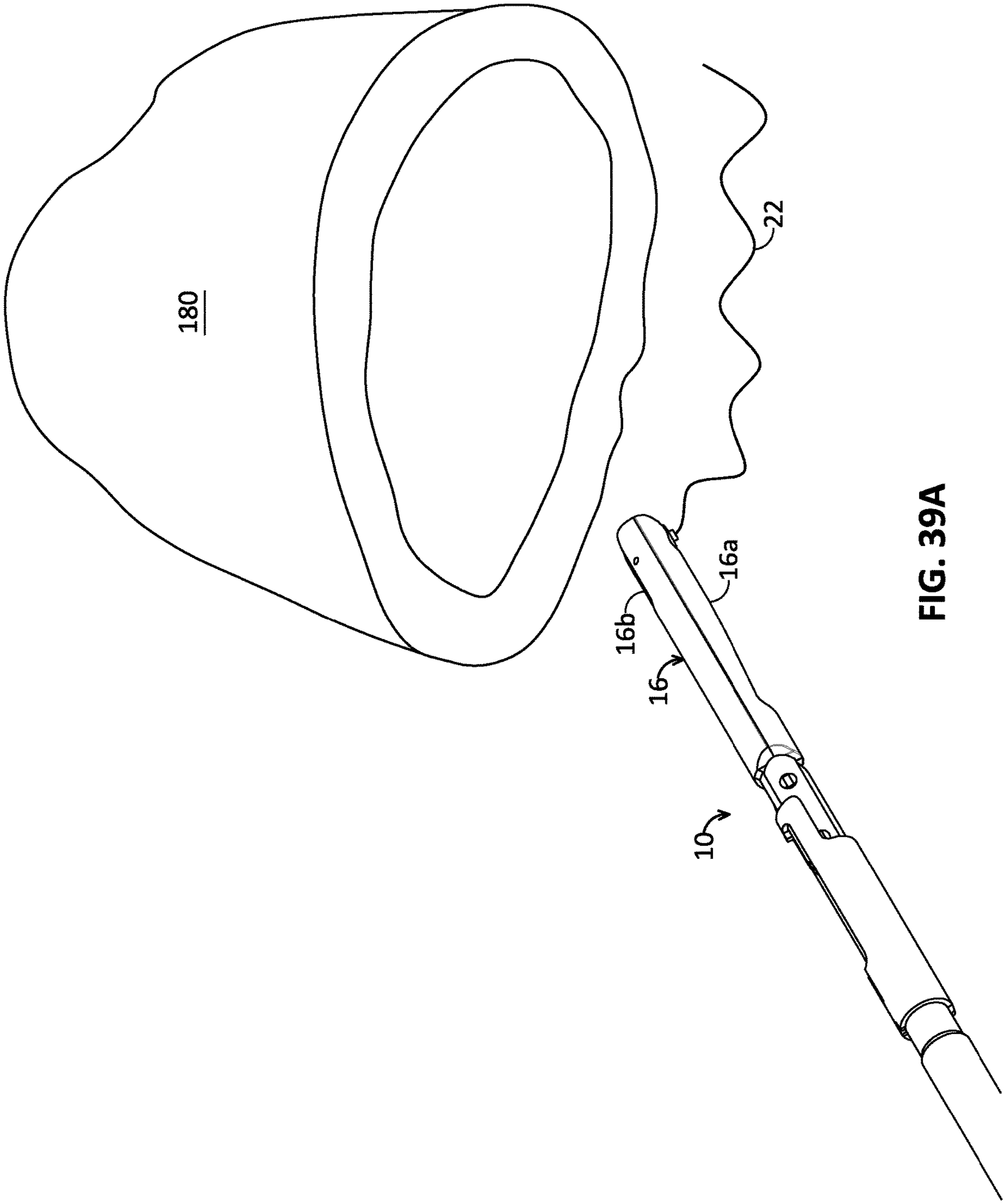
FIGS. 39A-39K are plan views illustrating the method of FIG. 38.
Figure 39B:
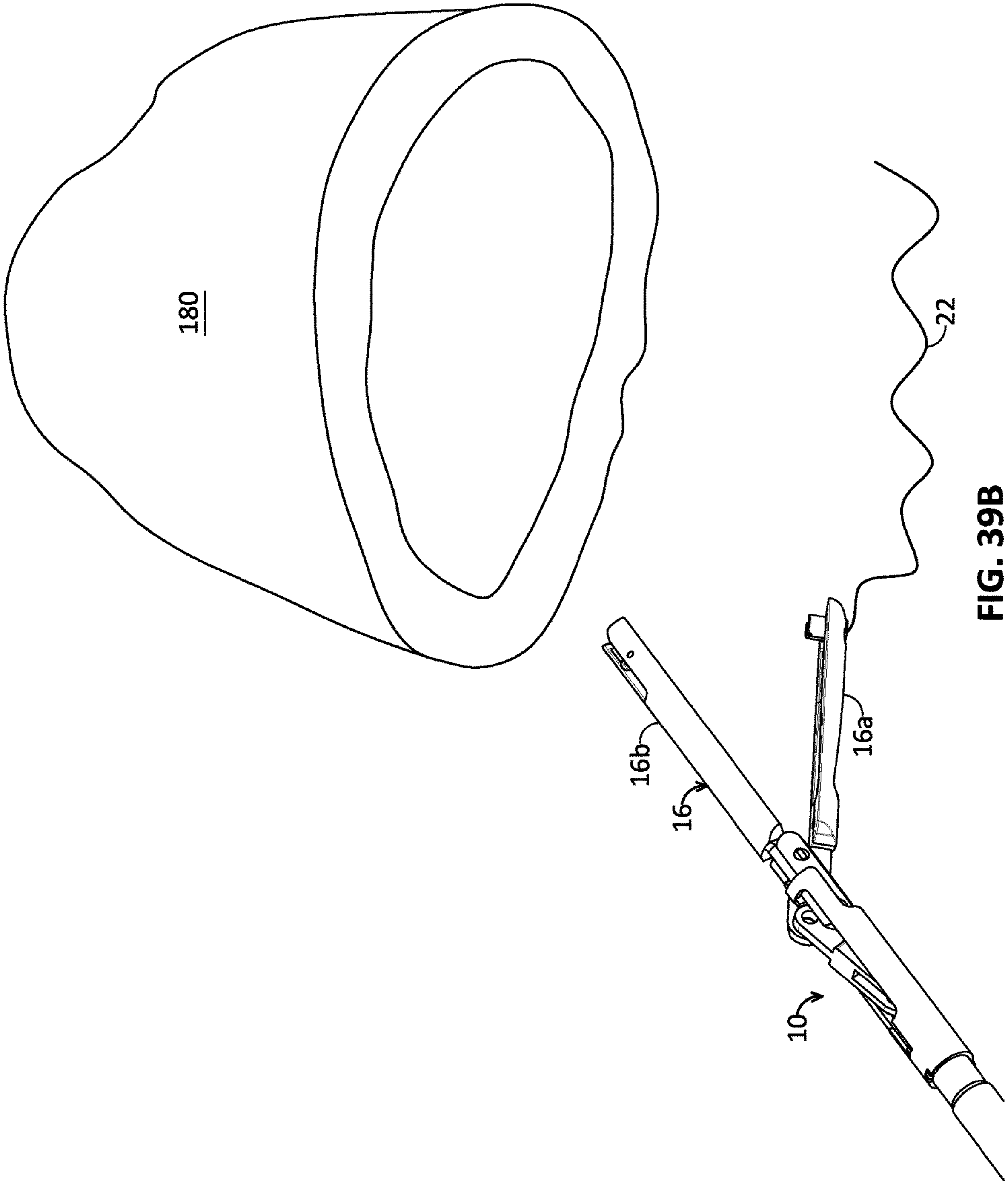
Figure 39C:
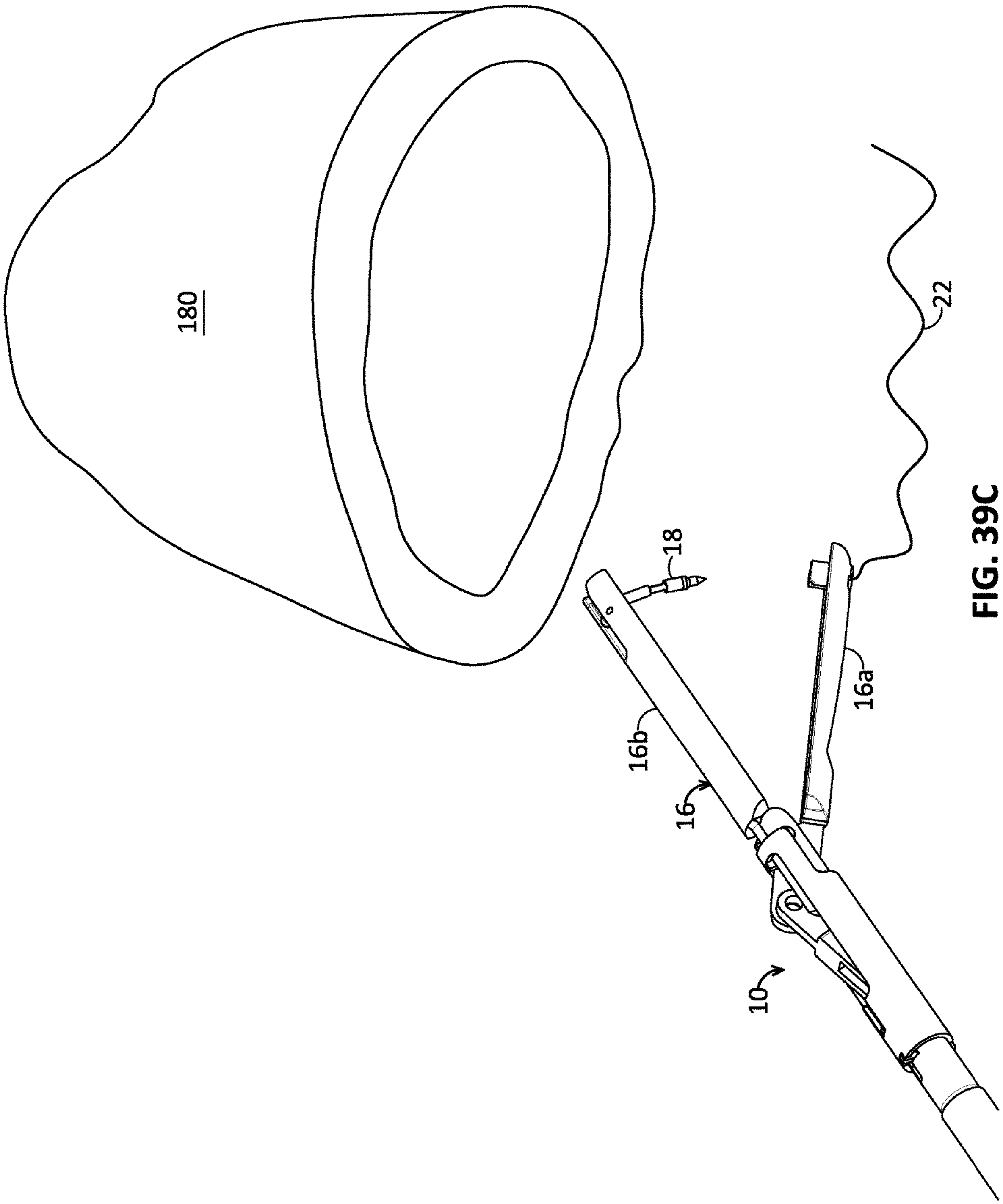
Figure 39D:
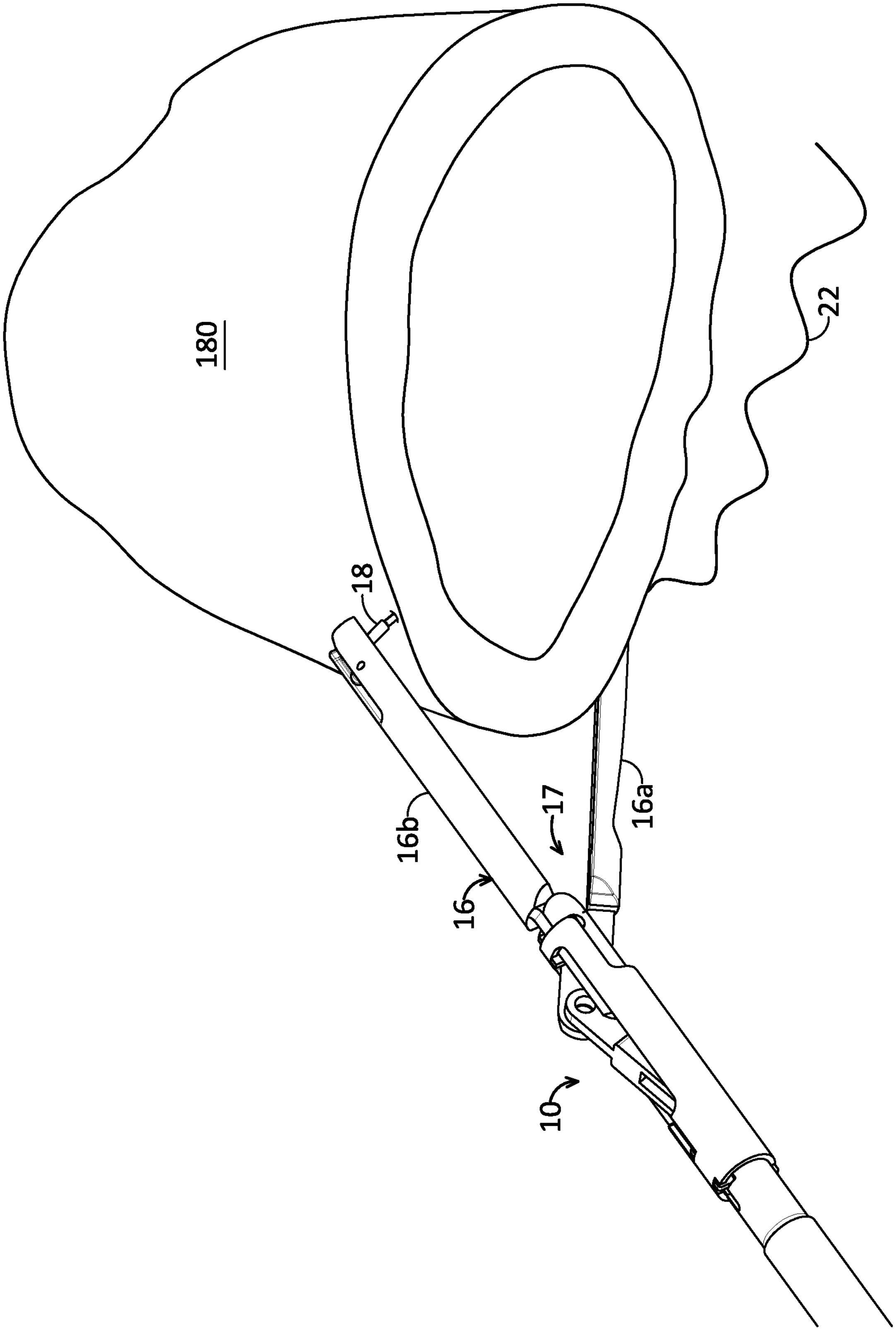
Figure 39E:
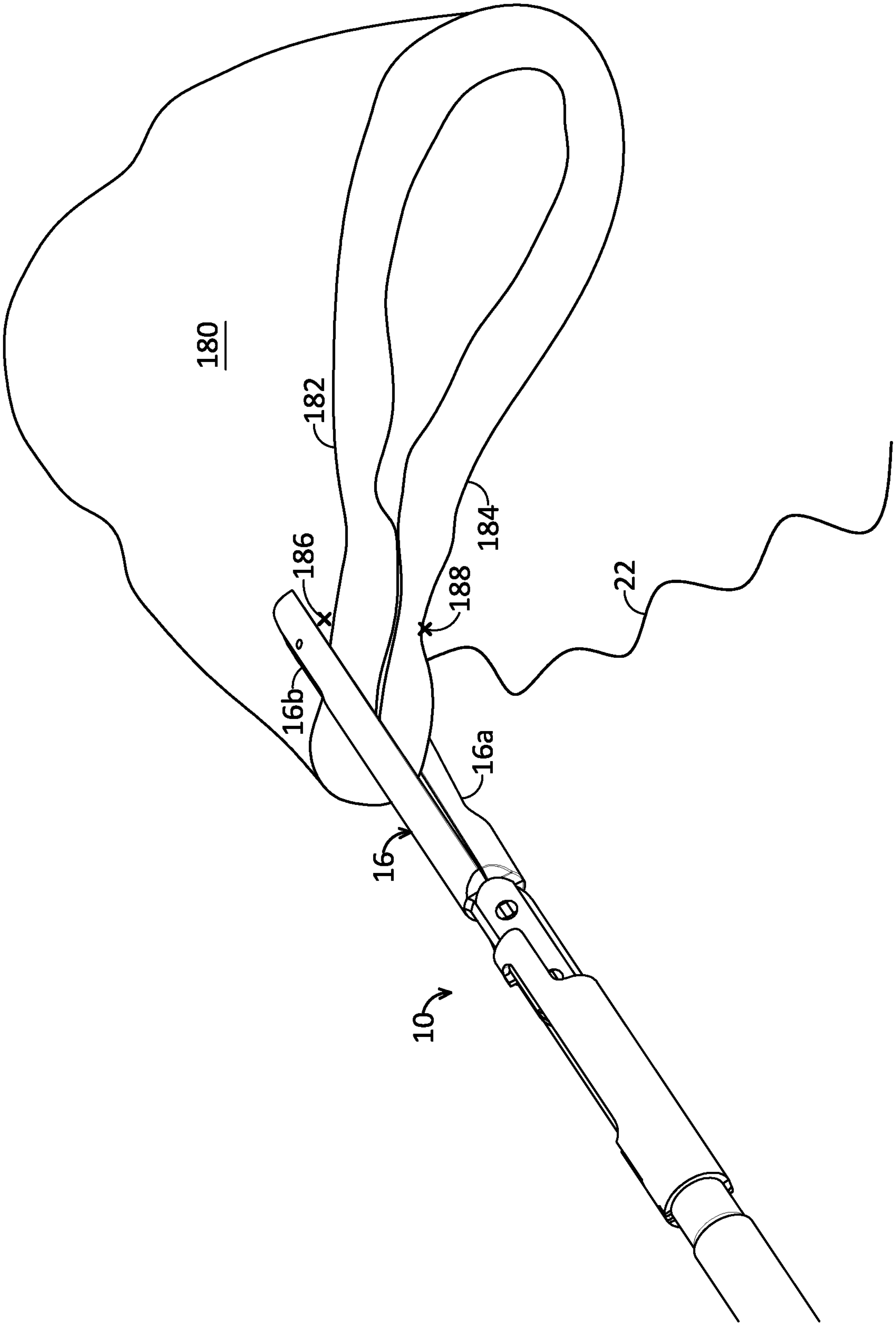
Figure 39F:
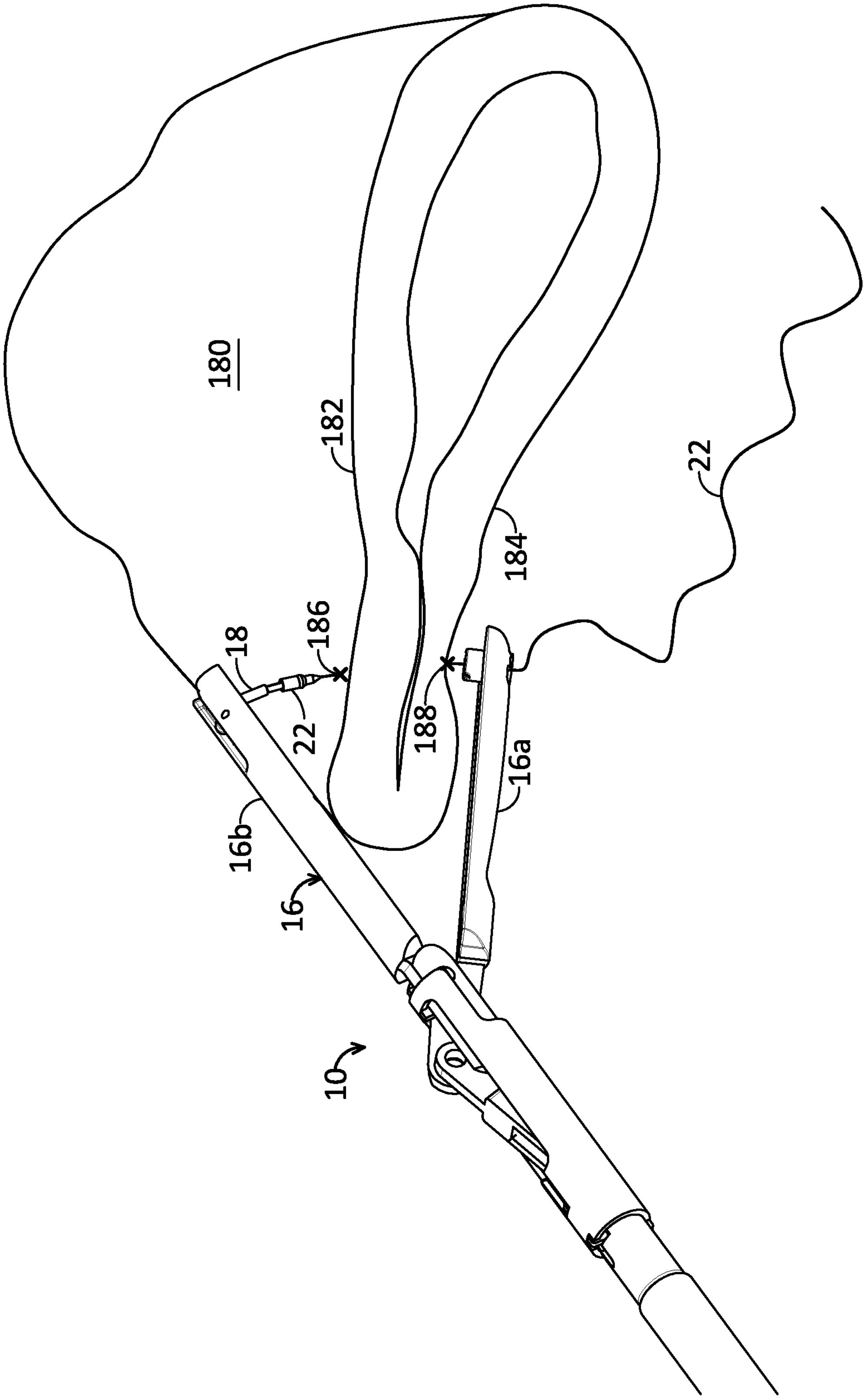
Figure 39G:
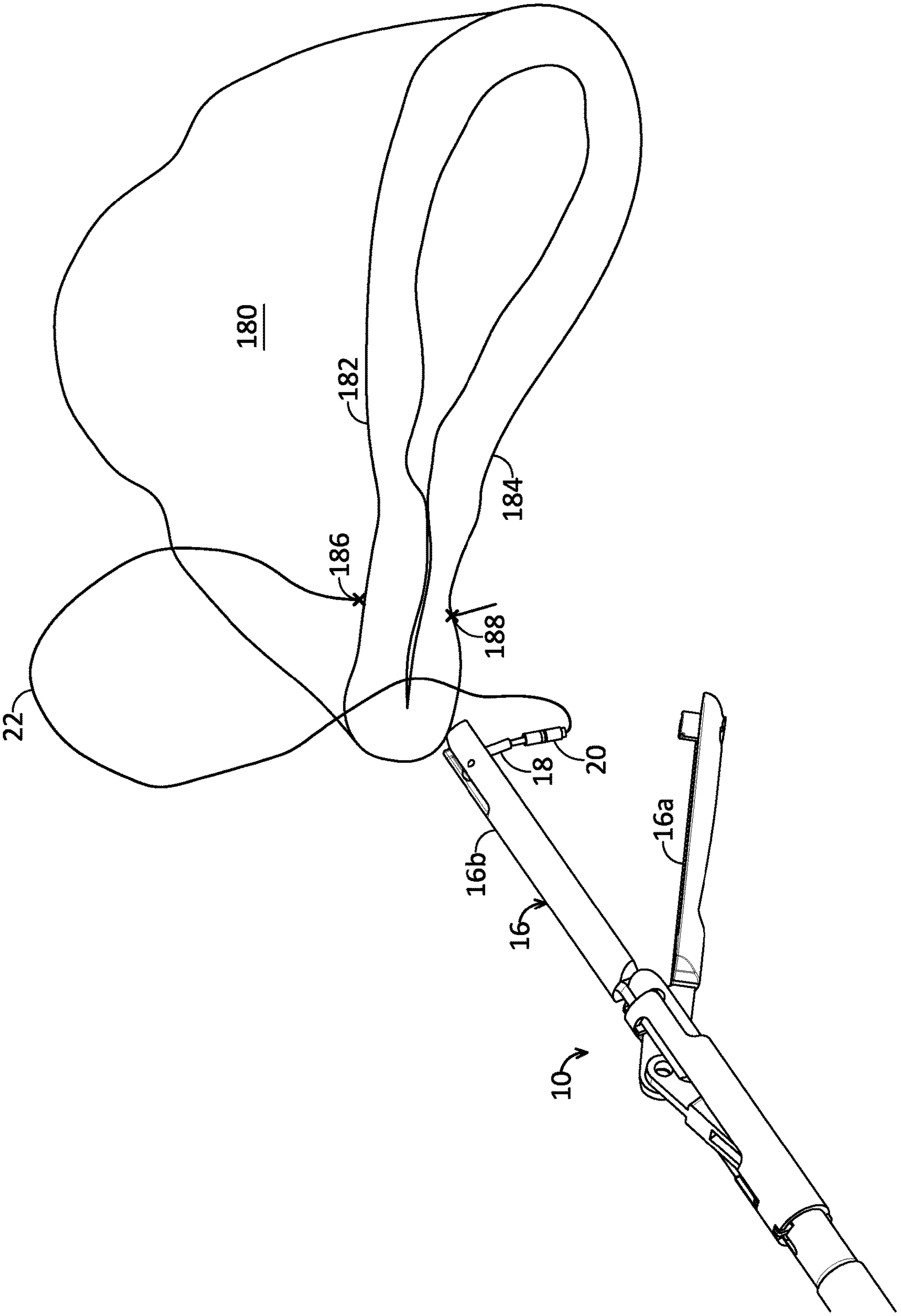
Figure 39H:
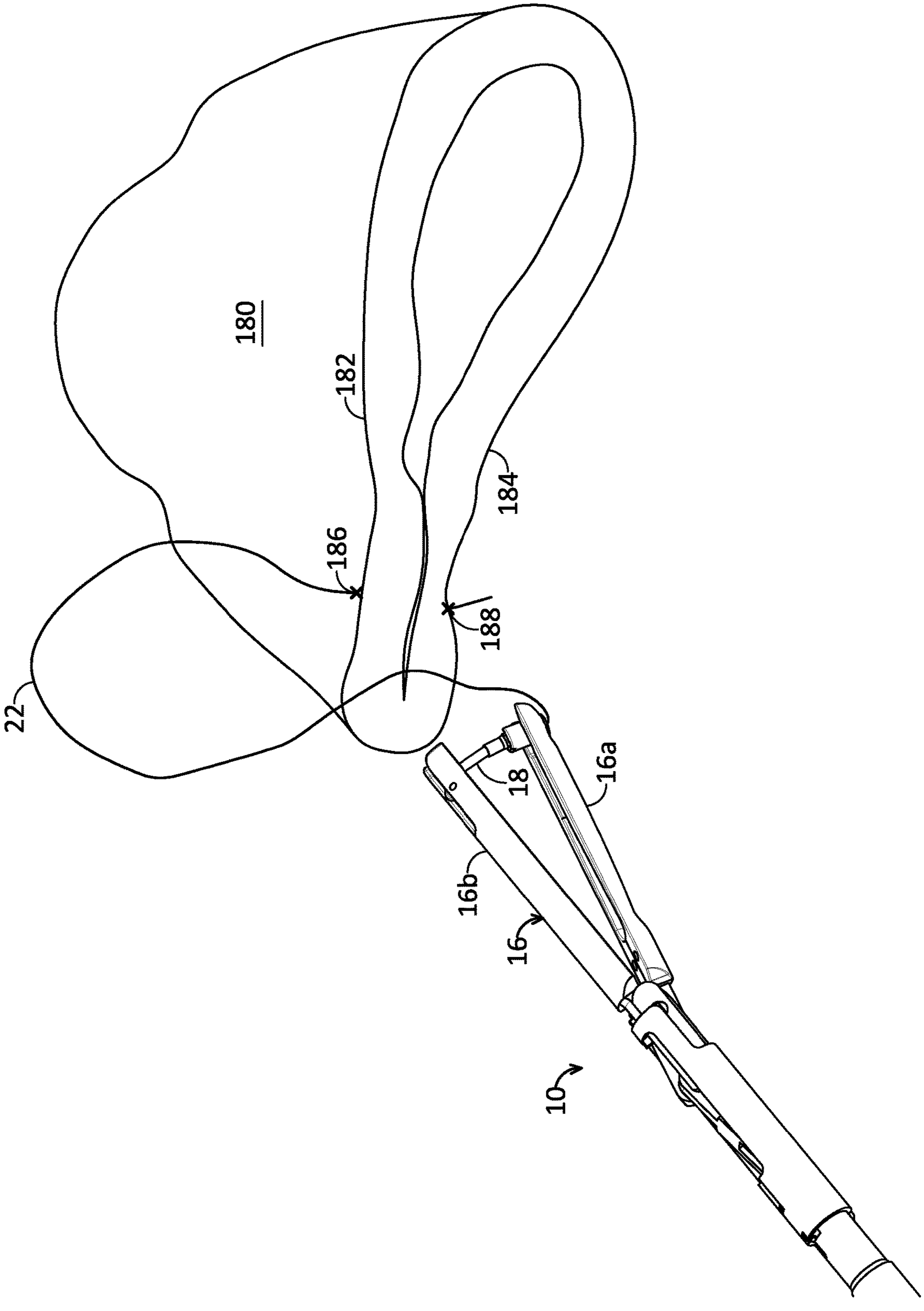
Figure 39I:
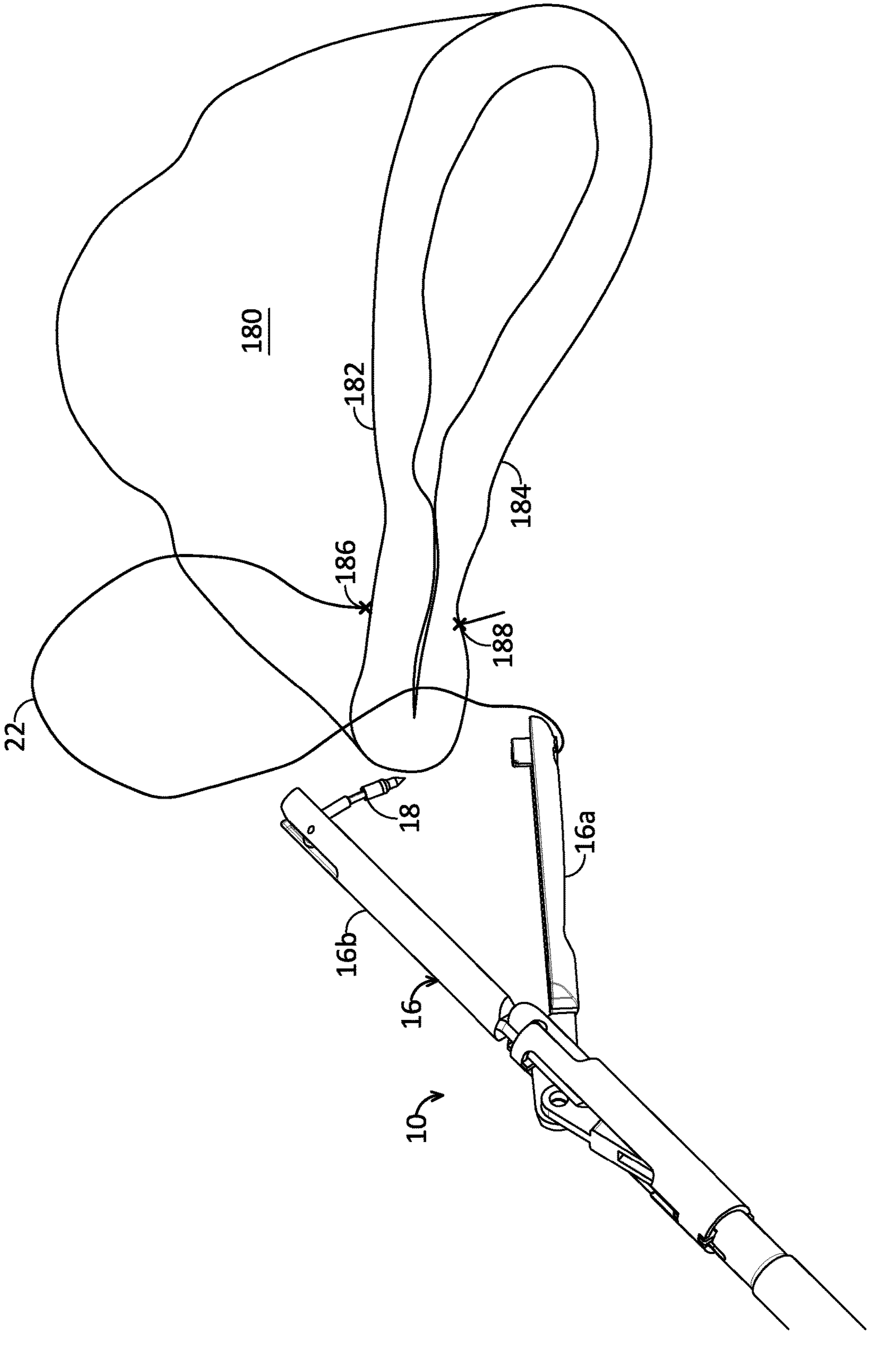

First, the laparoscopic tissue suturing instrument 10, while the jaw assembly 16 is in the closed state, is introduced through a conventional laparoscopic port into the insufflated abdomen of the patient (step 202) (see FIG. 39A).

Next, the jaw assembly 16 of the laparoscopic tissue suturing instrument 10 is transitioned from the closed state to the open state (i.e., the jaws 16*a*, 16*b* are translated away from each other) (see FIG. 39B) via manipulation of the finger piece 34 (shown in FIG. 1) (step 204), and the needle 18 is hinged from the retracted state to the deployed state (see FIG. 39C) via manipulation of the slider mechanism 80 (shown in FIG. 1) (step 206). Next, the vaginal cuff 180 is positioned within the tissue receiving gap 17 between the jaws 16*a*, 16*b* of the jaw assembly 16 (see FIG. 39D) (step 208). In an alternative method, the needle 18 may be hinged from the retracted state to the deployed state after the vaginal cuff 180 is located between the jaws 16*a*, 16*b*.

The jaw assembly 16 is then transitioned from the open state to the first intermediate state) (i.e., the jaws 16*a*, 16*b* are translated toward each other) via manipulation of the finger piece 34 (shown in FIG. 1), thereby grasping the vaginal cuff 180, passing the needle 18 through the vaginal cuff 180 (and specifically, through a first side 182 of the vaginal cuff 180 via a first entry point 186 and then through a second side 184 of the vaginal cuff 184 via a first exit point 188), inserting the needle 18 into and engaging the shuttling element 20, and transitioning the shuttling element retention cavity 122 from the retention state to the release state (and specifically, as best illustrated in FIGS. 37A-37D, inserting the shuttling element coupler 148 of the needle 18 into the cavity 152 of the shuttling element 20, and inserting the slidable sleeve 150 into the upper chamber 130 of the lower jaw 16*a*) (see FIG. 39E) (step 210).

Next, the jaw assembly 16 is transitioned from the first intermediate state back towards the open state (i.e., the jaws 16*a*, 16*b* are translated away from each other) via manipulation of the finger piece 34 (shown in FIG. 1), thereby decoupling the engaged shuttling element 20 from the lower jaw 16*a*, transitioning the shuttling element retention cavity 122 from the release state back to the retention state (and specifically, as best illustrated in FIGS. 37E-37G) by pulling the shuttling element 20 out of the expanded shuttling element retention cavity 122), and drawing the suture 22 through the vaginal cuff 180 (and specifically, back through the second side 184 of the vaginal cuff 182 via the first exit point 188 and then back through first side 182 of the vaginal cuff 180 via the first entry point 186) (see FIG. 39F) (step 212).

Then, the jaw assembly 16 is located, such that the vaginal cuff 180 is not within the tissue receiving gap 17 between the jaws 16*a*, 16*b* (see FIG. 39G) (step 214). As the jaw assembly 16 is located away from the vaginal cuff 180, the jaw assembly 16 may be manipulated, such that the suture 22 exits the suture clearance slot 123 (shown in FIG. 9). Preferably, the jaw assembly 16 is located away from the vaginal cuff 180 a sufficient distance to draw the end of the suture 22 adjacent to the exit point 188 in the vaginal cuff 180. The end of the suture 22 may have a knot or a loop to prevent the end of the suture 22 from entering the exit point 188 in the vaginal cuff 180.

Next, the jaw assembly 16 is transitioned from the open state to the second intermediate state (i.e., the jaws 16*a*, 16*b* are translated toward each other) via manipulation of the finger piece 34 (shown in FIG. 1), thereby recoupling the engaged shuttling element 20 to the lower jaw 16*a* while maintaining the shuttling element retention cavity 122 in the retention state (and specifically, as best illustrated in FIGS.

37H-371 by inserting the shuttling element 20 into the lower chamber 132 without inserting the slidable sleeve 150 into the upper chamber 130) (see FIG. 39H) (step 216).

Next, the jaw assembly 16 is transitioned from the second intermediate state to the open state (i.e., the jaws 16*a*, 16*b* are translated away from each other) via manipulation of the finger piece 34 (shown in FIG. 1), thereby removing the needle 18 from and disengaging the shuttling element 20 from the needle 18 (and specifically, as best illustrated in FIG. 37J, removing the shuttling element coupler 148 of the needle 18 from the cavity 152 of the shuttling element 20) (see FIG. 39I) (step 218).

Figure 39J:
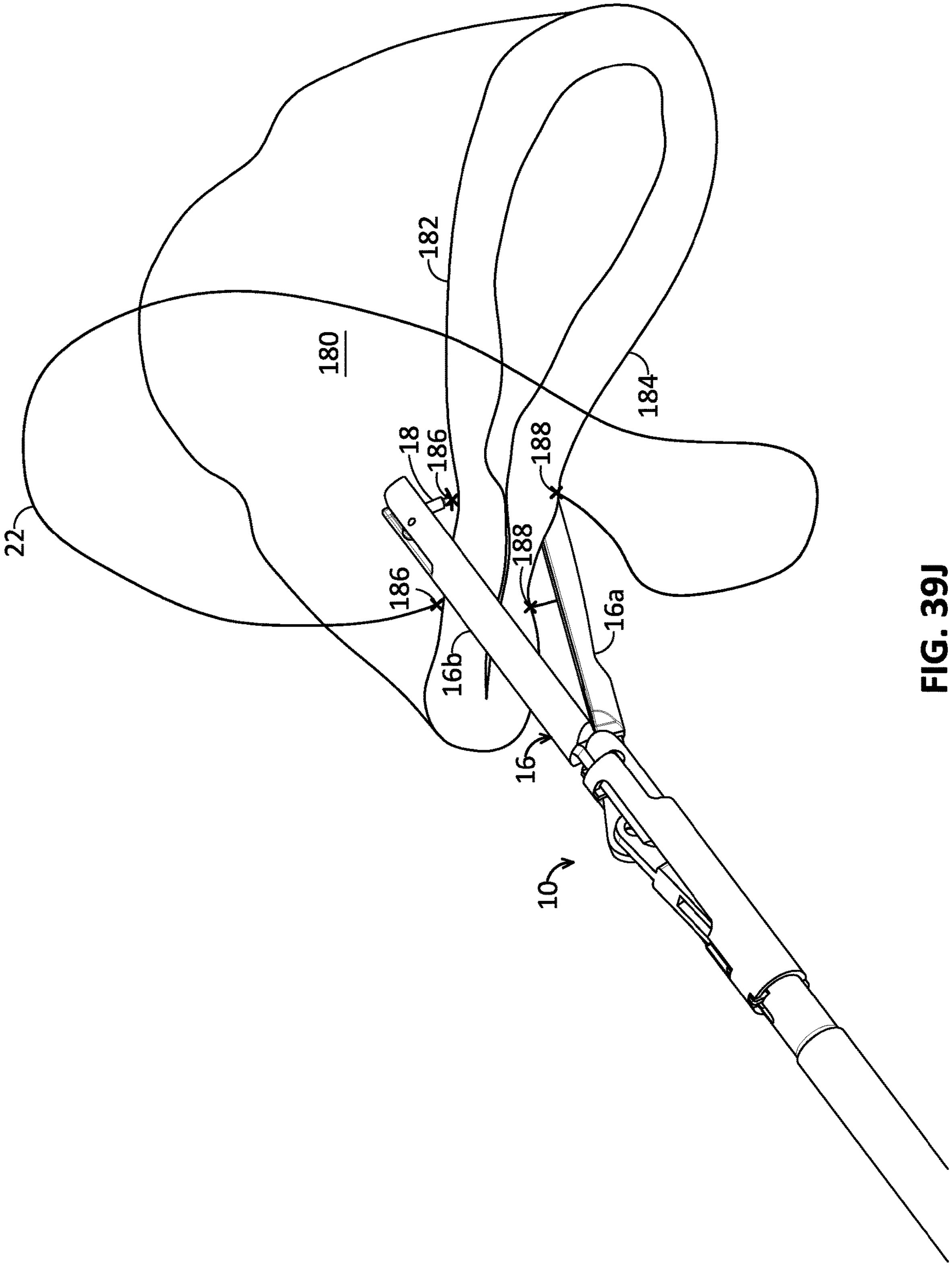
Figure 39K:
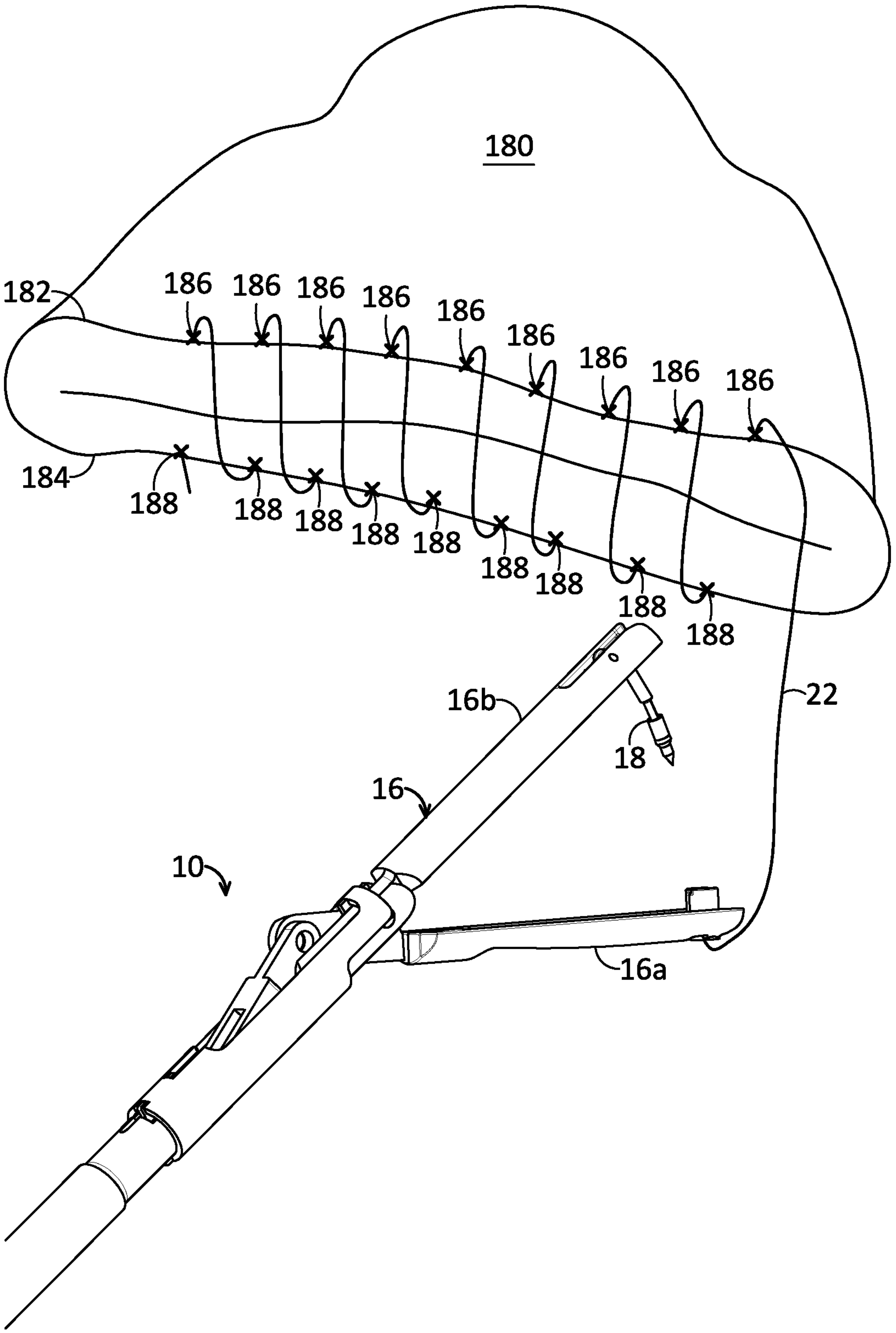

Next, as long as the vaginal cuff 180 is not completely sutured and closed (step 220), steps 208-218 are repeated at additional entry points 182 in the vaginal cuff 180 to create stitches 190 between the entry points 182 (see FIG. 39J). Once the vaginal cuff 180 is completely sutured and closed (step 220), the suture 22 is cut (e.g., using scissors introduced into the patient via another laparoscopic port (not shown) and tied (step 222) (see FIG. 39K), the needle 18 is hinged from the deployed state to the retracted state via manipulation of the slider mechanism 80 (shown in FIG. 1) (step 224), the jaw assembly 16 is transitioned from the open state to the closed state (i.e., the jaws 16*a*, 16*b* are translated toward each other) via manipulation of the finger piece 34 (shown in FIG. 1) (step 226), and the laparoscopic tissue suturing instrument 10 is removed from the insufflated abdomen of the patient via the laparoscopic port (step 228).

Referring to FIGS. 40, 40A, and 41-43, another embodiment of a laparoscopic tissue suturing instrument 310 generally comprises: an elongated rigid shaft 312 having a proximal end 324 and a distal end 326; a handle assembly 314 affixed to the proximal end 324 of the rigid shaft 312; a tissue grasper, and in particular, a single clamp arm 316 hingedly associated with the distal end 326 of the rigid shaft 312, such that clamp arm 316 may be transitioned (shown by the arrow 328) between an extended state (shown in solid in FIGS. 40 and 40A) and a retracted state (shown in phantom in FIGS. 40 and 40A) via manipulation of the handle assembly 314; a needle 318 operatively associated with the distal end 326 of the rigid shaft 312, such that the needle 318 may be transitioned (shown by the arrow 330) between a proximal position (or retracted state) (shown in phantom in FIGS. 45, 46, and 48) and one or more distal positions (or deployed state(s)) (shown in phantom in FIGS. 47 and 49) via manipulation of the handle assembly 314; a suture shuttling element 320 (shown best in FIG. 41) configured for being removably coupled to the clamp arm 316; and a suture 322 affixed to the shuttling element 320.

Figure 41:
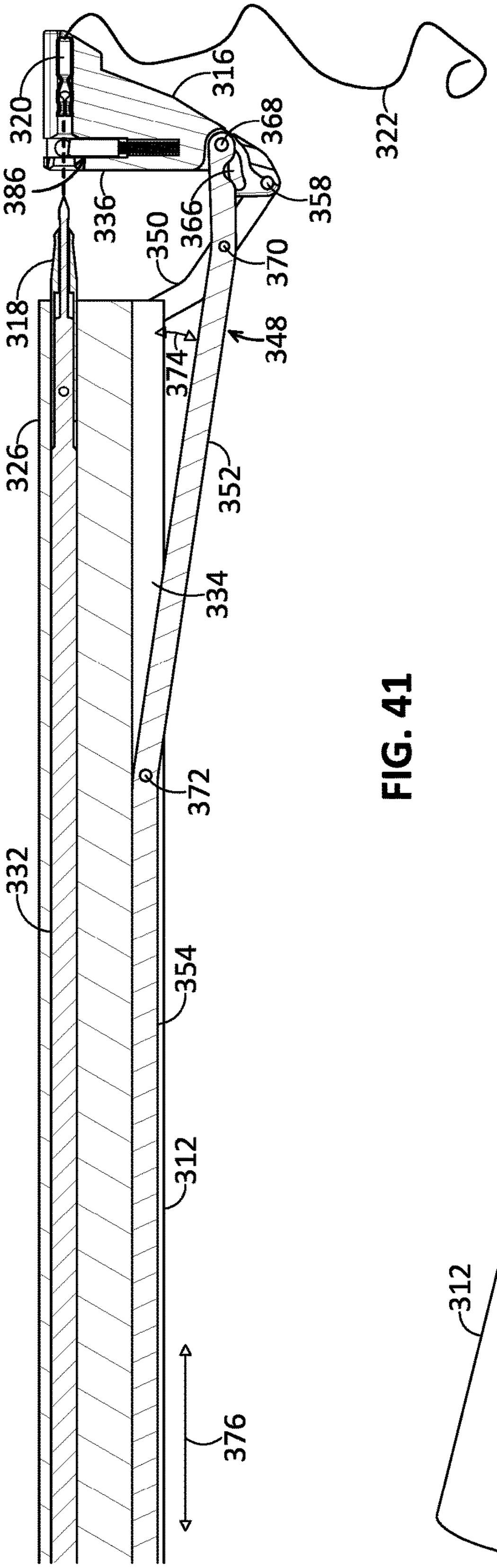
FIG. 41 is a longitudinal-sectional view of the distal end of the laparoscopic tissue suturing instrument of FIG. 40.

As best shown in FIG. 41, the rigid shaft 312 comprises a needle lumen 332 extending between proximal end 324 and distal end 326 of the rigid shaft 312, and a linkage channel 334 extending between proximal end 324 and distal end 326 of the rigid shaft 312. The needle lumen 332 accommodates the needle 318 for allowing the needle 318 to be transitioned between the proximal position and the distal position(s), whereas the linkage channel 334 accommodates a linkage (described in further detail below) for facilitating transition of the clamp arm 316 between the extended state and the retracted state. The rigid shaft 312 is preferably cylindrical (i.e., has a circular cross-section), although in alternative embodiments, the rigid shaft 312 may have any suitable cross-sectional geometry. The rigid shaft 312 is preferably narrow enough (e.g., less than 10 mm in diameter, and preferably 5 mm or less in diameter), such that the laparoscopic tissue suturing instrument 310 may be introduced through a separate conventional laparoscopic port (not shown) into the patient; and may have a suitable length, e.g., in the range of 18 cm-45 cm.

Figure 40:
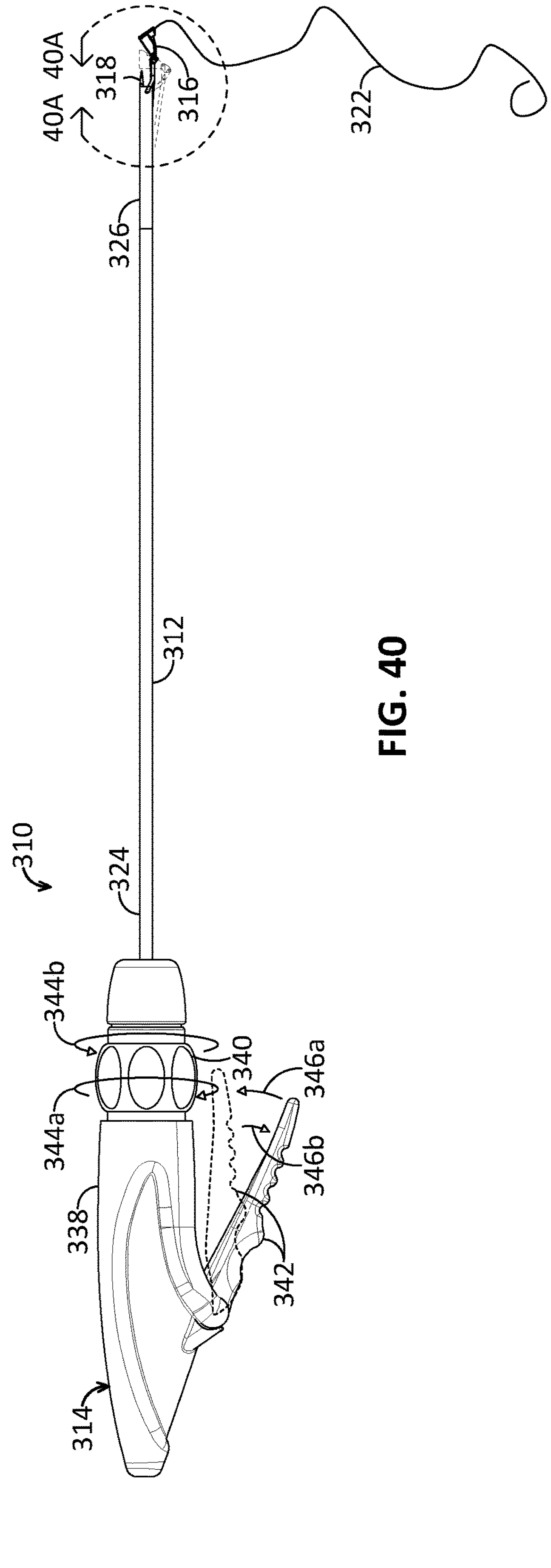
FIG. 40 is a schematic diagram of an exemplary laparoscopic tissue suturing instrument constructed in accordance with another embodiment of the disclosed inventions.
Figure 40A:
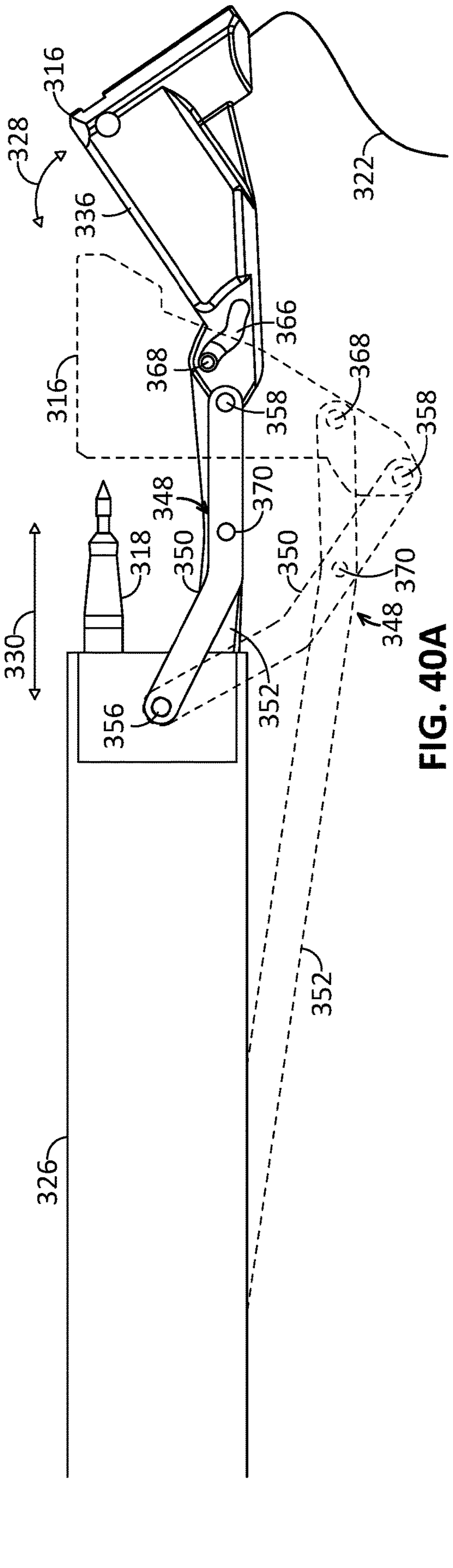
FIG. 40A a close-up view of the distal end of the laparoscopic tissue suturing instrument of FIG. 40, taken along the line 40A-40A.

The clamp arm 316, when in the extended state, is configured for placing the laparoscopic tissue suturing instrument 310 in a low-profile geometry, so that it can be introduced through a conventional laparoscopic port (not shown) into the patient. While in the extended state, the clamp arm 316 preferably has a profile that is equal to or larger than the diameter of the rigid shaft 312. The clamp arm 316, when in the retracted state, is configured for grasping tissue in a stable manner, thereby enabling the suturing functionality of the laparoscopic tissue suturing instrument 310. As best shown in FIGS. 40A and 41, the clamp arm 316 has a flat surface 336 configured for coming in firm contact with the tissue when the clamp arm 316 is in the retracted state. In an optional embodiment, the flat surface 336 may be textured or have teeth (not shown) to facilitate grasping of the tissue between the clamp arm 316 and the distal end 326 of the rigid shaft 312.

The handle assembly 314 comprises a handle 338 configured for being ergonomically grasped by the palm of a hand, a nut 340 configured for being ergonomically grasped between a forefinger and thumb of the hand, and a finger piece 342 configured for being ergonomically grasped by the fingers of the hand.

Figure 45:
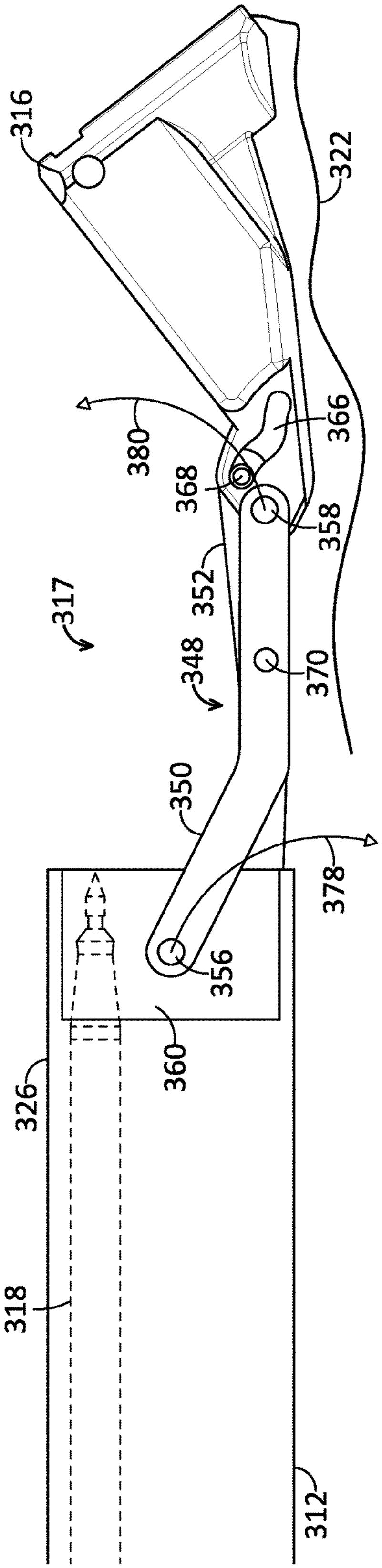
FIG. 45 is a profile view of the distal end of the laparoscopic tissue suturing instrument of FIG. 40, particularly showing a clamp arm of the laparoscopic tissue suturing instrument in an extended state, while a needle of the laparoscopic tissue suturing instrument is shown in phantom in a proximal position (or retracted state)
Figure 46:
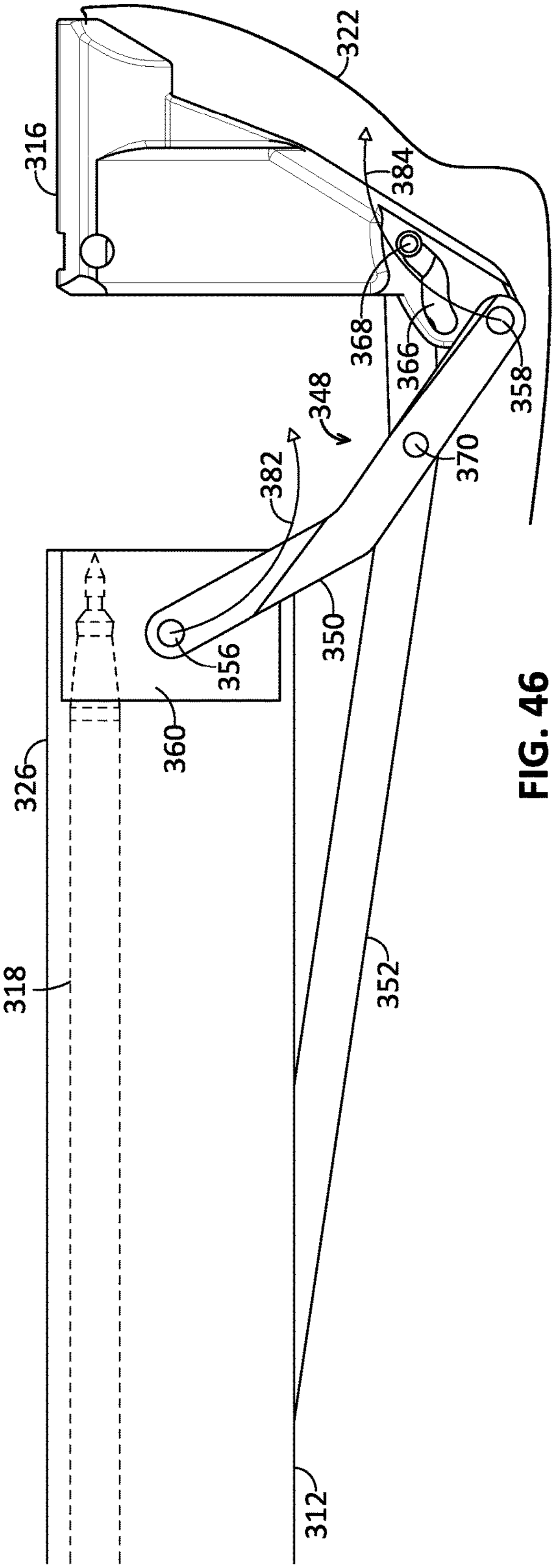
FIG. 46 is a profile view of the distal end of the laparoscopic tissue suturing instrument of FIG. 40, particularly showing the clamp arm in a retracted state, while the needle is shown in phantom in a proximal position (or retracted state)

The nut 340 is rotatably affixed to the handle 338 and is operably associated with the clamp arm 316 (e.g., using a threaded arrangement between the nut 340 and a linkage 348 (shown in FIGS. 40A and 41-43) connected to the clamp arm 316), such that rotation of the rotatable nut 340 relative to the handle 332 alternately transitions the clamp arm 316 between the extended state (shown in FIG. 45) and the retracted state (shown in FIG. 46). That is, manual rotation of the nut 340 about the handle 338 in one direction (in the direction 344*a*) pivots the clamp arm 316 towards the distal end 326 of the rigid shaft 312 to transition the clamp arm 316 from the extended state to the retracted state, whereas manual rotation of the nut 340 about the handle 332 in the opposite direction (in the direction 344*b*) pivots the clamp arm 316 away from the distal end 326 of the rigid shaft 312 to transition the clamp arm 316 from the retracted state to the extended state. In an optional embodiment, a slider mechanism or lever mechanism (not shown), instead of the nut 340, can be used to transition the clamp arm 316 between the extended state and the retracted state.

Referring specifically to FIGS. 40A and 41-43, the linkage 348 comprises a parallel hinge assembly 350 that hingedly couples the clamp arm 316 to the distal end 326 of the rigid shaft 312, a hinging link 352 hingedly affixed to the clamp arm 316, and a reciprocating link 354 (shown in FIG. 41) affixed between the hinging link 352 and the rotatable nut 340 of the handle assembly 314.

In particular, and with further reference to FIGS. 45-49, the proximal end of the parallel hinge assembly 350 is hingedly coupled to opposite sides of the distal end 326 of the rigid shaft 312 via opposing pins 356 (shown best in FIGS. 43-44) extending outward from the distal end 326 of the rigid shaft 312, while the distal end of the parallel hinge assembly 350 is hingedly coupled to opposite sides of the proximal end of the clamp arm 316 via pins 358. To accommodate the parallel hinge assembly 350, the exterior of the distal end 326 of the rigid shaft 312 has opposing cutouts 360 (shown best in FIG. 44) in which the proximal end of the parallel hinge assembly 350 may rotate. In this manner, the proximal end of the parallel hinge assembly 350 does not radially extend outside of the periphery of the rigid shaft 312 when the clamp arm 316 is in the extended state.

Figure 42:
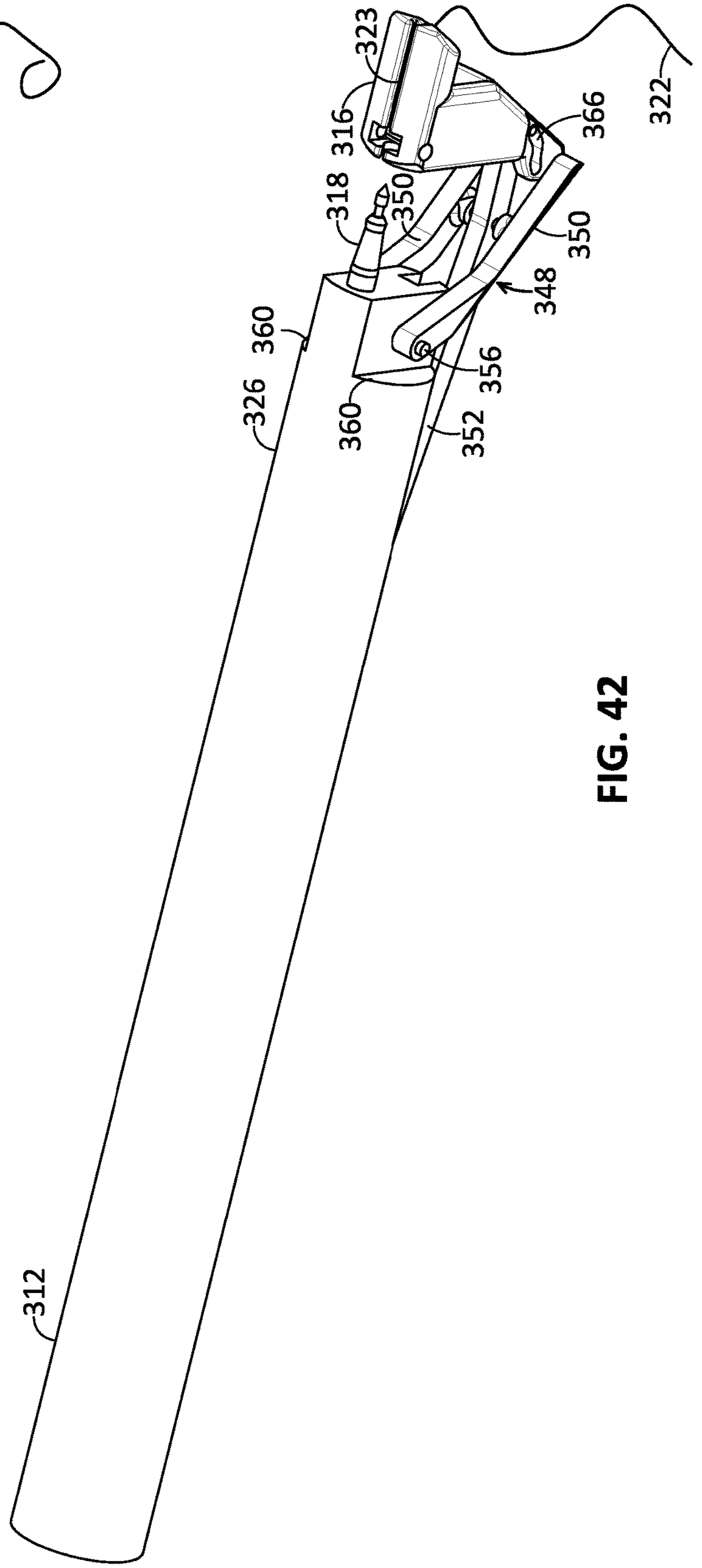
FIG. 42 is a perspective top view of the distal end of the laparoscopic tissue suturing instrument of FIG. 40.
Figure 43:
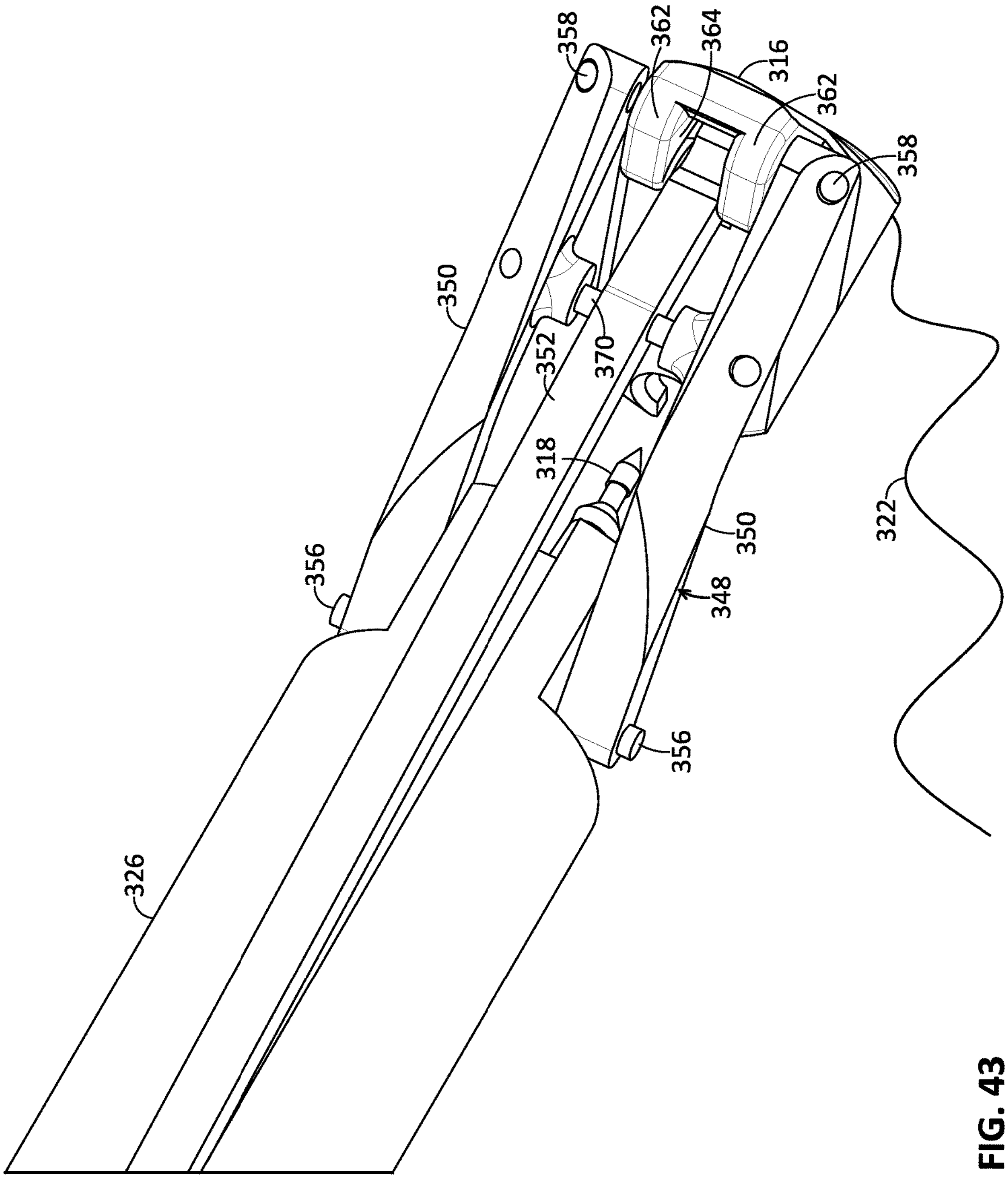
FIG. 43 is a perspective bottom view of the distal end of the laparoscopic tissue suturing instrument of FIG. 40.
Figure 44:
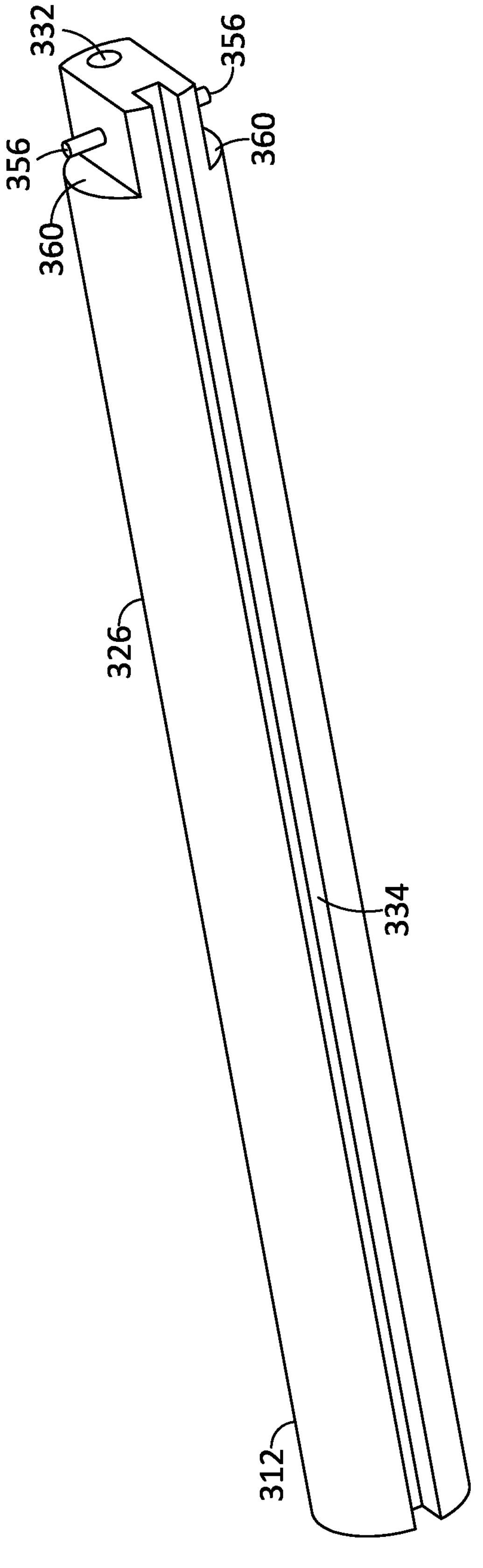
FIG. 44 is a perspective bottom view of the distal end of a rigid shaft of the laparoscopic tissue suturing instrument of FIG. 40.

Referring again to FIG. 41, the distal end of the hinging link 352 is hingedly and slidably coupled to the proximal end of the clamp arm 316. As best shown in FIG. 43, the clamp arm 316 comprises a pair of flanges 362 forming a recess 364 therebetween that accommodates the distal end of the hinging link 352. As best shown in FIGS. 41 and 42, the clamp arm 316 further comprises a pair of angled slots 366 (only one shown) formed within the respective pair of flanges 362, while the distal end of the hinging link 352 comprises a pair of opposing pins 368 (only one shown in FIGS. 45-49) configured for riding within the angled slots 366 as the clamp arm 316 is transitioned between the extended state and the retracted state. The distal end of the hinging link 352 is also hingedly coupled to the parallel hinge assembly 350 via a pin 370 (best shown in FIG. 43), such that the hinging link 352 actuates the hinging action of the parallel hinge assembly 350. As best shown in FIG. 41, the distal end of the reciprocating link 354 is hingedly coupled to the proximal end of the hinging link 352 via a pin 372, while the proximal end of the reciprocating link 354 is threadedly affixed to the rotatably nut 340 of the handle assembly 314. The hinging link 352 is configured for alternately hinging in and out of the linkage channel 334 (shown by the arrow 374), while the reciprocating link 354 is configured for translating along the linkage channel 334 (shown by the arrow 376).

Thus, when the nut 340 is rotated relative to the handle 338 in one direction 344*a* (see FIG. 40), the reciprocating link 354 is proximally translated within the linkage channel 334, thereby proximally displacing the hinging link 352, causing the parallel hinge assembly 350 to rotate about the distal end 326 of the rigid shaft 312 in the direction 378, and in turn, rotating the clamp arm 316 about the distal end of the parallel hinge assembly 350 in the direction 380 from its extended state (shown in FIG. 45) to its retracted state (shown in FIG. 46). In an optional embodiment, a locking mechanism or spring mechanism (not shown) may be employed in the handle 348 for locking the rotatable nut 340 in place, and thus, locking the clamp arm 316 in its retracted state. Rotation of the clamp arm 316 from its extended state to its retracted state also causes the parallel hinge assembly 350 to translate the shuttling element 320 retained within the clamp arm 316 into axial alignment with the needle 318, as illustrated in FIG. 41. When the clamp arm 316 is in the extended state, a tissue receiving gap 317 (best shown in FIG. 45) is defined between the clamp arm 316 and the distal end 326 of the rigid shaft 312.

Conversely, when the nut 340 is rotated relative to the handle 338 in another direction 344*b* (see FIG. 40), the reciprocating link 354 is distally translated within the linkage channel 334, thereby distally displacing the hinging link 352, causing the parallel hinge assembly 350 to rotate about the distal end 326 of the rigid shaft 312 in the direction 382, and in turn, rotating the clamp arm 316 about the distal end of the parallel hinge assembly 350 in the direction 384 from its retracted state (shown in FIG. 46) to its extended state (shown in FIG. 45).

Figure 47:
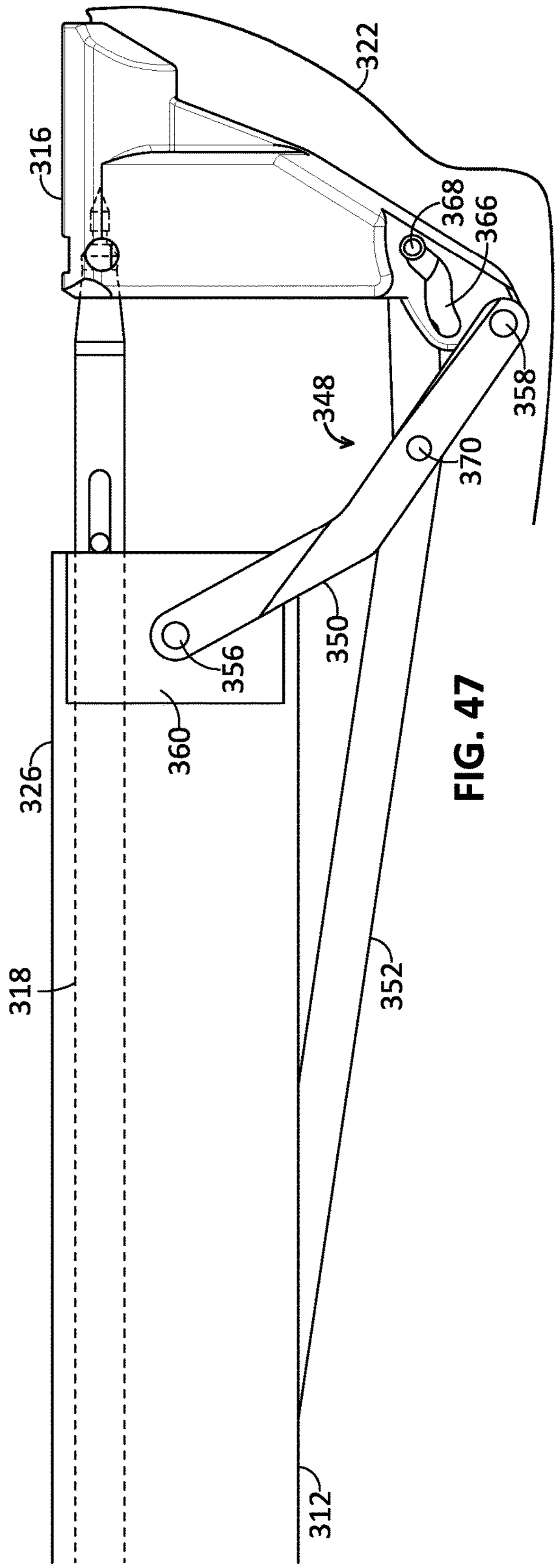
FIG. 47 is a profile view of the distal end of the laparoscopic tissue suturing instrument of FIG. 40, particularly showing the clamp arm in the retracted state, while the needle is partially shown in phantom in a first one of two distal positions (or a first deployed state) to engage a suture shuttling element coupled to the clamp arm.
Figure 48:
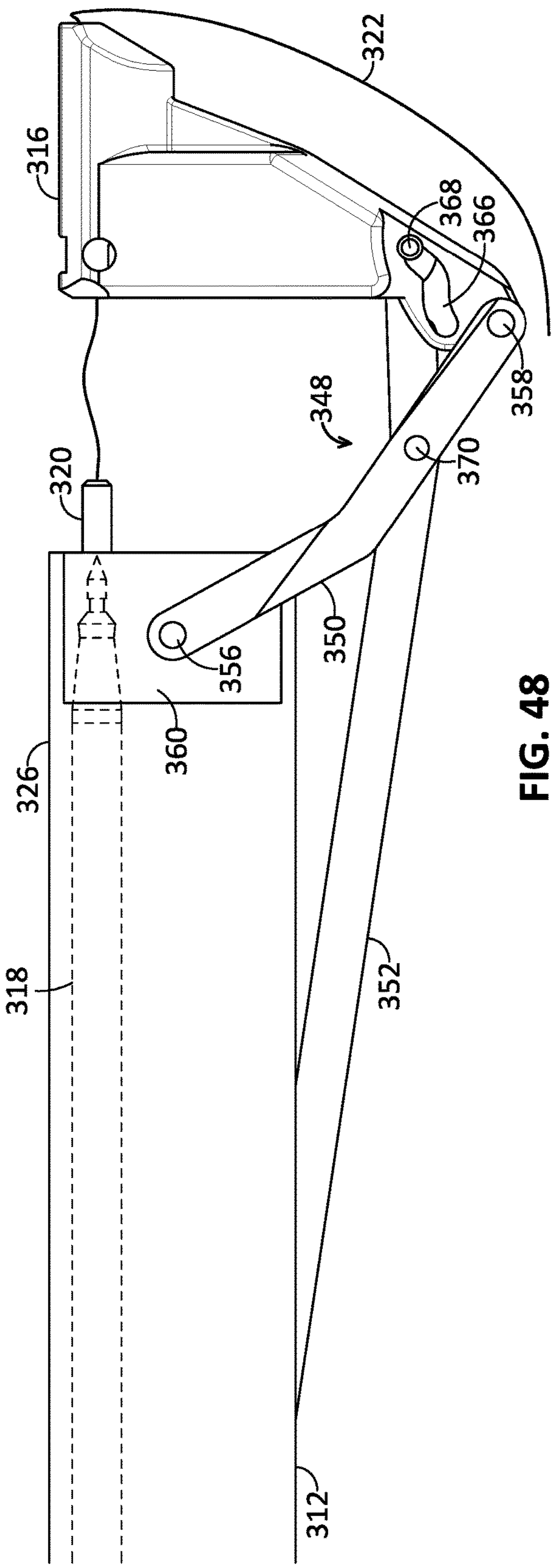
FIG. 48 is a profile view of the distal end of the laparoscopic tissue suturing instrument of FIG. 40, particularly showing the clamp arm in the retracted state, while the needle is shown in phantom in the proximal position after the shuttling element to decouple the shuttling element from the clamp arm.
Figure 49:
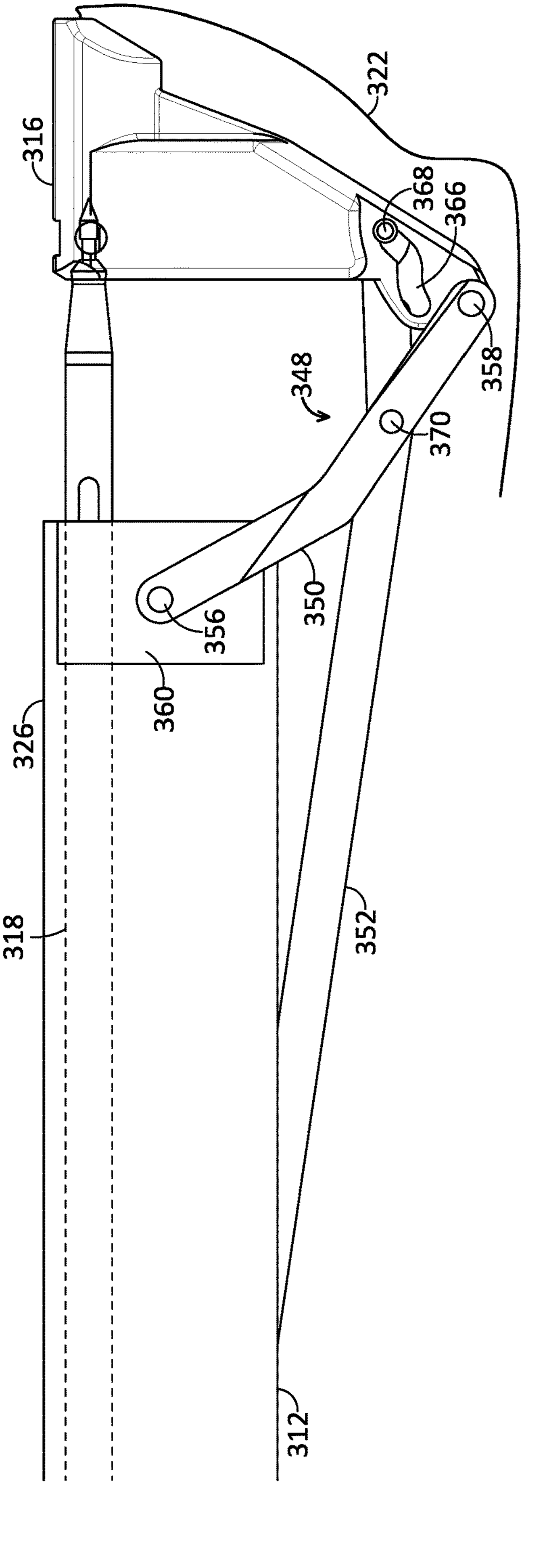
FIG. 49 is a profile view of the distal end of the laparoscopic tissue suturing instrument of FIG. 40, particularly showing the clamp arm in the retracted state, while the needle is partially shown in phantom in a second one of two distal positions (or a deployed state) and engaged with a shuttling element coupled to the clamp arm to recouple the shuttling element to the clamp arm.
Figure 51:
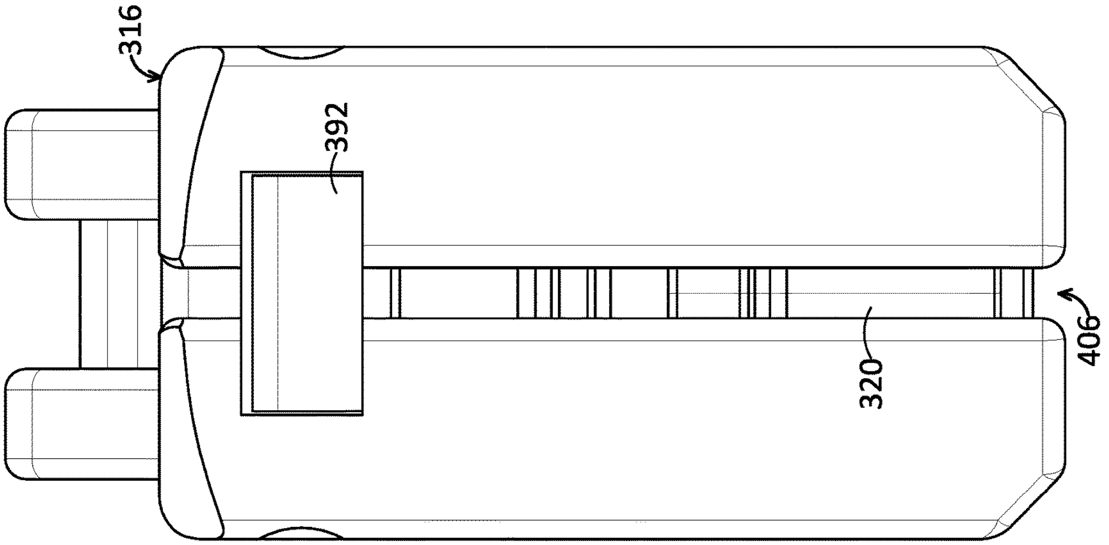
FIG. 51 is a top view of the clamp arm of FIG. 50.
Figure 50:
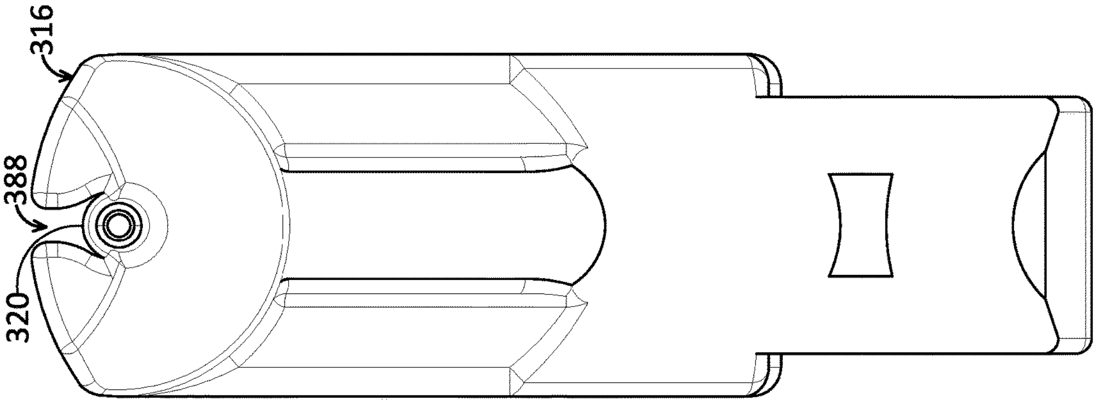
FIG. 50 is a front view of the clamp arm of the laparoscopic tissue suturing instrument of FIG. 40.

Referring back to FIG. 40, the finger piece 342 is pivotably affixed to the handle 338 and is operably associated with the needle 318 (e.g., using an interference arrangement between the finger piece 342 and the needle 318 (not shown), such that pivoting the finger piece 342 relative to the handle 338 alternately transitions the needle 318 within the needle lumen 332 of the rigid shaft 312 between the proximal position (in the illustrated embodiment, fully retracted within the rigid shaft 312, as shown in phantom in FIGS. 46 and 48) and the distal position(s), and as will be described in further detail below, two distal positions (shown in FIGS. 47 and 49). That is, manual pivoting of the finger piece 342 toward the handle 338 (in the direction 346*a*) distally translates the needle 318 to transition the needle 318 from the proximal position to either of the distal positions, whereas manual pivoting of the finger piece 342 away from the handle 338 (in the direction 346*b*) proximally translates the needle 318 from either of the distal positions to the proximal position. The finger piece 342 may be biased away from the handle 338, e.g., via a spring mechanism (not shown), such that the needle 318 is biased to the proximal position. In this case, the finger piece 342 may be manually pivoted towards the handle 338 (e.g., by firmly grasping the handle 338 with a single hand and squeezing the finger piece 342 with the fingers) in opposition to the biasing force applied by the spring mechanism to transition the needle 318 to either of the distal positions.

It should be appreciated that, although the pivotable finger piece 342 is described as actuating the needle 318 between the proximal position and the distal positions, any suitable proximal actuator and associated linkage may be used to alternately translate the needle 318 between the proximal position and the distal positions. For example, the handle assembly 314 may alternatively comprise a first finger ring (not shown) immovably affixed to the proximal end 324 of the rigid shaft 312, and a second finger ring (not shown) pivotably affixed to proximal end 324 of the rigid shaft 312, such that alternate manual translation of the finger rings towards and away from each other alternately translates the needle 318 within the needle lumen 332 of the rigid shaft 312.

The shuttling element 320 is removably coupled to the clamp arm 316 in a manner that allows the laparoscopic tissue suturing instrument 310 to pass the shuttling element 320 (and attached suture 322) back and forth between the clamp arm 316 and the distal end 326 of the rigid shaft 312 to thereby create a running stitch (i.e., a series of connected stitches) within tissue.

In particular, the needle 318, when the clamp arm 316 is in the retracted state, is configured for being inserted within and engaged to the shuttling element 320 coupled to the clamp arm 316 when the needle 318 is transitioned from the proximal position (see FIG. 46) to the first distal position (see FIG. 47); decoupling the engaged shuttling element 320 from the clamp arm 316 when the needle 318 is transitioned from the first distal position back to the proximal position, thereby drawing the suture 322 from the clamp arm 316 towards the distal end 326 of the rigid shaft 312 (see FIG. 48); recoupling the shuttling element 320 to the clamp arm 316 when the needle 318 is transitioned from the proximal position to the second distal position (see FIG. 49); and for being removed and disengaged from the shuttling element 320 when the needle 318 is transitioned from the second distal position back to the proximal position (see FIG. 46). In the illustrated embodiment, the first distal position and second distal position of the needle 318 are different from each other. As will be described below, the interaction between the needle 318 and the shuttling element 320 illustrated in FIGS. 46-49 can be repeatedly cycled to create a running stitch within the tissue.

In the illustrated embodiment, the laparoscopic tissue suturing instrument 310 comprises a shuttling element retainer mechanism 386 (shown in FIG. 41) that interacts with the needle 318, in conjunction with the complementary mechanical features between the clamp arm 316, needle 318, and shuttling element 320, in a manner that enables the needle 318 to alternately decouple the shuttling element 320 from the clamp arm 316 and recouple the shuttling element 320 to the clamp arm 316 in the manner illustrated in FIGS. 46-49.

In particular, referring to FIGS. 50-55, the clamp arm 316 defines a shuttling element retention cavity 388 configured for receiving the shuttling element 320. The shuttling element retention cavity 388 is further configured for being transformed between a retention state for securely retaining the shuttling element 320 (via non-interaction with the needle 318) and a release state for releasing the shuttling element 320 (via interaction with the needle 318), as will be described in further detail below.

Figure 53:
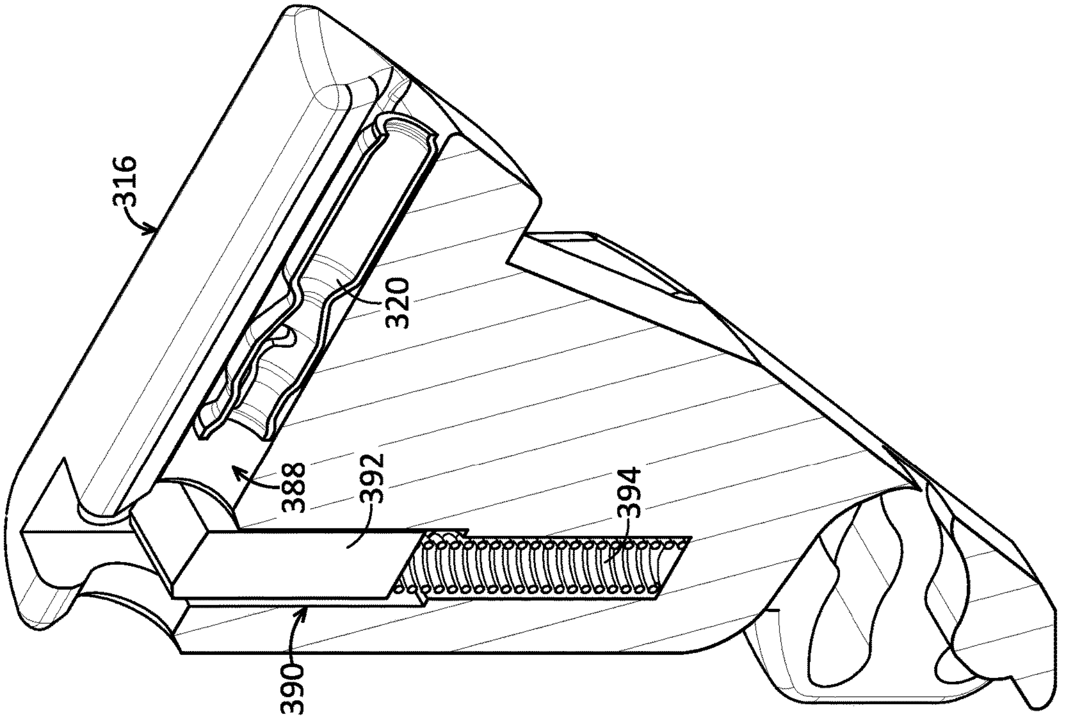
FIG. 53 is a longitudinal sectional view of the clamp arm of FIG. 50.
Figure 54:
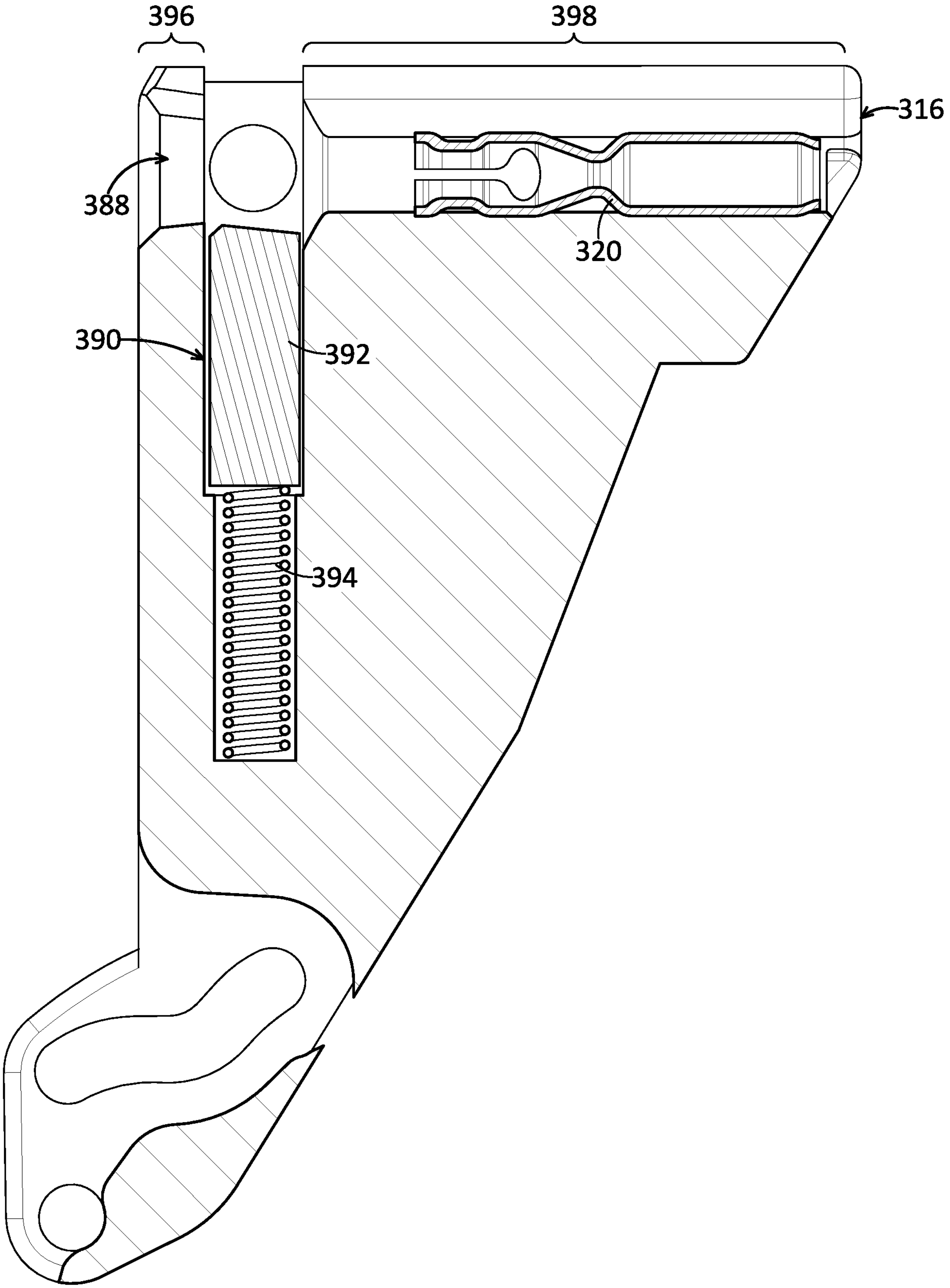
FIG. 54 is another longitudinal sectional view of the clamp arm of FIG. 50, particularly showing a shuttling element retention cavity of the clamp arm in a retention state.
Figure 55:
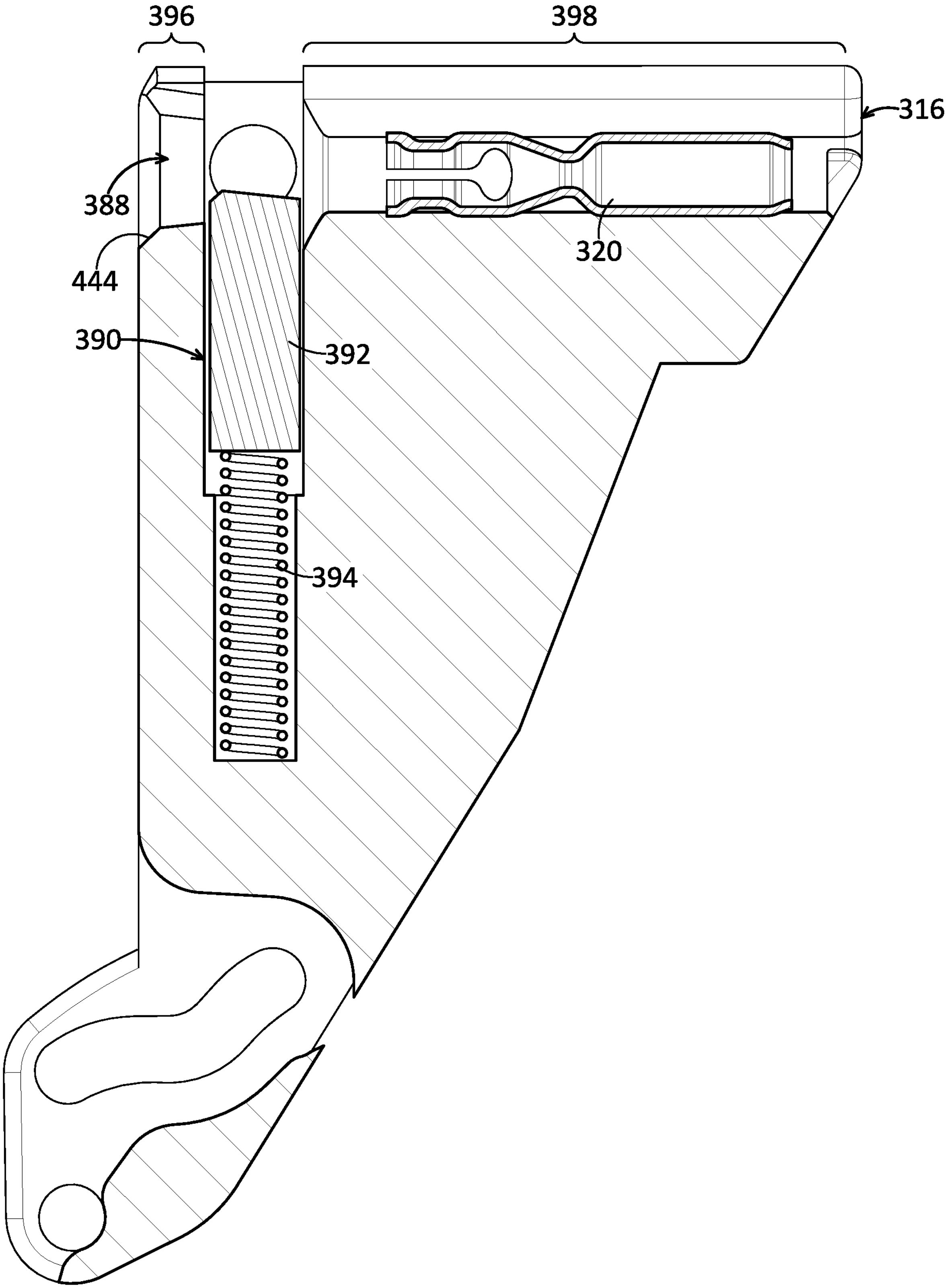
FIG. 55 is another longitudinal sectional view of the clamp arm of FIG. 50, particularly showing the shuttling element retention cavity of the clamp arm in a release state.

The clamp arm 316 further defines a cavity 390 orthogonal to the shuttling element retention cavity 388 for housing the shuttling element retainer mechanism 386 (best shown in FIGS. 53-55). The shuttling element retainer mechanism 386 comprises a latch 392 and a spring 394 configured for biasing the latch 392 from a recessed state (i.e., the latch 392 does not impinge into the shuttling element retention cavity 388, such that the shuttling element retention cavity 388 is in the release state, as shown in FIG. 54) to a deployed state (i.e., the latch 392 impinges into the shuttling element retention cavity 388, such that the shuttling element retention cavity 388 is in the retention state, as shown in FIG. 55). The latch 392 may be translated from the deployed state to the recessed state via interaction with the needle 318, as will be described in further detail below. As best shown in FIGS. 54-55, the shuttling element retention cavity 388 comprises a proximal chamber 396 and a distal chamber 398, the boundary between which is defined by the latch 392. For the purposes of this specification, the term "proximal" as it relates to a chamber is the chamber that is closest to the needle 318 when the clamp arm 316 is in the retracted state, and the term "distal" as it relates to a chamber is the chamber that is furthest from the needle 318 when the clamp arm 316 is in the retracted state.

Figure 56:
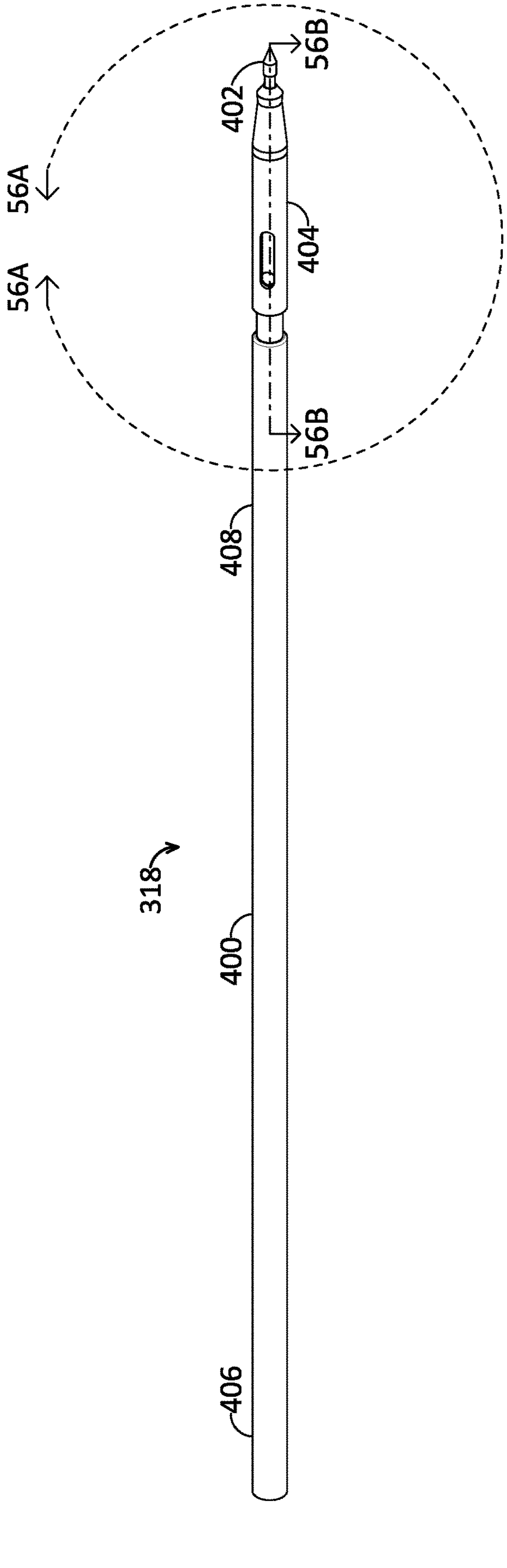
FIG. 56 is a perspective view of the needle of the laparoscopic tissue suturing instrument of FIG. 40.
Figure 57:
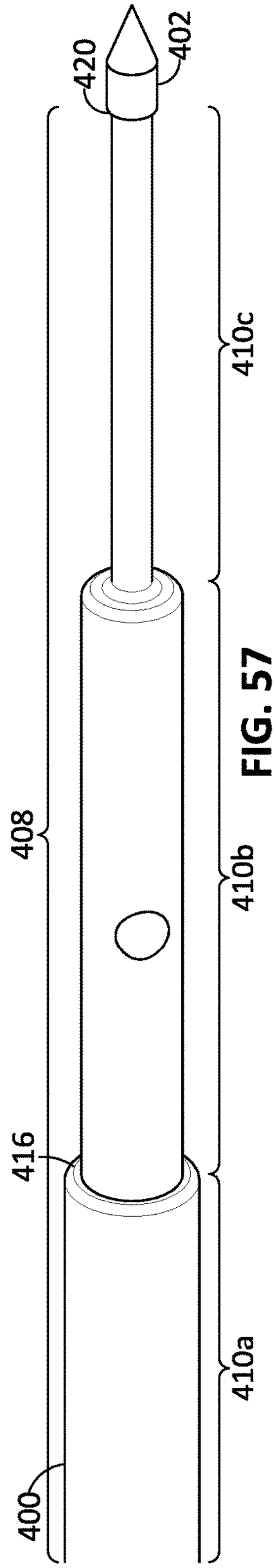
FIG. 57 is a close-up perspective view of the distal end of a shaft of the needle of FIG. 56.
Figure 58:
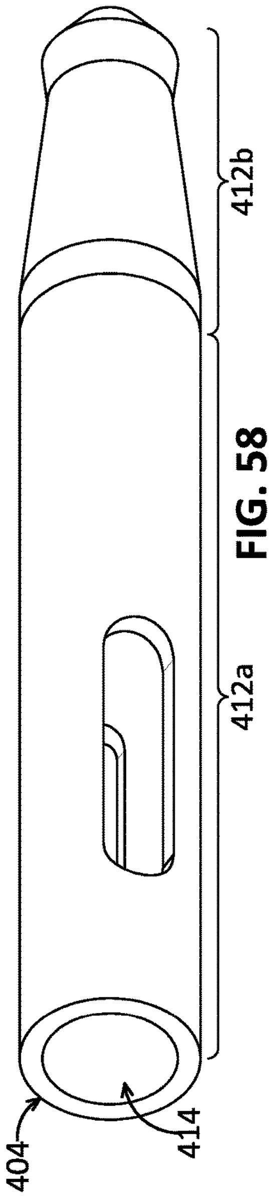
FIG. 58 is a perspective view of a slidable sleeve of the needle of FIG. 56.
Figure 59:
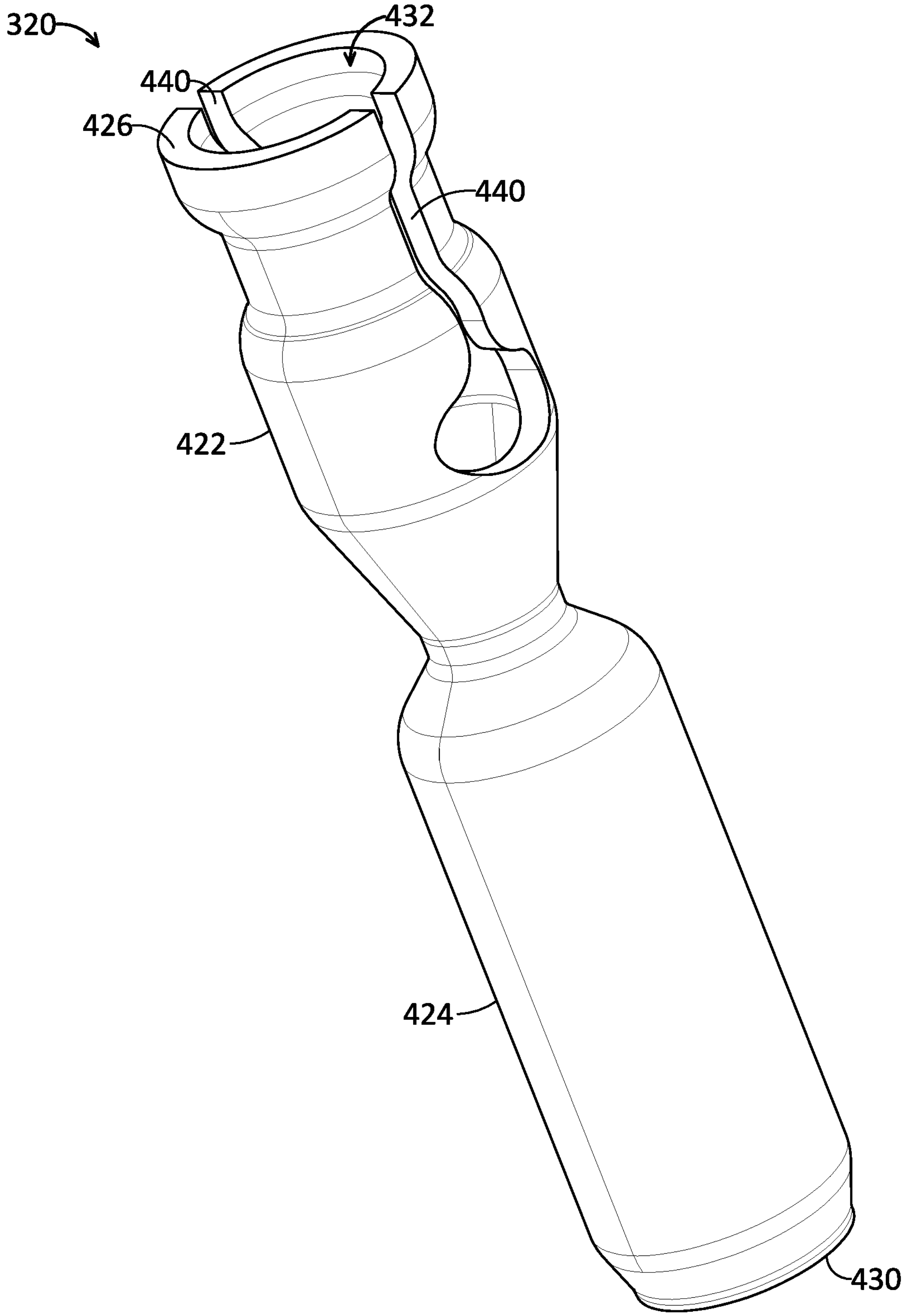
FIG. 59 is a perspective view of a suture shuttling element of the laparoscopic tissue suturing instrument of FIG. 40.
Figure 60:
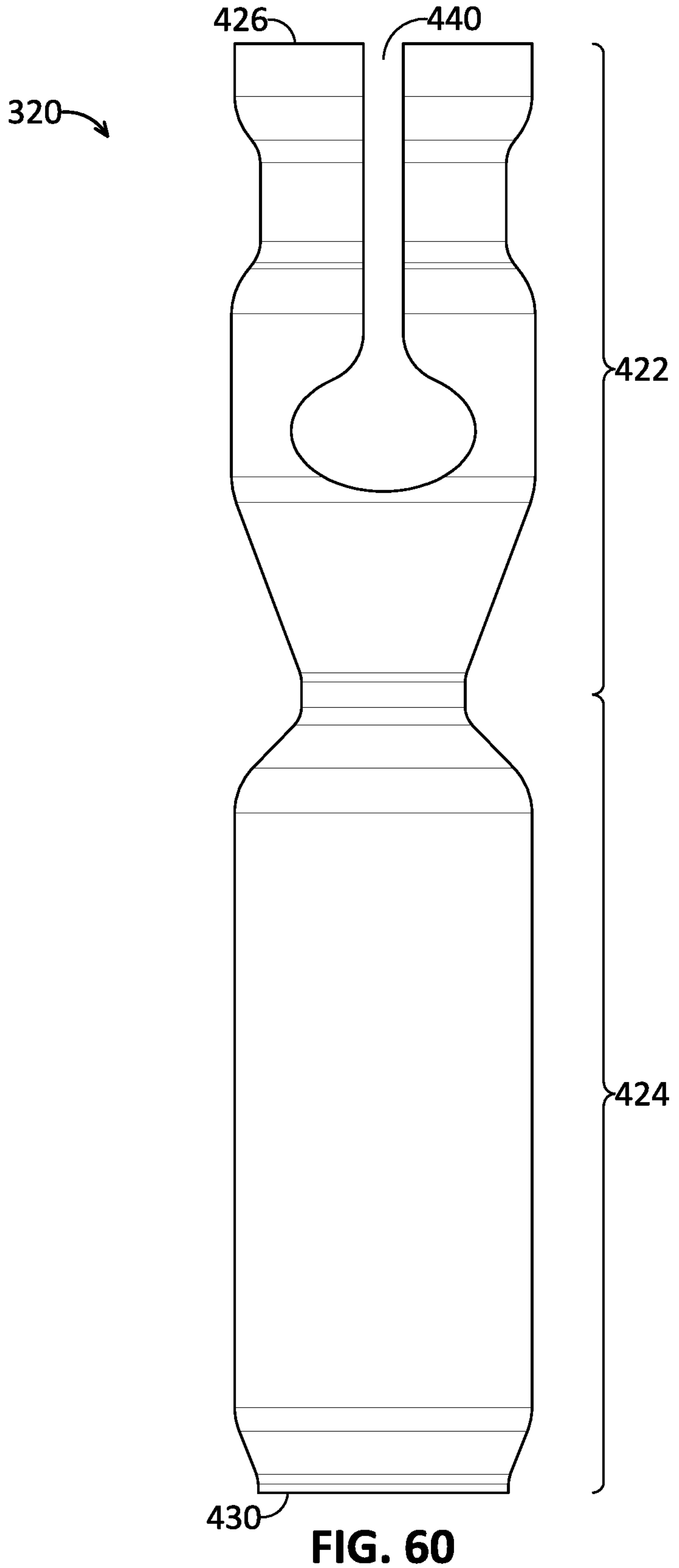
FIG. 60 is a profile view of the shuttling element of FIG. 59.

Referring now to FIGS. 56-58, the needle 318 comprises an elongated needle shaft 400 having a proximal end 406 and a distal end 408, a shuttling element coupler 402 disposed at the distal end 346 of the needle shaft 400, and a shuttling element release mechanism 404 slidably disposed on the needle shaft 400 just proximal to the shuttling element coupler 402. In the illustrated embodiment, the shuttling element release mechanism 404 takes the form of a slidable sleeve.

As will be described in further detail below, the shuttling element coupler 402 and slidable sleeve 404 operate in a similar manner as the shuttling element coupler 148 and slidable sleeve 150 described above with respect to the laparoscopic tissue suturing instrument 10, but instead of interacting with a jaw member, the shuttling element coupler 402 and slidable sleeve 404 interact with the clamp arm 316 to enable the suturing functionality of the laparoscopic tissue suturing instrument 310.

Figure 56A:
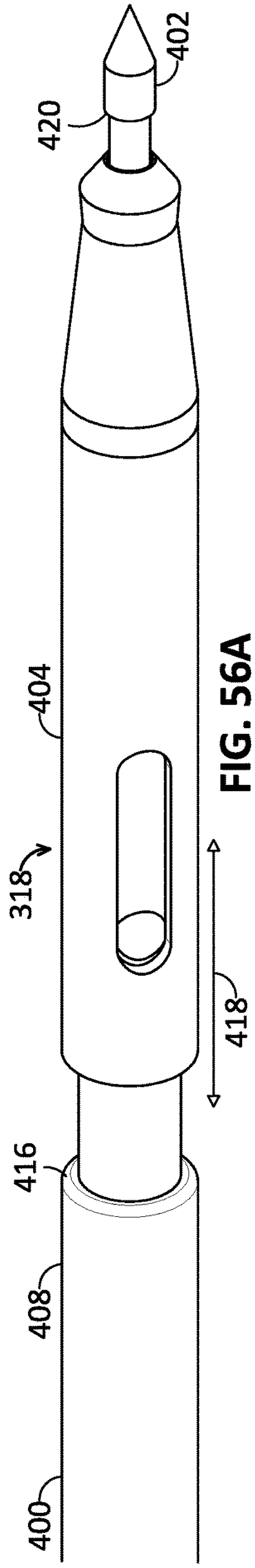
FIG. 56A is a perspective close-up view of the needle of FIG. 56, taken along the line 56A-56A.
Figure 56B:
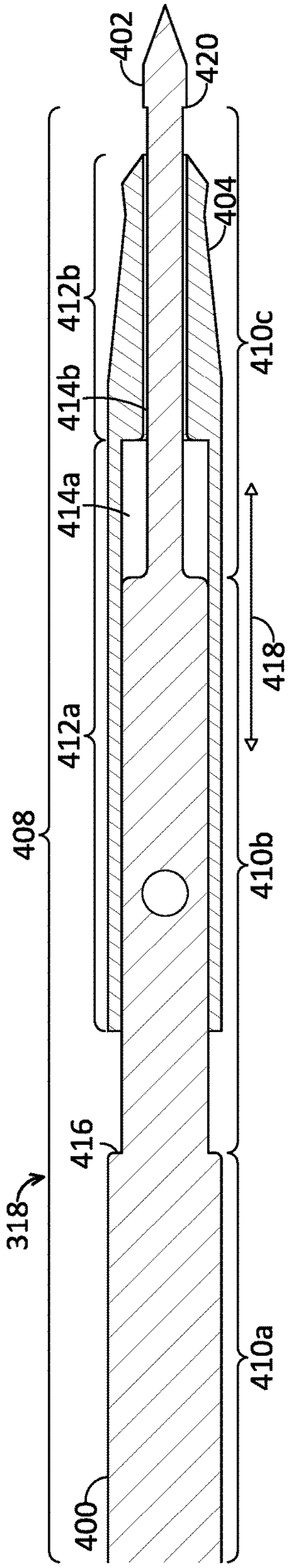
FIG. 56B is a longitudinal sectional view of the needle of FIG. 56, taken along the line 56B-56B.

The distal end of the needle 318 is specifically designed to provide a substantially continuous profile to facilitate insertion through tissue while allowing controlled slidability of the sleeve 404. In particular, the outer diameter of the needle shaft 400 and the needle lumen 332 of the rigid shaft 312 (shown in FIG. 41) are sized to match each other, such that the needle shaft 400 may smoothly slide in and out of the needle lumen 332 of the rigid shaft 312. Furthermore, as best shown in FIGS. 56A-56B and 57, the distal end 408 of the needle shaft 400 has a proximal needle shaft section 410*a*, a medial needle shaft section 410*b* having a diameter less than that of the proximal needle shaft section 410*a*, and a distal needle shaft section 410*c* having a diameter less than that of the medial needle shaft section 410*b*. The shuttling element coupler 402 is disposed at the tip of the distal needle shaft section 410*c*.

Figure 65:
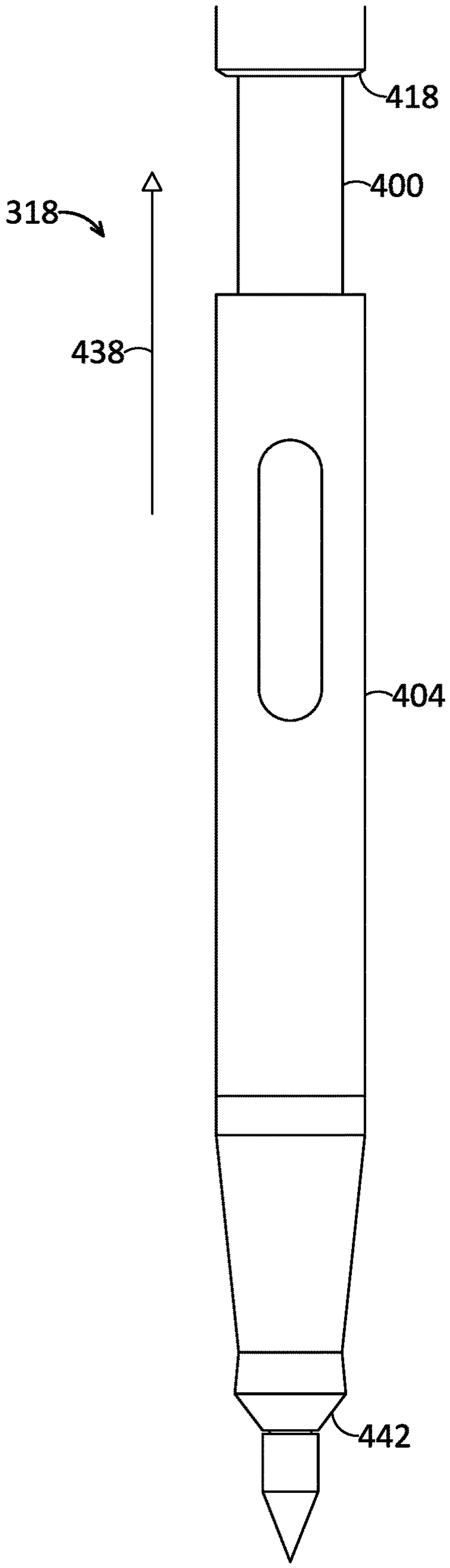
FIG. 65 is a profile view of the distal end of the needle of the laparoscopic tissue suturing instrument of FIG. 40, particularly showing the needle engaged with the shuttling element, particularly showing the slidable sleeve in its distal-most position.
Figure 66:
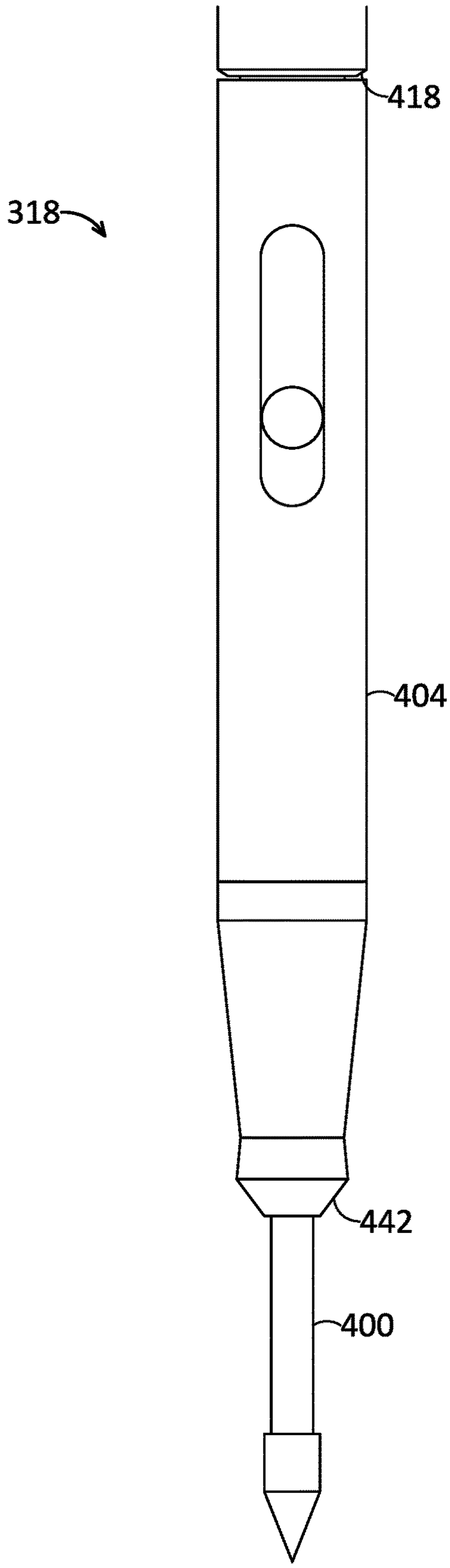
FIG. 66 is a profile view of the distal end of the needle of FIG. 65, particularly showing the slidable sleeve in its proximal-most position.

As best shown in FIGS. 56B and 58, the slidable sleeve 404 has a proximal cylindrical sleeve section 412*a* and a distal tapered sleeve section 412*b*. The outer diameter of the proximal cylindrical sleeve section 412*a* matches the outer diameter of the proximal needle shaft section 410*a*. The proximal cylindrical sleeve section 412*a* has a cavity 432 divided between a proximal sleeve cavity 414*a* in which the medial needle shaft section 410*b* is slidably disposed, and a distal sleeve cavity 414*b* in which the distal needle shaft section 410*c* is slidably disposed. The lengths of the medial needle shaft section 410*b* and distal needle shaft section 410*c* are respectively shorter than the lengths of the proximal sleeve cavity 414*a* and distal sleeve cavity 414*b* by a given distance, thereby allowing the sleeve 404 to proximally or distally slide along the distal end 408 of the needle shaft 400 (shown by the arrow 418). The diameter of the distal sleeve cavity 432*b* is less than the diameter of the proximal sleeve cavity 432*a*, such that the proximal sleeve cavity 432*a* and the medial needle shaft section 410*b* are tightly toleranced, while the distal sleeve cavity 432*b* and the distal needle shaft section 410*c* are tightly toleranced. As shown in FIGS. 65 and 66, the distal end 408 of the needle shaft 400 forms a stop 418 at a step transition between the proximal needle shaft section 410*a* and the medial needle shaft section 410*b*, which serves to limit the proximal travel of the slidable sleeve 404 along the distal end 408 of the needle shaft 400.

Figure 52:
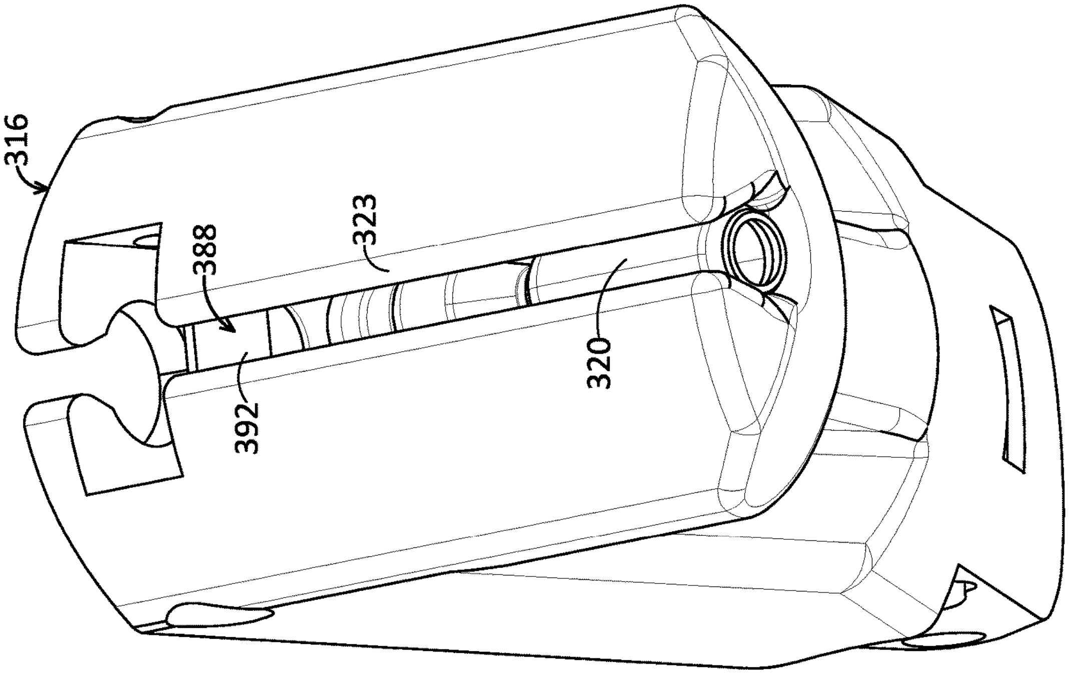
FIG. 52 is a perspective view of the clamp arm of FIG. 50.

As shown in FIGS. 56A-56B and 57, the shuttling element coupler 402 takes the form of an enlarged bullet-shaped tip, the outer diameter of which is greater than the outer diameter of the distal end 408 of the needle shaft 400, such that an outer annular ledge 420 is formed at a step transition between the shuttling element coupler 402 and the distal needle shaft section 410*c*, which serves to limit the distal travel of the slidable sleeve 404 along the distal end 408 of the needle shaft 400, as well as to facilitate engagement with the shuttling element 320, as will be described in further detail below. As best shown in FIGS. 42 and 52, the clamp arm 316 comprises a suture clearance slot 323 configured for allowing the suture 322 to be displaced from the shuttling element retention cavity 388, so that the suture 322 does not hinder recoupling of the suture sleeve 320 to the clamp arm 316.

Figure 61:
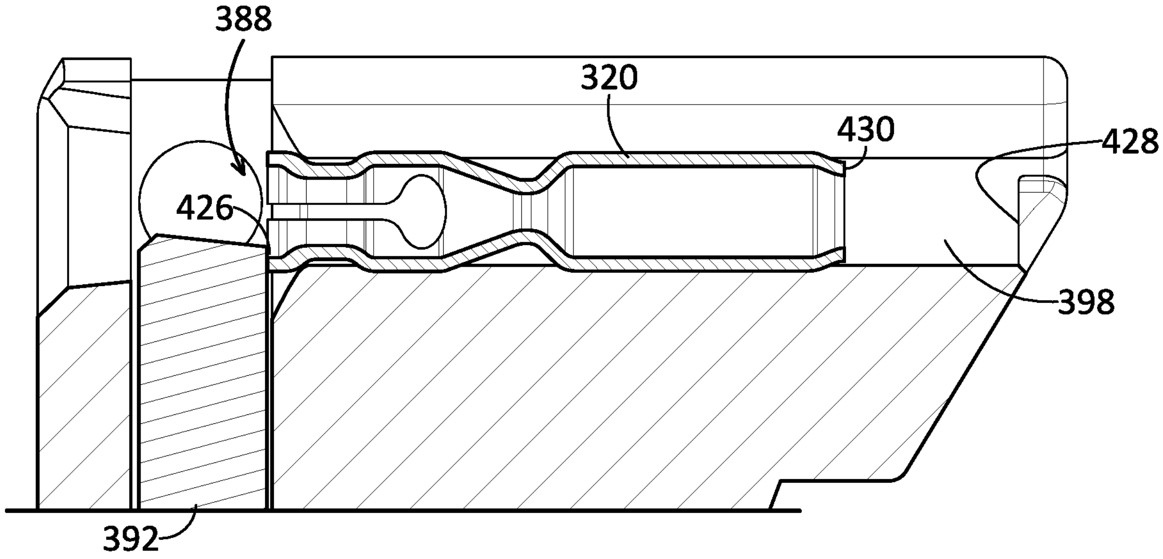
FIG. 61 is a partially cutaway cross-sectional view of the clamp arm of the laparoscopic tissue suturing instrument of FIG. 40, particularly showing the shuttling element in a proximal-most position in the clamp arm.
Figure 62:
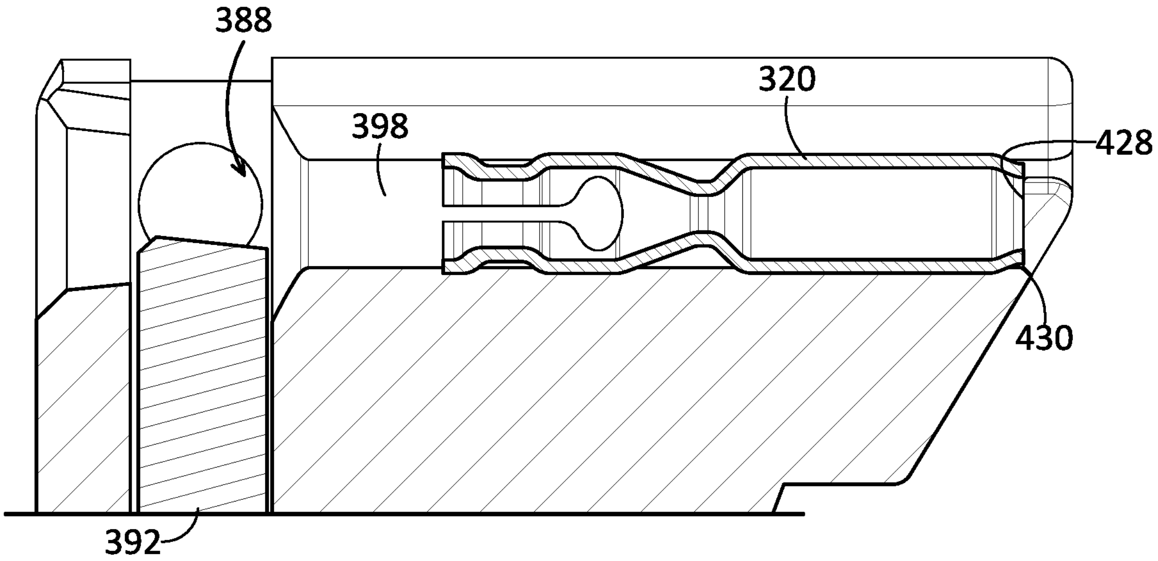
FIG. 62 is a partially cutaway cross-sectional view of the clamp arm of the laparoscopic tissue suturing instrument of FIG. 40, particularly showing the shuttling element in a distal-most position in the clamp arm.

Referring to FIGS. 59-62, the shuttling element 320 has a needle engagement portion 422 for interaction with the needle 318 and a suture affixation portion 424 to which the suture 322 (shown in FIGS. 40-42 and 45-49) is affixed. The outer diameter of the needle engagement portion 422 is less than the diameter of the shuttling element retention cavity 388, but is large enough, such that a proximal edge 426 of the shuttling element 320 may abut the latch 392 when the latch 392 is in its deployed state, as best illustrated in FIG. 61. Furthermore, the distal end of the shuttling element retention cavity 388 has a reduced diameter inner annular ledge 428 configured for abutting a distal edge 430 of the shuttling element 320, as best illustrated in FIG. 62, thereby serving to retain the shuttling element 320 within the distal chamber 398 of the shuttling element retention cavity 388. For purposes that will be described in further detail below, the length of the shuttling element 320 is less than the length of the distal chamber 398, such that shuttling element 320 may freely move in the distal chamber 398 in the linear direction. Thus, the proximal edge 426 of the shuttling element 320 may, at times, be spaced from the proximal extremity of the distal chamber 398, and the distal edge 430 of the shuttling element 320 may, at times be spaced from the distal extremity of the distal chamber 398, as shown in FIG. 56. As will be described in further detail below, the distal edge 430 of the shuttling element 320 is chamfered to urge the latch 392 downward into the latch cavity 390 as the shuttling element 320 enters retention cavity 388.

Figure 63:
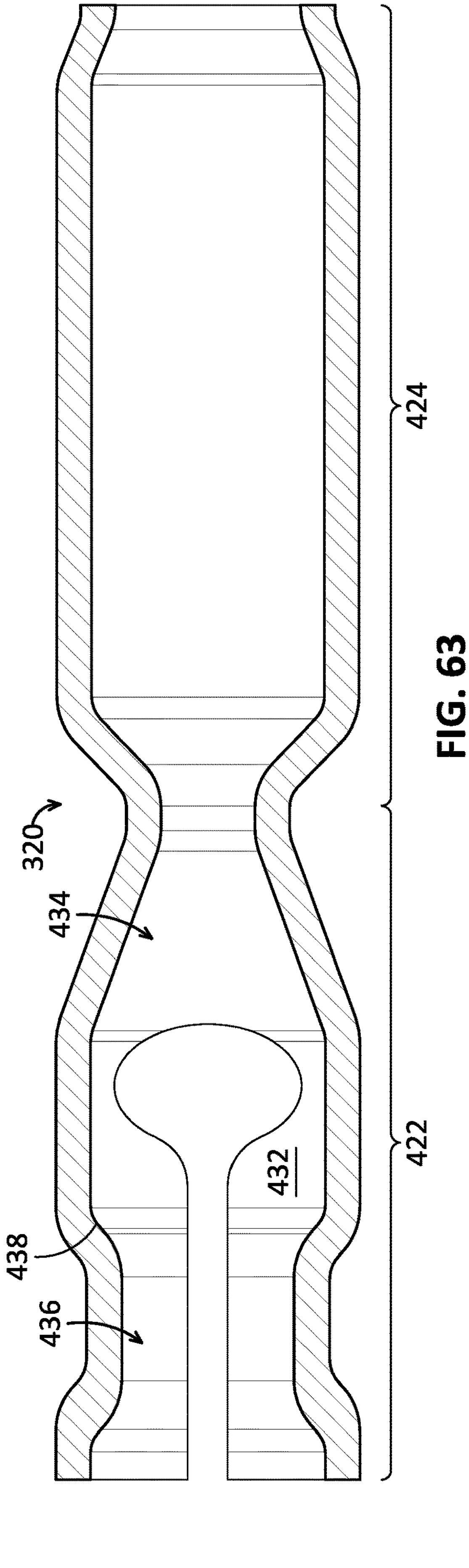
FIG. 63 is a longitudinal sectional view of the shuttling element of FIG. 59.
Figure 64:
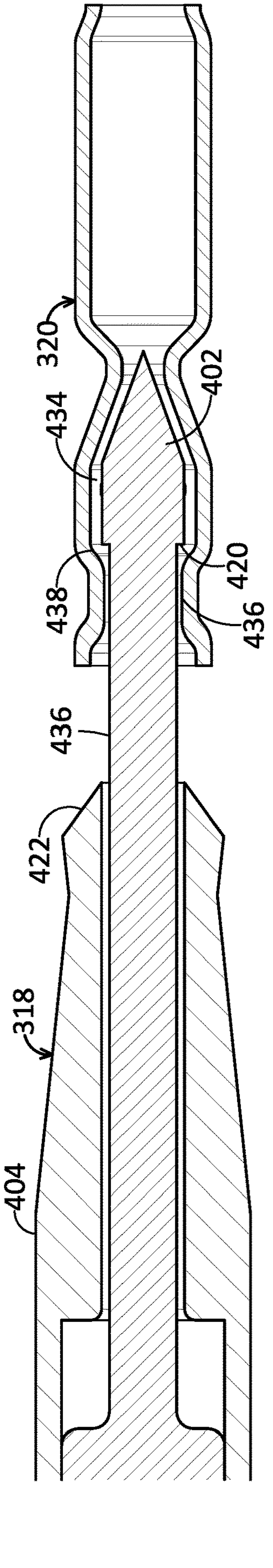
FIG. 64 is a cross-sectional view of the needle and shuttling element of the laparoscopic tissue suturing instrument of FIG. 40, particularly showing the needle engaged with the shuttling element.

Referring further to FIGS. 63 and 64, the needle engagement portion 422 of the shuttling element 320 defines a cavity 432 in which the shuttling element coupler 402 is configured for being disposed to engage the shuttling element 320. The cavity 432 has a bullet-shaped distal cavity portion 434 that complements the shape of the shuttling element coupler 402 of the needle 318, and a reduced diameter cylindrical proximal cavity portion 436 that complements the shape of the distal needle shaft section 410*c* of the needle 318. The transition between the distal cavity portion 434 and the proximal cavity portion 436 of the shuttling element 320 forms an inner annular ledge 438 within the cavity 432, such that the ledge 420 of the shuttling element coupler 402 is configured for abutting the ledge 438 of the shuttling element 320. The geometry of the cavity 432 closely matches the geometry of the shuttling element coupler 402 and the distal needle shaft section 410*c* of the needle 318, such that shuttling element coupler 402 may firmly engage the shuttling element 320.

The complementary shapes and sizes of the needle 318 and the cavity 432 of the shuttling element 320, and in particular, the ledge 420 of the shuttling element coupler 402 of the needle 318 and the ledge 438 of the shuttling element 320, can be selected to adjust the desired retention force of the shuttling element coupler 402 of the needle 318 within the cavity 432 of the shuttling element 320 (i.e., the minimum force require to prevent the shuttling element engagement 412 of the needle 318 from disengaging the shuttling element 320). In this manner, abutment between the ledge 420 of the shuttling element coupler 402 and the ledge 438 of the shuttling element 320 may prevent removal of the shuttling element coupler 402 from the cavity 432 in response to a relatively small opposing force (e.g., a slight frictional force applied on the shuttling element 320 by the walls of the shuttling element retention cavity 388 in response to transitioning the needle 318 from the first distal position towards the proximal position), while allowing removal of the shuttling element coupler 402 from the cavity 432 in response to a larger force (e.g., the force applied to the shuttling element 320 by the abutment between the proximal edge 426 of the shuttling element 320 and the latch 392 (shown in FIG. 61) in response to transitioning the needle 318 from the second distal position towards the proximal position). In the illustrated embodiment of the shuttling element 320 shown in FIG. 59, the needle engagement portion 422 comprises a pair of opposing cutouts 440 to decrease the amount of insertion force required for the shuttling element engagement 412 to be located in the cavity 432 of the shuttling element 320, and to decrease the retention force required for the shuttling element engagement 412 to be removed from the cavity 432.

Figure 67:
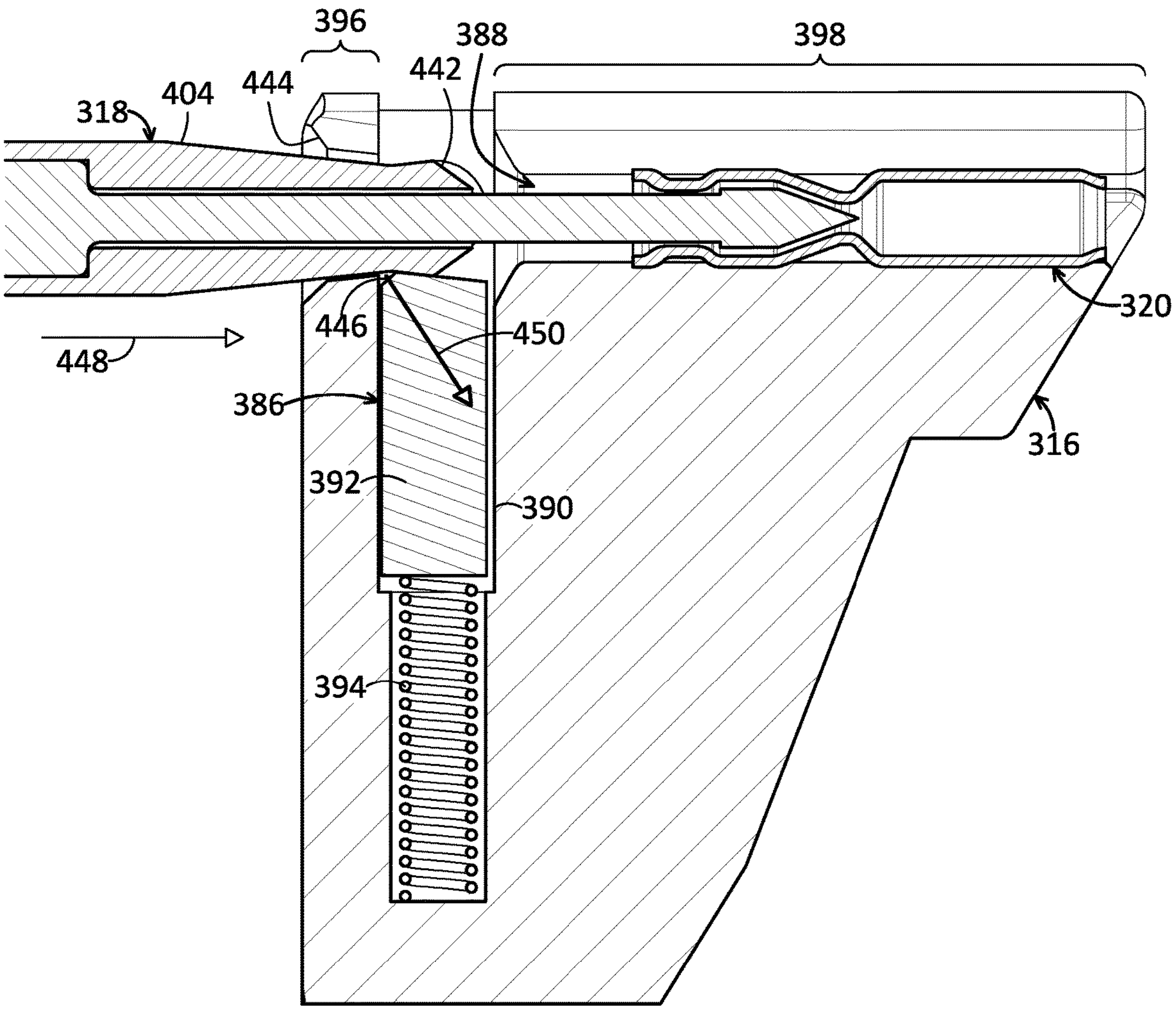
FIG. 67 is a longitudinal sectional view of the clamp arm of FIG. 50 and the needle of FIG. 56, particularly showing the needle engaged with the shuttling element.

As will be described in further detail below, the slidable sleeve 404 (as shown in FIG. 67) is configured for cooperating with the shuttling element retainer mechanism 386 to transition the latch 392 from the deployed state to the recessed state in opposition to the biasing force of the spring 394, thereby allowing the shuttling element coupler 402 to remove the shuttling element 320 from the shuttling element retention cavity 388 and decouple the shuttling element 320 from the clamp arm 316 when the needle 318 is transitioned from the first distal position toward the proximal position.

As best illustrated in FIGS. 65-66, the sleeve 404 is configured for sliding along the needle shaft 400 upward along arrow 438. Referring further to FIG. 67, the stop 418 of the needle 318 is configured for abutting the slidable sleeve 404 (shown in FIG. 66) to forcibly insert the slidable sleeve 404 into the proximal chamber 396 of the shuttling element retention cavity 388 (i.e., apply enough axial force to the slidable sleeve 404 to overcome the frictional forces applied to the slidable sleeve 404 by the proximal chamber 396). In the illustrated embodiment shown in FIG. 67, the slidable sleeve 404 and proximal chamber 396 have corresponding chamfered edges 442, 444 that engage each other to facilitate insertion of the slidable sleeve 404 into the proximal chamber 396. Forcible insertion of the slidable sleeve 404 further into the proximal chamber 396 urges the latch 392 of the shuttling element retainer mechanism 386 downward into the latch cavity 390 from the deployed state to the recessed state. The latch 392 has a proximal chamfered edge 446 that engages the chamfered edge 442 of the slidable sleeve 404 to redirect the axial force (shown by the arrow 448) applied by the slidable sleeve 404 to an oblique force (shown by the arrow 450) that urges the latch 392 downward into the latch cavity 390. Because the sleeve 404 is slidable relative to the needle shaft 400, the sleeve 404 is configured for maintaining the latch 392 in the recessed state to facilitate removal of the shuttling element 320 from the shuttling element retention cavity 398, and thus, decoupling of the shuttling element 320 from the clamp arm 316. Furthermore, the slidability of the sleeve 404 relative to the needle shaft 400 allows the shuttling element 320 to be reinserted into the shuttling element retention cavity 398 without inserting the sleeve 404 into the proximal chamber 396, thereby recoupling the shuttling element 320 to the clamp arm 316.

Referring to FIGS. 68A-68G, the interaction between the specific features of the clamp arm 316, needle 318, and shuttling element 320 will be described. When the clamp arm 316 is in the retracted state and the needle 318 is in the proximal position, the latch 392 of the shuttling element retainer mechanism 386 is in the deployed state within the shuttling element retention cavity 388 (biased by the spring 394), the slidable sleeve 404 is at a neutral position (somewhere between its most proximal position and most distal position, and the shuttling element 320 is retained within the distal chamber 398 of the shuttling element retention cavity 388 (shown in FIGS. 55 and 61-62) in a neutral position (somewhere between its most proximal position and its most distal position) (see FIG. 68A).

Figure 68A:
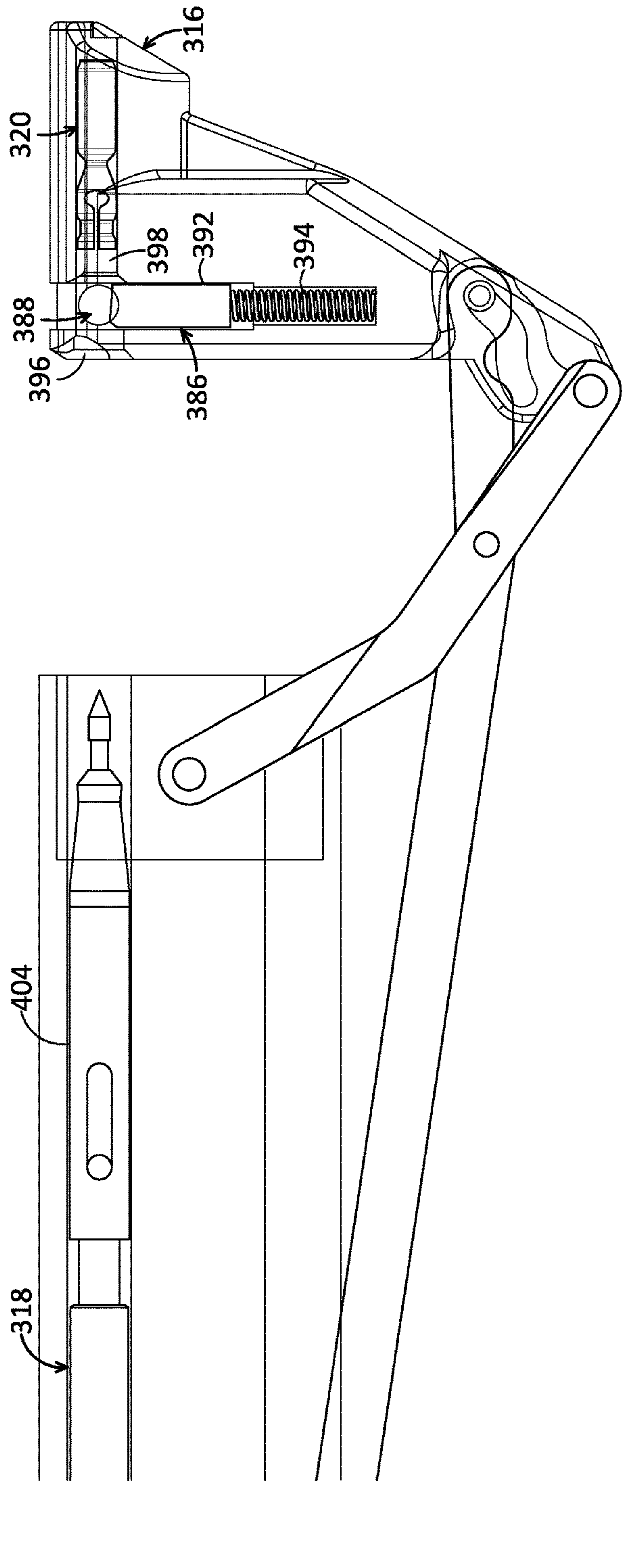
FIGS. 68A-68J are profile views of the distal end of the laparoscopic tissue suturing instrument of FIG. 1, particularly showing a sequence used to decouple the shuttling element from the clamp arm and recouple the shuttling element to the arm.
Figure 68B:
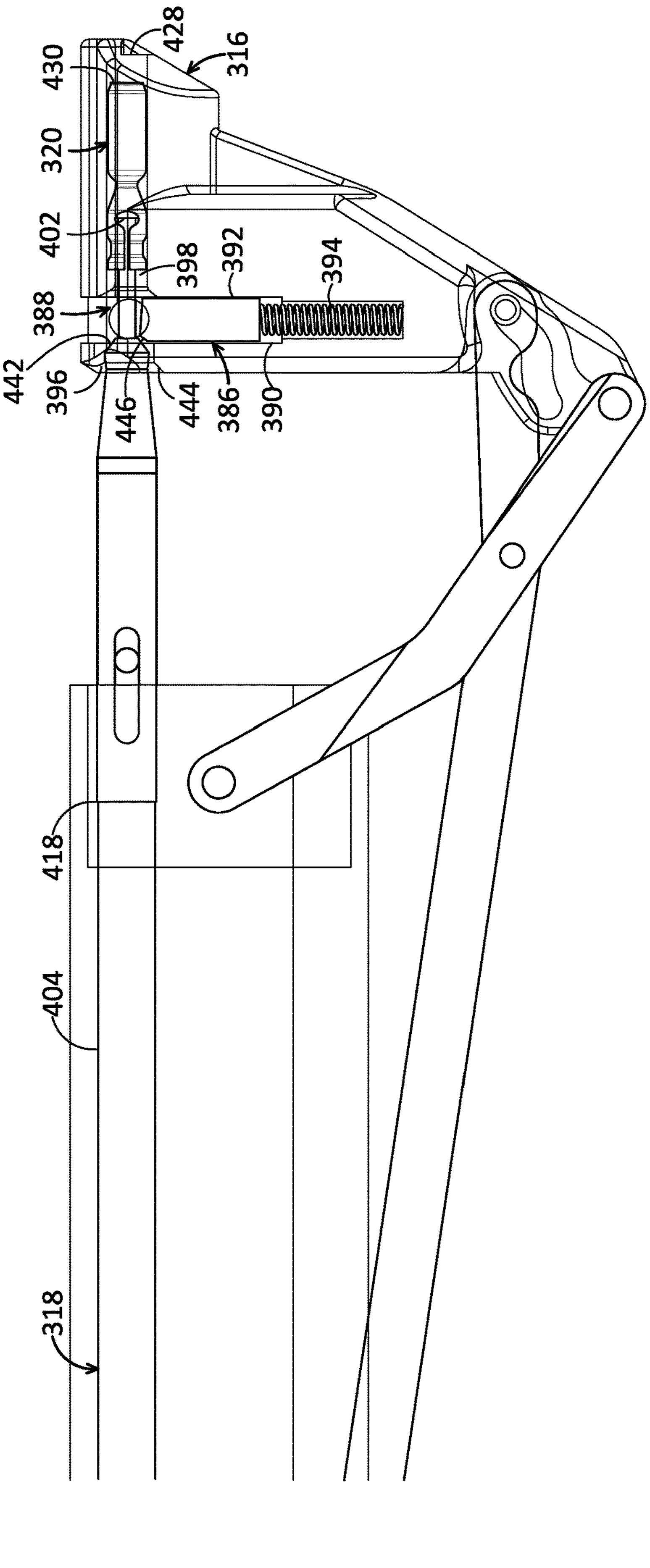

As the needle 318 is transitioned from the proximal position towards the first distal position, the needle 318 is translated toward the clamp arm 316, such that the shuttling element coupler 402 passes through the proximal chamber 396 and inserted into the cavity 432 of the shuttling element 320, thereby engaging the shuttling element 320 with the needle 318, while the slidable sleeve 404 is inserted into the proximal chamber 396 until the chamfered edge 442 of the slidable sleeve 404 contacts the proximal chamfered edge 446 of the latch 392 (see FIG. 68B). It should also be appreciated that, in the case where the slidable sleeve 404 is not at its most proximal position in contact with the stop 418, the slidable sleeve 404 will slide proximally along the needle shaft 400 in response to contact with the chamfered edge 444 of the proximal chamber 396 until the slidable sleeve 404 abuts the stop 418. The shuttling element coupler 402 fits within the cavity 432 of the shuttling element 320, such that translation of the needle 318 correspondingly translates the shuttling element 320 to which it is engaged.

Although, at this point, the shuttling element coupler 402 is shown as being inserted into the cavity 432 of the shuttling element 320, at times, the shuttling element coupler 402 may be passed into the distal chamber 398 without being inserted into the cavity 432 of the shuttling element 320 (e.g., if the shuttling element 320 is disposed more distally in the distal chamber 398 or if the force required to insert the shuttling element coupler 402 into the cavity 432 of the shuttling element 320 is greater than the frictional force between the shuttling element 320 and the distal chamber 398). In this case, the shuttling element coupler 402 will push the shuttling element 320 further into the distal chamber 398 until the distal edge 430 of the shuttling element 320 abuts the inner annular ledge 428 at the distal end of the shuttling element retention cavity 388, after which, such abutting force allows the shuttling element coupler 402 to be inserted into the cavity 432 of the shuttling element 320.

Furthermore, although the relatively small profile of the shuttling element coupler 402 may pass though the proximal chamber 396 without contacting the latch 392, in some cases, the shuttling element coupler 402 may contact the proximal chamfered edge 446 of the latch 392 (e.g., if the shuttling element coupler 402 has a larger profile or if the latch 392 impinges further into the proximal chamber 396), such that the latch 392 is at least slightly translated downward into the latch cavity 390 to provide clearance for the shuttling element coupler 402 as it passes though the proximal chamber 396 and into the distal chamber.

Figure 68C:
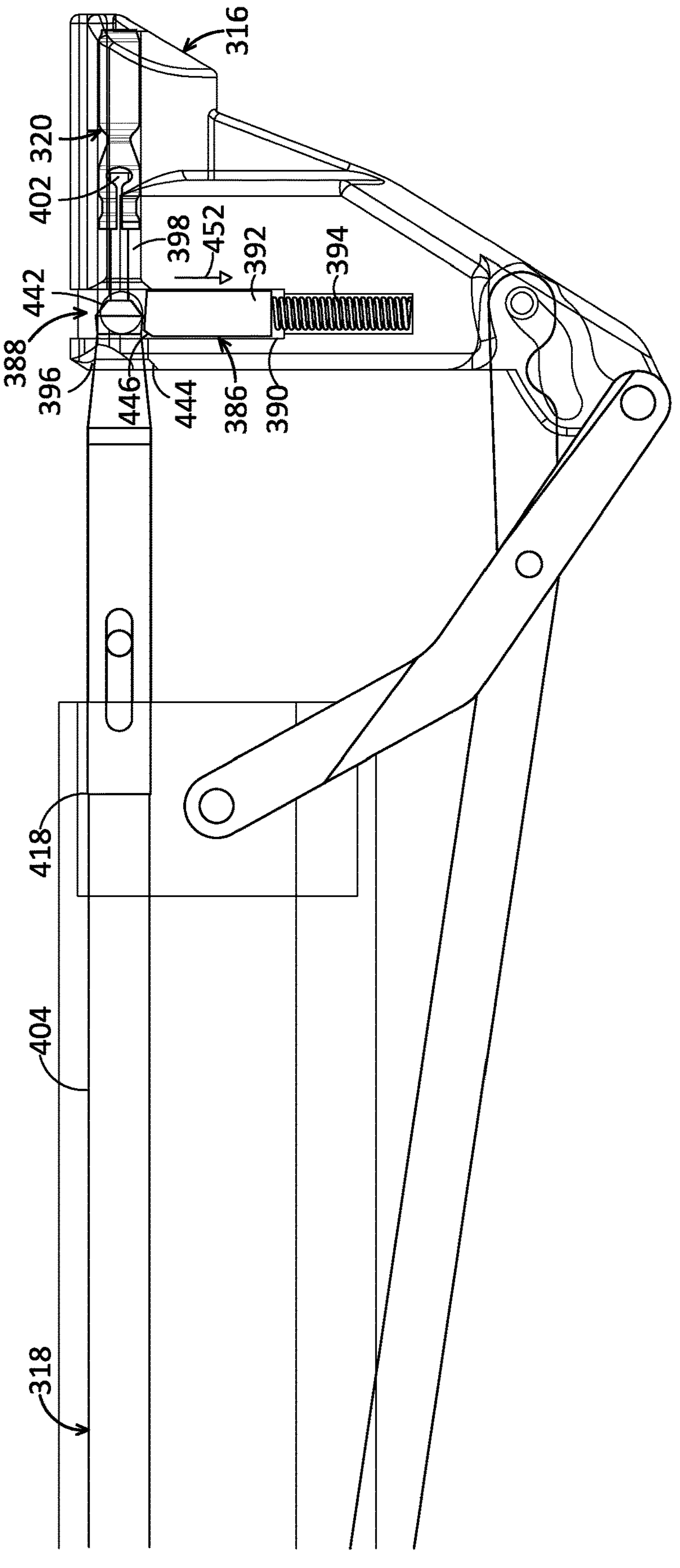

The needle 318 is further translated towards the first distal position, thereby causing the slidable sleeve 404 to urge the latch 392 downward from the deployed state into the recessed state within the latch cavity 390, thereby transitioning the shuttling element retention cavity 388 from the retention state to the release state (FIG. 68C). The stop 418 of the needle 318 forces the slidable sleeve 404 to exert sufficient axial force on the latch 392 to urge it downward (shown by the arrow 452) into the latch cavity 390 against the biasing force of the spring 394. That is, the chamfered edge 442 of the slidable sleeve 404 engages the proximal chamfered edge 446 of the latch 392, which redirects the axial force applied by the slidable sleeve 404 to an oblique force to urge the latch 392 downward into the latch cavity 390. Significantly, translation of the shuttling element coupler 402 within the distal chamber 398 causes the shuttling element 320 to be pushed towards the distal end of the shuttling element retention cavity 388, thereby allowing clearance for the needle 318 to insert the slidable sleeve 150 into the proximal chamber 396 and urge the latch 392 downward from the deployed state into the recessed state within the latch cavity 390.

Figure 68D:
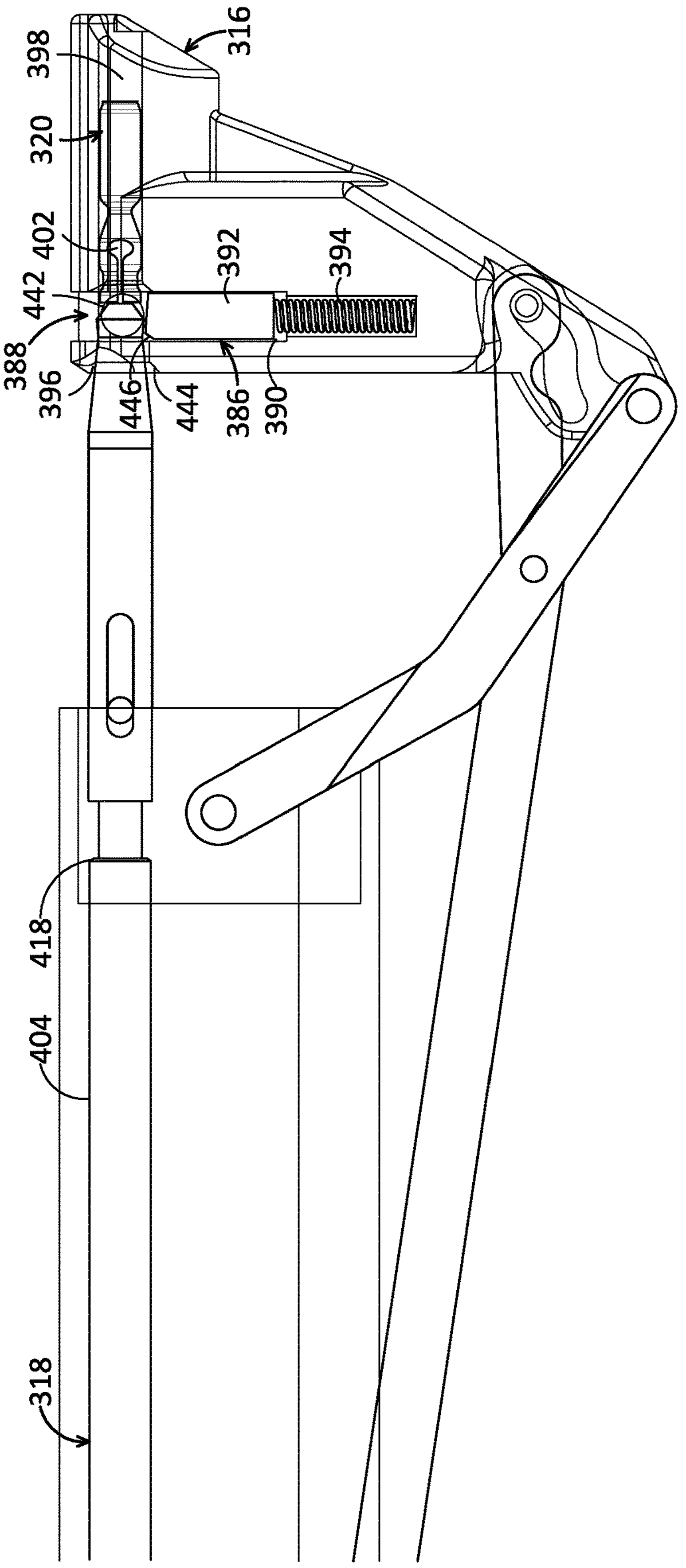

As the needle 318 is transitioned from the first distal position back towards the proximal position, the shuttling element coupler 402 pulls the shuttling element 320 (via abutting engagement between the ledge 420 of the shuttling element coupler 402 and the ledge 438 of the shuttling element 320 (shown best in FIG. 64)) partially out of the distal chamber 398 until the proximal edge 426 of the shuttling element 320 abuts the chamfered edge 442 of the slidable sleeve 404 (see FIG. 68D). As the needle 318 is transitioned from the first distal position back towards the proximal position, the sleeve 404 slides along the needle shaft 400, such that the sleeve 404 remains within the proximal chamber 396 to maintain the latch 392 in its recessed state (i.e., within the latch cavity 390).

Figure 68E:
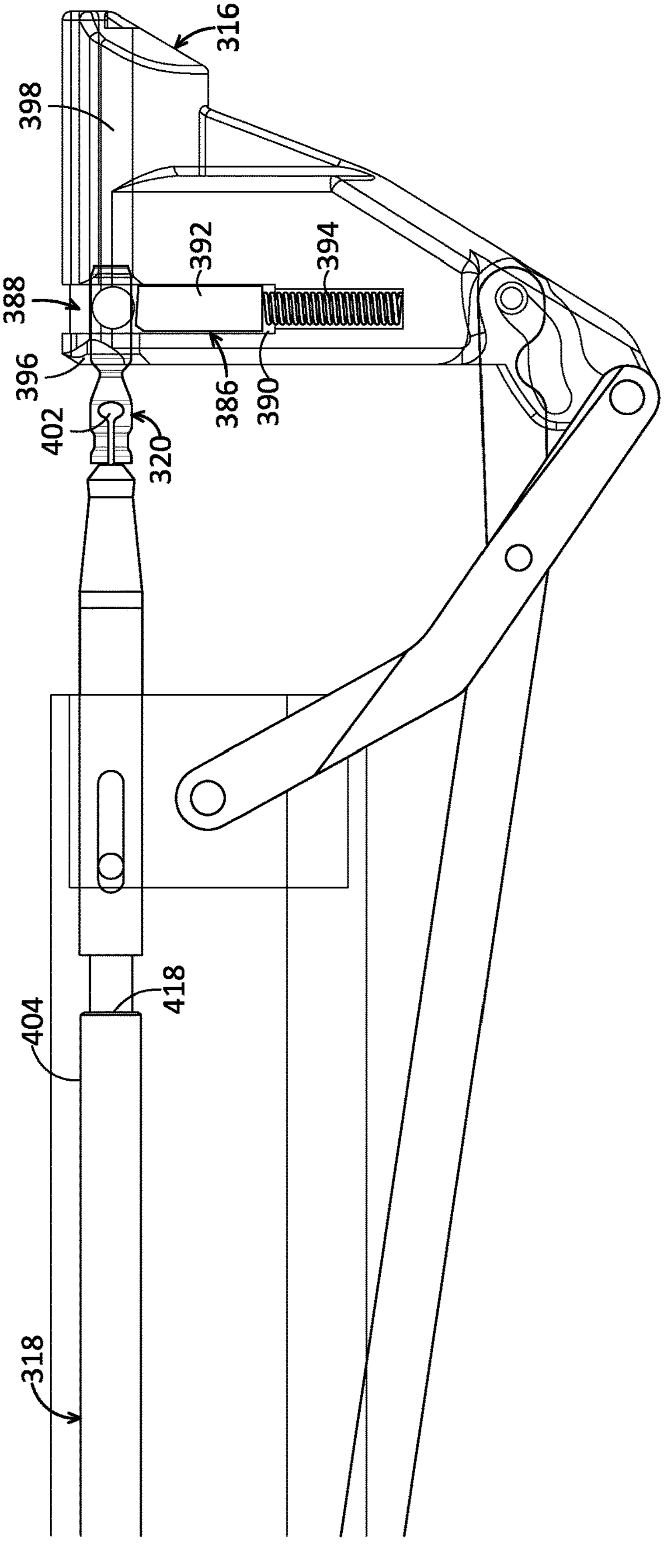

As the needle 318 is further transitioned toward the proximal position, the shuttling element coupler 402 pulls the shuttling element 320 (via abutting engagement between the ledge 420 of the shuttling element coupler 402 and the ledge 438 of the shuttling element 320 (shown best in FIG. 64)) completely from the distal chamber 398, past the recessed latch 392, and into the proximal chamber 396, while pushing the slidable sleeve 404 out of the proximal chamber 396 via abutting engagement between the proximal edge 426 of the shuttling element 320 and the chamfered edge 442 of the slidable sleeve 404 (see FIG. 68E).

Figure 68F:
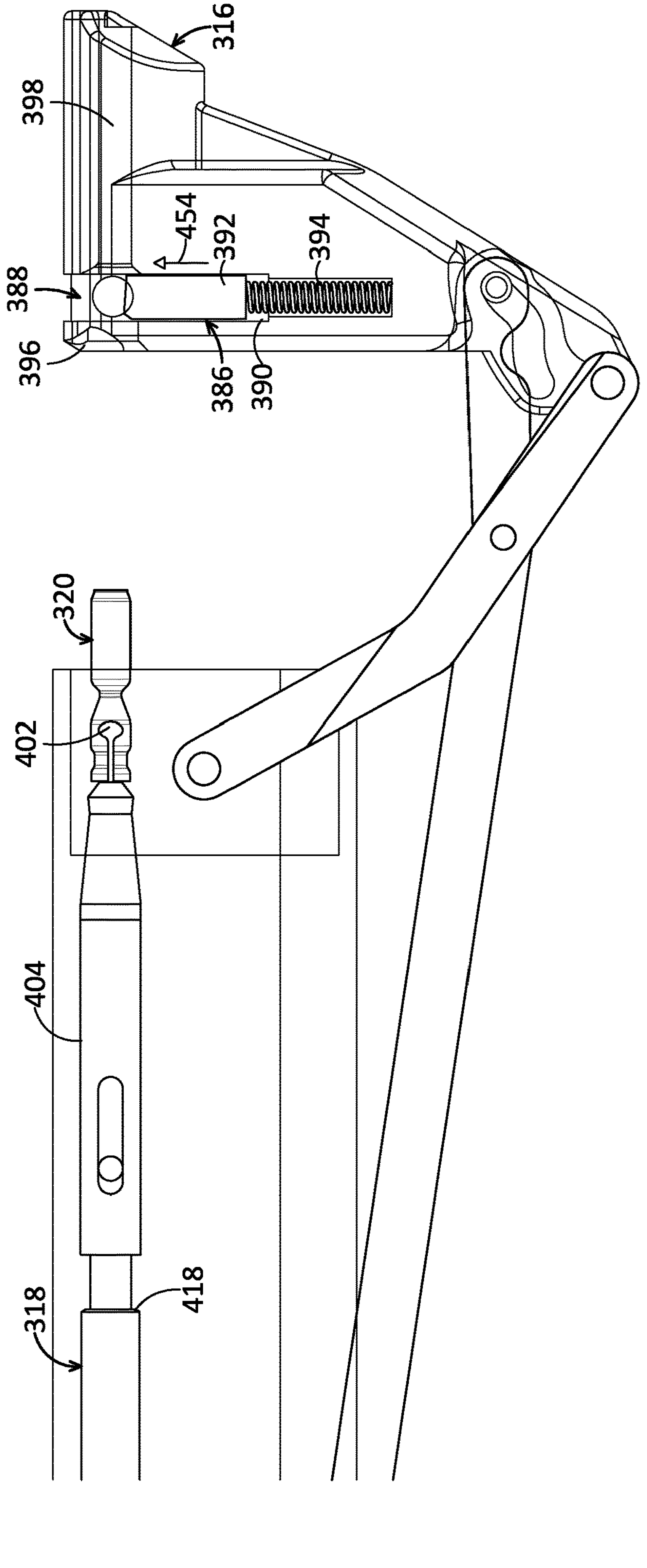

As the needle 318 is further transitioned to the proximal position, the shuttling element coupler 402 completely removes the shuttling element 320 from the shuttling element retention cavity 388, thereby decoupling the shuttling element 320 from the clamp arm 316, and allowing the latch 392 to be transitioned back from the recessed state to the deployed state within the proximal chamber 396 via the biasing force of the spring 394 (shown by arrow 454) (see FIG. 68F).

Figure 68G:
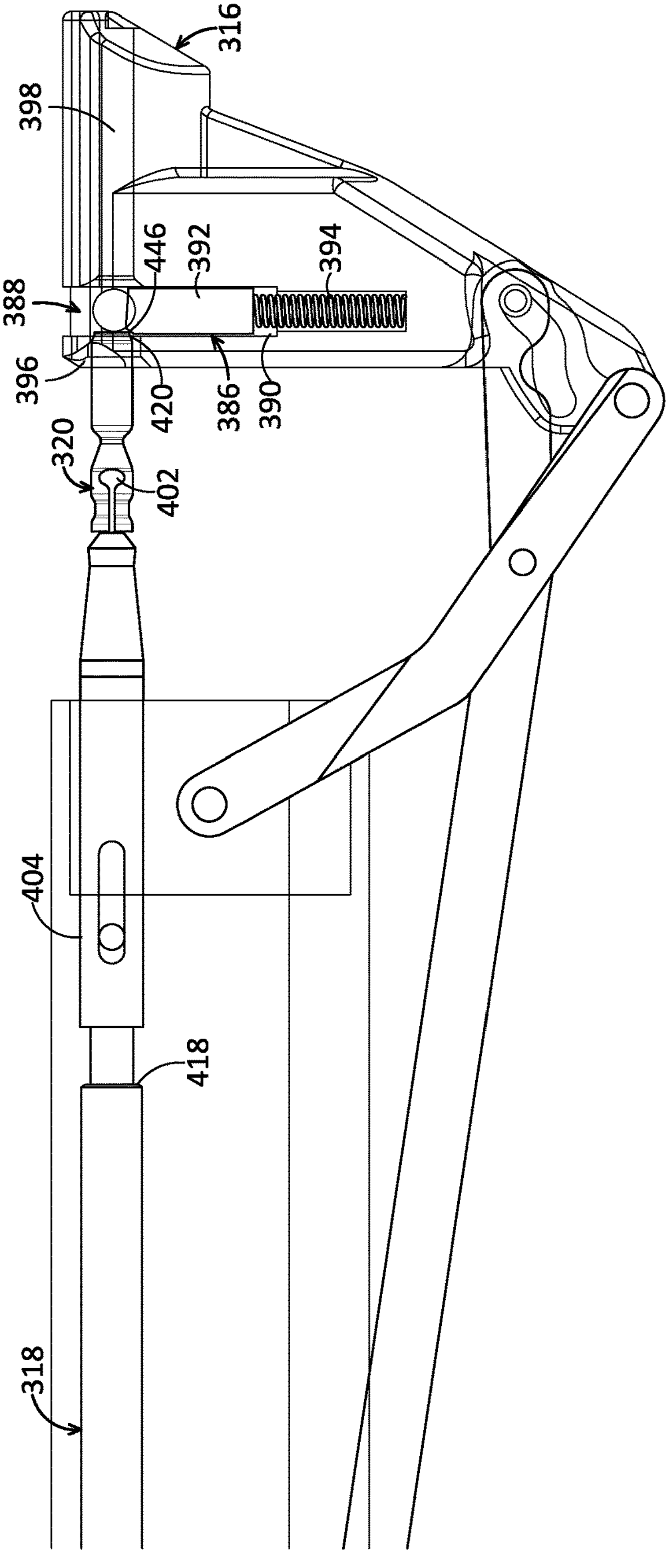

As the needle 318 is transitioned from the open state back towards the second distal position, the shuttling element 320 is inserted into the proximal chamber 396 (see FIG. 68G). The outer diameter of the shuttling element 320 is less than the diameter of the proximal chamber 396. In this manner, the shuttling element 320 may be easily inserted into the proximal chamber 396.

Figure 68H:
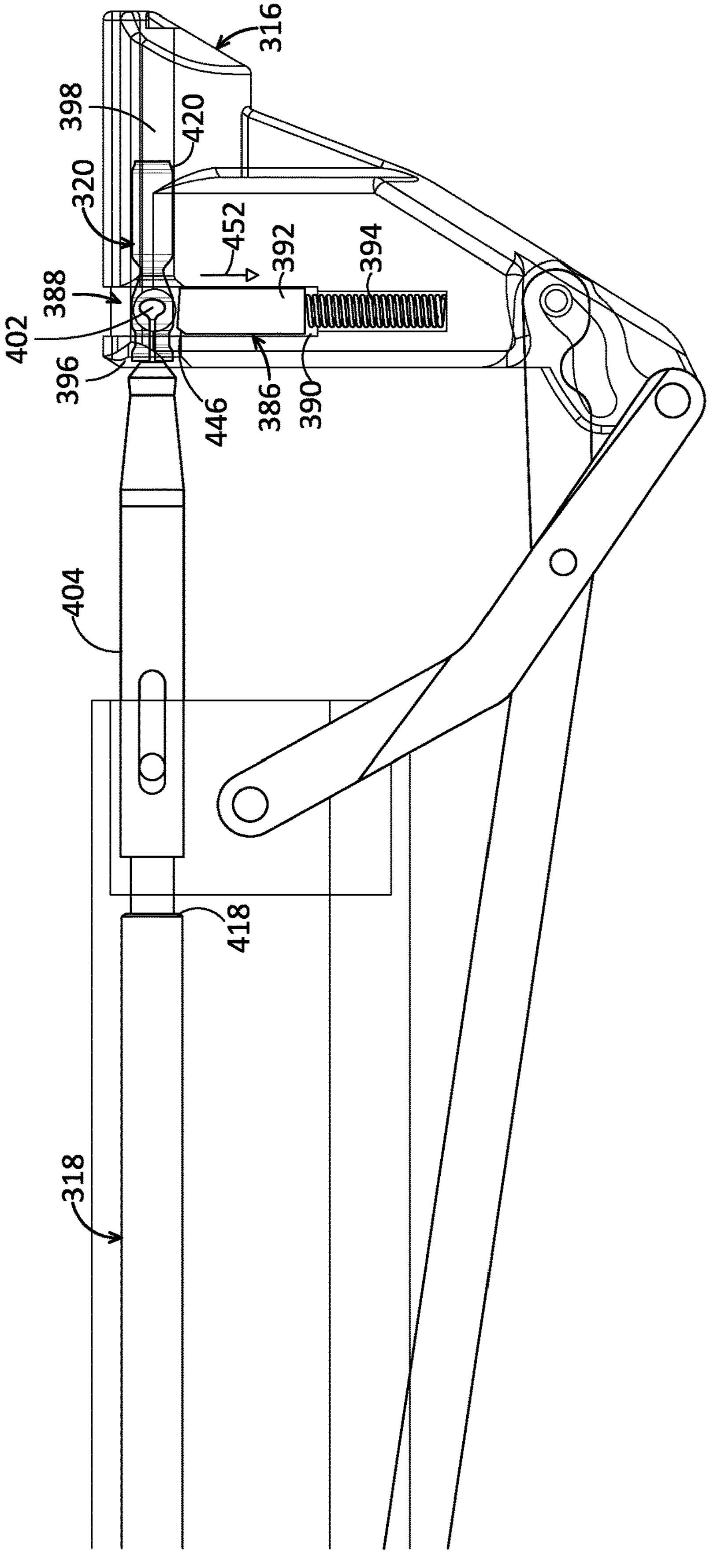
Figure 68I:
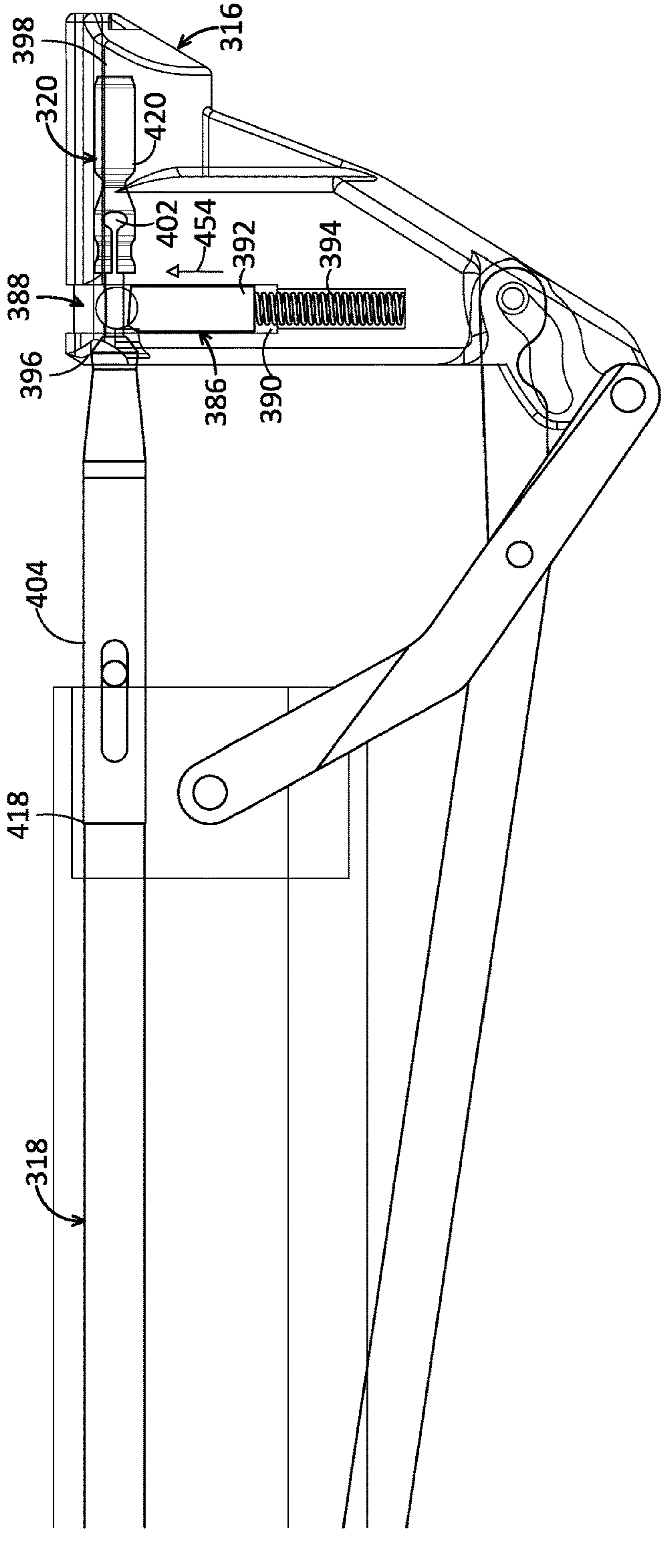

As the needle 318 is further transitioned into the second distal position, the shuttling element coupler 402 pushes the shuttling element 320 through the proximal chamber 396 and into the distal chamber 398, thereby recoupling the shuttling element 320 to the clamp arm 316. In order to pass from the proximal chamber 396 to the distal chamber 398, the chamfered edge 430 of the shuttling element 320 momentarily urges the latch 392 downward into the latch cavity 390. That is, in much the same way that the chamfered edge 442 of the slidable sleeve 404 engages the proximal chamfered edge 446 of the latch 392 to redirect the axial force applied by the slidable sleeve 404 to an oblique force to urge the latch 392 downward into the latch cavity 390 against the biasing force of the spring 394 (as described above with respect to FIG. 68C), the chamfered edge 430 of the shuttling element 320 engages the proximal chamfered edge 446 of the latch 392 (shown best in FIG. 68G) to redirect the axial force applied by the shuttling element 320 shuttling element 320 to an oblique force to urge the latch 392 downward (shown by the arrow 452) into the latch cavity 390 against the biasing force of the spring 394 (see FIG. 68H). As the shuttling element 320 passes completely into the distal chamber 398, the latch 392 is transitioned back from the recessed state to the deployed state within the proximal chamber 396 via the biasing force of the spring 394 (shown by arrow 454), thereby transitioning the shuttling element retention cavity 388 from the release state back to the retention state (see FIG. 68I). While the shuttling element 320 is being inserted through the proximal chamber 396 and into the distal chamber 398, the sleeve 404 slides along the needle shaft 400, such that the sleeve 404 does not enter the proximal chamber 396 when the needle 318 is in the second distal position. As long as the needle 318 is not further transitioned from the second distal position towards the first distal position, the sleeve 404 will not be inserted into the proximal chamber 396, and thus, the latch 392 will remain in the deployed state within the shuttling element retention cavity 388.

As the needle 318 is transitioned from the second distal position towards the open state, the shuttling element coupler 402 is removed from the cavity 432 of the shuttling element 320, thereby disengaging the needle 318 from the shuttling element 320 (see FIG. 37J). Notably, the retention force between the ledge 420 of the shuttling element coupler 402 and the ledge 438 of the shuttling element 320 shown best in FIG. 64) is less than the retention force between the deployed latch 392 within the shuttling element retention cavity 388 and the proximal edge 426 of the shuttling element 320 (i.e., the minimum force required to prevent the shuttling element 320 from being translated from the shuttling element retention cavity 388 in the proximal direction via mechanical interference between the proximal edge 426 of the shuttling element 320 and the latch 392). As such, the lower chamber 132 will retain the shuttling element 20 as the shuttling element coupler 402 of the needle 318 is pulled out of the cavity 432 of the shuttling element 320.

Referring to FIGS. 69 and 70A-70K, one exemplary method 500 of using the laparoscopic tissue suturing instrument 310 to perform a post-total laparoscopic hysterectomy (TLH) vaginal cuff suturing procedure on a patient will now be described. It is assumed that the uterus of the patient has been removed (either though a transvaginal hysterectomy or laparoscopic hysterectomy), leaving behind an open vaginal cuff 180 that requires suturing.

Figure 70A:
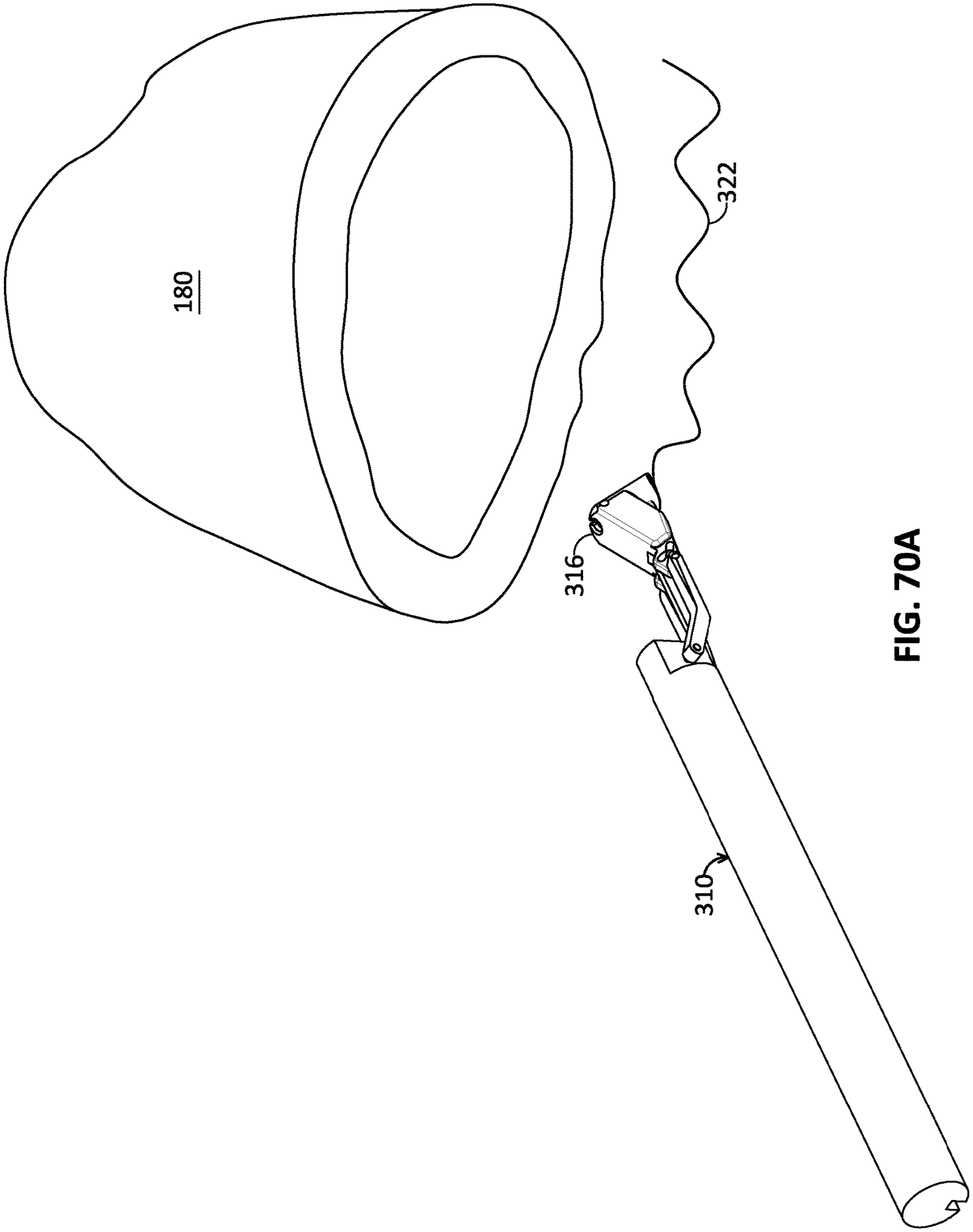
FIGS. 70A-70K are plan views illustrating the method of FIG. 69.
Figure 70B:
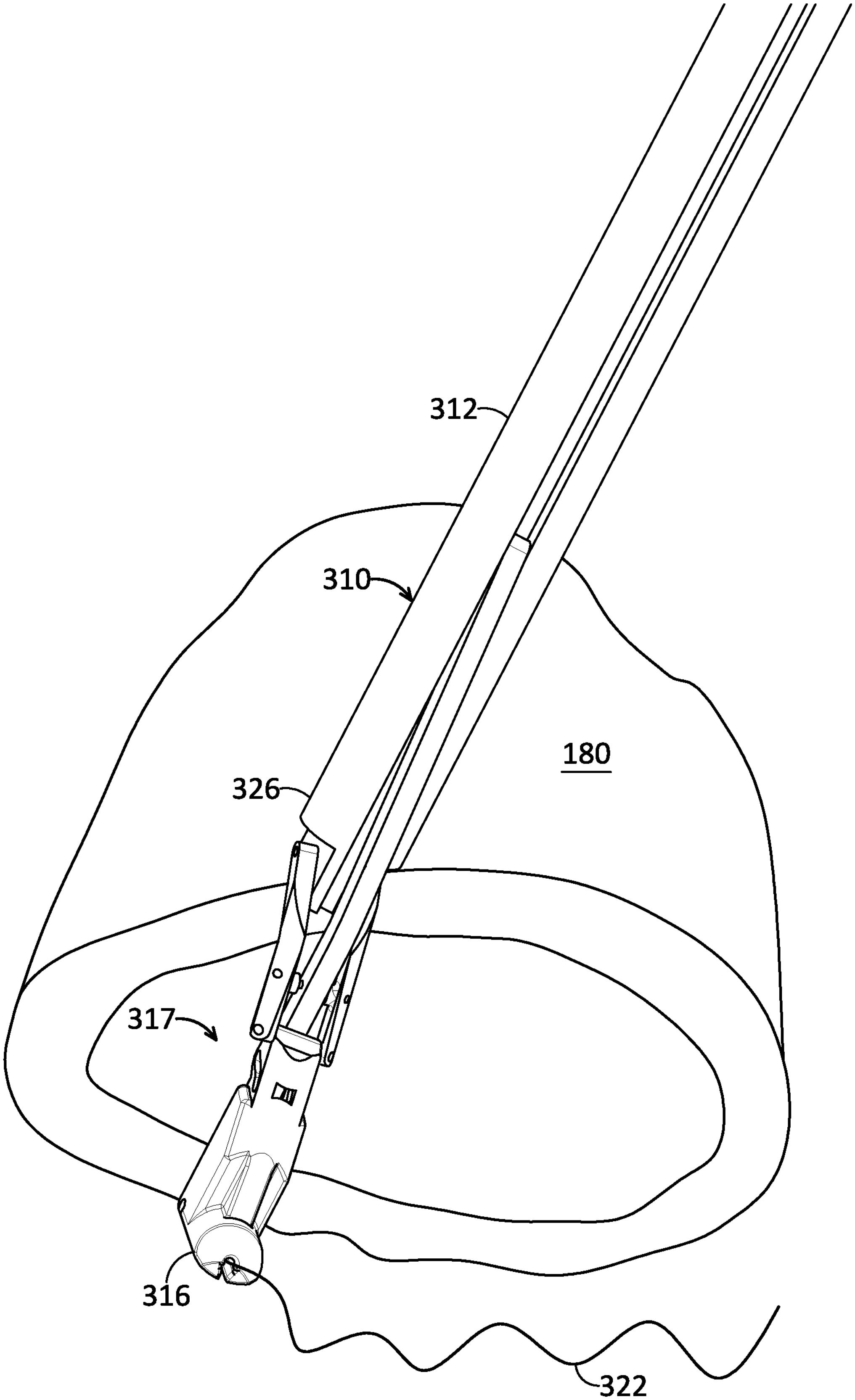
Figure 70C:
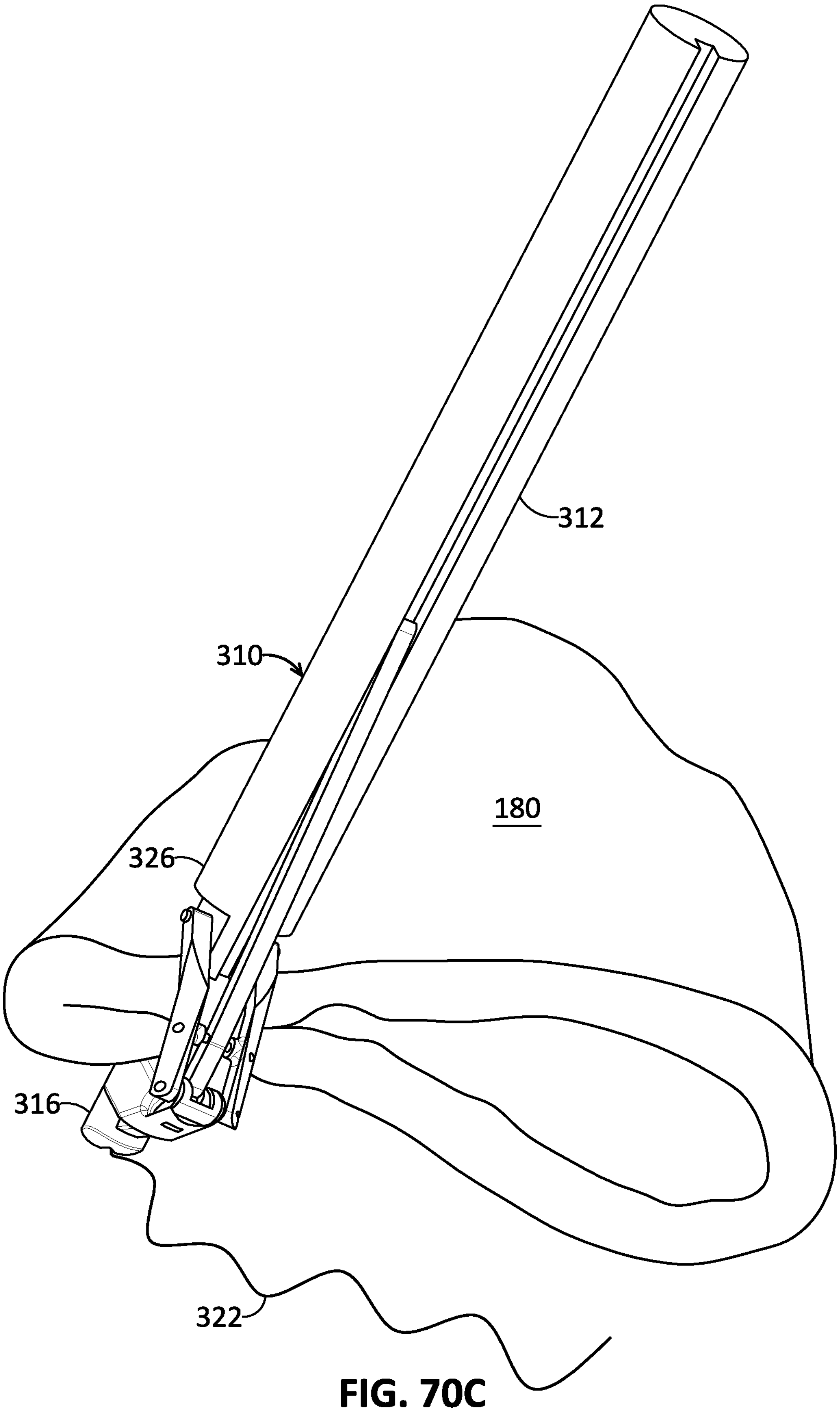
Figure 70D:
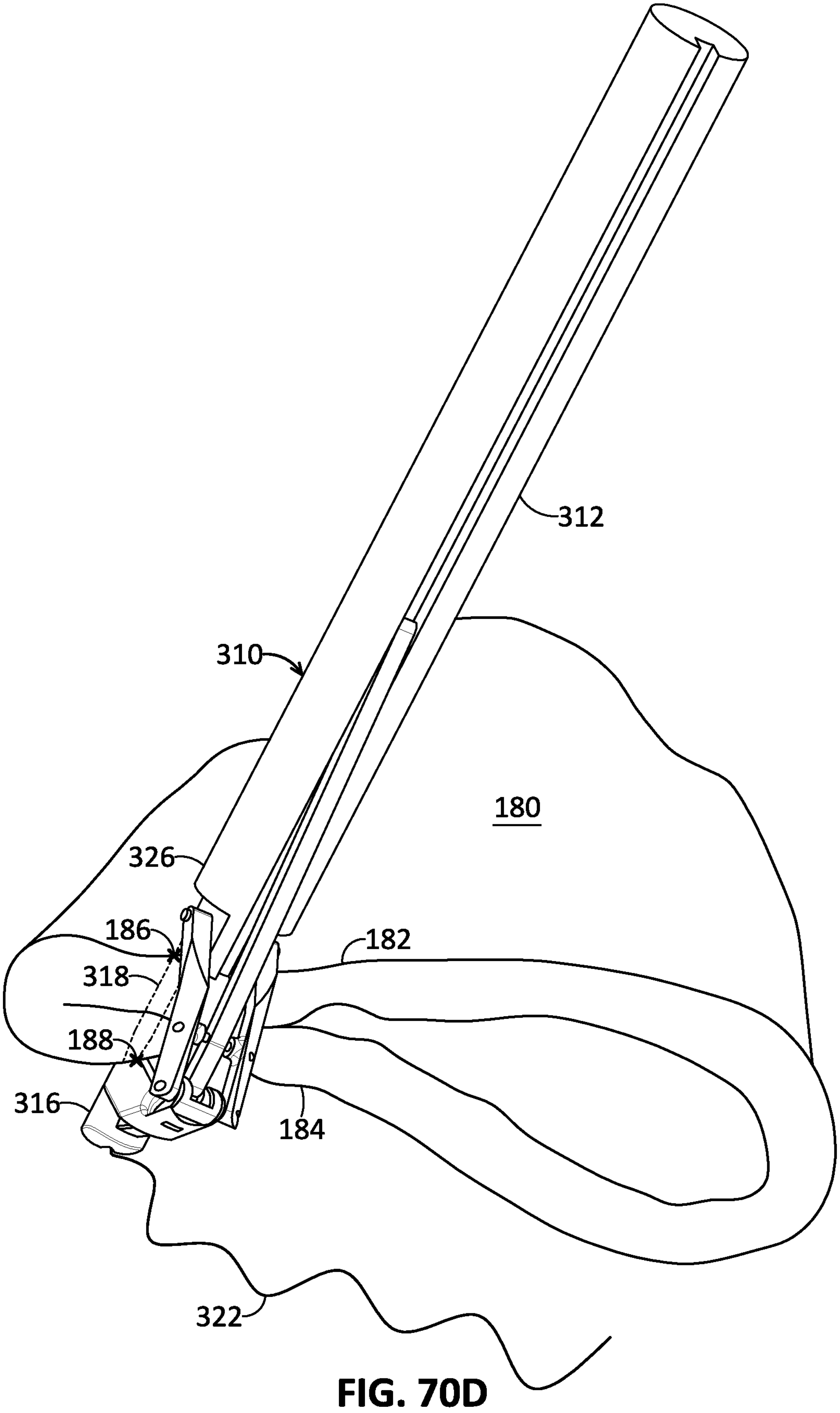
Figure 70E:
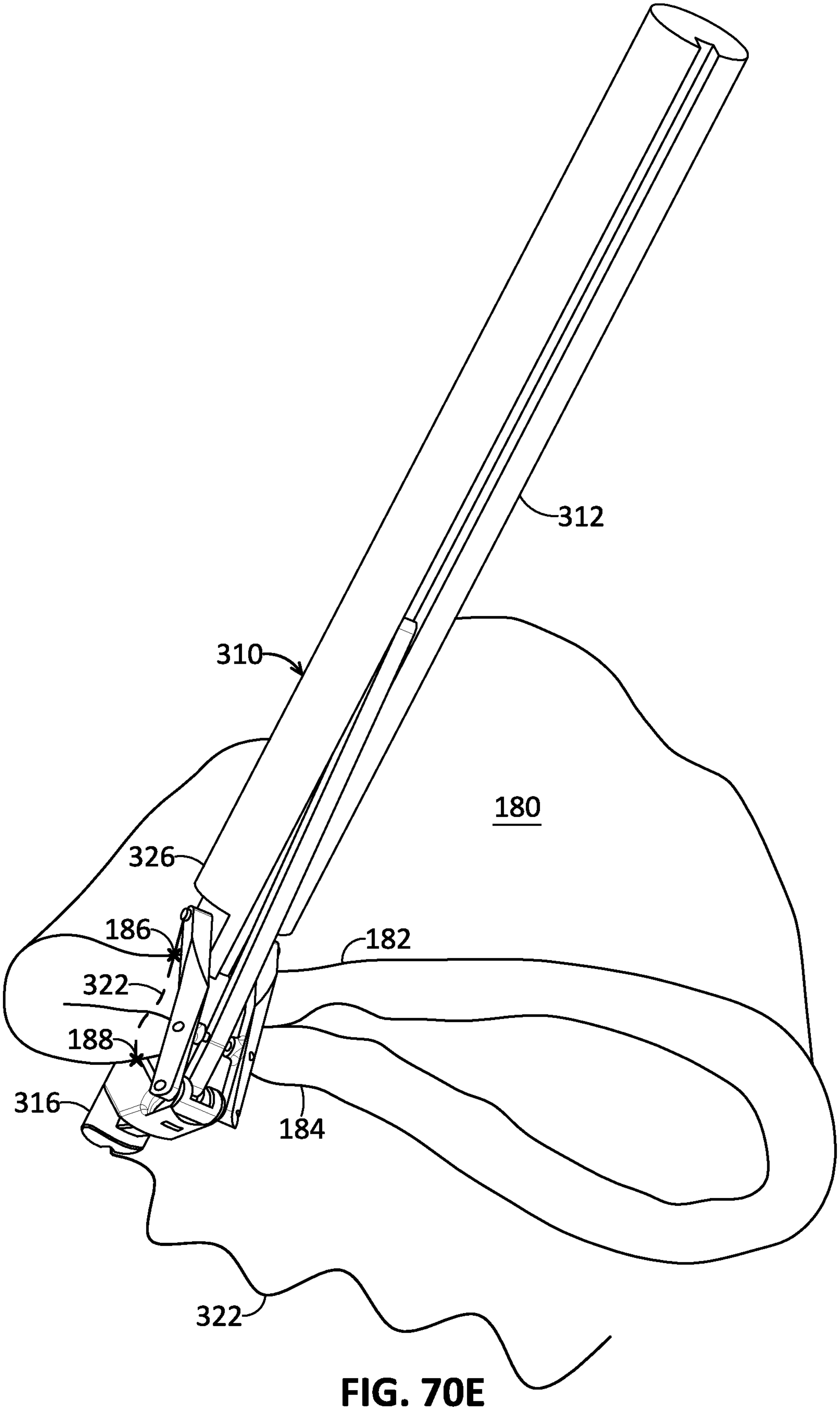
Figure 70F:
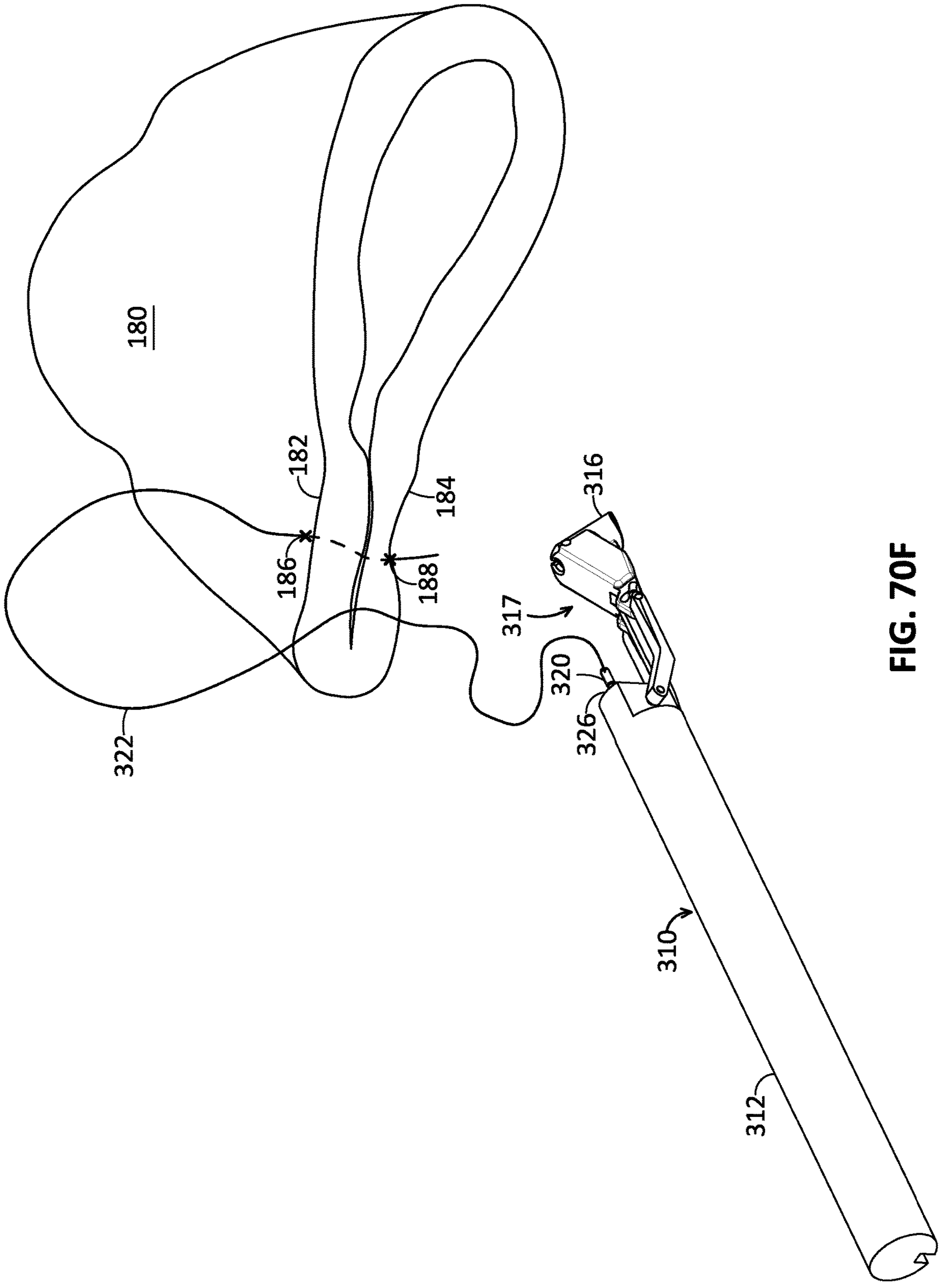
Figure 70G:
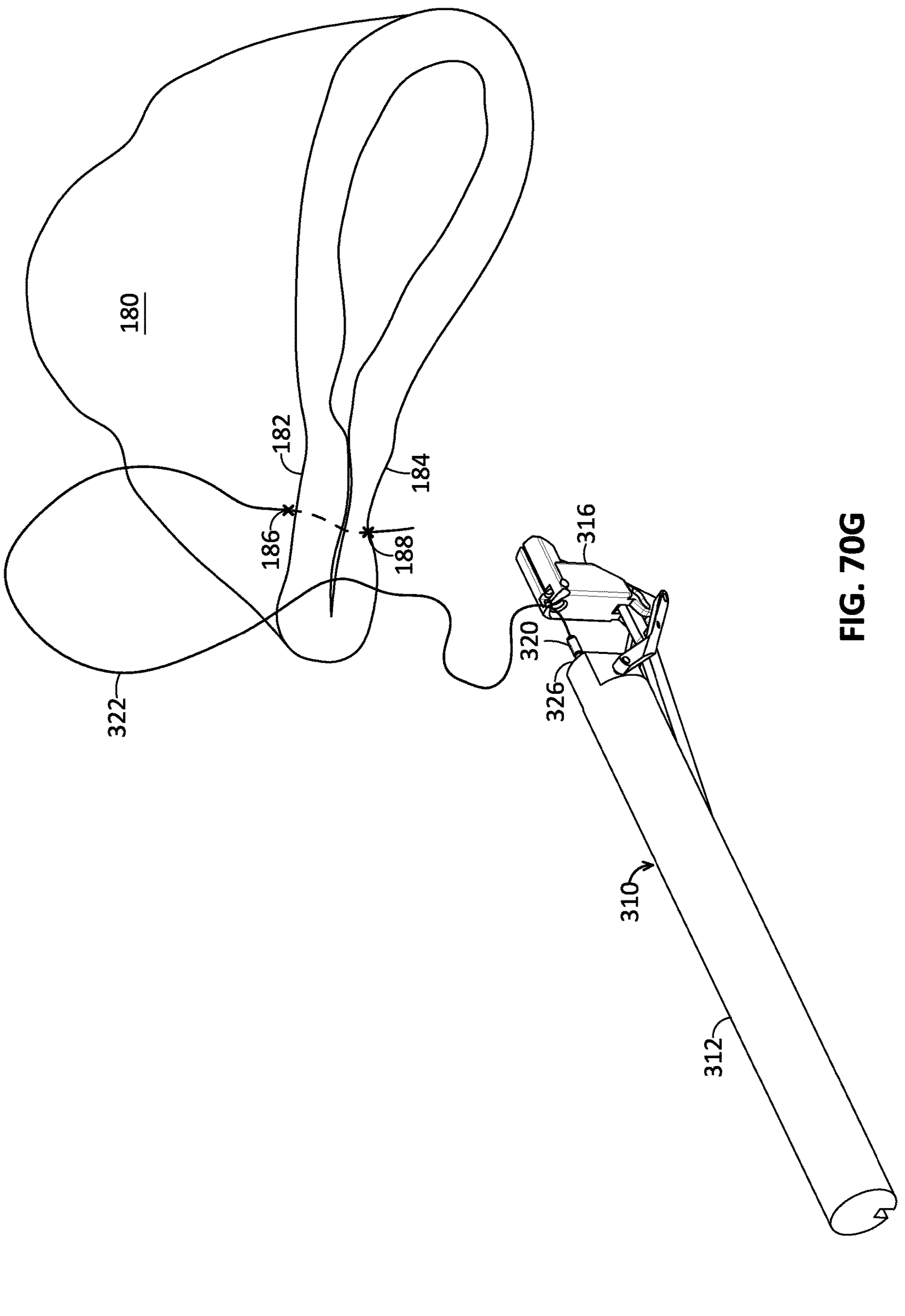
Figure 70H:
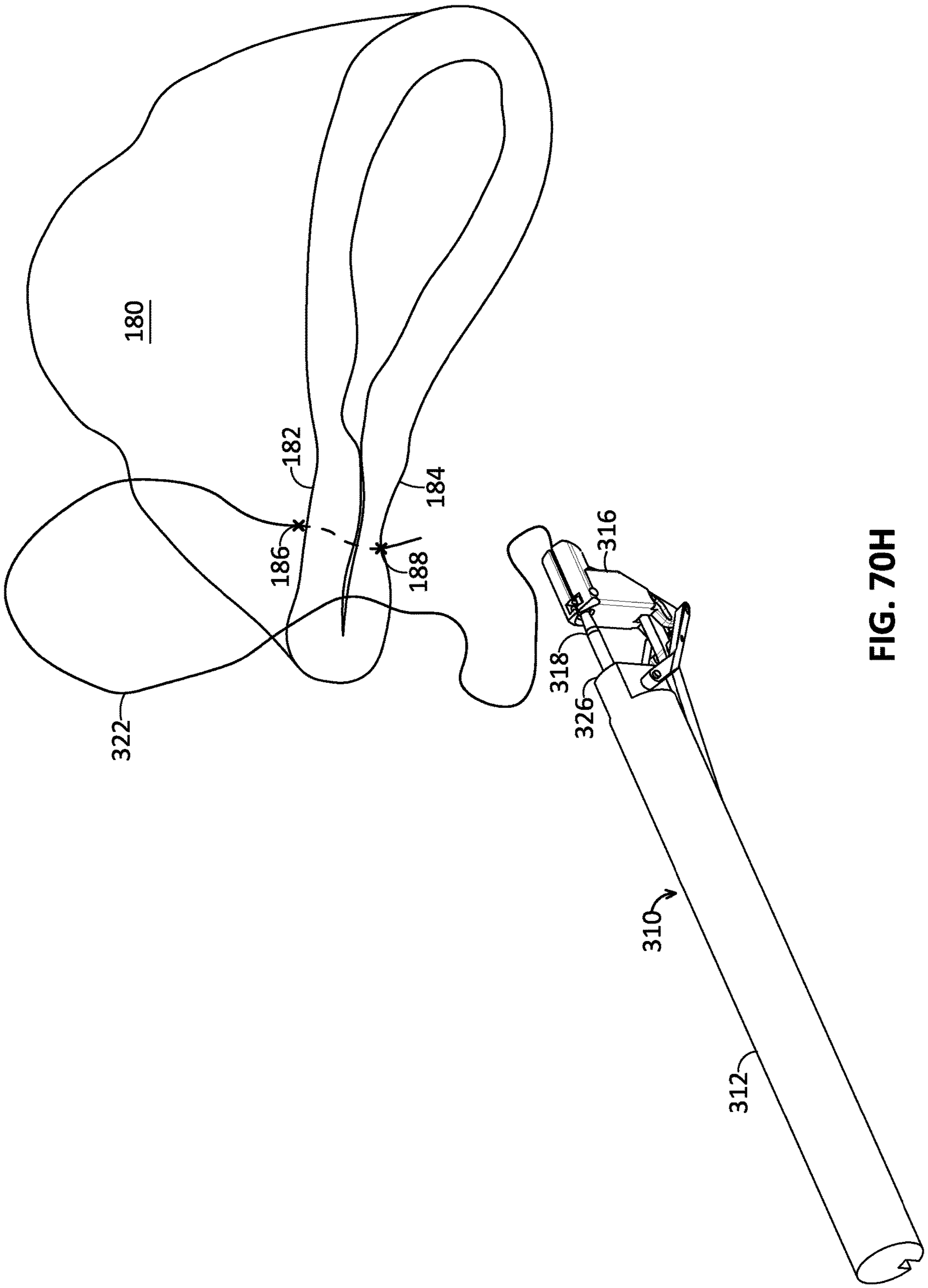
Figure 70I:
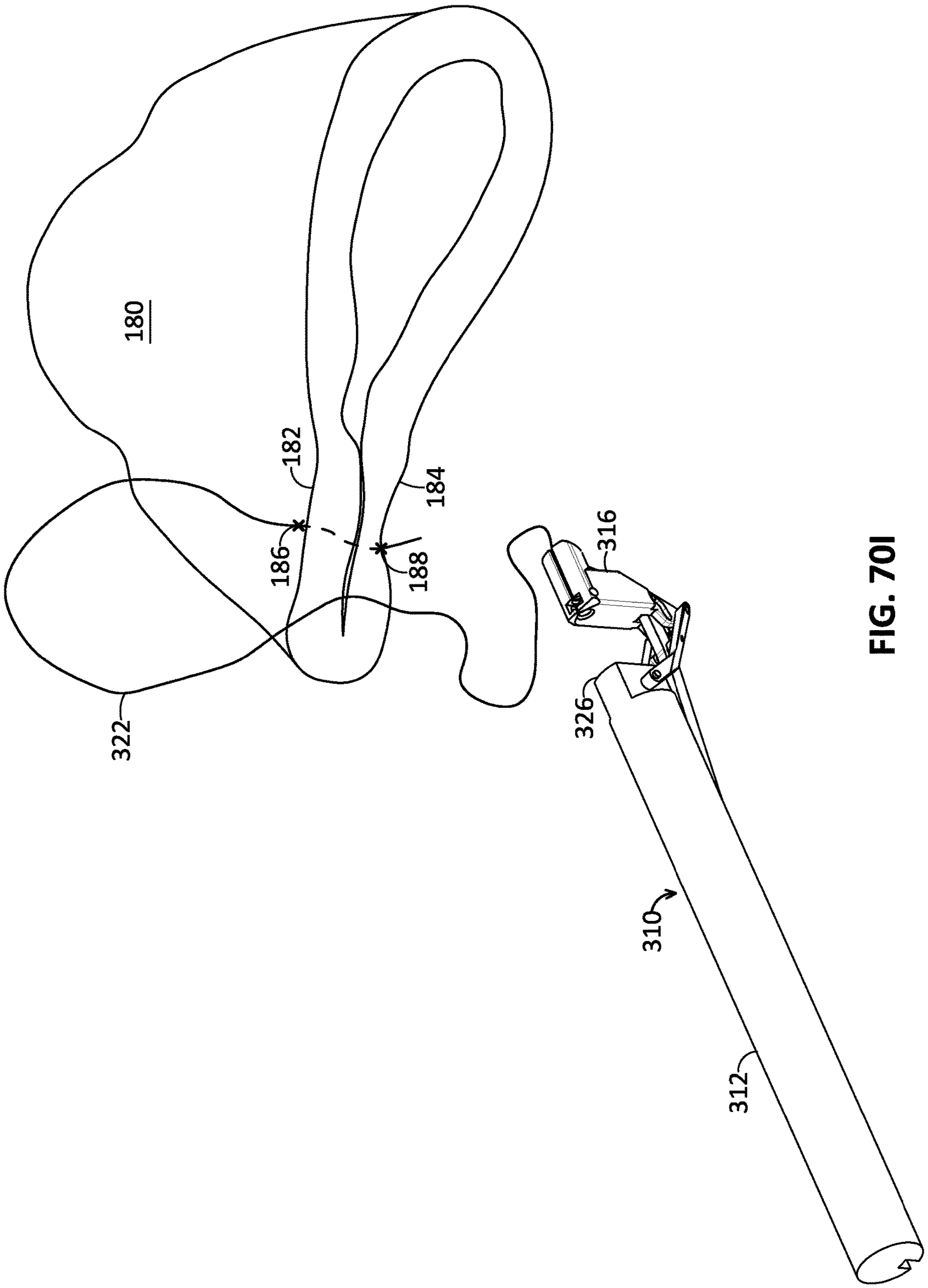

First, the laparoscopic tissue suturing instrument 310, while the clamp arm 316 is in the extended state, is introduced through a conventional laparoscopic port into the insufflated abdomen of the patient (step 502) (see FIG. 70A). Next, the vaginal cuff 180 is positioned within the tissue receiving gap 317 between the clamp arm 316 and the distal end 326 of the rigid shaft 312 (see FIG. 70B) (step 506). Then, the clamp arm 316 is transitioned from the extended state to the retracted state (see FIG. 70C) via manipulation of the rotatable nut 340 (shown in FIG. 40), thereby grasping the vaginal cuff 180 (step 504).

The needle 318 is then transitioned from the proximal position to the first distal position) via manipulation of the pivotable finger piece 342 (shown in FIG. 40), thereby passing the needle 318 (shown in phantom) through the grasped vaginal cuff 180 (and specifically, through a first side 182 of the vaginal cuff 180 via a first entry point 186 and then through a second side 184 of the vaginal cuff 184 via a first exit point 188) and inserting the needle 318 into and engaging the shuttling element 320, and transitioning the latch 392 from the deployed state to the recessed state, thereby transitioning the shuttling element retention cavity 388 of the clamp arm 316 from the retention state to the release state (and specifically, as best illustrated in FIGS. 68A-68C, inserting the shuttling element coupler 402 of the needle 318 into the cavity 432 of the shuttling element 320, and inserting the slidable sleeve 404 into the proximal chamber 396 of the clamp arm 316) (see FIG. 70D) (step 508).

Next, the needle 318 is transitioned from the first distal position back towards the proximal position via manipulation of the pivotable finger piece 342 (shown in FIG. 40), thereby decoupling the engaged shuttling element 320 from the clamp arm 316 (and specifically, as best illustrated in FIGS. 68D-68F) by pulling the shuttling element 320 out of the shuttling element retention cavity 388), allowing the spring 394 to bias the latch 392 from the recessed state into the deployed state within the shuttling element retention cavity 388, thereby transitioning the shuttling element retention cavity 388 from the release state to the retention state, and drawing the suture 322 (shown partially in phantom) through the vaginal cuff 180 (and specifically, back through the second side 184 of the vaginal cuff 182 via the first exit point 188 and then back through first side 182 of the vaginal cuff 180 via the first entry point 186) (see FIG. 70E) (step 510).

Then, the clamp arm 316 is transitioned from the retracted state to the extended state via manipulation of the rotatable nut 340 (shown in FIG. 40) (step 512), and the clamp arm 316 is located, such that the vaginal cuff 180 is not within the tissue receiving gap 317 between the clamp arm 316 and the distal end 326 of the rigid shaft 312 (see FIG. 70F) (step 514). As the clamp arm 316 is located away from the vaginal cuff 180, the clamp arm 316 may be manipulated, such that the suture 322 exits the suture clearance slot 323 (shown in FIGS. 42 and 52). Preferably, the clamp arm 316 is located away from the vaginal cuff 180 a sufficient distance to draw the end of the suture 322 adjacent to the exit point 188 in the vaginal cuff 180. The end of the suture 322 may have a knot or a loop to prevent the end of the suture 322 from entering the exit point 188 in the vaginal cuff 180.

Then, the clamp arm 316 is transitioned from the extended state to the retracted state (see FIG. 70G) via manipulation of the rotatable nut 340 (shown in FIG. 40) (step 516), and the needle 318 is transitioned from the recessed state to the second distal position via manipulation of the pivotable finger piece 342 (shown in FIG. 40), thereby recoupling the engaged shuttling element 320 to the clamp arm 316 (and specifically, as best illustrated in FIGS. 68G-681 by inserting the shuttling element 320 past the deployed latch 392 in the proximal chamber 396, and into the distal chamber 398 without inserting the slidable sleeve 404 into the proximal chamber 396 to maintain the latch 392 in the deployed state within the shuttling element retention cavity 388, and thus, the shuttling element retention cavity 388 in the retention state) (see FIG. 70H) (step 518). Notably, the latch 392 is momentarily transitioned from the deployed state to the recessed state by the passage of the shuttling element 320 through the proximal chamber 396, and then transitioned back from the recessed state to the deployed state by the biasing force of the spring 394 when the shuttling element 320 passes from the proximal chamber 392 into the distal chamber 396.

Figure 68J:
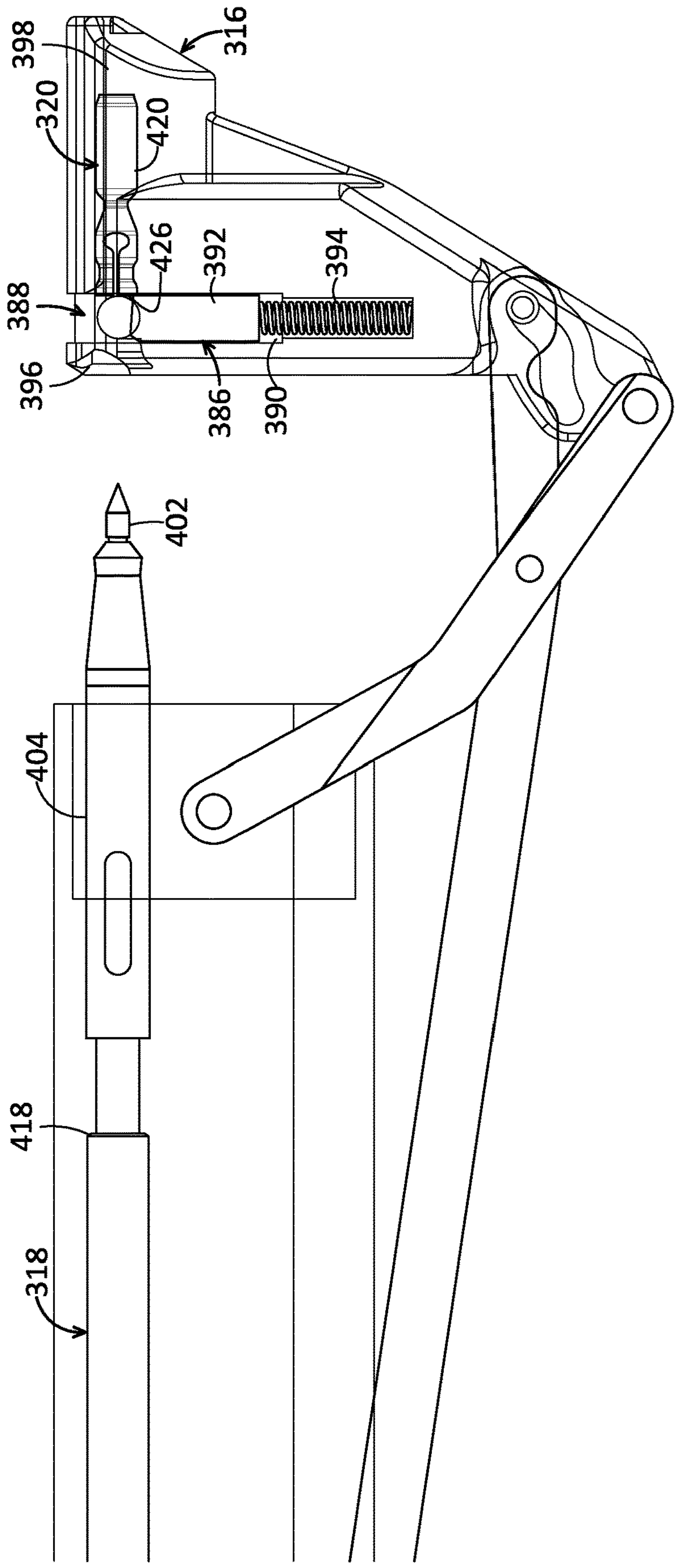
Figure 69:
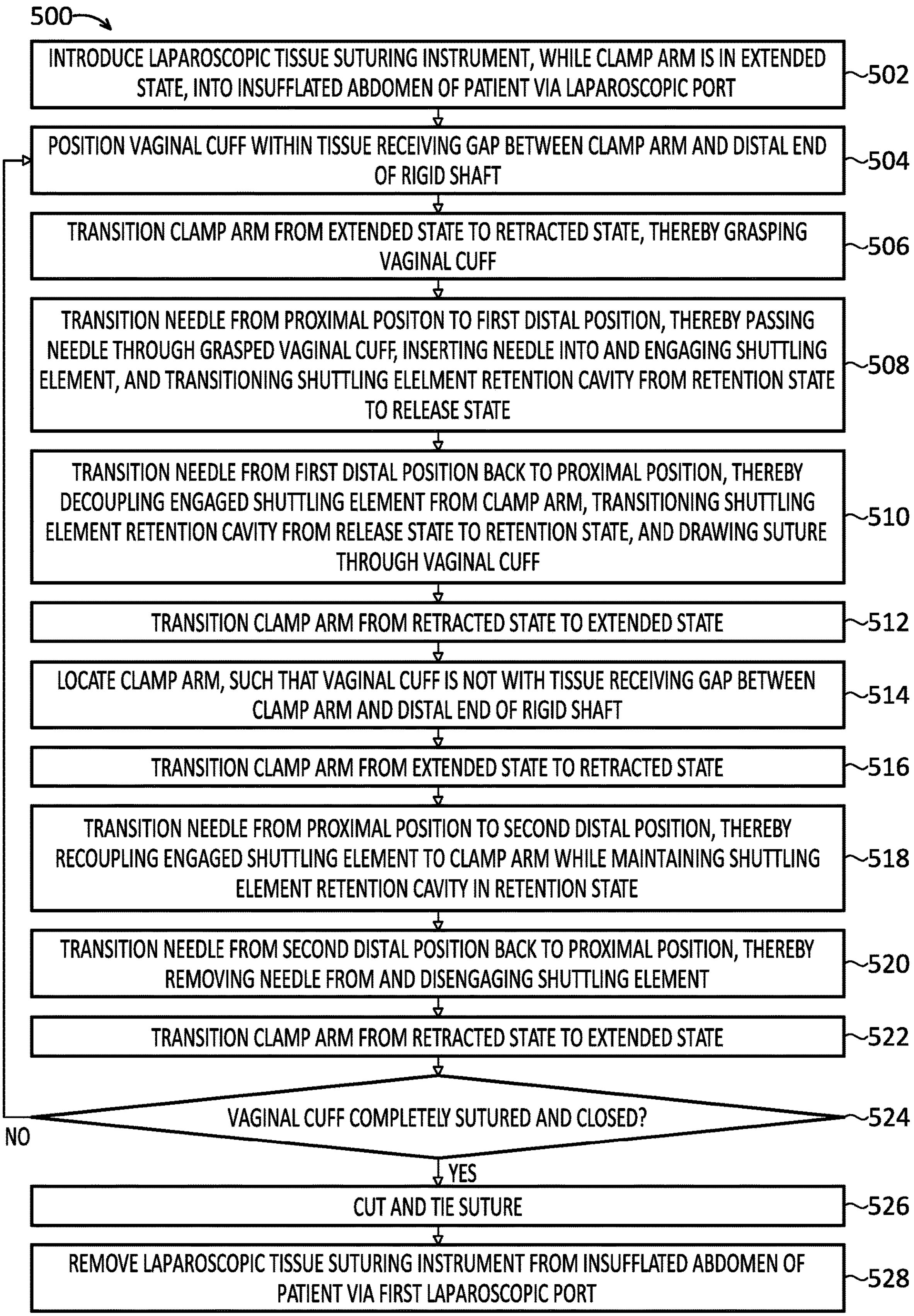
FIG. 69 is a flow diagram illustrating one exemplary method of operating the laparoscopic tissue suturing instrument of FIG. 40 to perform a TLH suturing procedure on a vaginal cuff of a patient.

Next, the needle 318 is transitioned from the second distal position to the proximal position via manipulation of the pivotable finger piece 342 (shown in FIG. 40), thereby removing the needle 318 from and disengaging the shuttling element 320 from the needle 318 (and specifically, as best illustrated in FIG. 68J, removing the shuttling element coupler 402 of the needle 318 from the cavity 432 of the shuttling element 320) (see FIG. 70I) (step 520).

Figure 70J:
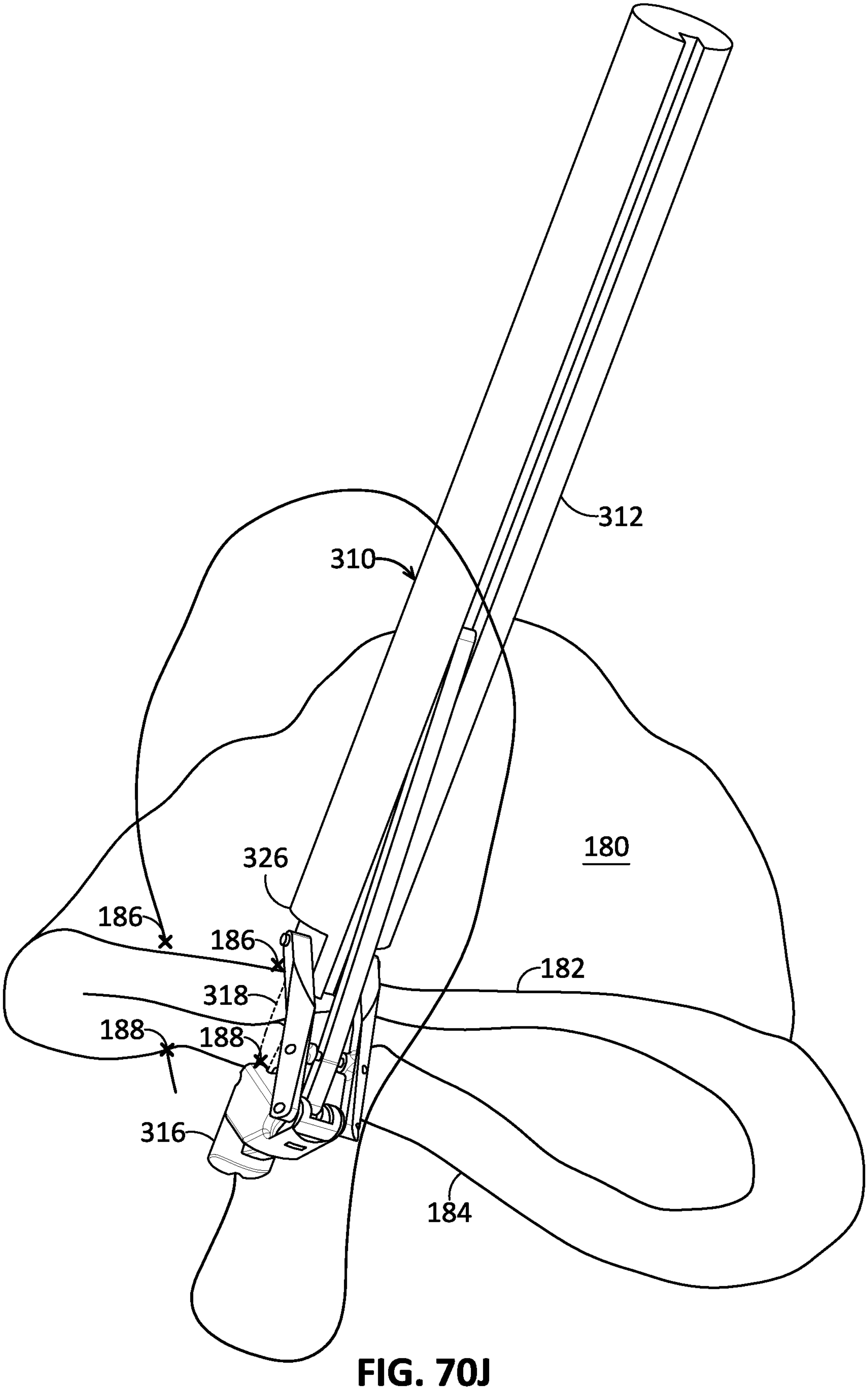
Figure 70K:
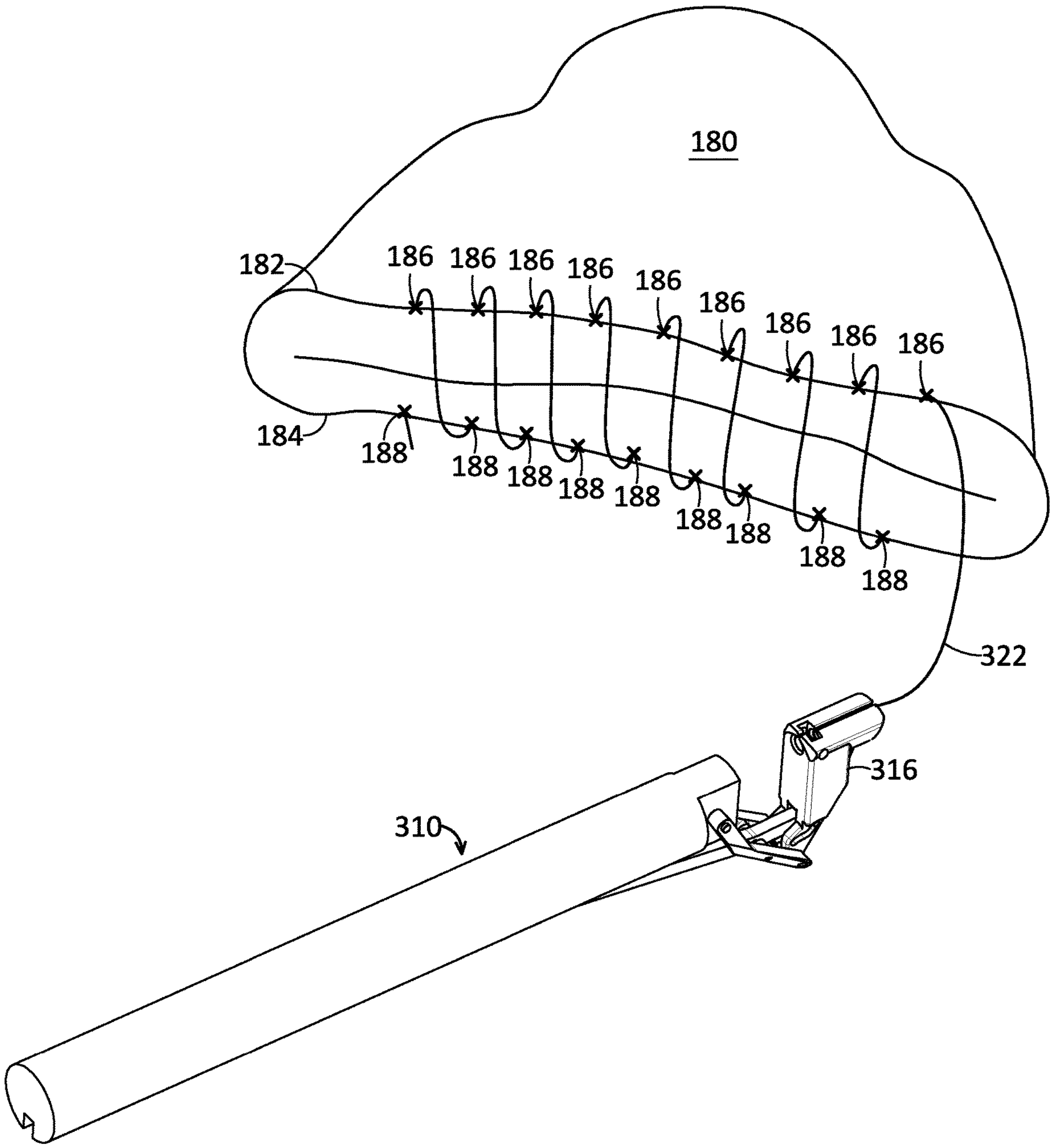

The clamp arm 316 is then transitioned from the retracted state to the extended state via manipulation of the rotatable nut 340 (shown in FIG. 40) (step 522), and as long as the vaginal cuff 180 is not completely sutured and closed (step 520), steps 504-518 are repeated at additional entry points 182 in the vaginal cuff 180 to create stitches 190 between the entry points 182 (see FIG. 70J). Once the vaginal cuff 180 is completely sutured and closed (step 522), the suture 322 is cut (e.g., using scissors introduced into the patient via another laparoscopic port (not shown) and tied (step 524) (see FIG. 70K), and the laparoscopic tissue suturing instrument 310 is removed from the insufflated abdomen of the patient via the laparoscopic port (step 526).

Although particular embodiments of the disclosed inventions have been shown and described herein, it should be understood that the embodiments are exemplary but not limiting, and it will be obvious to those skilled in the art that various changes and modifications may be made (e.g., the dimensions of various parts) without departing from the scope of the various disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A laparoscopic tissue suturing instrument, comprising:
an elongated shaft;
a tissue grasper coupled to a distal end of the elongated shaft, the tissue grasper defining a tissue receiving gap and defining a shuttling element retention cavity that removably retains a suture shuttling element;
a needle having a needle shaft, a shuttling element coupler disposed at a distal end of the needle shaft, and a shuttling element release mechanism disposed on the needle shaft proximal to the shuttling element coupler;
a shuttling element retainer mechanism adjacent to the shuttling element retention cavity, the shuttling element release mechanism interacting with the shuttling element retainer mechanism of the needle to alternately transition the shuttling element retention cavity between a retention state that securely retains the suture shuttling element, and a release state that releases the suture shuttling element;
wherein the shuttling element coupler:
engages the suture shuttling element when the needle shaft is transitioned from a proximal position to a first distal position, such that the shuttling element release mechanism interacts with shuttling element retainer mechanism to transition the shuttling element retention cavity from the retention state to the release state; and
removes the suture shuttling element from the shuttling element retention cavity when the needle shaft is transitioned from the first distal position to the proximal position, wherein the shuttling element release mechanism is slidably disposed along a length of the needle shaft, such that the shuttling element release mechanism continues to interact with the shuttling element retainer mechanism to maintain the shuttling element retention cavity in the release state as the shuttling element coupler removes the suture shuttling element from the shuttling element retention cavity.

2. The laparoscopic tissue suturing instrument of claim 1, wherein the shuttling element coupler:
inserts the suture shuttling element back into the shuttling element retention cavity when the needle shaft is transitioned from the proximal position to a second distal position proximal to the first distal position; and
disengages the suture shuttling element when the needle shaft is transitioned from the second distal position to the proximal position, wherein the shuttling element retention cavity retains the suture shuttling element after the shuttling element coupler has disengaged the suture shuttling element.

3. The laparoscopic tissue suturing instrument of claim 2, wherein the shuttling element retention cavity is biased to be maintained in the retention state;
wherein the shuttling element retention cavity returns from the release state to the retention state when the needle shaft is transitioned from the first distal position to the proximal position; and
the shuttling element release mechanism not interacting with the shuttling element retainer mechanism to maintain the shuttling element retention cavity in the retention state when the needle shaft is transitioned from the proximal position to the second distal position.

4. The laparoscopic tissue suturing instrument of claim 1, wherein the shuttling element release mechanism is a sleeve that is inserted within the shuttling element retention cavity and interacts with the shuttling element retainer mechanism when the needle shaft is transitioned from the proximal position to the first distal position.

5. The laparoscopic tissue suturing instrument of claim 1, wherein the needle further comprises a stop affixed to the needle shaft proximal to the shuttling element release mechanism, the stop abutting the shuttling element release mechanism to forcibly cause the shuttling element release mechanism to interact with the shuttling element retainer mechanism when the needle is transitioned from the proximal position to the first distal position.

6. The laparoscopic tissue suturing instrument of claim 1, wherein the suture shuttling element has a cavity, and the shuttling element coupler has a tip that is inserted into the cavity to engage the suture shuttling element, and that is removed from the cavity to disengage the suture shuttling element.

7. The laparoscopic tissue suturing instrument of claim 6, wherein the cavity of the suture shuttling element has an inner annular ledge, and the tip of the shuttling element coupler is an enlarged bullet-shaped tip, the enlarged bullet-shaped tip having an outer annular ledge that engages the inner annular ledge of the suture shuttling element, thereby allowing the shuttling element coupler to remove the suture shuttling element from the cavity.

8. The laparoscopic tissue suturing instrument of claim 1, wherein the tissue grasper comprises a jaw assembly having first and second jaws hingedly associated with each other, the jaw assembly transitions between an open state for grasping tissue and a closed state for delivery through a laparoscope.

9. The laparoscopic tissue suturing instrument of claim 8, wherein the shuttling element retainer mechanism comprises a pair of parallel resilient members formed on the first jaw, the shuttling element retention cavity comprises a pair of cavity portions formed on ends of the resilient members, the resilient members being flexed away from each other to translate the pair of cavity portions away from each other, thereby transitioning the shuttling element retention cavity from the retention state to the release state, and the resilient members being relaxed to translate the pair of cavity portions toward each other, thereby transitioning the shuttling element retention cavity from the released state to the retention state.

10. The laparoscopic tissue suturing instrument of claim 9, wherein the shuttling element release mechanism is inserted within the shuttling element retention cavity to flex the resilient members, and removed from the shuttling element retention cavity to relax the resilient members.

11. The laparoscopic tissue suturing instrument of claim 8, wherein the needle is hingedly coupled to the second jaw for, when the jaw assembly is in the open state, being alternately hinged between a retracted state, wherein the needle is stowed in the second jaw, and a deployed state, wherein the needle extends from the second jaw towards the first jaw.

12. The laparoscopic tissue suturing instrument of claim 1, wherein the tissue grasper comprises a clamp arm hingedly associated with the distal end of the elongated shaft, the clamp arm transitions between a retracted state for grasping tissue and an extended state for delivery through a laparoscope.

13. The laparoscopic tissue suturing instrument of claim 12, wherein the shuttling element retainer mechanism comprises a latch that translates from the shuttling element retention cavity, thereby transitioning the shuttling element retention cavity from the retention state to the release state, and translates into the shuttling element retention cavity, thereby transitioning the shuttling element retention cavity from the release state to the retention state.

14. The laparoscopic tissue suturing instrument of claim 13, wherein the shuttling element retainer mechanism further comprises a spring affixed to the latch, the spring being compressed to translate the latch from the shuttling element retention cavity, and the spring being relaxed to translate the latch into the shuttling element retention cavity.

15. The laparoscopic tissue suturing instrument of claim 14, wherein the shuttling element release mechanism is inserted within the shuttling element retention cavity to compress the spring, and removed from the shuttling element retention cavity to relax the spring.

16. The laparoscopic tissue suturing instrument of claim 12, wherein the needle is slidably coupled to the elongated shaft, such that the needle may be proximally slid between the proximal position, wherein the needle is stowed in the distal end of the elongated shaft, and the first and second distal positions.

17. The laparoscopic tissue suturing instrument of claim 1, further comprising a suture affixed to the suture shuttling element, such that the when the needle is transitioned from the first distal position to the proximal position, the suture is drawn from the tissue grasper to the distal end of the elongated shaft.

18. A laparoscopic tissue suturing instrument, comprising:

an elongated shaft;

a tissue grasper coupled to a distal end of the elongated shaft, the tissue grasper defining a tissue receiving gap and defining a shuttling element retention cavity that removably retains a suture shuttling element;

a needle having a needle shaft, a shuttling element coupler disposed at a distal end of the needle shaft, and a shuttling element release mechanism slidably disposed on the needle shaft proximal to the shuttling element coupler; and a shuttling element retainer mechanism adjacent to the shuttling element retention cavity, the shuttling element release mechanism interacting with the shuttling element retainer mechanism of the needle to alternately transition the shuttling element retention cavity between a retention state that securely retains the suture shuttling element, and a release state that releases the suture shuttling element;

wherein the shuttling element coupler:

engages the suture shuttling element when the needle shaft is transitioned from a proximal position to a first distal position, such that the shuttling element release mechanism interacts with shuttling element retainer mechanism to transition the shuttling element retention cavity from the retention state to the release state;

removes the suture shuttling element from the shuttling element retention cavity when the needle shaft is transitioned from the first distal position to the proximal position;

inserts the suture shuttling element back into the shuttling element retention cavity when the needle shaft is transitioned from the proximal position to a second distal position proximal to the first distal position; and disengages the suture shuttling element when the needle shaft is transitioned from the second distal position to the proximal position, wherein the shuttling element retention cavity retains the suture shuttling element after the shuttling element coupler has disengaged the suture shuttling element.

19. The laparoscopic tissue suturing instrument of claim 18, wherein the shuttling element retention cavity is biased to be maintained in the retention state;

wherein the shuttling element retention cavity returns from the release state to the retention state when the needle shaft is transitioned from the first distal position to the proximal position; and the shuttling element release mechanism does not interact with the shuttling element retainer mechanism to maintain the shuttling element retention cavity in the retention state when the needle shaft is transitioned from the proximal position to the second distal position.

20. A laparoscopic tissue suturing instrument, comprising:

an elongated shaft;

a jaw assembly coupled to a distal end of the elongated shaft, the jaw assembly comprising first and second jaws hingedly associated with each other, the jaw assembly configured for being transitioned between an open state for grasping tissue and a closed state for delivery through a laparoscopic port, the first jaw having a shuttling element retention cavity;

a suture shuttling element configured for being removably coupled to the first jaw;

a needle hingedly coupled to the second jaw for being alternately hinged between a retracted state, wherein the needle is stowed in the second jaw, and a deployed state; and a shuttling element release mechanism slidably disposed along a length of the needle for transitioning the shuttling element retention cavity between a release state and a retention state, wherein the needle is for being inserted within and engaged to the suture shuttling element retained within the shuttling element retention cavity of the first jaw when the jaw assembly is in a first one of at least one intermediate state between the open state and the closed state, such that the shuttling element release mechanism transitions the shuttling element retention cavity from the retention date to the release state, decoupling the engaged suture shuttling element from the first jaw by removing the engaged suture shuttling element from the shuttling element retention cavity of the first jaw when the jaw assembly is transitioned from the first intermediate state towards the open state, such that the shuttling element release mechanism transitions from the release state to the retention state, recoupling the suture shuttling element to the first jaw by inserting the suture shuttling element within the shuttling element retention cavity of the first jaw when the jaw assembly is transitioned from the open state to a second one of the at least one intermediate state, and for being removed and disengaged from the suture shuttling element when the jaw assembly is transitioned from the second intermediate state toward the open state.

* * * * *